(12) United States Patent
Punnonen et al.

(10) Patent No.: US 6,541,011 B2
(45) Date of Patent: *Apr. 1, 2003

(54) ANTIGEN LIBRARY IMMUNIZATION

(75) Inventors: Juha Punnonen, Palo Alto, CA (US); Steven H. Bass, Hillsborough, CA (US); Robert Gerald Whalen, Paris (FR); Russell Howard, Los Altos Hills, CA (US); Willem P. C. Stemmer, Los Gatos, CA (US)

(73) Assignee: Maxygen, Inc., Redwood City, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/247,890

(22) Filed: Feb. 10, 1999

(65) Prior Publication Data

US 2002/0198162 A1 Dec. 26, 2002

Related U.S. Application Data

(60) Provisional application No. 60/074,294, filed on Feb. 11, 1998, and provisional application No. 60/105,509, filed on Oct. 23, 1998.

(51) Int. Cl.[7] .................. A61K 39/12; C07K 1/00
(52) U.S. Cl. ................. 424/204.1; 424/218.1; 530/300; 530/350
(58) Field of Search ............ 424/204.1, 218.1; 530/300, 350

(56) References Cited

U.S. PATENT DOCUMENTS

| | | |
|---|---|---|
| 5,252,714 A | 10/1993 | Harris et al. |
| 5,264,563 A | 11/1993 | Huse .................. 536/25.3 |
| 5,338,665 A | 8/1994 | Schatz et al. |
| 5,348,867 A | 9/1994 | Georgiou et al. |
| 5,470,725 A | 11/1995 | Borriss et al. ........... 435/93 |
| 5,494,671 A | 2/1996 | Lai et al. |
| 5,512,463 A | 4/1996 | Stemmer |
| 5,514,588 A | 5/1996 | Varadaraj |
| 5,523,388 A | 6/1996 | Huse .................. 536/22.1 |
| 5,571,698 A | 11/1996 | Ladner et al. ......... 435/69.7 |
| 5,589,466 A | 12/1996 | Felgner et al. ........... 514/44 |
| 5,593,972 A | 1/1997 | Weiner et al. ........... 514/44 |
| 5,605,793 A | 2/1997 | Stemmer et al. ........... 435/6 |

(List continued on next page.)

FOREIGN PATENT DOCUMENTS

| | | |
|---|---|---|
| AU | 718740 B2 | 11/1996 |
| AU | 743414 B2 | 1/1998 |

(List continued on next page.)

OTHER PUBLICATIONS

Agren et al., "Genetically Engineered Nontoxic Vaccine Adjuvant That Combines B Cell Targeting with Immunomodulation by Cholera Toxin A1 Subunit," *J. Immunol.* 158:3936 (1997).

(List continued on next page.)

Primary Examiner—Hankyel T. Park
Assistant Examiner—Stacy S. Brown
(74) Attorney, Agent, or Firm—Margaret A. Powers; Norman J. Kruse; Quine Intellectual Property Law Group, P.C.

(57) ABSTRACT

This invention is directed to antigen library immunization, which provides methods for obtaining antigens having improved properties for therapeutic and other uses. The methods are useful for obtaining improved antigens that can induce an immune response against pathogens, cancer, and other conditions, as well as antigens that are effective in modulating allergy, inflammatory and autoimmune diseases.

47 Claims, 23 Drawing Sheets

U.S. PATENT DOCUMENTS

| | | | |
|---|---|---|---|
| 5,691,170 A | 11/1997 | Gritz et al. | 435/69.7 |
| 5,698,426 A | 12/1997 | Huse | 435/172.3 |
| 5,703,057 A | 12/1997 | Johnston et al. | 514/44 |
| 5,723,323 A | 3/1998 | Kauffman et al. | 435/172.3 |
| 5,744,141 A | 4/1998 | Paoletti et al. | |
| 5,763,192 A | 6/1998 | Kauffman et al. | 435/7.1 |
| 5,763,239 A | 6/1998 | Short et al. | |
| 5,770,434 A | 6/1998 | Huse | 435/252.33 |
| 5,783,386 A | 7/1998 | Jacobs, Jr. et al. | 435/6 |
| 5,789,228 A | 8/1998 | Lam et al. | |
| 5,808,022 A | 9/1998 | Huse | 536/22.1 |
| 5,811,238 A | 9/1998 | Stemmer et al. | 435/6 |
| 5,814,473 A | 9/1998 | Warren et al. | |
| 5,814,476 A | 9/1998 | Kauffman et al. | 435/69.1 |
| 5,817,483 A | 10/1998 | Kauffman et al. | 435/69.1 |
| 5,824,469 A | 10/1998 | Horwitz et al. | 435/6 |
| 5,824,514 A | 10/1998 | Kauffman et al. | 435/91.1 |
| 5,830,696 A | 11/1998 | Short | 435/69.1 |
| 5,830,721 A | 11/1998 | Stemmer et al. | 435/172.1 |
| 5,834,252 A | 11/1998 | Stemmer et al. | 435/91.1 |
| 5,837,458 A | 11/1998 | Minshull et al. | 435/6 |
| 5,862,514 A | 1/1999 | Huse et al. | |
| 5,866,344 A | 2/1999 | Georgiou | |
| 5,866,363 A | 2/1999 | Pieczenik | 435/69.1 |
| 5,871,974 A | 2/1999 | Huse | 435/69.7 |
| 5,876,997 A | 3/1999 | Kretz | |
| 5,882,883 A | 3/1999 | Egel-Mitani et al. | |
| 5,925,749 A | 7/1999 | Mathur et al. | |
| 5,928,905 A | 7/1999 | Stemmer et al. | 435/91.1 |
| 5,939,250 A | 8/1999 | Short | 435/4 |
| 5,939,300 A | 8/1999 | Robertson et al. | |
| 5,942,430 A | 8/1999 | Robertson et al. | |
| 5,948,666 A | 9/1999 | Callen et al. | |
| 5,955,358 A | 9/1999 | Huse | 435/328 |
| 5,958,672 A | 9/1999 | Short | 435/4 |
| 5,958,751 A | 9/1999 | Murphy et al. | |
| 5,962,258 A | 10/1999 | Mathur et al. | |
| 5,962,283 A | 10/1999 | Warren et al. | |
| 5,965,408 A | 10/1999 | Short | 435/91.1 |
| 5,976,862 A | 11/1999 | Kauffman et al. | 435/252.3 |
| 5,985,285 A | 11/1999 | Titball et al. | |
| 5,985,646 A | 11/1999 | Murphy et al. | |
| 5,989,553 A | 11/1999 | Johnston et al. | 424/190.1 |
| 6,001,574 A | 12/1999 | Short et al. | 435/6 |
| 6,001,613 A | 12/1999 | Donis et al. | |
| 6,004,788 A | 12/1999 | Short | 435/183 |
| 6,030,779 A | 2/2000 | Short | 435/6 |
| 6,043,303 A | 3/2000 | Beach et al. | |
| 6,054,267 A | 4/2000 | Short | 435/6 |
| 6,054,312 A | 4/2000 | Larocca et al. | |
| 6,057,103 A | 5/2000 | Short | 435/6 |
| 6,074,865 A | 6/2000 | Kelly et al. | |
| 6,087,341 A | 7/2000 | Khavari et al. | |
| 6,096,548 A | 8/2000 | Stemmer | 435/440 |
| 6,117,679 A | 9/2000 | Stemmer | 435/440 |
| 6,132,970 A | 10/2000 | Stemmer | 435/6 |
| 6,153,410 A | 11/2000 | Arnold et al. | |
| 6,156,511 A | 12/2000 | Schartz et al. | |
| 6,159,687 A | 12/2000 | Vind | |
| 6,159,688 A | 12/2000 | Borchert et al. | |
| 6,165,477 A | 12/2000 | Ivy et al. | |
| 6,165,718 A | 12/2000 | Borchert et al. | |
| 6,165,793 A | 12/2000 | Stemmer | |
| 6,168,919 B1 | 1/2001 | Short | |
| 6,171,820 B1 | 1/2001 | Short | |
| 6,171,854 B1 | 1/2001 | Galler et al. | |
| 6,174,673 B1 | 1/2001 | Short et al. | |
| 6,177,263 B1 | 1/2001 | Arnold et al. | |
| 6,180,406 B1 | 1/2001 | Stemmer | |
| 6,184,024 B1 | 2/2001 | Lai et al. | |
| 6,194,183 B1 | 2/2001 | Markvardsen et al. | |
| 6,238,884 B1 | 5/2001 | Short et al. | |
| 6,251,674 B1 | 6/2001 | Tobin et al. | |
| 6,261,561 B1 | 7/2001 | Stewart, Jr. et al. | |
| 6,271,354 B1 | 8/2001 | Srinivisan et al. | |
| 6,372,221 B2 | 4/2002 | Mannhalter et al. | |

FOREIGN PATENT DOCUMENTS

| | | | |
|---|---|---|---|
| EP | 0 125 228 B1 | 6/1984 | |
| EP | 0 725 081 A1 | 7/1996 | |
| EP | 0 544 809 B1 | 12/1998 | |
| EP | 0 563 296 B1 | 3/1999 | |
| EP | 0 911 396 A2 | 4/1999 | |
| EP | 0 911 396 A3 | 5/1999 | |
| EP | 0 934 999 A1 | 8/1999 | |
| EP | 00604566 B1 | 11/1999 | |
| EP | 0 876 509 B1 | 9/2001 | |
| WO | WO 90/14424 | 11/1990 | |
| WO | WO 90/14443 | 11/1990 | |
| WO | WO 91/07979 A1 | 6/1991 | |
| WO | WO 92/03461 | 3/1992 | |
| WO | WO 92/06176 | 4/1992 | |
| WO | WO 92/06204 | 4/1992 | |
| WO | WO 92/11272 | 7/1992 | |
| WO | WO 93/03763 A1 | 3/1993 | |
| WO | WO-9306214 A1 * | 4/1993 | |
| WO | WO 93/10214 A1 | 5/1993 | |
| WO | WO-9406421 A1 * | 3/1994 | |
| WO | WO 94/06911 | 3/1994 | |
| WO | WO 94/11496 | 5/1994 | |
| WO | WO 94/23738 A1 | 10/1994 | |
| WO | WO 94/25608 | 11/1994 | |
| WO | WO 94/26787 A1 | 11/1994 | |
| WO | WO 95/16027 A1 | 6/1995 | |
| WO | WO 95/22625 | 8/1995 | |
| WO | WO 95/26718 | 10/1995 | |
| WO | WO 96/11279 A1 | 4/1996 | |
| WO | WO 96/13250 A1 | 5/1996 | |
| WO | WO 96/23882 A1 | 8/1996 | |
| WO | WO 98/36080 | 8/1996 | |
| WO | WO 96/31613 | 10/1996 | |
| WO | WO 96/33207 | 10/1996 | |
| WO | WO 96/37221 A1 | 11/1996 | |
| WO | WO-9637624 A1 * | 11/1996 | |
| WO | WO 96/40933 A1 | 12/1996 | |
| WO | WO 97/04077 | 2/1997 | |
| WO | WO 97/07128 A1 | 2/1997 | |
| WO | WO 97/07205 | 2/1997 | |
| WO | WO 97/11605 A1 | 4/1997 | |
| WO | WO 97/20078 | 6/1997 | C12Q/1/68 |
| WO | WO 97/25410 | 7/1997 | |
| WO | WO 97/32987 A1 | 7/1997 | |
| WO | WO 97/35957 A1 | 10/1997 | |
| WO | WO 97/35966 | 10/1997 | |
| WO | WO 97/44361 | 11/1997 | |
| WO | WO 97/48416 | 12/1997 | |
| WO | WO 97/48717 | 12/1997 | |
| WO | WO 97/48794 | 12/1997 | |
| WO | WO 98/00526 | 1/1998 | |
| WO | WO 98/01581 | 1/1998 | |
| WO | WO 98/05764 | 2/1998 | |
| WO | WO 98/05765 | 2/1998 | |
| WO | WO 98/13485 | 4/1998 | |
| WO | WO 98/13487 | 4/1998 | |
| WO | WO 98/24799 | 6/1998 | |
| WO | WO 98/27230 | 6/1998 | |
| WO | WO 98/28416 | 7/1998 | |
| WO | WO 98/31816 | 7/1998 | |
| WO | WO 98/31837 | 7/1998 | |
| WO | WO 98/37911 A1 | 9/1998 | |
| WO | WO 98/41622 | 9/1998 | |

| | | |
|---|---|---|
| WO | WO 98/41623 | 9/1998 |
| WO | WO 98/41653 | 9/1998 |
| WO | WO 98/42727 | 10/1998 |
| WO | WO 98/42832 | 10/1998 |
| WO | WO 98/45444 | 10/1998 |
| WO | WO 98/48034 | 10/1998 |
| WO | WO 98/49286 | 11/1998 |
| WO | WO 98/58085 | 12/1998 |
| WO | WO 99/07837 | 2/1999 |
| WO | WO 99/08539 | 2/1999 |
| WO | WO 99/10472 | 3/1999 |
| WO | WO 99/10539 | 3/1999 |
| WO | WO 99/19506 | 4/1999 |
| WO | WO 99/19518 | 4/1999 |
| WO | WO 99/21979 | 5/1999 |
| WO | WO 99/23107 | 5/1999 |
| WO | WO 99/23236 | 5/1999 |
| WO | WO 99/29902 | 6/1999 |
| WO | WO 99/41366 | 8/1999 |
| WO | WO 99/41368 | 8/1999 |
| WO | WO 99/41369 | 8/1999 |
| WO | WO 99/41383 | 8/1999 |
| WO | WO 99/41402 | 8/1999 |
| WO | WO 99/45154 | 9/1999 |
| WO | WO 99/57128 | 11/1999 |
| WO | WO 99/65927 | 12/1999 |
| WO | WO 00/16984 | 3/2000 |
| WO | WO 00/18778 | 4/2000 |
| WO | WO 00/42560 | 7/2000 |
| WO | WO 00/42561 | 7/2000 |
| WO | WO 00/46344 | 8/2000 |
| WO | WO 00/53744 | 9/2000 |
| WO | WO 00/58517 | 10/2000 |
| WO | WO 01/00234 | 1/2001 |

OTHER PUBLICATIONS

Axon, A.T., "Treatment of *Helicobacter pylori*: future therapeutic and prophylactic perspectives," *Gut* 43(1):S70–3 (1998).

Bass, Steven et al., "Hormone Phage: An Enrichment Method for Variant Proteins With Altered Binding Properties," *Proteins: Structure, Function, and Genetics* 8:309–314 (1990).

Bhatnagar, Pradip K. et al., "Immune response to synthetic peptide analogues of hepatitis B surface antigen specific for the a determinant," *Proc. Nat'l. Acad. Sci. USA* 79:4400–4404 (1982).

Blaser, M.J. "*Helicobacter pylori* and gastric diseases," *BMJ* 316:1507–10 (1998).

Bray, Michael et al., "Mice Immunized with Recombinant Vaccinia Virus Expressing Dengue 4 Virus Structural Proteins with or without Nonstructural protein NS1 Are Protected against Fatal Dengue Virus Encephalitis," *J. Virol.* 63:2853–2856 (1989).

Brocke, Stefan et al., "Treatment of experimental encephalomyelitis with a peptide analogue of myelin basic protein," *Nature* 379:343–46 (1996).

Brubaker, Robert R. "The V Antigen of Yersiniae: An Overview," *Current Investigations of the Microbiology of Yersinae* 12:127–133 (1991).

Burton, Dennis R., "Phage display," *Immunotechnology* 1(2):87–94 (1995).

Christians, F.C. et al., "Directed evolution of thymidine kinase for AZT phosphorylation using DNA family shuffling," *Nature Biotechnology* 17:259–264 (1999).

Chu et al.,"A Vaccinia Virus–Vectored Hantaan Virus Vaccine Protects Hamsters from Challenge with Hantaan and Seoul Viruses but Not Puumala Virus," *J. Virol.* 69:6417 (1995).

Clackson, Tim and James A. Wells, "In vitro selection from protein and peptide libraries," *Trends Biotechnol.* 12(5):173–84 (1994).

Cote et al., "Protection of Chimpanzees from Type B Hepatitis by Immunization with Woodchuck Hepatitis Virus Surface Antigen," *J. Virol.* 60:895–901 (1986).

Crabtree, J.E., "Eradication of chronic *Helicobacter pylori* infection by therapeutic vaccination," *Gut* 43:7–8 (1998).

Crameri, A. et al., "Combinatorial Multiple Cassette Mutagenesis Creates All the Permutations of Mutant and Wild–Type Sequences," *Biotechniques* 18:194–195 (1995).

Crameri, A. et al., "Construction and evolution of antibody–phage libraries by DNA shuffling," *Nature Medicine* 2:100–103 (1996).

Crameri, A. et al., "DNA Shuffling of a family of genes from diverse species accelerates directed evolution," *Nature* 391:288–291 (1998).

Crameri, A. et al., "Improved Green Fluorescent Protein by Molecular Evolution Using DNA Shuffling," *Nature Biotechnology* 14:315–319 (1996).

Crameri, A. et al., "Molecular evolution of an arsenate detoxification pathway by DNA shuffling," *Nature Biotechnology* 15:436–438 (1997).

Cwirla, Steven E. et al., "Peptides on phage: A vast library of peptides for identifying ligands," *Proc. Natl. Acad. Sci. USA* 87:6378–6382 (1990).

Devlin, James J. et al., "Random Peptide Libraries: A Source of Specific Protein Binding Molecules," *Science* 249:404–406 (1990).

Donovan, William "Genes Encoding Spore Coat Polypeptides from *Bacillus subtilis*," *J. Mol. Biol.* 196:1–10 (1987).

Dubois, Andre et al., "Immunization against Natural *Helicobacter pylori* Infection in Nonhuman Primates," *Infect. Immun.* 66:4340–6 (1998).

Dunn, Ian S. "Phage display of proteins," *Curr. Opin. Biotechnol.* 7(5):547–53 (1996).

Felici, Franco et al., "Peptide and protein display on the surface of filamentous bacteriophage," *Biotechnol. Annu. Rev.* 1:149–83 (1995).

Fields, et al., "Crystal structure of a T–cell receptor B–chain complexed with a superantigen," *Nature* 384:188–192 (1996).

Francisco, Joseph A. et al., "Production and fluorescence–activated cell sorting of *Escherichia coli* expressing a functional antibody fragment on the external surface," *Proc. Nat'l. Acad. Sci. USA* 90:10444–10448 (1993).

Gates, C.M. et al., "Affinity Selective Isolation of Ligands from Peptide Libraries Through Display on a lac Repressor 'Headpiece Dimer'" *J. Mol. Biol.* 255:1–14 (1995).

Han, Xiaoliang et al., "Ligand–directed retroviral targeting of human breast cancer cells," *Proc. Natl. Acad. Sci USA* 92:9747–9751 (1995).

Hanes, Jozef and Andreas Pluckthun., "In vitro selection and evolution of functional proteins by using ribosome display," *Proc. Nat'l. Acad. Sci. USA* 94(10):4937–42 (1997).

He, Mingyue and Michael J. Taussig, "Antibody–ribosome–mRNA (ARM) complexes as efficient selection particles for in vitro display and evolution of antibody combining sites," *Nucl. Acids Res.* 25(24):5132–4 (1997).

Hill, H. Rachael and Peter G. Stockley et al., "Phage presentation," *Mol Microbiol* 20(4):685–92 (1996).

Holzmann, H. et al., "Molecular epidemiology of tick–borne encephalitis virus: cross–protection between European and Far Eastern subtypes," *Vaccine* 10:345 (1992).

Huang, Sharon K.S. et al., "Antibody Responses to Melanoma/Melanocyte Autoantigens in Melanoma Patients," *J. Invest. Dermatol.* 111:662–7 (1998).

Hui, George S.N. et al., "Dominance of Conserved B–Cell Epitopes of the *Plasmodium falciparum* Merozoite Surface Protein, MSP1, in Blood–Stage Infections of Naive Aotus Monkeys," *Infect Immun.* 64:1502–1509 (1996).

Iacono–Connors, Lauren C. et al., "Characterization of Langat virus antigenic determinants defined by monoclonal antibodies to E, NS1 and preM and identification of a protective, non–neutralizing preM–specific monoclonal antibody," *Virus Res.* 43:125–136 (1996).

Kay, B.K., et al., *Phage Display of Peptides and Proteins: A Laboratory Manual* Academic Press (1996).

Keenan et al., "Lack of Protection following immunisation with *H. pylori* outer membrane vesicles highlights antigenic differences between *H. felis* and *H. pylori*," *FEMS Microbiol Lett.* 161:21–7 (1998).

Kinney et al., "Recombinant Vaccinia Virus/Benezuelan Equine Encephalitis (VEE) Virus Protects Mice from Peripheral VEE Virus Challenge," *J. Virol.* 62:4697 (1998).

Kleanthous, Harry et al., "Vaccine development against infection with *Helicobacter pylori*," *Br. Med. Bull.* 54:229–41 (1998).

Kobyashi, Yuzuru et al., "Antigenic Analysis of Japanese Encephalitis Virus by Using Monoclonal Antibodies," *Infect. Immun.* 44:117 (1984).

Kochel, Tadeusz et al., "Inoculation of plasmids expressing the dengue–2 envelope gene elicit neutralizing antibodies in mice," *Vaccine* 15:547–552 (1997).

Konishi et al.,"A Highly Attenuated Host Range–Restricted Vaccinia Virus Strain, NYVAC, Encoding the prM, E and NS1 Genes of Japanese Encephalitis Virus Prevents JEV Viremia in Swine," *Virology* 190:454 (1992).

Leary et al.,"Active Immunization with Recombinent V Antigen from Yersinia Pestis Protects Mice against Plague," *Infect. Immun.* 3:2854 (1995).

Lee, Seung Woo et al., "Optimal Induction of Hepatitis C Virus Envelope–Specific Immunity by Bicistronic Plasmid DNA Inoculation with the Granulocyte–Macrophage Colony–Stimulating Facter Gene," *J. Virol* 72:8430–6 (1998).

Lowman, Henry B. and Jame A. Wells, "Affinity Maturation of Human Growth Hormone by Monovalent Phage Display," *J. Mol. biol.* 234:564–578 (1993).

Lowman, Henry B. and James A. Wells, "Monovalent Phage Display: A Method for Selecting Variant Proteins from Random Libraries," *Methods: A Companion to Methods Enz.* 3(3):205–216 (1991).

Lu, Zhijian et al., "Expression of Thioredoxin Random Peptide Libraries on the *Escherichia coli* Cell Surface as Functional Fusions to Flagellin: A System Designed for Exploring Protein–Protein Interactions," *Bio/Technology* 13:366–372 (1995).

Marchetti, Marta et al., "Protection against *Helicobacter pylori* infection in mice by intragastric vaccination with *H. pylori* antigens is achieved using a non–toxic mutant of *E. coli* heat–labile enterotoxin (LT) as adjuvant," *Vaccine* 16:33–7 (1998).

Mattheakis, Larry C. et al., "An in vitro polysome display system for identifying ligands from very large peptide libraries," *Proc. Nat'l. Acad. Sci. USA* 91(19):9022–6 (1994).

McAtee, C. Patrick et al., "Identification of Potential Diagnostic and Vaccine Candidates of *Helicobacter pylori* by Two–Dimensional Gel Electrophoresis, Sequence Analysis, and Serum Profiling," *Clin. Diagn. Lab. Immunol.* 5:537–42 (1998).

McAtee, C. Patrick et al., "Identification of Potential Diagnostic and Vaccine Candidates of *Helicobacter pylori* by "Proteome" Technologies," *Helicobacter* 3:163–9 (1998).

McCutcheon et al. "A senstive ELISPOT assay to detect low–frequency human T lymphocytes,", *J. Immunol. Methods* 210:149–66 (1997).

McGregor, Duncan, "Selection of Proteins and Peptides from Libraries Displayed on Filamentous Bacteriophage," *Mol Biotechnol.* 6(2):155–62 (1996).

Minshull, J. and Willem P.C. Stemmer, "Protein evolution by molecular breeding," *Current Opinion in Chemical Biology* 3:284–290 (1999).

Nemoto, Naoto et al., "In vitro virus: Bonding of mRNA bearing puromycin at the 3'–terminal end to the C–terminal end of its encoded protein on the ribosome in vitro," *FEBS Lett.* 414(2):405–8 (1997).

Neurath, A. R. et al., "Monoclonal Antibodies to Hepatitis BSurface Antigen (HBsAg) with Anti–a Specificity Recognize A Synthetic Peptide Analogue (S135–155) with Unmodified Lysine (141)," *J. Virol. Methods* 9:341–346 (1984).

Ni and Barrett, "Nucleotide and deduced amino acid sequence of the structural protein genes of Japanese encephalitis viruses from different geographical locations," *J. Gen. Virol.* 76:401 (1995).

O'Neil, Karyn T. et al., "Phage display: protein engineering by directed evolution," *Curr. Opin. Struct. Biol.* 5(4):443–9 (1995).

Oda, Kazumasa Ántigenic Characterization Among Strains of Japanese Encephalitis Virus Isolated in Hyogo Prefecture by the Antibody–Absorption Test, *Kobe J. Med. Sci.* 22:123 (1976).

Parren, Paul W.H.I. et al., "Relevance of the antibody response against human immunodeficiency virus type 1 envelope to vaccine design," *Immunol. Lett.* 57:105–112 (1997).

Patten, P.A. et al., "Applications of DNA Shuffling to Pharmaceuticals and Vaccines," *Current Opinion in Biotechnology,* 8:724–733 (1997).

Phizicky, Eric M. et al., "Protein–Protein Interactions: Methods for Detection and Analysis," *Microbiol Rev.* 59(1):94–123 (1995).

Racke, Michael K. et al., "Cytokine–induced Immune Deviation as a Therapy for Inflammatory Autoimmune Disease," *J. Exp. Med.* 180:1961–66 (1994).

Roggenkamp et al., "Passive Immunity to Infection with Yersinia spp. Mediated by Anti–Recombinant V Antigen is Dependent on Polymorphism of V Antigen," *Infect. Immun.* 65:446 (1997).

Schatz, Peter J. et al., "[10] Screening of Peptide Libraries Linked to Iac Repressor," *Methods Enzymol.* 267:171–91 (1996).

Schmaljohn, A.L. et al., "Non–neutralizing monoclonal antibodies can prevent lethal alphavirus encephalitis," *Nature* 297:70 (1982).

Scott, Jamie K. and George P. Smith, "Searching for Peptide Ligands with an Epitope Library," *Science* 249:386–388 (1990).
Stemmer, W.P.C. and N.W. Soong, "Molecular breeding of viruses for targeting and other clinical properties," *Tumor Targeting* 4:1–4 (1999).
Stemmer, W.P.C. et al., "Single–step assembly of a gene and entire plasmid from large numbers of oligodeoxyribonucleotides," *Gene* 164:49–53 (1995).
Stemmer, W.P.C., "DNA shuffling by random fragmentation and reassembly: In vitro recombination for molecular evolution," *Proc. Natl. Acad. Sci. USA* 91:10747–10751 (1994).
Stemmer, W.P.C., "Rapid evolution of a protien in vitro by DNA shuffling," *Nature* 370:389–391 (1994).
Stemmer, W.P.C., "Searching Sequence Space," *Biotechnology* 13:549–553 (1995).
Stemmer, W.P.C., "Sexual PCR and Assembly PCR," The Encyclopedia of Molecular Biology, VCH Publishers, New York pp. 447–457 (1996).
Stemmer, W.P.C., "The Evolution of Molecular Computation," *Science* 270:1510 (1995).
Tascon, Richard E. et al., "Vaccination against tuberculosis by DNA injection," *Nat. Med.* 2:888–92 (1996).
Tytgat, G.N.,"Review article: practical management issues for the *Helicobacter pylori*–infected patient at risk of gastric cancer," *Aliment. Pharmacol. Ther.* 12(1):123–8 (1998).
VanCott, Thomas C. et al., "Antibodies with Specificity to Native gp120 and Neutralization Activity against Primary Human Immunodeficiency Virus Type 1 Isolates Elicited by Immunization with Oligomeric gp160," *J. Virol.* 71:4319–4330 (1997).
Wermeille, Joel et al., "The eradication treatments of *Helicobacter pylori*," *Pharm. World Sci.* 20:1–17 (1998).
Woody, Mary Alice et al., "Staphylococcal enterotoxin B mutants (N23K and F44S): biological effects and vaccine potential in a mouse model," *Vaccine* 15(2):133–139 (1997).
Zamvil, Scott S. and Lawrence Steinman, "The T Lymphocyte in Experimental Allergic Encephalomyelitis," *Ann. Rev. Immunol.* 8:579–621 (1990).
Zhang, J. et al., "Directed evolution of a fucosidase from a galactosidase by DNA shuffling and screening," *Proc. Natl. Acad. Sci. USA* 94:4504–4509 (1997).
Zhong, Weimin et al., "Therapeutic passive vaccination against chronic Lyme disease in mice," *Proc. Nat'l. Acad. Sci. USA* 94:12533–12538 (1997).
Affholter & Stemmer (1998) "Directed evolutions of proteins and pathways by DNA shuffling." *Books of Abstracts* 216th ACS National Meeting Aug. 23–27, BIOT–042.
Ahmed (1995) J Bacteriology 177(14):3904–3910.
Ahn et al. (1996) "Human cytomegalovirus inhibits antigen presentation by a sequential multistep process." *Proc. Natl. Acad, Sci USA* 93:10990.
Attridge et al. (1997) "Oral delivery of foreign antigens by attenuated Salmonella: consequences of prior exposure to the vector strain." *Vaccine* 15(2): 155–162.
Baba et al., "Identification of CCR6, the Specific Receptor for a Novel Lymphocyte–directed CC Chemokine LARC," The J. of Biolog. Chem. 272 (23): 14893–14898 (1997).
Barry et al. (1995) "Protection against nycoplasma infection using expression–library immunization." *Nature* 377:632.
Beattie et al. (1990) "Cloning and characterization of T–cell– reactive protein anigens from Listeria monocytegenes." *Infection and Immunity* 58(9):2792–2803.

Beck et al., "DNA Sequence Analysis of 66 kb of the Human MHC Class II Region Encooding a Cluster of Genes for Antigen Processing," J. Mol. Biol. 228:433–441 (1992).
Bernard et al. (1994) "Transcriptional Control and Cell Type Specificity of HPV Gene Expression." *Arch Dermatol* 130:210.
Bielefeldt–Ohmann, H. et al., "Analysis of a recombinant dengue–2 virus–dengue–3 virus hybrid envelope protein expressed in a secretory baculovirus system," J. Gen. Virol. 78:2723–2733 (1997).
Bolhuis (1995) J. Biological Chamistry 270(3):26092–26098.
Burger et al. (1995) Proc. of thr Amer Assoc. for Cancer Research 36:522 Abst #3108.
Carter et al., "Improved oligonucleotide site–directed mutagenesis using M13 vectors," Nucl. Acids Res. 12:4431–4443 (1985).
Carter, "Improved Oligonucleotide–Directed Mutagenesis Using M13 Vectors," Methods in Enzymol. 154:382–403 (1987).
Carter, "Site–directed mutagenesis," Biochem. J. 237:1–7 (1986).
Chang, C., et al. (1999) "Evolution of a cytokine using DNA family shuffling." *Nature Biotechnology* 17:793–797.
Chen et al. "Regulatory T Cell Clones Induced by Oral Tolerance: Suppression of Autoimmune Encephalomyelitis." *Science* 265:1237–1240 (1994).
Chen et al., "Discontinuous epitopes of hepatitis B surface antigen derived from a filamentous phase peptide library," Proc. Nat'l. Acad. Sci. USA 93:1997–2001 (1996).
Choate and Khavari (1997) "Sustainability of Keratinocyte Gene Transfer and Cell Survival In Vivo." *Human Gene Therapy* 8:895–901.
Coco et al., (2001) "DNA shuffling method for generating highly recombined genes and evolved enzymes" *Nature Biotechnology* vol. 19 pp. 354–359.
Connry et al. (1994) "Immune response to a carinoembryonic antigen polynucleotide vassine." *Cancer Res.* 54:1164–1168.
Conry et al. (1996) "Selected strategies to augment polynucleotide immunization." Gene Therapy 3(1):67–74.
Coppel et al. (1993) "identification of a coda clone encoding a mature blood stage antigen of *Plasmodium falciparum* by immunization of mice with bacterial lysates." *EMBO Journal* 3)2):403–407.
Courvalin et al. (1995) "Gene transfer from bacteria to mammalian cells." *C.R. Acad. Sci III* 18:1207–1212.
Craiu et al., "Two distinct proteolytic processes in the generation of a major histocompatibility complex class I–presented peptide," Proc. Nat'l. Acad. Sci. USA 94:10850–10855 (1997).
Crameri & Stemmer (1993) "10(20)–fold aptamer library amplification without gel purification." *Nucleic Acids Research* 21(18): 4410.
Cresswell & Hughes, "Protein degradation: The ins and outs of of the matter,"Curr. Biol. 7:R552–R555 (1997).
Davis et al (1995) "DNA–based immunization." Molecular and Cell Biology of Human Gene Therapeutics 5:368–387.
Davis et al. (1997) "DNA–Based immunization against hepatitis B surface antigen (HBsAg) in Normal and HBsAg–transgenic mice." Vaccine 15(8) 849–822.
Deng et al. (1997) "Sustainable cutaneous gene delivery." *Nature Biotechnol* 15:1388–1391.

Dieu et al., "Selective Recruitment of Immature and Mature Dendritic Cells by Distinct Chemokines Expressed in Different Anatomic Sites," J. Exp. Med. 188:373–386 (1998).

Eghtedarzadeh and Henikoff, "Use of oligonucleotides to generate large deletions," Nucl. Acids Res. 14:5115 (1986).

Fox et al. (1996) "Anerobic bacteria as a delivery system for cancer gene therapy: In vitro activation of 5–fluorocytosine by genetically engineered clostridia." Gene Ther 3:173–178.

Fritz (1996) "Gene Transfer into Mammalian Cells Using Histone–Condenced Plasmid DNA." Human Gene Therapy 7:1395–1404.

Fritz et al. "Oligonucleotide–directed construction of mutations: a gapped duplex DNA procedure without enzymatic reactions in vitro," Nucl. Acids Res. 167:6987–6999 (1988).

Gaczynska et al., Proteasome Subunits X and Y alter Peptidase Activities in Opposite Ways to the Interferon–γ–induced Subunits LMP2 and LMP7*, J. Biol. Chem. 271:17275–17280 (1996).

Galoncha et al. (1997) "The Active Site of ICP47, a Herpes Simple Virus–encoded Inhibitor of the Major Histocompatibility Complex . . . " J. Exp. Med 185:1565–1572.

Groettrup et al. "The subunits MECL–1 and LMP2 are mutually required for incorporation into the 20S proteasome," Proc. Nat'l. Acad. Sci. USA 94:8970–8975 (1997).

Groettrup et al., "A third interferon –γ–induced subunit exchange in the 20S proteasome," Eur. J. Immunol. 26:863–869 (1997).

Groux et al., "A CD4+ T–cell subset inhibits antigen–specific T–cell responses and prevents colitis," Nature 389:737 (1997).

Grundstrom et al., "Oligonucleotide–directed mutagenesis by microscale 'shot–gun' gene synthesis," Nucleic Acids Res. 13:3305–3316 (1985).

Halminen et al. (1997) "Expression of MXA Protein in Blood Lymphocytes Discriminates between Viral and Bacterial Infections in Febrile Children." Pediatric Research 41:647–650.

Hilgers et al. (1990) "Caco–2 Cell Monolayers as a Model for Drug Transport Across the Intestinal Mucosa." Pharmaceutical Res. 7(9):902–910.

Hohol et al. (1996) "Three–year Open Protocol Continuation Study of Oral Tolerization with Myelin Antigens in Multiple Sclerosis and Design of a phase III Pivotal Trial." Ann. N.Y. Acad Sci. 778:243–250.

Hourvitz et al. (1996) "Reactogenicity and immunogenicity of a new recombinant hepatitis B Vaccine containing Pre S Antigens." J Virol. Hepatitis 3:37–42.

Howard (1998) "Chemistry of the future: Exploitation of the power of biology." Book of Abstracts, 216th ACS National Meeting, Boston, Aug. 23–27, BTEC–045 Apst #: 528494.

Irvine, K.R. et al., "Cytokine Enhancement of DNA Immunization Leads to Effective Treatment of Established Pulmonary Metastases," Journal of Immunology, 156:238–245 (1996).

Jiang et al., "Subtraction hybridization identified a novel melanoma differentiation associated gene, mda–7, modulated during human melanoma differentiation, growth and progression," Oncogene 11:2477 (1995).

Jiang et al., "The melanoma differentiation associated gene mda–7 suppresses cancer cell growth," Proc. Nat'l. Acad. Sci. USA 93:9160 (1996).

Karandikar et al.,"CTLA–4: A Negative Regulator of Autoimmune Disease," J. Exp. Med. 184:783 (1996).

Khavari and Krueger (1997) "Cutaneous Gene Therapy." Adv Clin Res Dermatologic Clinics 15(1): 27–35.

Khusmith et al. (1991) "Protection against malaria by vaccination with sporozoite surface protein 2 plus CS protein." Science 252:715.

Kim et al., "In Vivo Engineering of a Cellular Immune Response by Coadministration of IL–12 Expression Vector with a DNA Immunogen," J. Immunol. 158:816 (1997).

Klinman et al., "CpG motifs present in bacterial DNA rapidly induce lymphocytes to secrete interleukin 6, interleukin 12 and interferon □," Proc. Nat'l. Acad. Sci. USA 93:2879 (1996).

Klinman, D.M. et al., "Contribution of CpG Motifs to the Immunogenicity of DNA Vaccines," Journal of Immunology, 158:3635–3639 (1997).

Kobayashi et al.,"Identification and Purification of Natural Killer Cell Stimulatory Factor (NKSF), A Cytokine with Multiple Biologic Effects an Human Lymphocytes," J. Exp. Med. 170:827 (1989).

Kodama et al., "Type I macrophage scavenger receptor contains –helical and collagen–like coiled coils," Nature 343:531–535 (1990).

Koopman et al., "Generation, intracellular transport and loading of peptides associated with MHC class 1 molecules," Curr. Opin. Immunol. 9:80–88 (1997).

Kramer and Fritz, "Oligonucleotide–Directed Construction of Mutations via Gapped Duplex DNA," Methods in Enzymol. 154:350–367 (1987).

Kramer et al. "Improved Enzymatic in vitro reactions in the gapped duplex DNA approach to oligonucleotide–directed construction of mutations," Nucl. Acids Res. 16:7207 (1988).

Kramer et al., "Different Base/Base Mismatches Are Corrected with Different Efficiencies by the Methyl Directed DNA Mismatch–Repair System of E. coli," Cell 38:879–887 (1984).

Kramer et al., "The gapped duplex DNA approach to oligonucleotide–directed mutation construction," Nucl. Acids Res. 12:9441–9456 (1984).

Krieg et al., "CpG motifs in bacterial DNA trigger direct B–cell activation," Nature 374:546 (1995).

Krieger, M. et al., "Molecular Flypaper, Atherosclerosis, and Host Defense: Structure and Function of the Macrophage Scavenger Receptor," Cold Spring Harbor Symposia on Quantitative Biology 57:605–609 (1992).

Kruse et al., "Conversion of human interleukin–4 into a high affinity antagonist by a single amino acid replacement," EMBO J. 11:3237–3244 (1992).

Kuchroo et al., "B7–1 and B7–2 Costimulatory Molecules Activate Differentially the Th1/Th2 Developmental Pathways: Application to Autoimmune Disease Therapy," Cell 80:707 (1995).

Kunkel et al., "Rapid and Efficient Site–Specific Mutagenesis without Phenotypic Selection," Methods in Enzymol. 154:367–382 (1985).

Kunkel, "The efficiency of oligonucleotide directed mutagenesis" Nucleic acids & Molecular Biology 2: 124–135 (1988).

Kunkel, "Rapid and Efficient Site–Specific Mutagenesis without Phenotypic Selection," Proc. Nat'l. Acad. Sci. USA 82:488–492 (1985).

Larsen et al., Long Term acceptance of Skin and Cardiac Allografts After Blocking CD40 and CD28 Pathways, Nature 381: 434 (1996).

Laud et al., Human Immunol. 50:91–102 (1996).
Leung et al. (1989) Technique 1(1):11–15.
Li et al.,"Cloning and functional characterization of a subunit of the transporter associated with antigen processing," Proc. Natl. Acad. Sci USA 94: 8708–8713 (1997).
Liao et al. (1990) Gene 107–111.
Liao et al., STRL22 is a Receptor for the CC Chemokine MIP–3α, Biochem. and Biophys. Comms. 236: 212–217 (1997).r.
Liem et al. (1994) Nucleic Acids Res 22(9):1613–1619.
Lieschke et al.,"Bioactive murine and human interleukin–12 fusion proteins which retain antitumor activity in vivo," Nature Biotech. 15:35 (1997).
MacKay et al. (1981) "Production of immunology active surface of hepatitis B virus by *Escherichia coli*." *Proc. Natl. Acad. Sci USA* 78:4510–4514.
Marusina et al.,"Allelic Variation in the Mouse Tap–1 and Tap–2 Transporter Genes," J. Immunol. 158:5251–5256 (1997).
Metz et al. (1996) "Bicistronic and Two–Gene Retroviral Vectors for Using MDR1 as a Selectable Market and a Therapeutic Gene." *Virology* 217:230–241.
Monaco, "Pathways for the processing and presentation of antigens to T cells," J. Leukocyte Biol. 57:543–57 (1995).
Mosmann and Coffman, Adv. Immunol. 46:111 (1989).
Nakamaye and Eckstein, "Inhibition of restriction endonuclease Nci I cleavage by phosphorothioate groups and its application to oligonucleotide–directed mutagenesis," Nucl. Acids Res. 14:9679–9698 (1986).
Nambiar et al.,"Total Synthesis and Cloning of a Gene Coding for the Ribonuclease S Protein," Science 223:1299–1301 (1984).
Ness, J. et al., (1999) "DNA shuffling of subgenominc sequences of subtilisin." *Nature Biotechnology* 17:893–896.
Oggioni, M.R. and Pozzi, G., "A host–vector system for heterologous gene expression in *Streptococcus gordonii*," Gene 169:85–90 (1996).
Ortmann et al.,"A Critical Role for Tapasin in the Assembly and Function of Multimeric MHC Class 1–TAP Complexes," Science 277: 1306–1309 (1997).
Parronchi et al., "IL–4 and IFN (☐ and ☐) Exert Opposite Regulatory Effects on the Development of Cytolytic Potential by Th1 or Th2 Human T Cell Clones," J. Immunol. 149:2977 (1992).
Pascopella et al. (1994) "Identification of a genomc fragment of *Mycobacterium tuberculosis*." *Infectious Agents & Disease* 2:282–284.
Pascopella et al. (1994) "Use of In Vivo complementation in *Mycobacterium tuberculosis* to identify a genomic fragment associated with virulence." *Infection & Immunity* 62(4):1313–1319.
Paul and Seder, "Lymphocyte Responses and Cytokines," Cell 76:241 (1994).
Paulusma et al. (1996) "Congenital jaundice in rats with a mutation in a multidrug resistance–associated protein gene." *Science* 271:1126–1128.
Pelletier, Joelle N., (2001) "A Rachitt for our toolbox" *Nature Biotechnology* vol. 19, p. 314–315.
Pisetsky, D.S., "Immune Activation by Bacterial DNA: A New Genetic Code," Immunity 5: 303–310 (1996).
Pletnev, A.G. et al., Chimeric Tick–Borne Encephalitis and Dengue Type 4 Viruses: Effects of Mutations on Neurovirulence in Mice, J. Virol. 67(8):4956–4963 (1993).
Porcelli (1995) *Adv. Immunol* 59:1.

Powis et al.,"Polymorphism in a second ABC transporter gene located within the class II region of the human major hisotcompatibility complex,"Proc. Nat'l. Acad. Sci. USA 89:1463–1467 (1996).
Premack et al. (1996) *Nature Med.* 2:1174.
Punnonen et al (1998) "Evolution of genetic vaccines by DNA shuffling." Keystone Symposia on Molecular and Cellular Biology, Molecular Aspects of Viral Immunity, Abstract #227, Tamarron, CO, Feb. 16–20, 1998.
Punnonen et al. (1997) "Evolution of DNA Vaccine vectors by gene shuffling." The First Gordon Conference on Genetic Vaccines/DNA Vaccines, Plymouth State College, Plymouth, NH, Jul. 20–25, 1997.
Punnonen et al. *J. Exp Med.* 185:993–1004 (1997).
Punnonen et al., "Interleukin 13 induces interleukin 4–independent IgG4 and IgE synthesis and CD23 expression by human B cells," Proc. Nat'l. Acad. Sci. USA 90:3730 (1993).
Rahden–staron et al. (1991) Biochem & Biophy Res. & Commun. 177(2):597–602.
Reiser et al., "Cloning and expression of a cDNA for the T–cell–activating protein TAP," Proc. Nat'l. Acad. Sci. USA 85:2255–2259 (1988).
Roncarolo et al. "Human T– and B–cell functions in SCID–hu mice," Semin. Immunol. 8: 207 (1996).–.
Saggio et al. (1995) "CNFT Variants with increased biological potency and receptor selectivity define a functional site of receptor interaction." EMBO Journal 14(13):3045–3054.
Sakmar and Khorana, Total synthesis and expression of a gene for the a–subunit of bovine rod outer segment guanine nucleotide–binding protein (transducin), Nucl. Acids Res. 14:6361–6372 (1988).
Sayers et al. "Strand specific cleavage of phosphorothioate–containing DNA by reaction with restriction endonucleases in the presence of ethidium bromide,", Nucl. Acids Res. 16:803–814 (1988).
Sayers et al., "5'–3' Exonucleases in phosphorothioate––based oligonucleotide–directed mutagenesis," Nucl. Acids Res. 16:791–802 (1988).
Seliger et al., "TAP off—tumors on," Immunol. Today 18: 292–299 (1997).
Sheu et al. (1995) "Deletion or alteration of hydrophobic amino acids at the third transmembrane domains of Hepatitis B Surface antigen enhances its production in *Escherichia coli*." 160(2):179–184.
Shouval et al. (1994) "Improved immunogenicity in Mice of a mammalian cell–derived recombinant hepatitis B Vaccine containing pre–S1 and Pre–S2 antigens as compared with conventional yeast–derived vaccines." Vaccine 12(15):1453–1459.
Sizemore et al., "Attenuated Shigella as a DNA Delivery Vehicle for DNA–Mediated Immunization," Science 270:299–302 (1995).
Smith, "In Vitro Mutagenesis," Ann. Rev. Genet. 19:423–462 (1985).
Sokolic et al. (1996) "A Bicistronic Retrovirus Vector Containing a Picornavirus InternationalRibosome Entry Site Allows for Correct of X–Linked CGD Selection for MDR1 Expression." Blood 87:42–50.
Soong et al. (1998) "DNA shuffling as a tool to evolve desired retrovial phenotypes." Abstracts of papers presented at the 1998 meeting on Gene Therapy, p. 228 Cold Spring Harbor Laboratory, Cold Spring Harbor, New York, Sep. 23–27, 1998.

Stemmer et al. (1991) "Expression of antibody Fv Fragments specific for a heavy metal chelate (indium–EDTA) in *E. coli.*" *Journal of Cellular Biotechnology Supplement* 0 (15 Part G):217.

Stemmer (1991) "A 20–Minute ethidium bromide/high–salt extraction protocol for plasmid DNA." *BioTechniques* 10(96): 726.

Stemmer et al. (1992) "Enzymatic inverse PCR: a restriction site independent, single–fragment method for high–efficiency, site–directed mutagenesis." *Bio Techniques* 13(2): 214, 216, 218–220.

Stemmer et al. (1993) "Increased antibody expression from *Escherichia coli* through wobble–base library mutagenesis by enzymatic inverse PCR>" *Gene* 123(1): 1–7.

Stemmer et al. (1993) "Selection of an active single chain Fv antibody from a protein linker library prepared by enzymatic inverse PCR>" Biotechniques 14(2): 256–265.

Stemmer (1994) "Rapid evolution of a protein in vitro by DNA shuffling." Nature 370:389–391.

Stemmer (1996) "DNA sequence evolution by sexual PCR." Experientia (Basel) 52(ABSTR): A25 28$^{th}$ Annual Meeting of the Swiss Society Societies for Experimental Biology, Mar. 27–29, 1996.

Stemmer et al. (1997) "Molecular evolution of genetic vaccines by DNA shuffling." FASEB Journal 11(9): A1124, 17TH International Congress of Biochem . . . San Francisco, CA USA (2/24–29,).

Stemmer (1998) "Directed evolution of proteins, pathways, episomes and viruses by DNA shuffling," FASEB Journal 12(8): A1303.

Stern et al., "Purification to homogeneity and partial characterization of cytotoxic lymphocyte maturation factor from human B–lymphoblastoid cells," Proc. Nat'l. Acad. Sci. USA 87:6808 (1990).

Stohwasser et al., "Molecular cloning of the mouse proteasome subunits MC14 and MECL–1: reciprocally regulated tissue expression of interferon –γ–modulated proteasome subunits," Eur. J. Immunol. 27:1182–1187 (1997).

Sugimoto et al. (1995) Retroviral Coexpression of a Multidrug Resistance Gene (MDR1) and Human a–Galactosidase A for Gene Therapy of Febry Disease. *Human Gene Ther* 6:905–915.

Tahara et al., "IL–12 Gene Therapy Using Direct Injection of Tumors with Genetically Engineered Autologous Fibroblasts," Human Gene Therapy 6:1607 (1995).

Tan et al., "Characterizationof Recombinant Extracellular Domain of Human Interleukin–10 Receptor," J. Biol. Chem. 270:12906 (1995).

Tang et al. (1992) "Genetic immunization is a simole method for eliciting an immune response." *Nature* 356:152.

Tang et al., "Vaccination onto bare skin," Nature 388: 729–730 (1997).

Tano et al. (1990) Proc. Nat'l Acad Sci USA 87:686–690.

Taylor et al., "The use of phosphorothioate–modified DNA in restriction enzyme reactions to prepare nicked DNA," Nucl. Acids Res. 13:8749–8764 (1985).

Thierfelder et al. "Requirement for Stat4 in interleukin–1–2–mediated responses of natural killer and T cells", Nature 382:171 (1996).

Trudel et al., "pGATA: A Positive Selection Vector Based on the Toxicity of the Transcription Factor GATA–1 to Bacteria," Biotechniques 20:684–693 (1996).

Ugen et al. (1994) "DNA inoculation as a novel vaccination method against retroviruses with rheumatic disease associations." *Immunol. Res.* 13:154–162.

Ulmer et al. (1993) "Heterologous protection against influenza by injection of DNA encoding a viral protein." *Science* 259:1745.

Ulmer et al. (1996) "ELI's coming: expression library immunization and vaccine antigen discovery." *Trends im Microbiology* 4(5):170–171.

Villinger et al., "Comparative Sequence Analysis of Cytokine Genes from Human and Nonhuman Primates," J. Immunol. 155:3946–3954 (1995).

Walther et al. (1996) "Cell type specific and inducible promoters for vectors in gene therapy as an approach for cell targeting." *J. Mol. Med.* 74:379–392.

Walunas et al., "CTLA–4 Can Function as a Negative Regulator of T Cell Activation," Immunity 1:405 (1994).

Wang et al. (1993) "DNA inoculation induces cross clade anti–HIV–1 responses." *Annals New York Acad. Sci* 186–196.

Wang et al. (1993) "Gene inoculation generates immune responses against human deficiency virus type 1." *Proc. Nat'l Acad. Sci. USA* 90:4156–4160.

Wells et al., "Cassette mutagenesis: an efficient method for generation of multiple mutations at defined sites," Gene 34:315–323 (1985).

Wells et al., "Importance of hydrogen–bond formation in stabilizing the transition state of subtilisin," Phil. Trans. R. Soc. Lond. A317:415–423 (1986).

Whitacre et al.,"Treatment of Autoimmune Disease by Oral Tolerance to Autoantigens," Clin. Immunol. Immunopathol. 80: S31–9 (1996).

Wiertz et al., "SEC61–mediated transfer of a membrane protein from the endoplasmic reticulum to the proteasome for destruction," Nature 384: 432 (1996).

Wiertz et al., "The Human Cytomegalovirus US11 Gene Product Dislocates MHC Class 1 Heavy Chains from the Endoplasmic Reticulum to the Cytosol," Cell 84: 769–779 (1996).

Williams et al. (1993) "Genetic Infection Induces Protective In Vivo Immune Response." *DNA & Cell Biology* 12(8):675–683.

Williams et al. (1994) "Immunotherapeutic strategies targeting rheumatoid synovial T–cell receptors by DNA inoculation." *Immunol. Res* 13:145–153.

Wisniak et al. (1974) "Hydrogen Solubililty in Joboba Oil." *JAOCA* 51:482–485.

Wloch et al., "The Influence of DNA Sequence on the Immunostimulatory Properties of Plasmid DNA Vectors," Hum. Gene Ther. 9:1439–1447 (1998).

Xiang et al. (1994) "A Simple method to test the ability of individual viral proteins to induce immune responses." *J. Virological Methods* 47:103–116.

Xiang, Z. et al., "Manipulation of the Immune Response to a Plasmid–Encoded Viral Antigen by Coinoculation with Plasmids Expressing Cytokines," Immunity 2:129–135 (1995).

Zanelli et al. (1993) "Epitope mapping of human thyroid peroxidase defined seven epitopes reconized by sera from patients with thyroid pathologies." *Cell. & Mol Biol.* 39(5):491–501.

Zoller and Smith, "Oligonucleotide–directed mutagenesis using M13–derived vectors: an efficinet and general procedure for the production of point mutations in any fragment of DNA," Nucl. Acids res. 10:6487–6500 (1982).

Zoller and Smith, "Oligonucleotide–Directed Mutagenesis: A Simple Method using Two Oligonucleotide Primers and a Single–Stranded DNA Template," Methods in Enzymol. 154:329–350 (1987).

Zoller and Smith, "Oligonucleotide–Directed Mutagenesit of DNA Fragments Cloned into M13 Vectors," Methods in Enzymol. 100:468–500 (1983).

Zou et al. (1995) "Structure–function analysis of the p35 subunit of mouse interleukin 12." J. Bio. Chem. 270(11):5864–5871.

Aizaki et al. (1998) "Full–Length Complementary DNA of Hepatitis C Virus Genome From an Infectious Blood Sample." *Hepatology* 27:621–627 (1998).

Aldovini & Young (1991) "Humoral and cell–mediated immune response to live recombinant BCG–HIV vaccines." *Nature* 351:479–482.

Ambriovic, A. et al. (1997) "Efficacy of Replication–Defective Adenovirus–Vectored Vaccines: Protection Following Intramuscular Injection Is Linked to Promoter Efficiency in Muscle Representative Cells" Virology 238:, 327–335.

Appel and Harris (1998) "Antibody titers in domestic ferret fills and kits to canine distemper virus vaccines." *JAVMA* 193:332–333.

Atkins et al. (1996) "Manipulation of the Semliki Forest Virus Genome and Its Potential for Vaccine Construction." *Mol Biotechnol* 5:33–38.

Barry et al. (1994) "Production of monoclonal antibodies by genetic immunization." *Short Te\echnical Reports in Biotechniques* 16(4):616.

Behrens et al. (1996) "Identification and properties of the RNA–dependent RNA polymerase of hepatitis C virus." *EMBO J.* 15:12–22.

Benham et al. (1997) "Proteasome activity limits the assembly f HMC class 1 molecules after IFN–gamma stimulation." J. Immol 159(2):5896–5904.

Berkhout et al. (1999) "Genetic Instability of Live, Attenuated Human Immunodeficiency Virus Type I Vaccine Strains." *J. Virology* 73(2):1138–1145.

Blachere et al., "Heat Shock Protein–Peptide Complexes, Reconstituted In Vitro, Elicit Peptide–specific Cytotoxic T Lymphocyte Response and Tumor Immunity," J. Exp. Med. 186:1315–22 (1997).

Blanchard et al. (1998) "Modified vaccinia virus Ankara undergoes limited replication in human cells and lacks several immunomodulatory proteins . . . " *J. Gen. Virol* 79:1159–1167.

Bloom et al. (1993) Characterization of Chimeric Full--Length Molecular Clones of Aleutian Mink Disease Parvovirus (ADV) . . . *J. Virol* 67(10):5976–5988.

Botstein and Shortle, "Strategies and Applications of in Vitro Mutagenesis," Science 229:1193–1201 (1985).

Boursnell et al. (1997) "A Genetically Inactivated Herpes Simplex Virus Type 2 (Hsv–2) Vaccine Provides Effective Protection against Primary & Recurrent HSV-2 Disease." *J. Infect. Dis* 175:16–25.

Bridgen and Elliot (1996) "Rescue of a segmented negative–strand RNA virus entirely from cloned complementary DNA's." *Proc. Nat'l Acad. Sci USA* 93:15400–15404.

Burke et al. (1999) "Formulation, Stability and Delivery of Live Attenuated Vaccines for Human Use." *Crit. Rev. Ther Drig. Carrier Syst* 16:1–83.

Carroll and Moss (1997) "Host range and Cytopathogenicity of the Highly Attenuated MVA Strain of Vaccinia Virus . . . " *Virology* 238:198–211.

Casal (1999) "Use of parvovirus–like particles for vacation and induction of multiple immune response." *Biotechnol Appl. Biochem* 29:–141–150.

Cathomen et al. (1998) "A matrix–less measles virus is infectious and extensive cell fusion: consequences for propagation in the brain." *EMBO J.* 17(14):3899–3908.

Chin et al. (1993) "Functions and Regulation of the Human Miltidrug Resistance Gene." *Adv. Cancer Res.* 60:157–180.

Collman et al. (1992) "An Infectious Molecular Clone of an Unusual Macrophage–Topic and Highly Cytopathic Strain of Human Immunodeficiency Virus Type 1." *J. Virol* 66(12):7517–7521.

Davis et al. (1989) "In vitro Synthesis of Infectious Venezuelar Equine Encephalitis Virus RNA from a cDNA Clone: Analysis of a Viable Deletion Mutant." *Virology* 171:189–204.

Di Marco et al. (1997) "Agnostic and antagonistic variants of ciliary neurothrophic Factor (CNTF) Reveal functional differences between mambrean–bound and soluble CNTF Alpha–receptors." J Biol. Chem. 272(37):23069–23075.

Drabkin et al. (1996) "Amber Suppression in Mammalian Cells Dependent upon Expression of an *Escherichia coli* Aminoacyl–tRNA Synthetase Gene." *Mol Cell. Biol.* 16(3):907–913.

Engels and Ackermann (1996) "Pathogenesis of ruminant herpesvirus infections." *Vet Microbiol* 53:3–15.

HCJ Ertl et al., (1996) "Genetic Immunization" *Viral Immunization* vol. 9, No. 1, pp. 1–9.

Frankel and Young (1998) "HIV–1 Fifteen Proteins and an RNA." *Annu. Rev. Biochem* 67:1–25.

Freeman et al., "B7–1 and B7–2 Do Not Deliver Identical Costimulatory Signals, Since B7–2 but Not B7–1 Preferentially Costimulates the Initial Production of IL–4," Immunity 2:523 (1995).

Galler et al. (1997) "The Yellow fever 17D vaccine virus: molecular basis of viral attnuation and its use as an expression vector." *J. Med Biol. Res.* 30:157–168.

Garnett and Grenfell (1992) "The epidemiology of varicella–zoster virus infections: the influence of varicella on the prevalence of herpes zoster." *Epidemiol. Infect* 108:513–528.

Geigenmuller et al. (1997) "Construction of a Genome–Length cDNA Clone for Human Astrovirus Serotype 1 and Synthesis of Infectious RNA Transcrips." *J. Virol* 71:1713–1717.

Goldman et al. (1999) Molecular Cloning and Expression of Major Structural Protein . . . *J. Virol.* 73:4465–4469.

Gritsun et al. (1998) "Development and analysis of a tick-–bone encephalitis virus infectious clone using a novel and rapid strategy." *J Virol. Methods* 76:109–120.

Gualano et al. (1998) "Identification of a major determinant of mouse neurovirulence of dengue virus typw 2 using stably cloned genomic–length cDNA." *J. Gen. Virol.* 79:437–466.

Guo et al. (1998) "Susceptibility to recombination rearrangements of a chimeric plum pox potyvirus genome after insertion of a foreign gene." *Virus Res* 57:183–195.

Haq et al. (1995) "Oral Immunization with a Recombinant Bacterial Antigen Produced in Transgenic Plants." *Science* 268:714–716.

Haralambiev (1967) "Immunogenicity Studies on a Inactivated IBR Vaccine Administered Into the Nasal Mucosa." *Acta Vet Acad Sci Hung* 26:215–217.

Harrington et al. (1992) "An outbreak of Respiratory Syncytial Virus in a Bone Marrow Transplant Center." *J. Infect Dis.* 176:987–993.

He et al. (1998) "The Paramyxovirus SV5 Small Hydrobhobic (SH) Protein Is Not Essential for Virus Growth In Tissue Culture Cells." *Virology* 250:30–40.

Hensel and Lubitz (1997) Vaccination by Aerosols: Modulation of Clearance Mechanism in the Lung. *Behring. Inst. Mitt.* 98:212–219.

Hoffman and Banerjee (1997) "An Infectious Clone of Human Parainfluenza Virus Type 3." *J. Virol.* 71:4272–4277.

Hopkins and Yoder (1986) "Reversion to Virulence of Chicken–Passaged Infectious Bronchitis Vaccine Virus." *Avain Dis.* 30:221–223.

Hristov and Karadjov (1975) *Vet Med Nauki* 13:5.

Hulskotte et al. (1998) "Towards an HIV–1 vaccine: lessons from studies in macaque models." *Vaccine* 16:904–915.

Hurtado et al. (1996) "Identification of Domains in Canine Parvovirus VP2 Essential for the Accembly of Virus–Like Particles." *J. Virol* 70:5422–5429.

Jia et al. (1995) "A Novel virant of avian infectious bronchitis virus resulting from recombination among three different strains." *Arch Virol* 140:259–271.

Jiang et al. (1999) "Heterotypic protection from rotavirus infection in mice vaccinated with virus–like particles." *Vaccine* 17:1005–1013.

Jin et al. (1998) "Recombinant Human Respiratory Synctial Virus (RSV) from cDNA and Construction of Subgroup A and B Chimeric RSV." *Virology* 251:206–214.

Johnston, et al. (1997) "Genetic to genomic vaccination" vol. 15, No. 8 pp. 808–809.

Kang et al. (1999) "Development of HIV/AIDS Vaccine Using Chimeric gag–env Virus–like Particles." *Biol. Chem* 380:353–364.

Keck. Et al. (1988) "In Vivo RNA–RNA Recombination of Coronavirus in Mouse Brain." *J. Virol.* 62:1810–1813.

Khavari, (1997) "Therapeutic gene delivery to the skin" Molecular Medicine Today, Dec. 1997: 533538.

Kim, et al. (1997) "Development of a multicomponent candidate vaccine for HIV–1" Vaccine, vol. 15 No. 8 pp 879–883.

Kinney et al. (1997) "Construction of Infectious cDNA Clones for Dengue 2 Virus: Strain 16681 and Its Attenuated Vaccine Derivative, Strain PDK–53." *Virology* 230:300–308.

Lagranderie et al. (1993) "BCG–induced protection in guinea pigs vaccinated and challenged via the respiratory route." *Tubercle and Lung Disease* 74:38–46.

Lai et al. (1991) "Infectious RNA transcribed from stabily cloned full–length cDNA of dengue type 4 Virus." *Proc. Nat'l Acad. Sci. USA* 88:5139–5143.

Lanar et al. (1996) "Attanuated Vaccinia Virus–Circumsporoziote Protein Recombinants Confer Protection against Rodent Malaria." *Infect Immun* 64:1666–1671.

Lanciotti et al. (1994) "Molecular evolution and epidemology of dengue–3 viruses." *J Gen Virol.* 75:65–75.

Lee et al., (1997) "Generation of an Infectious cDNA of a highly cardiovirulent coxsakievirus B3(CVB3m) and comparasion to other infectious CVB cDNAs." *Virus Res* 50:255–235.

Lehrer et al. (1998) "Immunotherapy with *Mycobacterium vaccae* in the treatment of psoriasis." *FEMS Immunol. Med. Microbiol.* 21:71–77.

Li et al. (1997) "Expression of the Human Papillomavirus Type 11 L1 Capsid Protein in *Escherichia coli*. . ." *J. Virol* 71(4):2988–2995.

Liblau et al. "Th1 and Th2 CD4+ cells in thepathogenesis of organ–specific autoimmune diseases," Immunol. Today 16:34–38 (1995).

Limbach and Paoletti (1996) "Non–replicating expression vectors: applications in vaccine development and gene therapy." *Epidemol. Infect.* 116:241–256.

Lowe et al. (1997) "Human Papillamavirus Typw 2 (HPV–11) Nutralizing Antibobies in the Serum and Genitial Mucosal Secretions of African Green Monkeys Immunized with HPV–11 Virus–like particles Expressed in Yeast." *J. Invect Dis* 176:1141–1145.

Luytjes et al. (1989) "Amplification, Expressionand Packaging of a Foreign Gene by Influenza Virus." *Cell* 59:1107–1113.

Mandl et al. (1997) "Infectious cDNA clones of tick–borne encephalitis virus European subtype protopic strain Neudoerfl and high virulence strain Hypr." *J. Gen. Virol* 78:1049–1057.

Melen et al., "Enzymatic Characterization of Interferon–Induced Antiviral GTPases Murine Mx1 and Human MxA Proteins," J. Biol, Chem. 269: 2009–2015 (1994).

Meulenberg et al. (1998) "An Infectious cDNA Clone Porcine Reproductive and Respiratory Syndrome Virus." *Coronaviruses and Arteriviruses* 440:199–206.

Meulenberg et al. (1998) "Infectious Transcrips from Cloned Genome–Length cDNA of Porcine Reproductive and Respiratory Syndrome Virus." *J. Virol.* 72:380–387.

Meyer et al. (1998) "Bovine herpesvirus type 1 glycoprotein H is essential for penetration and and propagation in cell culture." *J. Gen. Virol.* 79:1983–1987.

N. Miller et al., (1995) "Targeted vectors for gene therapy," FASEB J., 9, pp. 190–199.

Mittelholzer et al. (1997) "Generation of cytopathogenic RNA of Classical swine fevor in persistently infected porcine cell lines." *Virus Res* 51:125–137.

Morita et al. (1987) "Recombinant vaccinia virus LC16m0 or LC1m8 that expresses hepatitis B surface antigen while preserving the attention of the parental virus." *Vaccine* 5:65–70.

Moss (1994) "Replicating and Host–Restricted Non–Replicating Vaccina Virus Vectors for Vaccine Development." *Dev. Biol. Stand* 82:55–63.

Mundt and Vakharia (1996) "Synthetic transcripts of double–stranded Birnavirus genome are infectious." *Proc Nat'l Acad. Sci USA* 93:11131–11136.

Nazerian et al. (1996) "Protection and synerhism by Recombinant Fowl Pox Vaccines Expressing Genes from Marek's Disease Virus." *Avian Dis.* 40:368–376.

Notka et al. (1999) "Constructon and Characterization of Recombinant VLPs and Semliki–Forest Virus Live Vectors for Comparative Evaluation in the SHIV Monkey Model." *Biol Chem* 380:341–352.

Orme (1997) "Progress in the development of new vaccines against tuberculosis." *Int J. Tuberc. Jung. Dis* 1:95–100.

Paoletti et al. (1995) "Highly Attenuated Poxvirus: HYVAC, ALVAC and TROVAC," *Dev Biol Stand* 84:159–163.

Park and RajBhandary (1998) "Tatracycline–Regulated Suppression of Amber Codons in Mammalian Cells." *Mol Cell Biol* 18:4418–4425.

Peng et al. (1998) "Papillomavirus Virus–like Particles Can Deliver Defined CTL Epitopes to the MHC Class 1 Pathway." *Virology* 240:147–157.

Penzes et al. (1996) "Replication and Packaging of Coronavirus Infectious Bronchitis Defective RNSa Lacking a Long Open Reading Frame." *J. Virol* 70:86660–8668.

Polo et al. (1999) "Stable alphavirus packaging cell lines for Sidbis virus–and Semlike Forest virus–derived vectors." *Proc Nat'l Acad. Sci USA>* 96:4598–4603.

Pryor et al. (1998) "Growth restriction of dengue virus type 2 by site–specific mutagenesis of virus–encoded glycoproteins." *J. Gen Virol.* 79:2631–2639.

Puri et al. (1998) "Complete Nucleotide Sequences Analysis of a Western Pacific Dengue–1 Virus Strain." *Virus Genes* 17:85–88.

Raj and Jones (1997) "Growth of infectious bronchitis virus vaccines in oviducts derived from oestrogen–treated chicks and embryos." *Vaccine* 15:163–168.

Roden et al. (1996) "In Vitro Generation and TypeSpecific Neutralization of a Human Papillomavirus Type 16 Viron Pseudotype." *J. Virol.* 70:5875–5883.

Sagazio et al. (1998) "Antigenic characterization of canine parovirus strains isolated in Italy." *J. Virol. Methods* 73:197–200.

Sanz et al. (1994) "Genetic heterogeneity of the attachment glycoprotein G among A respiratory syncytial virusus." *Virus Res* 33:203–217.

Saurmann et al. (1990) "Molecular Cloning and Characterization of a German HIV–1 Isolate." *AIDS Res. Hum Retroviruses* 6:813–823.

Schwarz et al. (1957) "Modification of Infevtious Bovine Rhinotrachetis (IBR) Virus in Tissue Culture and Development of a Vaccine." *Proc Soc Exp. Biol Med.* 96:453–458.

Schwarz et al. (1958) "Propagation and Modification of Infactious Bovine Rhinotrachetis (BR) Virus in Porcine Kidney Tissue Culture." *Proc Soc. Exp. Biol. Med* 97:680–683.

Sharma and Graham (1982) "Influence of Material Antibody on Efficacy of Embryo Vaccination with Cell–Associated ans Cell–Free Marek's Disease Vaccine." *Avian Dis.* 26:860–870.

Soong et al. (1998) "Directed evolution of novel retroviral tropisms by DNA shuffling." Abstract #97, Programs & Absracts, 1st Annual Meeting of the American Society of Gene Therapy, Seattle, Washington, May 28–31, 1998.

Soong et al. (1998) "Directed evolution of novel retroviral tropisms by DNA shuffling." Abstracts of papers presented at the 1998 meeting on Retroviruses, Cold Springs Harbor Laboratory, Cold Spring Harbor, New York, May 26–31, 1998.

Sosnovtsev et al. (1998) "Cleavage of the Feline Calicivirus Capsid Precurrsor Is Mediated by a Virus–Encoded Proteinase." *J. Virol* 72:3051–3059.

Srinivasan et al. (1987) "Molecular characterization of human immunodeiciency virus from Zaire." *Gene* 52:71–82.

Subbaroa et al. (1993) Rescue of an Influenza A Virus Wild–type PB2 Gene and a Mutant Derivative Bearing a Site–Specific Temperature–sensitive and Attenuating Mutation. *J. Virol.* 67:7223–7228.

Sugimoto et al. (1994) "Characteristics of an attenuated vaccinia virus strain, LC16m0 and It's recombinant virus vaccines." *Vaccine* 12:675–681.

Tartagila et al. (1992) "NYVAC: A Highly Attenuated Strain of Vaccinia Virus." *Virology* 188:217–232.

\* cited by examiner

Figure 7A

```
                    1                                                           60
HSV-1_gD-1      ATGGGGGGGACTGCCGCGCCAGGTTGGGGGCCGTGATTTTGTTTGTCGTCATAGTGGGCCTC
HSV-2_gD_seq    ATGGGGCGTTTGACCTCCGGCGTCCGGACGGCGGCGGCCCTGCTAGTTGTCGCGGTGGACTC
HSV-2_gD-2_seq  ATGGGGCGTTTGACCTCCGGCGTCCGGACGGCGGCGGCCCTGCTAGTTGTCGCGGTGGACTC 61                                                          120
HSV-1_gD-1      CATGGGGTCCGCGGCAAATATGCCTTGGCGGATGCCTCTCTCAAGATGGCCGACCCCCAAT
HSV-2_gD_seq    CGCGTCGTCTGCGCGCCAAATACGCCTTAGCAGACGCCTCGCTTAAGATGGCCGATCCCAAT
HSV-2_gD-2_seq  CGCGTCGTCTGCGCGCCAAATACGCCTTAGCAGACGCCTCGCTTAAGATGGCCGATCCCAAT 121                                                         180
HSV-1_gD-1      CGCTTTCGCGGCAAAGACCTTCCGGTCCTGGACCAGCTGACCGACCCTCCGGGGGTCCGG
HSV-2_gD_seq    CGATTTCGCGGGAAGAACCTTCCGGTTTGGACCAGCTGACCGACCCCCGACCCCGGGGTGAAG
HSV-2_gD-2_seq  CGATTTCGCGGGAAGAACCTTCCGGTTTGGACCAGCTGACCGACCCCCGACCCCGGGGTGAAG 181                                                         240
HSV-1_gD-1      CGCGTGTACCACATCCAGGCGGGCCTACCGGACCCCGTTCCAGCCCCCAGCCTCCCGATC
HSV-2_gD_seq    CGTGTTTACCACATTCAGCCGCCTGGAACGTGCTGCCGCCGCCTGCGTTCCAGCCATCCCGATC
HSV-2_gD-2_seq  CGTGTTTACCACATTCAGCCGCCTGGAACGTGCTGCCGCCGCCTGCGTTCCAGCCATCCCGATC 241                                                         300
HSV-1_gD-1      ACGGTTTACTACGCCGTGTTGGAGCGCGCCCTGCCGCCAGCGTGCTCCTAAACGCACCGTCG
HSV-2_gD_seq    ACTGTGTACTACGCAGTGCTGGAACGTGCTGCCGCCGCCTGCGTGCTCCTACATGCCCCATCG
HSV-2_gD-2_seq  ACTGTGTACTACGCAGTGCTGGAACGTGCTGCCGCCGCCTGCGTGCTCCTACATGCCCCATCG 301                                                         360
HSV-1_gD-1      GAGGCCCCCCAGATTGTCCGCGGGCCTCCGAAGACGTCCGGAAACAACCCTACAACCTG
HSV-2_gD_seq    GAGGCCCCCCAGATCGTCGCGCGGGCTTCGGACGAGCGCCGAAAGCACACGTACAACCTG
HSV-2_gD-2_seq  GAGGCCCCCCAGATCGTCGCGCGGGCTTCGGACGAGCGCCGAAAGCACACGTACAACCTG
```

Figure 7B

```
               361
HSV-1_gD-1     ACCATCGCTTGGTTTCGGATGGGAGGCAACTGTGCTATCCCCATCACGGTCATGGAGTAC
HSV-2_gD_seq   ACCATCGCCTGGTATCGCATGGCATGGAGACACAATTGCGCTATCCCCATCACGGTTATGGAATAC
HSV-2_gD-2_seq ACCATCGCCTGGTATCGCATGGGAGAGACAATTGCGCTATCCCCATCACGGTTATGGAATAC
                                                                                420

421
HSV-1_gD-1     ACCGAATGCTCCTACACAACAAGTCTCTGGGGGCCTGTCCCATCCGAACGCAGCCCCGCTGG
HSV-2_gD_seq   ACCGAGTGCCCCTACAACAAGTCGTTGGGGGTCTGCCCATCCGAACGCAGCCCCGCTGG
HSV-2_gD-2_seq ACCGAGTGCCCCTACAACAAGTCGTTGGGGGTCTGCCCATCCGAACGCAGCCCCGCTGG
                                                                                480

481
HSV-1_gD-1     AACTACTATGACAGCTTCAGCGCCCGTCAGCGGAGGATAACCTGGGGTTCCTGATGCACGCC
HSV-2_gD_seq   AGCTACTATGACAGCTTTAGCGCCCGTCAGCGGAGGATAACCTGGATTCCTGATGCACGCC
HSV-2_gD-2_seq AGCTACTATGACAGCTTTAGCGCCCGTCAGCGGAGGATAACCTGGATTCCTGATGCACGCC
                                                                                540

541
HSV-1_gD-1     CCCGCGTTTGAGACCGCCGGCACGTACCTGCGCTCGTGAAGATAAACGACTGGACGGAG
HSV-2_gD_seq   CCCGCCTTCGAGACCGCCGGGCGGGTACGTACCTGCGGTAGTGAAGATAAACGACTGGACGGAG
HSV-2_gD-2_seq CCCGCCTTCGAGACCGCCGGGCGGGTACGTACCTGCGGTAGTGAAGATAAACGACTGGACGGAG
                                                                                600

601
HSV-1_gD-1     ATTACACAGTTTATCCTGGAGCACCGAGCCAAGGGCTCCTGTAAGTACGCCCTCCCGCTG
HSV-2_gD_seq   ATCACACAATTTATCCTGGAGCACCGGAGCACCGGGCCGCCTCCTGCAAGTACGCTCTCCCCCTG
HSV-2_gD-2_seq ATCACACAATTTATCCTGGAGCACCGGAGCACCGGGCCGCCTCCTGCAAGTACGCTCTCCCCCTG
                                                                                660

661
HSV-1_gD-1     CGCATCCCCCCCGTCAGCCTCTCCCCCCAGGCCTACCAGCAGGGGGTGACGGTGGAC
HSV-2_gD_seq   CGCATCCCCCGGCAGCGTGCCTCACCTGAAGGCCTACCAACAGGGCGTGACGGTCGAC
HSV-2_gD-2_seq CGCATCCCCCCGGCAGCGTGCCTCACCTGAAGGCCTACCAACAGGGCGTGACGGTCGAC
                                                                                720
```

Figure 7C

```
              721                                                           780
HSV-1_gD-1    AGCATCGGGATGCTGCCCCGCTTCATCCCCGAGAACCAGCGCACCGTGCCGTATACAGC
HSV-2_gD_seq  AGCATCGGGATGTTACCCCGCTTTACTCCCGAAAACCAGCGCACCGTCGCCTATACAGC
HSV-2_gD-2_seq AGCATCGGGATGTTACCCCGCTTTATCCCGAAAACCAGCGCACCGTCGCCTATACAGC 781                                                           840
HSV-1_gD-1    TTGAAGATCGCCGGGTGGCACGGGCCCAAGGCCCCATACACGAGACACCCTGCTGCCCCG
HSV-2_gD_seq  TTAAAAATCGCCGGGTGGCACGGCCACCGCCCAAGCCCCCGTACACCAGCCCTGCTGCCCCG
HSV-2_gD-2_seq TTAAAAATCGCCGGGTGGCACGGCCACCGCCCAAGCCCCCGTACACCAGCCCTGCTGCCCCG 841                                                           900
HSV-1_gD-1    GAGCTGTCCGAGAGACCCCCAACGCCAGCGCCAGAACTCGCCCCGGAAGACCCCGAGGAT
HSV-2_gD_seq  GAGCTGTCCGACACCACCACCACCAACGCCAACCCGAACTCGTTCCGAAGACCCCGAGGAC
HSV-2_gD-2_seq GAGCTGTCCGACACCACCACCACCAACGCCAACCCGAACTCGTTCCGAAGACCCCGAGGAC 901                                                           960
HSV-1_gD-1    TCGGCCCCTCTTGGAGGACCCCGTGGGGGACGGGGTGGCGCCGCAAATCCCACCAAACTGGCAC
HSV-2_gD_seq  TCGGCCCCTCTTTAGAGGATCCCGCCGGACGTCGCGCCGCGGTGTCTTCGCAGATCCCCCAAACTGGCAC
HSV-2_gD-2_seq TCGGCCCCTCTTTAGAGGATCCCGCCGGACGTCGCGCCGCGGTGTCTTCGCAGATCCCCCAAACTGGCAC 961                                                           1020
HSV-1_gD-1    ATCCCGTCGATCCAGGACGCGCCGACGCCTTACCATCCCCCGGCCACCCCGAACAACATG
HSV-2_gD_seq  ATCCCGTCGATCCAGGACGTCGCGCCGC...ACCACGCCCCCGCCGCCCAGCCAACCCG
HSV-2_gD-2_seq ATCCCGTCGATCCAGGACGTCGCGCCGC...ACCACGCCCCCGCCGCCCAGCCAACCCG 1021                                                          1080
HSV-1_gD-1    GGCCTGATCGCCGGGCGGCGGTGGGCGCAGTCTCCTGGCAGCCCTGGTCATTTGCGGAATT
HSV-2_gD_seq  GGCCTGATCATCGGCCGGCTGCCGGCAGTACCCTGGCCGCTGGTCATGCCGGGTATT
HSV-2_gD-2_seq GGCCTGATCATCGGCCGGCTGCCGGCAGTACCCTGGCCGCTGGTCATGCCGGGTATT
```

Figure 7D

```
                1081                                                      1140
  HSV-1_gD-1    GTGTACTGGATGCACGCCG.CACTCGGAAAGCCCCAAAGCGCATACGCCTCCCCCACAT
  HSV-2_gD_seq  GCGTTTTGGGTACGCCGCCG.CGCCGGCGCTCAG.TGGCCCCCAAGCGCCTACGTCCCCACAT
  HSV-2_gD-2_seq GCGTTTTGGGTACGCCGCCG.CGCTCAGATGGCCCCAAGCGCCTACGCCTCTCCCCACAT 1141                                                      1200
  HSV-1_gD-1    CCGGGAAGACGACCAGCCCGTCCTCGCACCAGCCCTTGTTTTACTAG............
  HSV-2_gD_seq  CCGGGATGACGACGACGCGCCCCCCTCGCACCAGCCAGCCATTGTTTTACT.........
  HSV-2_gD-2_seq CCGGGATGACGACGACGCGCCCCCCCCTCGCACCAGCCATTGTTTTACTAGAGGAGTTTCCCGT 1201                                                 1246
  HSV-1_gD-1    ............................................................
  HSV-2_gD_seq  ............................................................
  HSV-2_gD-2_seq TCCCGTGTACCTCTCGGGCCCGTGTGGGAGGGTGGCCGGGGTATTTG
```

Figure 8A

Expression of shuffled envelope gp120 protein in a genetic vaccine

Insert BssH2 site in place of ATG
(ATGCAA to GGCGCGC)

Make a silent mutation to introduce unique, blunt restriction site

BssH2 ■■■■■■■■■■■■■■■■■■■ Blunt    Sequences to be shuffled

Figure 8B
PCR primers for genetic vaccine for HIV 6221, the beginning of gp120    7747, the end of gp120

| 6025F | CAAGCTTCTCTATCAAAGCAGTAAGTAGTAC | Primers to generate shuffling materials |
| 7773R | CTTCCTGCTGCTCCCAAGAACCCAA | |

| 6196F | ATAGAAAGAGCAGAAGACAGTGGCA | Primers to amplify shuffled materials |
| 7746R | AACAAAGCTCCTATTCCCACTGCTC | |

BssH2 →                                      ← EcoR1

BssH2-6205F  ttgcgcGCAGAAGACAGTGGCAATGAGAGTG
Ends next to the unique blunt site to be ibtroduced to the vector Primers to clone the PCR fragment into genetic vaccine vector

Figure 9

Domain Structure of Hepadnavirus Envelope Genes

| preS1 | preS2 | S |
|-------|-------|---|

Figure 10

Isolate genes coding for proteins in which the immunogenicity of one antigenic domain is improved:

++++       -       -

| preS1 | preS2 | S |
|-------|-------|---|

-       ++++       -

| preS1 | preS2 | S |
|-------|-------|---|

-       -       ++++

| preS1 | preS2 | S |
|-------|-------|---|

Figure 11

Shuffle genes for which the immunogenicity of one antigenic domain is improved:

| ++++ | - | - |
|------|------|------|
| preS1 | preS2 | S |

| - | ++++ | - |
|------|------|------|
| preS1 | preS2 | S |

| - | - | ++++ |
|------|------|------|
| preS1 | preS2 | S |

Second round of shuffling

| ++++ | ++++ | ++++ |
|------|------|------|
| preS1 | preS2 | S |

Transmembrane organization of the HBsAg polypeptide

Phage Display for Allergens not Recognized by Pre-existing IgE

- Remove variants that bind to IgE der

Screening of Allergen Variants that Efficiently Activate Th cells from Atopics

Screening of Cancer Antigens that Efficiently Activate T cells from Patients

Figure 17A

M38454, HPBADR1CG Hepatitis B virus, complete genome. Shown is HBsAg coding region (SEQ ID NO: 9); PreS2 starts at 1811 of complete genome sequence, S starts at 1976, end at 2656.

ATGCAGTGGAACTCCACAACATTCCACCAAGCTCTGCTAGACCCCAGAGTGAGGGGCCTATA
CTTTCCTGCTGGTGGCTCCAGTTCCGGAACAGTAAACCCTGTTCCGACTACTGCCTCACCCA
TATCGTCAATCTTCTCGAGGACTGGGGACCCTGCACCGAACATGGAGAACACAACATCAGGA
TTCCTAGGACCCCTGCTCGTGTTACAGGCGGGGTTTTTCTTGTTGACAAGAATCCTCACAAT
ACCACAGAGTCTACACTCGTGGTGGACTTCTCTCAATTTTCTAGGGGCAGCACCCACGTGTC
TTGGCCAAAATTCGCAGTCCCCAACCTCCAATCACTCACCAACCTCTTGTCCTCCAATTTGT
CCTGGTTATCGTTGGATGTGTCTGCGGCGTTTTATCATATTCCTCTTCATCCTGCTGCTATG
CCTCATCTTCTTGTTGGTTCTTCTGGACTACCAAGGTATGTTGTCTGTTTGTCCTCTACTTC
CAAGAACATCAACTACCAGCACGGGACCATGCAAGACCTGCACGATTCCTGCTCAAGGAACC
TCTATGTTTCCCTCTTCTTGCTGTACAAAACCTTCGGACGGAAACTGCACTTGTATTCCCAT
CCCATCATCTTGGGCTTTCGCAAGATTCCTATGGGAGTGGGCCTCAGTCCGTTTCTCCTGGC
TCAGTTTACTAGTGCCATTTGTTCAGTGGTTCGTAGGGCTTTCCCCCACTGTTTGGCTTTCA
GTTATATGGATGATGTGGTATTGGGGGCCAAGTCTGTACAACATCTTGAGTCCCTTTTTACC
TCTATTACCAATTTTCTTTTGTCTTTGGGTATACATTTGA

HBsAg Protein adr (SEQ ID NO: 10):
MQWNSTTFHQALLDPRVRGLYFPAGGSSSGTVNPVPTTASPISSIFSRTGDPAPNMENTTSG
FLGPLLVLQAGFFLLTRILTIPQSLHSWWTSLNFLGAAPTCLGQNSQSPTSNHSPTSCPPIC
PGYRWMCLRRFIIFLFILLLCLIFLLVLLDYQGMLSVCPLLPRTSTTSTGPCKTCTIPAQGT
SMFPSSCCTKPSDGNCTCIPIPSSWAFARFLWEWASVRFSWLSLLVPFVQWFVGLSPTVWLS
VIWMMWYWGPSLYNILSPFLPLLPIFFCLWVYIZ

Figure 17B

J02203; HPBAYW Hepatitis B Virus ayw. (SEQ ID NO: 11)

ATGCAGTGGAATTCCACAACCTTCCACCAAACTCTGCAAGATCCCAGAGTGAGAGGCCTGTA
TTTCCCTGCTGGTGGCTCCAGTTCAGGAACAGTAAACCCTGTTCTGACTACTGCCTCTCCCT
TATCGTCAATCTTCTCGAGGATTGGGGACCCTGCGCTGAACATGGAGAACATCACATCAGGA
TTCCTAGGACCCCTTCTCGTGTTACAGGCGGGGTTTTTCTTGTTGACAAGAATCCTCACAAT
ACCGCAGAGTCTAGACTCGTGGTGGACTTCTCTCAATTTTCTAGGGGGAACTACCGTGTGTC
TTGGCCAAAATTCGCAGTCCCCAACCTCCAATCACTCACCAACCTCTTGTCCTCCAACTTGT
CCTGGTTATCGCTGGATGTGTCTGCGGCGTTTTATCATCTTCCTCTTCATCCTGCTGCTATG
CCTCATCTTCTTGTTGGTTCTTCTGGACTATCAAGGTATGTTGCCCGTTTGTCCTCTAATTC
CAGGATCCTCAACAACCAGCACGGGACCATGCCGGACCTGCATGACTACTGCTCAAGGAACC
TCTATGTATCCCTCCTGTTGCTGTACCAAACCTTCGGACGGAAATTGCACCTGTATTCCCAT
CCCATCATCCTGGGCTTTCGGAAAATTCCTATGGGAGTGGGCCTCAGCCCGTTTCTCCTGGC
TCAGTTTACTAGTGCCATTTGTTCAGTGGTTCGTAGGGCTTTCCCCCACTGTTTGGCTTTCA
GTTATATGGATGATGTGGTATTGGGGGCCAAGTCTGTACAGCATCTTGAGTCCCTTTTTACC
GCTGTTACCAATTTTCTTTTGTCTTTGGGTATACATTTAA

Forward HBV ayw PCR Primer (with 2 natural EcoRI sites) (SEQ ID NO: 13):
5'-CCGG<u>GAATTC</u>CTCGACACCATGCAGTGG<u>AATTC</u>CACAACC-3'

Reverse HBV ayw PCR Primer (with added KpnI site) (SEQ ID NO: 14):
5'-CCGG<u>GGTACC</u>CAAAGACAAAAGAAAATTGGTAACAGCGG-3'

HBsAg Protein ayw (SEQ ID NO: 12):
MQWNSTTFHQTLQDPRVRGLYFPAGGSSSGTVNPVLTTASPLSSIFSRIGDPALNMENITSG
FLGPLLVLQAGFFLLTRILTIPQSLDSWWTSLNFLGGTTVCLGQNSQSPTSNHSPTSCPPTC
PGYRWMCLRRFIIFLFILLLCLIFLLVLLDYQGMLPVCPLIPGSSTTSTGPCRTCMTTAQGT
SMYPSCCCTKPSDGNCTCIPIPSSWAFGKFLWEWASARFSWLSLLVPFVQWFVGLSPTVWLS
VIWMMWYWGPSLYSILSPFLPLLPIFFCLWVYIZ

Figure 17C

J04514 OHVHEPBA Woodchuck hepatitis B virus genome (WHV8) (SEQ ID NO: 15) (PNAS 86, 1846-1849, 1989). ATCC No. 45097. EcoRI site at pos. 1 cuts the PreS1 region. HBs(S) ORF: 296-964. PreS2 starts at 116; PreS1 starts at 3039.

ATGAAAAATCAGACTTTTCATCTCCAGGGGTTCGTAGACGGATTACGAGACTTGACAACAAC
GGAACGCCAACACAATGCCTATGGAGATCCTTTTACAACACTAAGCCCTGCGGTTCCTACTG
TATCCACCATATTGTCTCCTCCCTCGACGACTGGGGACCCTGCACTGTCACCGGAGATGTCA
CCATCAAGTCTCCTAGGACTCCTCGCAGGATTACAGGTGGTGTATTTCTTGTGGACAAAAAT
CCTAACAATAGCTCAGAATCTAGATTGGTGGTGGACTTCTCTCAGTTTTCCAGGGGGCATAC
CAGAGTGCACTGGCCAAAATTCGCAGTTCCAAACTTGCAAACACTTGCCAACCTCCTGTCCA
CCAACTTGCAATGGCTTTCGTTGGATGTATCTGCGGCGTTTTATCATATACCTATTAGTCCT
GCTGCTGTGCCTCATCTTCTTGTTGGTTCTCCTGGACTGGAAAGGTTTAATACCTGTCTGTC
CTCTTCAACCCACAACAGAAACAACAGTCAATTGCAGACAATGCACAATCTCTGCACAAGAC
ATGTATACTCCTCCTTACTGTTGTTGTTTAAAACCTACGGCAGGAAATTGCACTTGTTGGCC
CATCCCTTCATCATGGGCTTTAGGAAATTACCTATGGGAGTGGGCCTTAGCCCGTTTCTCTT
GGCTCAATTTACTAGTGCCCTTGCTTCAATGGTTAGGAGGAATTTCCCTCATTGCGTGGTTT
TTGCTTATATGGATGATTTGGTTTTGGGGGCCCGCACTTCTGAGCATCTTACCGCCATTTAT
TCCCATATTTGTTCTGTTTTTCTTGATTTGGGTATACATTTGA

Forward WHV PCR Primer (with added EcoRI site) (SEQ ID NO: 17):
5'-CCGGGAATTCTCATCTCCAGGGGTTCGTAGACGGATTACG-3'

Reverse WHV PCR Primer (with added KpnI site) (SEQ ID NO: 18):
5'-CCGGGGTACCCAAATCAAGAAAAACAGAACAAATATGGG-3'

WHV Surface Antigen Protein (SEQ ID NO: 16):
MKNQTFHLQGFVDGLRDLTTTERQHNAYGDPFTTLSPAVPTVSTILSPPSTTGDPALSPEMS
PSSLLGLLAGLQVVYFLWTKILTIAQNLDWWWTSLSFPGGIPECTGQNSQFQTCKHLPTSCP
PTCNGFRWMYLRRFIIYLLVLLLCLIFLLVLLDWKGLIPVCPLQPTTETTVNCRQCTISAQD
MYTPPYCCCLKPTAGNCTCWPIPSSWALGNYLWEWALARFSWLNLLVPLLQWLGGISLIAWF
LLIWMIWFWGPALLSILPPFIPIFVLFFLIWVYIZ

Figure 18

Primers for PCR amplification of the large fragments containing the S2S coding sequences (primers are about 200 bp outside the desired sequences)

AYWSHFOR (SEQ ID NO: 19)
5'-GCCGGCAGGAAGGAAATGGG-3' (13GC + 7AT = Tm 66)

AYWSHREV (SEQ ID NO: 20)
5'-CTGCTATTGTCTTCCCAATCCTC-3' (11GC + 12AT = Tm 68)

WHVSHFOR (SEQ ID NO: 21)
5'-CGGGACATACCACGTGGTTTAG-3' (12GC + 10AT = Tm 68)

WHVSHREV (SEQ ID NO: 22)
5'-GGCATTAAAGCAGCGTATCCAC-3' (11GC + 11AT = Tm 66)

Figure 19: Alignment of amino acid sequences of different HBV subtypes.

adr (SEQ ID NO: 10) vs. ayw (SEQ ID NO: 12)

```
ayw: MQNNSTFHQTLQDPRVRGLYFPAGGSSSGTVNPVLTTASPLSSIFSRIGDPALNMENITSGFLGPLLVLQAGFFLLTRILTIPQSLDSWWTSLNFLGGTVCLGQNSQSPTSNHSPTSCPPTCPGYRWMCLRRFIIFLFI
adr: MQNNSTFHQALLDPRVRGLYFPAGGSSSGTVNPVPTTASPLSSIFSRTGDPAPNMENITSGFLGPLLVLQAGFFLLTRILTIPQSLHSWWTSLNFLGEAPTCLGQNSQSPTSNHSPTSCPPICPGYRWMCLRRFIIFLFI
         •      •               •        •  •                              •           • •       •            • ayw: LLLCLIFLLVLLDYQGMLPVCPLIPGSSTTSTGPCRTCMTPAQGTSMYPSCCCTKPSDGNCTCIPIPSSWAFGKFLWEWASARFSWLSLLVPFVQWFVGLSPTVWLSVIWMMWYWGPSLYSILSPFLPLLPIFFCLWVYIZ
adr: LLLCLIFLLVLLDYQGMLSVCPLLPRTSTSTGPCKTCTTPAQGTSMFPSSCCCTKPSDGNCTCIPIPSSWAFAPAFLWEWASVRFSWLSLLVPFVQWFVGLSPTVWLSVIWMMWYWGPSLYNILSPFLPLLPIFFCLWVYIZ
                    •    •  •           • •           •                  • • •      •                              •
```

ANTIGEN LIBRARY IMMUNIZATION

CROSS-REFERENCE TO RELATED APPLICATIONS

This application claims benefit of U.S. Provisional Application No. 60/074,294, filed Feb. 11, 1998, and U.S. Provisional Application No. 60/105,509, filed Oct. 23, 1998, which applications are incorporated herein by reference for all purposes.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

1. Field of the Invention

This invention pertains to the field of methods for developing immunogens that can induce efficient immune responses against a broad range of antigens.

2. Background

The interactions between pathogens and hosts are results of millions of years of evolution, during which the mammalian immune system has evolved sophisticated means to counterattack pathogen invasions. However, bacterial and viral pathogens have simultaneously gained a number of mechanisms to improve their virulence and survival in hosts, providing a major challenge for vaccine research and development despite the powers of modern techniques of molecular and cellular biology. Similar to the evolution of pathogen antigens, several cancer antigens are likely to have gained means to downregulate their immunogenicity as a mechanism to escape the host immune system.

Efficient vaccine development is also hampered by the antigenic heterogeneity of different strains of pathogens, driven in part by evolutionary forces as means for the pathogens to escape immune defenses. Pathogens also reduce their immunogenicity by selecting antigens that are difficult to express, process and/or transport in host cells, thereby reducing the availability of immunogenic peptides to the molecules initiating and modulating immune responses. The mechanisms associated with these challenges are complex, multivariate and rather poorly characterized. Accordingly, a need exists for vaccines that can induce a protective immune response against bacterial and viral pathogens. The present invention fulfills this and other needs.

SUMMARY OF THE INVENTION

The present invention provides recombinant multivalent antigenic polypeptides that include a first antigenic determinant from a first disease-associated polypeptide and at least a second antigenic determinant from a second disease-associated polypeptide. The disease-associated polypeptides can be selected from the group consisting of cancer antigens, antigens associated with autoimmunity disorders, antigens associated with inflammatory conditions, antigens associated with allergic reactions, antigens associated with infectious agents, and other antigens that are associated with a disease condition.

In another embodiment, the invention provides a recombinant antigen library that contains recombinant nucleic acids that encode antigenic polypeptides. The libraries are typically obtained by recombining at least first and second forms of a nucleic acid which includes a polynucleotide sequence that encodes a disease-associated antigenic polypeptide, wherein the first and second forms differ from each other in two or more nucleotides, to produce a library of recombinant nucleic acids.

Another embodiment of the invention provides methods of obtaining a polynucleotide that encodes a recombinant antigen having improved ability to induce an immune response to a disease condition. These methods involve: (1) recombining at least first and second forms of a nucleic acid which comprises a polynucleotide sequence that encodes an antigenic polypeptide that is associated with the disease condition, wherein the first and second forms differ from each other in two or more nucleotides, to produce a library of recombinant nucleic acids; and (2) screening the library to identify at least one optimized recombinant nucleic acid that encodes an optimized recombinant antigenic polypeptide that has improved ability to induce an immune response to the disease condition.

These methods optionally further involve: (3) recombining at least one optimized recombinant nucleic acid with a further form of the nucleic acid, which is the same or different from the first and second forms, to produce a further library of recombinant nucleic acids; (4) screening the further library to identify at least one further optimized recombinant nucleic acid that encodes a polypeptide that has improved ability to induce an immune response to the disease condition; and (5) repeating (3) and (4), as necessary, until the further optimized recombinant nucleic acid encodes a polypeptide that has improved ability to induce an immune response to the disease condition.

In some embodiments, the optimized recombinant nucleic acid encodes a multivalent antigenic polypeptide and the screening is accomplished by expressing the library of recombinant nucleic acids in a phage display expression vector such that the recombinant antigen is expressed as a fusion protein with a phage polypeptide that is displayed on a phage particle surface; contacting the phage with a first antibody that is specific for a first serotype of the pathogenic agent and selecting those phage that bind to the first antibody; and contacting those phage that bind to the first antibody with a second antibody that is specific for a second serotype of the pathogenic agent and selecting those phage that bind to the second antibody; wherein those phage that bind to the first antibody and the second antibody express a multivalent antigenic polypeptide.

The invention also provides methods of obtaining a recombinant viral vector which has an enhanced ability to induce an antiviral response in a cell. These methods can include the steps of: (1) recombining at least first and second forms of a nucleic acid which comprise a viral vector, wherein the first and second forms differ from each other in two or more nucleotides, to produce a library of recombinant viral vectors; (2) transfecting the library of recombinant viral vectors into a population of mammalian cells; (3) staining the cells for the presence of Mx protein; and (4) isolating recombinant viral vectors from cells which stain positive for Mx protein, wherein recombinant viral vectors from positive staining cells exhibit enhanced ability to induce an antiviral response.

BRIEF DESCRIPTION OF THE FIGURES

In FIG. 3A, wild-type immunogenic polypeptides from the pathogens A, B, and C provide protection against the corresponding pathogen from which the polypeptide is derived, but little or no cross-protection against the other pathogens (left panel). After shuffling, an A/B/C chimeric polypeptide is obtained that can induce a protective immune response against all three pathogen types (right panel). In FIG. 3B, shuffling is used with substrate nucleic acids from two pathogen strains (A, B), which encode polypeptides that are protective only against the corresponding pathogen. After shuffling, the resulting chimeric polypeptide can induce an immune response that is effective against not only the two parental pathogen strains, but also against a third strain of pathogen (C).

FIGS. 7A–7D show an alignment of the nucleotide sequences of glycoprotein D (gD) from HSV-1 (SEQ ID NO: 1) and HSV-2 (gD-1 (SEQ ID NO: 2) and gD-2 (SEQ ID NO: 3)), illustrating the feasibility of family shuffling when evolving gD.

FIG. 8A shows a diagram of a method for expressing HIV gp120 using genetic vaccine vectors and generation of a library of shuffled gp120 genes. FIG. 8B shows PCR primers that are useful for obtaining gp120 nucleic acid substrates for DNA shuffling reactions. Primers suitable for generating substrates include 6025F (SEQ ID NO: 4), 7773R (SEQ ID NO: 5), and primers suitable for amplifying the shuffled nucleic acids include 6196F (SEQ ID NO: 6) and 7746R (SEQ ID NO: 7). The primer BssH2-6205F (SEQ ID NO: 8) can be used to clone the resulting fragment into a genetic vaccine vector.

FIG. 9 shows the domain structure of hepadnavirus envelope genes.

FIG. 10 shows a schematic representation of the use of shuffling to obtain hepadnavirus proteins in which the immunogenicity of one antigenic domain is improved.

FIG. 11 shows a strategy in which genes that encode the hepadnavirus proteins having one antigenic domain that has improved immunogenicity are shuffled to obtain recombinant proteins in which all three domains have improved immunogenicity.

In FIG. 16A, each individual shuffled epitope-encoding nucleic acid is linked to a single promoter, and multiple promoter-epitope gene constructs can be placed in a single vector. The scheme shown in FIG. 16B involves linking multiple epitope-encoding nucleic acids to a single promoter.

FIGS. 17A–17C show the sequences of PreS2-S coding regions (SEQ ID NOS:9 and 11) and corresponding amino acid sequences (SEQ ID NOS: 10 and 12) of different hepatitis B surface antigen HBsAg) or woodchuck hepatis B (WHV) proteins. Primners suitable for amplification of this region are also shown.

FIG. 18 shows primers that are suitable for amplification of large fragments that contain the S2S coding sequences. The primers hybridize to regions that are approximately 200 bp outside the desired sequences.

FIG. 19 shows an alignment of the amino acid sequences of surface antigens from different HBV subtypes (SEQ ID NOS: 10 and 12).

DETAILED DESCRIPTION

Definitions

Figure 1:
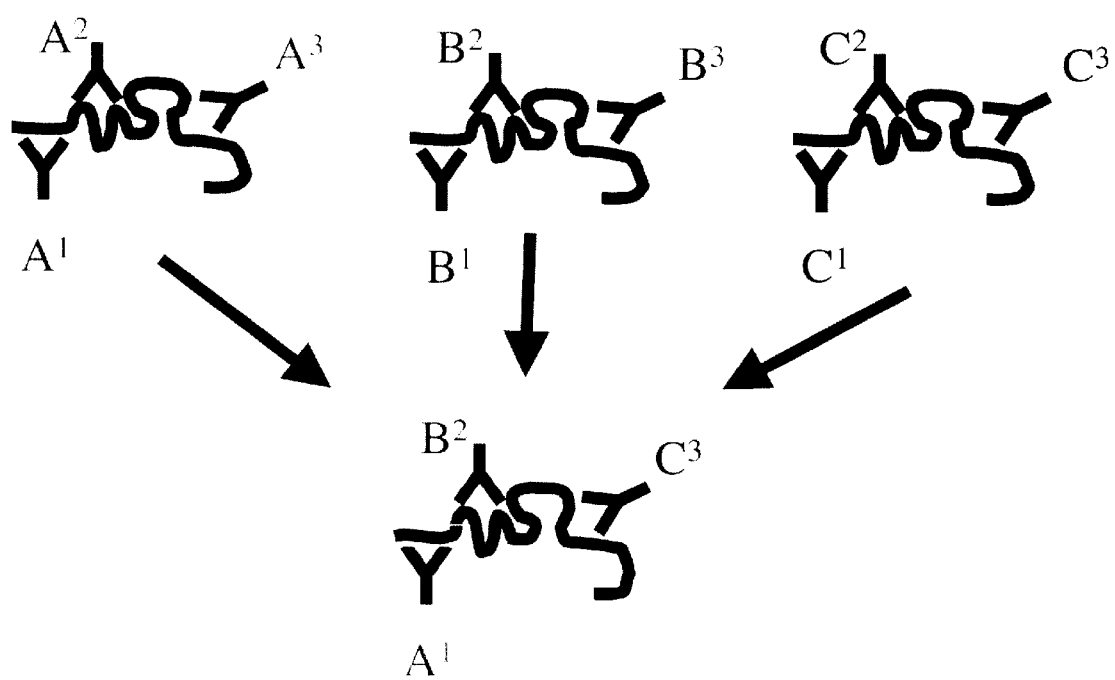
FIG. 1 shows a schematic representation of a method for generating a chimeric, multivalent antigen that has immunogenic regions from multiple antigens. Antibodies to each of the non-chimeric parental immunogenic polypeptides are specific for the respective organisms (A, B, C). After carrying out the recombination and selection methods of the invention, however, a chimeric immunogenic polypeptide is obtained that is recognized by antibodies raised against each of the three parental immunogenic polypeptides.

The term "screening" describes, in general, a process that identifies optimal antigens. Several properties of the antigen can be used in selection and screening including antigen expression, folding, stability, immunogenicity and presence of epitopes from several related antigens. Selection is a form of screening in which identification and physical separation are achieved simultaneously by expression of a selection marker, which, in some genetic circumstances, allows cells expressing the marker to survive while other cells die (or vice versa). Screening markers include, for example, luciferase, beta-galactosidase and green fluorescent protein. Selection markers include drug and toxin resistance genes, and the like. Because of limitations in studying primary immune responses in vitro, in vivo studies are particularly useful screening methods. In these studies, the antigens are first introduced to test animals, and the immune responses are subsequently studied by analyzing protective immune responses or by studying the quality or strength of the induced immune response using lymphoid cells derived from the immunized animal. Although spontaneous selection can and does occur in the course of natural evolution, in the present methods selection is performed by man.

A "exogenous DNA segment", "heterologous sequence" or a "heterologous nucleic acid", as used herein, is one that originates from a source foreign to the particular host cell, or, if from the same source, is modified from its original form. Thus, a heterologous gene in a host cell includes a gene that is endogenous to the particular host cell, but has been modified. Modification of a heterologous sequence in the applications described herein typically occurs through the use of DNA shuffling. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

The term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The term "isolated", when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

The term "naturally-occurring" is used to describe an object that can be found in nature as distinct from being artificially produced by man. For example, a polypeptide or polynucleotide sequence that is present in an organism (including viruses, bacteria, protozoa, insects, plants or mammalian tissue) that can be isolated from a source in nature and which has not been intentionally modified by man in the laboratory is naturally-occurring.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19: 5081; Ohtsuka et al. (1985) *J. Biol. Chem.* 260: 2605–2608; Cassol et al. (1992); Rossolini et al. (1994) *Mol. Cell. Probes* 8: 91–98). The term nucleic acid is used interchangeably with gene, cDNA, and mRNA encoded by a gene.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample.

A nucleic acid is "operably linked" when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

A specific binding affinity between two molecules, for example, a ligand and a receptor, means a preferential binding of one molecule for another in a mixture of molecules. The binding of the molecules can be considered specific if the binding affinity is about $1 \times 10^4$ $M^{-1}$ to about $1 \times 10^6$ $M^{-1}$ or greater.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

A "multivalent antigenic polypeptide" or a "recombinant multivalent antigenic polypeptide" is a non-naturally occurring polypeptide that includes amino acid sequences from more than one source polypeptide, which source polypeptide is typically a naturally occurring polypeptide. At least some of the regions of different amino acid sequences constitute epitopes that are recognized by antibodies found in a mammal that has been injected with the source polypeptide. The source polypeptides from which the different epitopes are derived are usually homologous (i.e., have the same or a similar structure and/or function), and are often from different isolates, serotypes, strains, species, of organism or from different disease states, for example.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In some embodiments, the sequences are substantially identical over the entire length of the coding regions.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to", refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

"Stringent hybridization conditions" and "stringent hybridization wash conditions" in the context of nucleic acid hybridization experiments such as Southern and northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology—Hybridization with Nucleic Acid Probes* part I chapter 2 "Overview of principles of hybridization and the strategy of nucleic acid probe assays", Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra., for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0 M $Na^+$ ion, typically about 0.01 to 1.0 M $Na^+$ ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

A further indication that two nucleic acid sequences or polypeptides are substantially identical is that the polypeptide encoded by the first nucleic acid is immunologically cross reactive with, or specifically binds to, the polypeptide encoded by the second nucleic acid. Thus, a polypeptide is typically substantially identical to a second polypeptide, for example, where the two peptides differ only by conservative substitutions.

The phrase "specifically (or selectively) binds to an antibody" or "specifically (or selectively) immunoreactive with", when referring to a protein or peptide, refers to a binding reaction which is determinative of the presence of the protein, or an epitope from the protein, in the presence of a heterogeneous population of proteins and other biologics. Thus, under designated immunoassay conditions, the specified antibodies bind to a particular protein and do not bind in a significant amount to other proteins present in the sample. The antibodies raised against a multivalent antigenic polypeptide will generally bind to the proteins from which one or more of the epitopes were obtained. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) *Antibodies, A Laboratory Manual,* Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following five groups each contain amino acids that are conservative substitutions for one another:

Aliphatic: Glycine (G), Alanine (A), Valine (V), Leucine (L), Isoleucine (I);

Aromatic: Phenylalanine (F), Tyrosine (Y), Tryptophan (W);

Sulfur-containing: Methionine (M), Cysteine (C);

Basic: Arginine (R), Lysine (K), Histidine (H);

Acidic: Aspartic acid (D), Glutamic acid (E), Asparagine (N), Glutamine (Q).

See also, Creighton (1984) *Proteins,* W.H. Freeman and Company, for additional groupings of amino acids. In addition, individual substitutions, deletions or additions which alter, add or delete a single amino acid or a small percentage of amino acids in an encoded sequence are also "conservatively modified variations".

A "subsequence" refers to a sequence of nucleic acids or amino acids that comprise a part of a longer sequence of nucleic acids or amino acids (e.g., polypeptide) respectively.

Description of the Preferred Embodiments

The invention provides a new approach to vaccine development, which is termed "antigen library immunization." No other technologies are available for generating libraries of related antigens or optimizing known protective antigens. The most powerful previously existing methods for identification of vaccine antigens, such as high throughput sequencing or expression library immunization, only explore the sequence space provided by the pathogen genome. These approaches are likely to be insufficient, because they generally only target single pathogen strains, and because natural evolution has directed pathogens to downregulate their own immunogenicity. In contrast, the immunization protocols of the invention, which use shuffled antigen libraries, provide a means to identify novel antigen sequences. Those antigens that are most protective can be selected from these pools by in vivo challenge models. Antigen library immunization dramatically expands the diversity of available immunogen sequences, and therefore, these antigen chimera libraries can also provide means to defend against newly emerging pathogen variants of the future. The methods of the invention enable the identification of individual chimeric antigens that provide efficient protection against a variety of existing pathogens, providing improved vaccines for troops and civilian populations.

The methods of the invention provide an evolution-based approach, such as DNA shuffling in particular, that is an optimal approach to improve the immunogenicity of many types of antigens. For example, the methods provide means of obtaining optimized cancer antigens useful for preventing and treating malignant diseases. Furthermore, an increasing number of self-antigens, causing autoimmune diseases, and allergens, causing atopy, allergy and asthma, have been characterized. The immunogenicity and manufacturing of these antigens can likewise be improved with the methods of this invention.

The antigen library immunization methods of the invention provide a means by which one can obtain a recombinant antigen that has improved ability to induce an immune response to a pathogenic agent. A "pathogenic agent" refers to an organism or virus that is capable of infecting a host cell. Pathogenic agents typically include and/or encode a molecule, usually a polypeptide, that is immunogenic in that an immune response is raised against the immunogenic polypeptide. Often, the immune response raised against an immunogenic polypeptide from one serotype of the pathogenic agent is not capable of recognizing, and thus protecting against, a different serotype of the pathogenic agent, or other related pathogenic agents. In other situations, the polypeptide produced by a pathogenic agent is not produced in sufficient amounts, or is not sufficiently immunogenic, for the infected host to raise an effective immune response against the pathogenic agent.

These problems are overcome by the methods of the invention, which typically involve recombining two or more forms of a nucleic acid that encode a polypeptide of the pathogenic agent, or antigen involved in another disease or condition. These recombination methods, referred to herein as "DNA shuffling", use as substrates forms of the nucleic acid that differ from each other in two or more nucleotides, so a library of recombinant nucleic acids results. The library is then screened to identify at least one optimized recombinant nucleic acid that encodes an optimized recombinant antigen that has improved ability to induce an immune response to the pathogenic agent or other condition. The resulting recombinant antigens often are chimeric in that they are recognized by antibodies (Abs) reacting against multiple pathogen strains, and generally can also elicit broad spectrum immune responses. Specific neutralizing antibodies are known to mediate protection against several pathogens of interest, although additional mechanisms, such as cytotoxic T lymphocytes, are likely to be involved. The concept of chimeric, multivalent antigens inducing broadly reacting antibody responses is further illustrated in FIG. 1.

Figure 2:
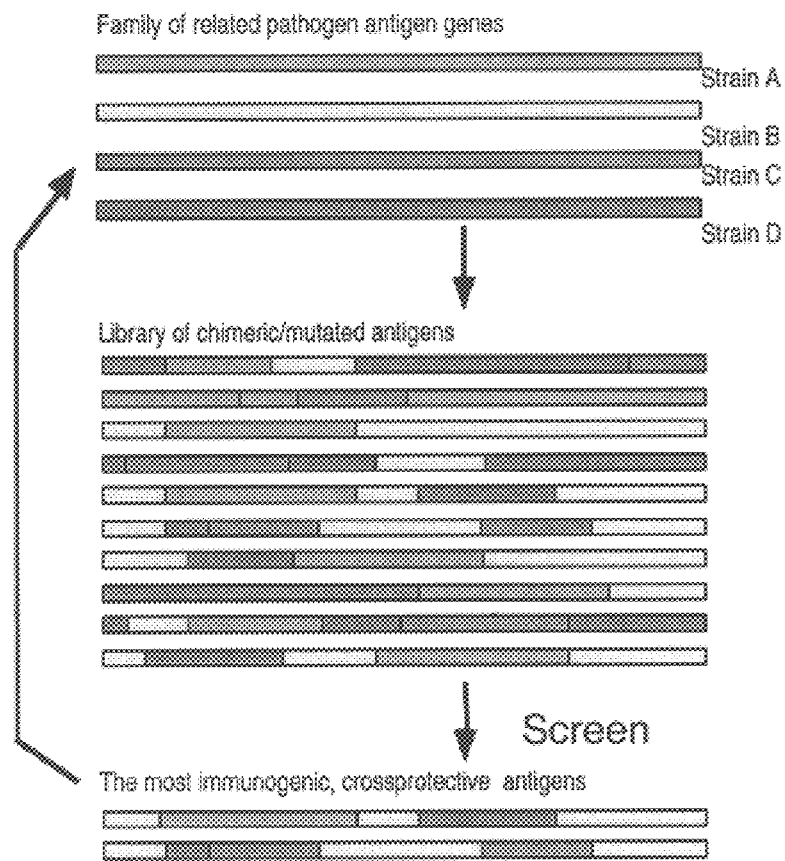
FIG. 2 shows the principle of family DNA shuffling. A family of antigen genes from related pathogens are subjected to shuffling, which results in a library of chimeric and/or mutated antigens. Screening methods are employed to identify those recombinant antigens that are the most immunogenic and/or cross-protective. These can, if desired, be subjected to additional rounds of shuffling and screening.
Figure 3:
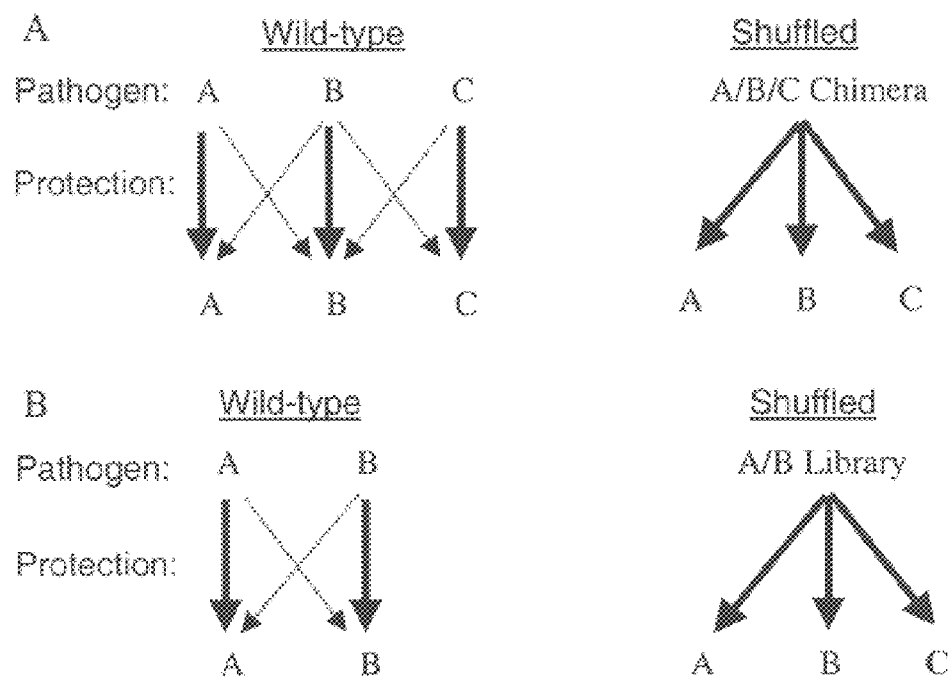
FIG. 3A–FIG. 3B shows a schematic for a method by which one can obtain recombinant polypeptides that can induce a broad-spectrum immune response.

In preferred embodiments, the different forms of the nucleic acids that encode antigenic polypeptides are obtained from members of a family of related pathogenic agents. This scheme of performing DNA shuffling using nucleic acids from related organisms, known as "family shuffling," is described in Crameri et al. ((1998) *Nature* 391: 288–291) and is shown schematically in FIG. 2. Polypeptides of different strains and serotypes of pathogens generally vary between 60–98%, which will allow for efficient family DNA shuffling. Therefore, family DNA shuffling provides an effective approach to generate multivalent, crossprotective antigens. The methods are useful for obtaining individual chimeras that effectively protect against most or all pathogen variants (FIG. 3A). Moreover, immunizations using entire libraries or pools of shuffled antigen chimeras can also result in identification of chimeric antigens that protect against pathogen variants that were not included in the starting population of antigens (for example, protection against strain C by shuffled library of chimeras/mutants of strains A and B in FIG. 3B). Accordingly, the antigen library immunization approach enables the development of immunogenic polypeptides that can induce immune responses against poorly characterized, newly emerging pathogen variants.

Sequence recombination can be achieved in many different formats and permutations of formats, as described in further detail below. These formats share some common principles. For example, the targets for modification vary in different applications, as does the property sought to be acquired or improved. Examples of candidate targets for acquisition of a property or improvement in a property include genes that encode proteins which have immunogenic and/or toxigenic activity when introduced into a host organism.

The methods use at least two variant forms of a starting target. The variant forms of candidate substrates can show substantial sequence or secondary structural similarity with each other, but they should also differ in at least one and preferably at least two positions. The initial diversity between forms can be the result of natural variation, e.g., the different variant forms (homologs) are obtained from different individuals or strains of an organism, or constitute related sequences from the same organism (e.g., allelic variations), or constitute homologs from different organisms (interspecific variants). Alternatively, initial diversity can be induced, e.g., the variant forms can be generated by error-prone transcription, such as an error-prone PCR or use of a polymerase which lacks proof-reading activity (see, Liao (1990) *Gene* 88:107–111), of the first variant form, or, by replication of the first form in a mutator strain (mutator host cells are discussed in further detail below, and are generally well known). A mutator strain can include any mutants in any organism impaired in the functions of mismatch repair. These include mutant gene products of mutS, mutT, mutH, mutL, ovrD, dcm, vsr, umuC, umuD, sbcB, recj, etc. The impairment is achieved by genetic mutation, allelic replacement, selective inhibition by an added reagent such as a small compound or an expressed antisense RNA, or other techniques. Impairment can be of the genes noted, or of homologous genes in any organism. Other methods of generating initial diversity include methods well known to those of skill in the art, including, for example, treatment of a nucleic acid with a chemical or other mutagen, through spontaneous mutation, and by inducing an error-prone repair system (e.g., SOS) in a cell that contains the nucleic acid. The initial diversity between substrates is greatly augmented in subsequent steps of recombination for library generation.

Properties Involved in Immunogenicity

The effectiveness of an antigen in inducing an immune response against a pathogen can depend upon several factors, many of which are not well understood. Most previously available methods for increasing the effectiveness of antigens are dependent upon understanding the molecular basis for these factors. However, DNA shuffling and antigen library immunization according to the methods of the invention are effective even where the molecular bases are unknown. The methods of the invention do not rely upon a priori assumptions.

Figure 4:
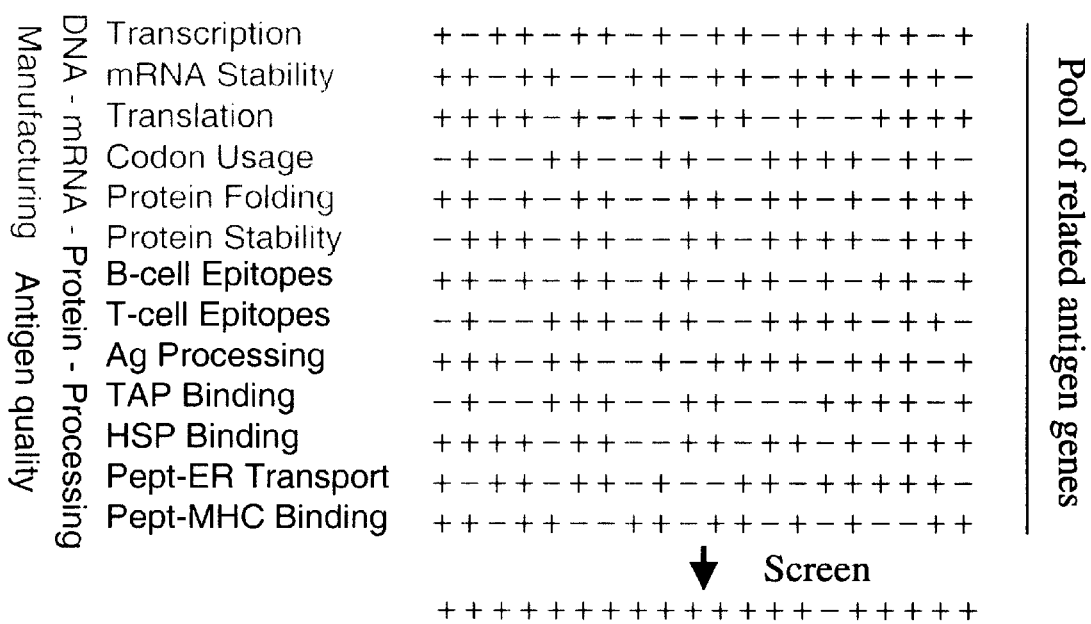
FIG. 4 diagrams some of the possible factors that can determine whether a particular polynucleotide encodes an immunogenic polypeptide having a desired property, such as enhanced immunogenicity and/or cross-reactivity. Those sequence regions that positively affect a particular property are indicated as plus signs along the antigen gene, while those sequence regions that have a negative effect are shown as minus signs. A pool of related antigen genes are shuffled and screened to obtain those that recombinant nucleic acids that have gained positive sequence regions and lost negative regions. No pre-existing knowledge as to which regions are positive or negative for a particular trait is required.

Polynucleotide sequences that can positively or negatively affect the immunogenicity of an antigen encoded by the polynucleotide are often scattered throughout the entire antigen gene. Several of these factors are shown diagranmmatically in FIG. 4. By recombining different forms of polynucleotide that encode the antigen using DNA shuffling, followed by selection for those chimeric polynucleotides that encode an antigen that can induce an improved immune response, one can obtain primarily sequences that have a positive influence on antigen immunogenicity. Those sequences that negatively affect antigen immunogenicity are eliminated (FIG. 4). One need not know the particular sequences involved.

DNA Shuffling Methods

Generally, the methods of the invention entail performing DNA recombination ("shuffling") and screening or selection to "evolve" individual genes, whole plasmids or viruses, multigene clusters, or even whole genomes (Stemmer (1995) *Bio/Technology* 13:549–553). Reiterative cycles of recombination and screening/selection can be performed to further evolve the nucleic acids of interest. Such techniques do not require the extensive analysis and computation required by conventional methods for polypeptide engineering. Shuffling allows the recombination of large numbers of mutations in a minimum number of selection cycles, in contrast to natural pair-wise recombination events (e.g., as occur during sexual replication). Thus, the sequence recombination techniques described herein provide particular advantages in that they provide recombination between mutations in any or all of these, thereby providing a very fast way of exploring the manner in which different combinations of mutations can affect a desired result. In some instances, however, structural and/or functional information is available which, although not required for sequence recombination, provides opportunities for modification of the technique.

The DNA shuffling methods of the invention can involve at least one of at least four different approaches to improve immunogenic activity as well as to broaden specificity. First, DNA shuffling can be performed on a single gene. Secondly, several highly homologous genes can be identified by sequence comparison with known homologous genes. These genes can be synthesized and shuffled as a family of homologs, to select recombinants with the desired activity. The shuffled genes can be cloned into appropriate host cells, such as *E. coli*, yeast, plants, fungi, animal cells, and the like, and those that encode antigens having the desired properties can be identified by the methods described below. Third, whole genome shuffling can be performed to shuffle genes that encode antigenic polypeptides (along with other genomic nucleic acids). For whole genome shuffling approaches, it is not even necessary to identify which genes are being shuffled. Instead, e.g., bacterial cell or viral genonies are combined and shuffled to acquire recombinant polypeptides that have enhanced ability to induce an immune response, as measured in any of the assays described below. Fourth, antigenic polypeptide-encoding genes can be codon modified to access mutational diversity not present in any naturally occurring gene. Details on each of these procedures can be found below.

Exemplary formats and examples for sequence recombination, sometimes referred to as DNA shuffling, evolution, or molecular breeding, have been described by the present inventors and co-workers in co-pending applications U.S. patent application Ser. No. 08/198,431, filed Feb. 17, 1994, Serial No. PCT/US95/02126, filed, Feb. 17, 1995, Ser. No. 08/425,684, filed Apr. 18, 1995, Ser. No. 08/537,874, filed Oct. 30, 1995, Ser. No. 08/564,955, filed Nov. 30, 1995, Ser. No. 08/621,859, filed Mar. 25, 1996, Ser. No. 08/621,430, filed Mar. 25, 1996, Serial No. PCT/US96/05480, filed Apr. 18, 1996, Ser. No. 08/650,400, filed May 20, 1996, Ser. No. 08/675,502, filed Jul. 3, 1996, Ser. No. 08/721, 824, filed Sep. 27, 1996, Serial No. PCT/US97/17300, filed Sep. 26, 1997, and Serial No. PCT/US97/24239, filed Dec. 17, 1997; Stenmmer, *Science* 270:1510 (1995); Stenmmer et al., *Gene* 164:49–53 (1995); Stemmer, *Bio/Technology* 13:549–553 (1995); Stemmer, *Proc. Natl. Acad. Sci. U. S. A.* 91:10747–10751 (1994); Stemmer, *Nature* 370:389–391 (1994); Crameri et al., *Nature Medicine* 2(1):1–3 (1996); Crameri et al., *Nature Biotechnology* 14:315–319 (1996), each of which is incorporated by reference in its entirety for all purposes.

Other methods for obtaining recombinant polynucleotides and/or for obtaining diversity in nucleic acids used as the substrates for shuffling include, for example, homologous recombination (PCT/US98/05223; Publ. No. WO98/42727); oligonucleotide-directed mutagenesis (for review see, Smith, *Ann. Rev. Genet.* 19: 423–462 (1985); Botstein and Shortle, *Science* 229: 1193–1201 (1985); Carter, *Biochem. J.* 237: 1–7 (1986); Kunkel, "The efficiency of oligonucleotide directed mutagenesis" in *Nucleic acids & Molecular Biology*, Eckstein and Lilley, eds., Springer Verlag, Berlin (1987)). Included among these methods are oligonucleotide-directed mutagenesis (Zoller and Smith, *Nucl. Acids Res.* 10: 6487–6500 (1982), *Methods in Enzymol.* 100: 468–500 (1983), and *Methods in Enzymol.* 154: 329–350 (1987)) phosphothioate-modified DNA mutagenesis (Taylor et al., *Nuc. Acids Res.* 13: 8749–8764 (1985); Taylor et al., Nuc. Acids Res. 13: 8765–8787 (1985); Nakamaye and Eckstein, *Nucl. Acids Res.* 14: 9679–9698 (1986); Sayers et al., *Nucl. Acids Res.* 16: 791–802 (1988); Sayers et al., *Nucl. Acids Res.* 16: 803–814 (1988)), mutagenesis using uracil-containing templates (Kunkel, *Proc. Natl Acad. Sci. USA* 82: 488–492 (1985) and Kunkel et al., *Methods in Enzymol.* 154: 367–382)); mutagenesis using gapped duplex DNA (Kramer et al., *Nucl. Acids Res.* 12: 9441–9456 (1984); Kramer and Fritz, *Methods in Enzymol.* 154: 350–367 (1987); Kramer et al., *Nucl. Acids Res.* 16: 7207 (1988)); and Fritz et al., *Nucl. Acids Res.* 16: 6987–6999 (1988)). Additional suitable methods include point mismatch repair (Kramer et al., *Cell* 38: 879–887 (1984)), mutagenesis using repair-deficient host strains (Carter et al., *Nucl. Acids Res.* 13: 4431–4443 (1985); Carter, *Methods in Enzymol.* 154: 382–403 (1987)), deletion mutagenesis (Eghtedarzadeh and Henikoff, *Nucl. Acids Res.* 14: 5115 (1986)), restriction-selection and restriction-purification (Wells et al., *Phil. Trans. R. Soc. Lond.* A 317: 415–423 (1986)), mutagenesis by total gene synthesis (Nambiar et al., *Science* 223: 1299–1301 (1984); Sakamar and Khorana, *Nucl. Acids Res.* 14: 6361–6372 (1988); Wells et al., *Gene* 34: 315–323 (1985); and Grundstrom et al., *Nucl. Acids Res.* 13: 3305–3316 (1985). Kits for mutagenesis are commercially available (e.g., Bio-Rad, Amersham International, Anglian Biotechnology).

The breeding procedure starts with at least two substrates that generally show some degree of sequence identity to each other (i.e., at least about 30%, 50%, 70%, 80% or 90% sequence identity), but differ from each other at certain positions. The difference can be any type of mutation, for example, substitutions, insertions and deletions. Often, different segments differ from each other in about 5–20 positions. For recombination to generate increased diversity relative to the starting materials, the starting materials must differ from each other in at least two nucleotide positions. That is, if there are only two substrates, there should be at least two divergent positions. If there are three substrates, for example, one substrate can differ from the second at a single position, and the second can differ from the third at a different single position. The starting DNA segments can be natural variants of each other, for example, allelic or species variants. The segments can also be from nonallelic genes showing some degree of structural and usually functional relatedness (e.g., different genes within a superfamily, such as the family of Yersinia V-antigens, for example). The starting DNA segments can also be induced variants of each other. For example, one DNA segment can be produced by error-prone PCR replication of the other, the nucleic acid can be treated with a chemical or other mutagen, or by substitution of a mutagenic cassette. Induced mutants can also be prepared by propagating one (or both) of the segments in a mutagenic strain, or by inducing an error-prone repair system in the cells. In these situations, strictly speaking, the second DNA segment is not a single segment but a large family of related segments. The different segments forming the starting materials are often the same length or substantially the same length. However, this need not be the case; for example; one segment can be a subsequence of another. The segments can be present as part of larger molecules, such as vectors, or can be in isolated form.

The starting DNA segments are recombined by any of the sequence recombination formats provided herein to generate a diverse library of recombinant DNA segments. Such a library can vary widely in size from having fewer than 10 to more than $10^5$, $10^9$, $10^{12}$ or more members. In some embodiments, the starting segments and the recombinant libraries generated will include full-length coding sequences and any essential regulatory sequences, such as a promoter and polyadenylation sequence, required for expression. In other embodiments, the recombinant. DNA segments in the library can be inserted into a common vector providing sequences necessary for expression before performing screening/selection.

Substrates for Evolution of Optimized Recombinant Antigens

The invention provides methods of obtaining recombinant polynucleotides that encode antigens that exhibit improved ability to induce an immune response to a pathogenic agent. The methods are applicable to a wide range of pathogenic agents, including potential biological warfare agents and other organisms and polypeptides that can cause disease and toxicity in humans and other animals. The following examples are merely illustrative, and not limiting.

1. Bacterial Pathogens and Toxins

In some embodiments, the methods of the invention are applied to bacterial pathogens, as well as to toxins produced by bacteria and other organisms. One can use the methods to obtain recombinant polypeptides that can induce an immune response against the pathogen, as well as recombinant toxins that are less toxic than native toxin polypeptides. Often, the polynucleotides of interest encode polypeptides that are present on the surface of the pathogenic organism.

Among the pathogens for which the methods of the invention are useful for producing protective immunogenic recombinant polypeptides are the Yersinia species. *Yersinia pestis*, the causative agent of plague, is one of the most virulent bacteria known with $LD_{50}$ values in mouse of less than 10 bacteria. The pneumonic form of the disease is readily spread between humans by aerosol or infectious droplets and can be lethal within days. A particularly preferred target for obtaining a recombinant polypeptide that can protect against Yersinia infection is the V antigen, which is a 37 kDa virulence factor, induces protective immune responses and is currently being evaluated as a subunit vaccine (Brubaker (1991) *Current Investigations of the Microbiology of Yersinae,* 12: 127). The V-antigen alone is not toxic, but Y pestis isolates that lack the V-antigen are avirulent. The Yersinia V-antigen has been successfully produced in *E. coli* by several groups (Leary et al. (1995) *Infect. Immun.* 3: 2854). Antibodies that recognize the V-antigen can provide passive protection against homologous strains, but not against heterologous strains. Similarly, immunization with purified V antigen protects against only homologous strains. To obtain cross-protective recombinant V antigen, in a preferred embodiment, V antigen genes from various Yersinia species are subjected to family shuffling. The genes encoding the V antigen from *Y. pestis, Y. enterocolitica,* and *Y. pseudotuberculosis,* for example, are 92–99% identical at the DNA level, making them ideal for optimization using family shuffling according to the methods of the invention. After shuffling, the library of recombinant nucleic acids is screened and/or selected for those that encode recombinant V antigen polypeptides that can induce an improved immune response and/or have greater cross-protectivity.

*Bacillus anthracis,* the causative agent of anthrax, is another example of a bacterial target against which the methods of the invention are useful. The anthrax protective antigen (PA) provides protective immune responses in test animals, and antibodies against PA also provide some protection. However, the immunogenicity of PA is relatively poor, so multiple injections are typically required when wild-type PA is used. Co-vaccination with lethal factor (LF) can improve the efficacy of wild-type PA vaccines, but toxicity is a limiting factor. Accordingly the DNA shuffling and antigen library immunization methods of the invention can be used to obtain nontoxic LF. Polynucleotides that encode LF from various *B. anthracis* strains are subjected to family shuffling. The resulting library of recombinant LF nucleic acids can then be screened to identify those that encode recombinant LF polypeptides that exhibit reduced toxicity. For example, one can inoculate tissue culture cells with the recombinant LF polypeptides in the presence of PA and select those clones for which the cells survive. If desired, one can then backcross the nontoxic LF polypeptides to retain the immunogenic epitopes of LF. Those that are selected through the first screen can then be subjected to a secondary screen. For example, one can test for the ability of the recombinant nontoxic LF polypeptides to induce an immune response (e.g., CTL or antibody response) in a test animal such as mice. In preferred embodiments, the recombinant nontoxic LF polypeptides are then tested for ability to induce protective immunity in test animals against challenge by different strains of *B. anthracis.*

The protective antigen (PA) of *B. anthracis* is also a suitable target for the methods of the invention. PA-encoding nucleic acids from various strains of *B. anthracis* are subjected to DNA shuffling. One can then screen for proper folding in, for example, *E. coli,* using polyclonal antibodies. Screening for ability to induce broad-spectrum antibodies in a test animal is also typically used, either alone or in addition to a preliminary screening method. In presently preferred embodiments, those recombinant polynucleotides that exhibit the desired properties can be backcrossed so that the immunogenic epitopes are maintained. Finally, the selected recombinants are tested for ability to induce protective immunity against different strains of *B. anthracis* in a test animal.

The *Staphylococcus aureus* and Streptococcus toxins are another example of a target polypeptide that can be altered using the methods of the invention. Strains of *Staphylococcus aureus* and group A Streptococci are involved in a range of diseases, including food poisoning, toxic shock syndrome, scarlet fever and various autoimmune disorders. They secrete a variety of toxins, which include at least five cytolytic toxins, a coagulase, and a variety of enterotoxins. The enterotoxins are classified as superantigens in that they crosslink MHC class II molecules with T cell receptors to cause a constitutive T cell activation (Fields et al. (1996) *Nature* 384: 188). This results in the accumulation of pathogenic levels of cytokines that can lead to multiple organ failure and death. At least thirty related, yet distinct enterotoxins have been sequenced and can be phylogenetically grouped into families. Crystal structures have been obtained for several members alone and in complex with MHC class II molecules. Certain mutations in the MHC class II-binding site of the toxins strongly reduce their toxicity and can form the basis of attenuated vaccines (Woody et al. (1997) *Vaccine* 15: 133). However, a successful immune response to one type of toxin may provide protection against closely related family members, whereas little protection against toxins from the other families is observed. Family shuffling of enterotoxin genes from various family members can be used to obtain recombinant toxin molecules that have reduced toxicity and can induce a cross-protective immune response. Shuffled antigens can also be screened to identify antigens that elicit neutralizing antibodies in an appropriate animal model such as mouse or monkey. Examples of such assays can include ELISA formats in which the elicited antibodies prevent binding of the enterotoxin to the MHC complex and/or T cell receptors on cells or purified forms. These assays can also include formats where the added antibodies would prevent T cells from being cross-linked to appropriate antigen presenting cells.

Cholera is an ancient, potentially lethal disease caused by the bacterium *Vibrio cholerae* and an effective vaccine for its prevention is still unavailable. Much of the pathogenesis of this disease is caused by the cholera enterotoxin. Ingestion of microgram quantities of cholera toxin can induce severe diarrhea causing loss of tens of liters of fluid. Cholera toxin is a complex of a single catalytic A subunit with a pentameric ring of identical B subunits. Each subunit is inactive on its own. The B subunits bind to specific ganglioside receptors on the surface of intestinal epithelial cells and trigger the entry of the A subunit into the cell. The A subunit ADP-ribosylates a regulatory G protein initiating a cascade of events causing a massive, sustained flow of electrolytes and water into the intestinal lumen resulting in extreme diarrhea.

The B subunit of cholera toxin is an attractive vaccine target for a number of reasons. It is a major target of protective antibodies generated during cholera infection and contains the epitopes for antitoxin neutralizing antibodies. It is nontoxic without the A subunit, is orally effective, and stimulates production of a strong IgA-dominated gut mucosal immune response, which is essential in protection against cholera and cholera toxin. The B subunit is also being investigated for use as an adjuvant in other vaccine preparations, and therefore, evolved toxins may provide general improvements for a variety of different vaccines. The heat-labile enterotoxins (LT) from enterotoxigenic *E. coli* strains are structurally related to cholera toxin and are 75% identical at the DNA sequence level. To obtain optimized recombinant toxin molecules that exhibit reduced toxicity and increased ability to induce an immune response that is protective against *V. cholerae* and *E. coli*, the genes that encode the related toxins are subjected to DNA shuffling.

The recombinant toxins are then tested for one or more of a several desirable traits. For example, one can screen for improved cross-reactivity of antibodies raised against the recombinant toxin polypeptides, for lack of toxicity in a cell culture assay, and for ability to induce a protective immune response against the pathogens and/or against the toxins themselves. The shuffled clones can be selected by phage display and/or screened by phage ELISA and ELISA assays for the presence of epitopes from the different serotypes. Variant proteins with multiple epitopes can then be purified and used to immunize mice or other test animal. The animal serum is then assayed for antibodies to the different B chain subtypes and variants that elicit a broad cross-reactive response will be evaluated further in a virulent challenge model. The *E. coli* and *V. cholerae* toxins can also act as adjuvants that are capable of enhancing mucosal immunity and oral delivery of vaccines and proteins. Accordingly, one can test the library of recombinant toxins for enhancement of the adjuvant activity.

Shuffled antigens can also be screened for improved expression levels and stability of the B chain pentamer, which may be less stable than when in the presence of the A chain in the hexameric complex. Addition of a heat treatment step or denaturing agents such as salts, urea, and/or guanidine hydrochloride can be included prior to ELISA assays to measure yields of correctly folded molecules by appropriate antibodies. It is sometimes desirable to screen for stable monomeric B chain molecules, in an ELISA format, for example, using antibodies that bind monomeric, but not pentameric B chains. Additionally, the ability of shuffled antigens to elicit neutralizing antibodies in an appropriate animal model such as mouse or monkey can be screened. For example, antibodies that bind to the B chain and prevent its binding to its specific ganglioside receptors on the surface of intestinal epithelial cells may prevent disease. Similarly antibodies that bind to the B chain and prevent its pentamerization or block A chain binding may be useful in preventing disease.

The bacterial antigens that can be improved by DNA shuffling for use as vaccines also include, but are not limited to, *Helicobacter pylori* antigens CagA and VacA (Blaser (1996) *Aliment. Pharmacol. Ther.* 1: 73–7; Blaser and Crabtree (1996) *Am. J. Clin. Pathol.* 106: 565–7; Censini et al. (1996) *Proc. Nat'l . Acad. Sci. USA* 93: 14648–14643). Other suitable *H. pylori* antigens include, for example, four immunoreactive proteins of 45–65 kDa as reported by Chatha et al. (1997) *Indian J. Med. Res.* 105: 170–175 and the *H. pylori* GroES homologue (HspA) (Kansau et al. (1996) *Mol. Microbiol.* 22: 1013–1023. Other suitable bacterial antigens include, but are not limited to, the 43-kDa and the fimbrilin (41 kDa) proteins of *P. gingivalis* (Boutsl et al. (1996) *Oral Microbiol. Immunol.* 11: 236–241); pneumococcal surface protein A (Briles et al. (1996) *Ann. NY Acad. Sci.* 797: 118–126); *Chlamydia psittaci* antigens, 80–90 kDa protein and 110 kDa protein (Buendia et al. (1997) *FEMS Microbiol. Lett.* 150: 113–9); the chlamydial exoglycolipid antigen (GLXA) (Whittum-Hudson et al. (1996) *Nature Med.* 2: 1116–1121); *Chlamydia pneumoniae* species-specific antigens in the molecular weight ranges 92–98, 51–55, 43–46 and 31.5–33 kDa and genus-specific antigens in the ranges 12, 26 and 65–70 kDa (Halme et al. (1997) *Scand. J. Immunol.* 45: 378–84); *Neisseria gonorrhoeae* (GC) or *Escherichia coli* phase-variable opacity (Opa) proteins (Chen and Gotschlich (1996) *Proc. Nat'l . Acad. Sci. USA* 93: 14851–14856), any of the twelve immunodominant proteins of *Schistosoma mansoni* (ranging in molecular weight from 14 to 208 kDa) as described by Cutts and Wilson (1997) *Parasitology* 114: 245–55; the 17-kDa protein antigen of *Brucella abortus* (De Mot et al. (1996) *Curr. Microbiol.* 33: 26–30); a gene homolog of the 17-kDa protein antigen of the Gram-negative pathogen *Brucella abortus* identified in the nocardioform actinomycete Rhodococcus sp. NI86/21 (De Mot et al. (1996) *Curr. Microbiol.* 33: 26–30); the staphylococcal enterotoxins (SEs) (Wood et al. (1997) *FEMS Immunol. Med. Microbiol.* 17: 1–10), a 42-kDa *M. hyopneumoniae* NrdF ribonucleotide reductase R2 protein or 15-kDa subunit protein of *M. hyopneumoniae* (Fagan et al. (1997) Infect. Immun. 65: 2502–2507), the meningococcal antigen PorA protein (Feavers et al. (1997) *Clin. Diagn. Lab. Immunol.* 3: 444–50); pneumococcal surface protein A (PspA) (McDaniel et al. (1997) *Gene Ther.* 4: 375–377); *F. tularensis* outer membrane protein FopA (Fulop et al. (1996) *FEMS Immunol. Med. Microbiol.* 13: 245–247); the major outer membrane protein within strains of the genus Actinobacillus (Hartmann et al. (1996) *Zentralbl. Bakteriol.* 284: 255–262); p60 or listeriolysin (Hly) antigen of *Listeria monocytogenes* (Hess et al. (1996) *Proc. Nat'l. Acad. Sci. USA* 93: 1458–1463); flagellar (G) antigens observed on *Salmonella enteritidis* and *S. pullorum* (Holt and Chaubal (1997) *J. Clin. Microbiol.* 35: 1016–1020); *Bacillus anthracis* protective antigen (PA) (Ivins et al. (1995) *Vaccine* 13: 1779–1784); *Echinococcus granulosus* antigen 5 (Jones et al. (1996) *Parasitology* 113: 213–222); the rol genes of *Shigella dysenteriae* 1 and *Escherichia coli* K-12 (Klee et al. (1997) *J. Bacteriol.* 179: 2421–2425); cell surface proteins Rib and alpha of group B streptococcus (Larsson et al. (1996) *Infect. Immun.* 64: 3518–3523); the 37 kDa secreted polypeptide encoded on the 70 kb virulence plasmid of pathogenic Yersinia spp. (Leary et al. (1995) *Contrib. Microbiol. Immunol.* 13: 216–217 and Roggenkamp et al. (1997) *Infect. Immun.* 65: 446–51); the OspA (outer surface protein A) of the Lyme disease spirochete *Borrelia burgdorferi* (Li et al. (1997) *Proc. Nat'l. Acad. Sci. USA* 94: 3584–3589, Padilla et al. (1996) *J. Infect. Dis.* 174: 739–746, and Wallich et al. (1996) *Infection* 24: 396–397); the *Brucella melitensis* group 3 antigen gene encoding Omp28 (Lindler et al. (1996) *Infect. Immun.* 64: 2490–2499); the PAc antigen of *Streptococcus mutans* (Murakami et al. (1997) *Infect. Immun.* 65: 794–797); pneumolysin, Pneumococcal neuraminidases, autolysin, hyaluronidase, and the 37 kDa pneumococcal surface adhesin A (Paton et al. (1997) *Microb. Drug Resist.* 3: 1–10); 29–32, 41–45, 63–71×10(3) MW antigens of *Salmonella typhi* (Perez et al. (1996) *Immunology* 89: 262–267); K-antigen as a marker of *Klebsiella pneumoniae* (Priamukhina and Morozova (1996) *Klin. Lab. Diagn.* 47–9); nocardial antigens of molecular mass approximately 60, 40, 20 and 15–10 kDa (Prokesova et al. (1996) *Int. J. Immunopharmacol.* 18: 661–668); *Staphylococcus aureus* antigen ORF-2 (Rieneck et al. (1997) *Biochim Biophys Acta* 1350: 128–132); GlpQ antigen of *Borrelia hermsii* (Schwan et al. (1996) *J. Clin. Microbiol.* 34: 2483–2492); cholera protective antigen (CPA) (Sciortino (1996) *J. Diarrhoeal Dis. Res.* 14: 16–26); a 190-kDa protein antigen of *Streptococcus mutans* (Senpuku et al. (1996) *Oral Microbiol. Immunol.* 11: 121–128); Anthrax toxin protective antigen (PA) (Sharma et al. (1996) *Protein Expr. Purif.* 7: 33–38); *Clostridium perfringens* antigens and toxoid (Strom et al. (1995) *Br. J. Rheumatol.* 34: 1095–1096); the SEF14 fimbrial antigen of *Salmonella enteritidis* (Thoms et al. (1996) *Microb. Pathog.* 20: 235–246); the *Yersinia pestis* capsular antigen (F1 antigen) (Titball et al. (1997) *Infect. Immun.* 65: 1926–1930); a 35-kilodalton protein of *Mycobacterium leprae* (Triccas et al. (1996) *Infect. Immun.* 64: 5171–5177); the major outer membrane protein, CD, extracted from Moraxella (Branhamella) catarrhalis (Yang et al. (1997) *FEMS Immunol. Med. Microbiol.* 17: 187–199); pH6 antigen (PsaA protein) of *Yersinia pestis* (Zav'yalov et al. (1996) *FEMS Immunol. Med. Microbiol.* 14: 53–57); a major surface glycoprotein, gp63, of *Leishmania major* (Xu and Liew (1994) *Vaccine* 12: 1534–1536; Xu and Liew (1995) *Immunology* 84: 173–176); mycobacterial heat shock protein 65, mycobacterial antigen (*Mycobacterium leprae* hsp65) (Lowrie et al. (1994) *Vaccine* 12: 1537–1540; Ragno et al. (1997) *Arthritis Rheum.* 40: 277–283; Silva (1995) *Braz. J. Med. Biol. Res.* 28: 843–851); *Mycobacterium tuberculosis* antigen 85 (Ag85) (Huygen et al. (1996) *Nat. Med.* 2: 893–898); the 45/47 kDa antigen complex (APA) of *Mycobacterium tuberculosis, M. bovis* and BCG (Horn et al. (1996) *J. Immunol. Methods* 197: 151–159); the mycobacterial antigen, 65-kDa heat shock protein, hsp65 (Tascon et al. (1996) *Nat. Med.* 2: 888–892); the mycobacterial antigens MPB64, MPB70, MPB57 and alpha antigen (Yamada et al. (1995) *Kekkaku* 70: 639–644); the *M. tuberculosis* 38 kDa protein (Vordermeier et al. (1995) *Vaccine* 13: 1576–1582); the MPT63, MPT64 and MPT-59 antigens from *Mycobacterium tuberculosis* (Manca et al. (1997) *Infect. Immun.* 65: 16–23; Oettinger et al. (1997) *Scand. J. Immunol.* 45: 499–503; Wilcke et al. (1996) *Tuber. Lung Dis.* 77: 250–256); the 35-kilodalton protein of *Mycobacterium leprae* (Triccas et al. (1996) *Infect. Immun.* 64: 5171–5177); the ESAT-6 antigen of virulent mycobacteria (Brandt et al. (1996) *J. Immunol.* 157: 3527–3533; Pollock and Andersen (1997) *J. Infect. Dis.* 175: 1251–1254); *Mycobacterium tuberculosis* 16-kDa antigen (Hspl6. 3) (Chang et al. (1996) *J. Biol. Chem.* 271: 7218–7223); and the 18-kilodalton protein of *Mycobacterium leprae* (Baumgart et al. (1996) *Infect. Immun.* 64: 2274–2281).

2. Viral Pathogens

The methods of the invention are also useful for obtaining recombinant nucleic acids and polypeptides that have enhanced ability to induce an immune response against viral pathogens. While the bacterial recombinants described above are typically administered in polypeptide form, recombinants that confer viral protection are preferably administered in nucleic acid form, as genetic vaccines.

One illustrative example is the Hantaan virus. Glycoproteins of this virus typically accumulate at the membranes of the Golgi apparatus of infected cells. This poor expression of the glycoprotein prevents the development of efficient genetic vaccines against these viruses. The methods of the invention solve this problem by performing DNA shuffling on nucleic acids that encode the glycoproteins and identifying those recombinants that exhibit enhanced expression in a host cell, and/or for improved immunogenicity when administered as a genetic vaccine. A convenient screening method for these methods is to express the recombinant polynucleotides as fusion proteins to PIG, which results in display of the polypeptides on the surface of the host cell (Whitehom et al. (1995) *Biotechnology* (N Y) 13:1215–9). Fluorescence-activated cell sorting is then used to sort and recover those cells that express an increased amount of the antigenic polypeptide on the cell surface. This preliminary screen can be followed by immunogenicity tests in mammals, such as mice. Finally, in preferred embodiments, those recombinant nucleic acids are tested as genetic vaccines for their ability to protect a test animal against challenge by the virus.

The flaviviruses are another example of a viral pathogen for which the methods of the invention are useful for obtaining a recombinant polypeptide or genetic vaccine that is effective against a viral pathogen. The flaviviruses consist of three clusters of antigenically related viruses: Dengue 1–4 (62–77% identity), Japanese, St. Louis and Murray Valley encephalitis viruses (75–82% identity), and the tick-borne encephalitis viruses (77–96% identity). Dengue virus can induce protective antibodies against SLE and Yellow fever (40–50% identity), but few efficient vaccines are available. To obtain genetic vaccines and recombinant polypeptides that exhibit enhanced cross-reactivity and immunogenicity, the polynucleotides that encode envelope proteins of related viruses are subjected to DNA shuffling. The resulting recombinant polynucleotides can be tested, either as genetic vaccines or by using the expressed polypeptides, for ability to induce a broadly reacting neutralizing antibody response. Finally, those clones that are favorable in the preliminary screens can be tested for ability to protect a test animal against viral challenge.

Viral antigens that can be evolved by DNA shuffling for improved activity as vaccines include, but are not limited to, influenza A virus N2 neuraminidase (Kilbourne et al. (1995) *Vaccine* 13: 1799–1803); Dengue virus envelope (E) and premembrane (prM) antigens (Feighny et al. (1994) *Am. J. Trop. Med. Hyg.* 50: 322–328; Putnak et al. (1996) *Am. J. Trop. Med. Hyg.* 55: 504–10); HIV antigens Gag, Pol, Vif and Nef (Vogt et al. (1995) *Vaccine* 13: 202–208); HIV antigens gp120 and gp160 (Achour et al. (1995) *Cell. Mol. Biol.* 41: 395–400; Hone et al. (1994) *Dev. Biol. Stand.* 82: 159–162); gp41 epitope of human immunodeficiency virus (Eckhart et al. (1996) *J. Gen. Virol.* 77: 2001–2008); rotavirus antigen VP4 (Mattion et al. (1995) *J. Virol.* 69: 5132–5137); the rotavirus protein VP7 or VP7sc (Emslie et al. (1995) *J. Virol.* 69: 1747–1754; Xu et al. (1995) *J. Gen. Virol.* 76: 1971–1980); herpes simplex virus (HSV) glycoproteins gB, gC, gD, gE, gG, gH, and gI (Fleck et al. (1994) *Med. Microbiol. Immunol. (Berl)* 183: 87–94 [Mattion, 1995]; Ghiasi et al. (1995) *Invest. Ophthalmol. Vis. Sci.* 36: 1352–1360; McLean et al. (1994) *J. Infect. Dis.* 170: 1100–1109); immediate-early protein ICP47 of herpes simplex virus-type I (HSV-1) (Banks et al. (1994) *Virology* 200: 236–245); immediate-early (IE) proteins ICP27, ICP0, and ICP4 of herpes simplex virus (Manickan et al. (1995) *J. Virol.* 69: 4711–4716); influenza virus nucleoprotein and hemagglutinin (Deck et al. (1997) *Vaccine* 15: 71–78; Fu et al. (1997) *J. Virol.* 71: 2715–2721); B19 parvovirus capsid proteins VP1 (Kawase et al. (1995) *Virology* 211: 359–366) or VP2 (Brown et al. (1994) *Virology* 198: 477–488); Hepatitis B virus core and e antigen (Schodel et al. (1996) *Intervirology* 39: 104–106); hepatitis B surface antigen (Shiau and Murray (1997) *J. Med. Virol.* 51: 159–166); hepatitis B surface antigen fused to the core antigen of the virus (Id. ); Hepatitis B virus core-preS2 particles (Nemeckova et al. (1996) *Acta Virol.* 40: 273–279); HBV preS2-S protein (Kutinova et al. (1996) *Vaccine* 14: 1045–1052); VZV glycoprotein I (Kutinova et al. (1996) *Vaccine* 14: 1045–1052); rabies virus glycoproteins (Xiang et al. (1994) *Virology* 199: 132–140; Xuan et al. (1995) *Virus Res.* 36: 151–161) or ribonucleocapsid (Hooper et al. (1994) *Proc. Nat'l. Acad. Sci. USA* 91: 10908–10912); human cytomegalovirus (HCMV) glycoprotein B (UL55) (Britt et al. (1995) *J. Infect. Dis.* 171: 18–25); the hepatitis C virus (HCV) nucleocapsid protein in a secreted or a nonsecreted form, or as a fusion protein with the middle (pre-S2 and S) or major (S) surface antigens of hepatitis B virus (HBV) (Inchauspe et al. (1997) *DNA Cell Biol.* 16: 185–195; Major et al. (1995) *J. Virol.* 69: 5798–5805); the hepatitis C virus antigens: the core protein (pC); El (pEl) and E2 (pE2) alone or as fusion proteins (Saito et al. (1997) *Gastroenterology* 112: 1321–1330); the gene encoding respiratory syncytial virus fusion protein (PFP-2) (Falsey and Walsh (1996) *Vaccine* 14: 1214–1218; Piedra et al. (1996) *Pediatr. Infect. Dis. J.* 15: 23–31); the VP6 and VP7 genes of rotaviruses (Choi et al. (1997) *Virology* 232: 129–138; Jin et al. (1996) *Arch. Virol.* 141: 2057–2076); the E1, E2, E3, E4, E5, E6 and E7 proteins of human papillomavirus (Brown et al. (1994) Virology 201: 46–54; Dillner et al. (1995) *Cancer Detect. Prev.* 19: 381–393; Krul et al. (1996) *Cancer Immunol. Immunother.* 43: 44–48; Nakagawa et al. (1997) *J. Infect. Dis.* 175: 927–931); a human T-lymphotropic virus type I gag protein (Porter et al. (1995) *J. Med. Virol.* 45: 469–474); Epstein-Barr virus (EBV) gp340 (Mackett et al. (1996) *J. Med. Virol.* 50: 263–271); the Epstein-Barr virus (EBV) latent membrane protein LMP2 (Lee et al. (1996) *Eur. J. Immunol.* 26: 1875–1883); Epstein-Barr virus nuclear antigens I and 2 (Chen and Cooper (1996) *J. Virol.* 70: 4849–4853; Khanna et al. (1995) *Virology* 214: 633–637); the measles virus nucleoprotein (N) (Fooks et al. (1995) *Virology* 210: 456–465); and cytomegalovirus glycoprotein gB (Marshall et al. (1994) *J. Med. Virol.* 43: 77–83) or glycoprotein gH (Rasmussen et al. (1994) *J. Infect. Dis.* 170: 673–677).

3. Parasites

Antigens from parasites can also be optimized by the methods of the invention. These include, but are not limited to, the schistosome gut-associated antigens CAA (circulating anodic antigen) and CCA (circulating cathodic antigen) in *Schistosoma mansoni, S. haematobium* or *S. japonicum* (Deelder et al. (1996) *Parasitology* 112: 21–35); a multiple antigen peptide (MAP) composed of two distinct protective antigens derived from the parasite *Schistosoma mansoni* (Ferru et al. (1997) *Parasite Immunol.* 19: 1–11); Leishmania parasite surface molecules (Lezama-Davila (1997) *Arch. Med. Res.* 28: 47–53); third-stage larval (L3) antigens of L. loa (Akue et al. (1997) *J. Infect. Dis.* 175: 158–63); the genes, Tams1-1 and Tams1-2, encoding the 30-and 32-kDa major merozoite surface antigens of Theileria annulata (Ta) (d'Oliveira et al. (1996) *Gene* 172: 33–39); *Plasmodium falciparum* merozoite surface antigen 1 or 2 (al-Yaman et al. (1995) *Trans. R. Soc. Trop. Med. Hyg.* 89: 555–559; Beck et al. (1997) *J. Infect. Dis.* 175: 921–926; Rzepczyk et al. (1997) *Infect. Immun.* 65: 1098–1100); circumsporozoite (CS) protein-based B-epitopes from *Plasmodium berghei*, $(PPPPNPND)_2$ (SEQ ID NO:23) and *Plasmodium yoelii*, $(QGPGAP)_3QG$ (SEQ ID NO:24), along with a *P. berghei* T-helper epitope KQIRDSITEEWS (SEQ ID NO:25) (Reed et al. (1997) *Vaccine* 15: 482–488); NYVAC-Pf7 encoded *Plasmodium falciparum* antigens derived from the sporozoite (circumsporozoite protein and sporozoite surface protein 2), liver (liver stage antigen 1), blood (merozoite surface protein 1, serine repeat antigen, and apical membrane antigen 1), and sexual (25-kDa sexual-stage antigen) stages of the parasite life cycle were inserted into a single NYVAC genome to generate NYVAC-Pf7 (Tine et al. (1996) *Infect. Immun.* 64: 3833–3844); *Plasimodium falciparum* antigen Pfs230 (Williamson et al. (1996) *Mol. Biochem. Parasitol.* 78: 161–169); *Plasimodium falciparum* apical membrane antigen (AMA-I) (Lal et al. (1996) *Infect. Immun.* 64: 1054–1059); *Plasmodium* falciparum proteins Pfs28 and Pfs25 (Duffy and Kaslow (1997) Infect. Immun. 65: 1109–1113); Plasimodium falciparum merozoite surface protein, MSP1 (Hui et al. (1996) Infect. Immun. 64: 1502–1509); the malaria antigen Pf332 (Ahlborg et al. (1996) Immunology 88: 630–635); Plasmodium falciparum erythrocyte membrane protein 1 (Baruch et al. (1995) Proc. Nat'l. Acad. Sci. USA 93: 3497–3502; Baruch et al. (1995) Cell 82: 77–87); Plasmodium falciparum merozoite surface antigen, PfMSP-1 (Egan et al. (1996) J. Infect. Dis. 173: 765–769); Plasmodium falciparum antigens SERA, EBA-175, RAP1 and RAP2 (Riley, (1997) J. Pharm. Pharmacol. 49: 21–27); Schistosoma japonicum paramyosin (Sj97) or fragments thereof (Yang et al. (1995) Biochem. Biophys. Res. Commun. 212: 1029–1039); and Hsp70 in parasites (Maresca and Kobayashi (1994) Experientia 50: 1067–1074).

4. Allergy

The invention also provides methods of obtaining reagents that are useful for treating allergy. In one embodiment, the methods involve making a library of recombinant polynucleotides that encode an allergen, and screening the library to identify those recombinant polynucleotides that exhibit improved properties when used as immunotherapeutic reagents for treating allergy. For example, specific immunotherapy of allergy using natural antigens carries a risk of inducing anaphylaxis, which can be initiated by cross-linking of high-affinity IgE receptors on mast cells. Therefore, allergens that are not recognized by pre-existing IgE are desirable. The methods of the invention provide methods by which one can obtain such allergen variants. Another improved property of interest is induction of broader immune responses, increased safety and efficacy.

Synthesis of polyclonal and allergen-specific IgE requires multiple interactions between B cells, T cells and professional antigen-presenting cells (APC). Activation of naive, unprimed B cells is initiated when specific B cells recognize the allergen by cell surface immunoglobulin (sIg). However, costimulatory molecules expressed by activated T cells in both soluble and membrane-bound forms are necessary for differentiation of B cells into IgE-secreting plasma cells. Activation of T helper cells requires recognition of an antigenic peptide in the context of MHC class II molecules on the plasma membrane of APC, such as monocytes, dendritic cells, Langerhans cells or primed B cells. Professional APC can efficiently capture the antigen and the peptide-MHC class II complexes are formed in a post-Golgi, proteolytic intracellular compartment and subsequently exported to the plasma membrane, where they are recognized by T cell receptor (TCR) (Whitton (1998) Curr. Top. Microbiol. Immunol. 232: 1–13). In addition, activated B cells express CD80 (B7-1) and CD86 (B7-2, B70), which are the counter receptors for CD28 and which provide a costimulatory signal for T cell activation resulting in T cell proliferation and cytokine synthesis. Since allergen-specific T cells from atopic individuals generally belong to the $T_H2$ cell subset, activation of these cells also leads to production of IL-4 and IL-13, which, together with membrane-bound costimulatory molecules expressed by activated T helper cells, direct B cell differentiation into IgE-secreting plasma cells.

Mast cells and eosinophils are key cells in inducing allergic symptoms in target organs. Recognition of specific antigen by IgE bound to high-affinity IgE receptors on mast cells, basophils or eosinophils results in crosslinking of the receptors leading to degranulation of the cells and rapid release of mediator molecules, such as histamine, prostaglandins and leukotrienes, causing allergic symptoms.

Immunotherapy of allergic diseases currently includes hyposensibilization treatments using increasing doses of allergen injected to the patient. These treatments result skewing of immune responses towards $T_H1$ phenotype and increase the ratio of IgG/IgE antibodies specific for allergens. Because these patients have circulating IgE antibodies specific for the allergens, these treatments include significant risk of anaphylactic reactions. In these reactions, free circulating allergen is recognized by IgE molecules bound to high-affinity IgE receptors on mast cells and eosinophils. Recognition of the allergen results in crosslinking of the receptors leading to release of mediators, such as histamine, prostaglandins, and leukotrienes, which cause the allergic symptoms, and occasionally anaphylactic reactions. Other problems associated with hyposensibilization include low efficacy and difficulties in producing allergen extracts reproducibly.

The methods of the invention provide a means to obtain allergens that, when used in genetic vaccines, provide a means of circumventing the problems that have limited the usefulness of previously known hyposensibilization treatments. For example, by expressing antigens on the surface of cells, such as muscle cells, the risk of anaphylactic reactions is significantly reduced. This can be conveniently achieved by using genetic vaccine vectors that encode transmembrane forms of allergens. The allergens can also be modified in such a way that they are efficiently expressed in transmembrane forms, further reducing the risk of anaphylactic reactions. Another advantage provided by the use of genetic vaccines for hyposensibilization is that the genetic vaccines can include cytokines and accessory molecules which further direct the immune responses towards the $T_H1$ phenotype, thus reducing the amount of IgE antibodies produced and increasing the efficacy of the treatments. To further reduce IgE production, one can administer the shuffled allergens using vectors that have been evolved to induce primarily IgG and IgM responses, with little or no IgE response (see, e.g., U.S. patent application Ser. No. 09/021,769, filed Feb. 11, 1998).

In these methods, polynucleotides encoding known allergens, or homologs or fragments thereof (e.g., immunogenic peptides) are inserted into DNA vaccine vectors and used to immunize allergic and asthmatic individuals. Alternatively, the shuffled allergens are expressed in manufacturing cells, such as E. coli or yeast cells, and subsequently purified and used to treat the patients or prevent allergic disease. DNA shuffling or other recombination method can be used to obtain allergens that activate T cells but cannot induce anaphylactic reactions. For example, a library of recombinant polynucleotides that encode allergen variants can be expressed in cells, such as antigen presenting cells, which are than contacted with PBMC or T cell clones from atopic patients. Those library members that efficiently activate $T_H$ cells from the atopic patients can be identified by assaying for T cell proliferation, or by cytokine synthesis (e.g., synthesis of IL-2, IL-4, IFN-γ. Those recombinant allergen variants that are positive in the in vitro tests can then be subjected to in vivo testing.

Examples of allergies that can be treated include, but are not limited to, allergies against house dust mite, grass pollen, birch pollen, ragweed pollen, hazel pollen, cockroach, rice, olive tree pollen, fungi, mustard, bee venom. Antigens of interest include those of animals, including the mite (e.g., Dermatophagoides pteronyssinus, Dermatophagoides farinae, Blomia tropicalis), such as the allergens der p1 (Scobie et al. (1994) Biochem. Soc. Trans. 22: 448S; Yssel et al. (1992) J. Immunol. 148: 738–745), der p2 (Chua et al.

(1996) *Clin. Exp. Allergy* 26: 829–837), der p3 (Smith and Thomas (1996) *Clin. Exp. Allergy* 26: 571–579), der p5, der p V (Lin et al. (1994) *J. Allergy Clin. Immunol.* 94: 989–996), der p6 (Bennett and Thomas (1996) *Clin. Exp. Allergy* 26: 1150–1154), der p 7 (Shen et al. (1995) *Clin. Exp. Allergy* 25: 416–422), der f2 (Yuuki et al. (1997) *Int. Arch. Allergy Immunol.* 112: 44–48), der f3 (Nishiyama et al. (1995) *FEBS Lett.* 377: 62–66), der f7 (Shen et al. (1995) *Clin. Exp. Allergy* 25: 1000–1006); Mag 3 (Fujikawa et al. (1996) *Mol. Immunol.* 33: 311–319). Also of interest as antigens are the house dust mite allergens Tyr p2 (Eriksson et al. (1998) *Eur. J. Biochem.* 251: 443–447), Lep dl (Schmidt et al. (1995) *FEBS Lett.* 370: 11–14), and glutathione S-transferase (O'Neill et al. (1995) *Immunol. Lett.* 48: 103–107); the 25,589 Da, 219 amino acid polypeptide with homology with glutathione S-transferases (O'Neill et al. (1994) *Biochim. Biophys. Acta.* 1219: 521–528); Blo t 5 (Arruda et al. (1995) *Int. Arch. Allergy Immunol.* 107: 456–457); bee venom phospholipase A2 (Carballido et al. (1994) *J. Allergy Clin. Immunol.* 93: 758–767; Jutel et al. (1995) *J Immunol.* 154: 4187–4194); bovine dermal/dander antigens BDA 11 (Rautiainen et al. (1995) *J. Invest. Dermatol.* 105: 660–663) and BDA20 (Mantyjarvi et al. (1996) *J. Allergy Clin. Immunol.* 97: 1297–1303); the major horse allergen Equ cl (Gregoire et al. (1996) *J. Biol. Chem.* 271: 32951–32959); Jumper ant *M. pilosula* allergen Myr p I and its homologous allergenic polypeptides Myr p2 (Donovan et al. (1996) *Biochem. Mol. Biol. Int.* 39: 877–885); 1–13, 14, 16 kD allergens of the mite *Blomia tropicalis* (Caraballo et al. (1996) *J. Allergy Clin. Immunol.* 98: 573–579); the cockroach allergens Bla g Bd90K (Helm et al. (1996) *J. Allergy Clin. Immunol.* 98: 172–80) and Bla g 2 (Arruda et al. (1995) *J. Biol. Chem.* 270: 19563–19568); the cockroach Cr-PI allergens (Wu et al. (1996) *J. Biol. Chem.* 271: 17937–17943); fire ant venom allergen, Sol i 2 (Schmidt et al. (1996) *J. Allergy Clin. Immunol.* 98: 82–88); the insect *Chironomus thummi* major allergen Chi t 1–9 (Kipp et al. (1996) *Int. Arch. Allergy Immunol.* 110: 348–353); dog allergen Can f 1 or cat allergen Fel d 1 (Ingram et al. (1995) *J. Allergy Clin. Immunol.* 96: 449–456); albumin, derived, for example, from horse, dog or cat (Goubran Botros et al. (1996) *Immunology* 88: 340–347); deer allergens with the molecular mass of 22 kD, 25 kD or 60 kD (Spitzauer et al. (1997) *Clin. Exp. Allergy* 27: 196–200); and the 20 kd major allergen of cow (Ylonen et al. (1994) *J. Allergy Clin. Immunol.* 93: 851–858).

Pollen and grass allergens are also useful in vaccines, particularly after optimization of the antigen by the methods of the invention. Such allergens include, for example, Hor v9 (Astwood and Hill (1996) *Gene* 182: 53–62, Lig v1 (Batanero et al. (1996) *Clin. Exp. Allergy* 26: 1401–1410); Lolp 1 (Muller et al. (1996) *Int. Arch. Allergy Immunol.* 109: 352–355), Lol p II (Tamborini et al. (1995) *Mol. Immunol.* 32: 505–513), Lol pVA, Lol pVB (Ong et al. (1995) *Mol. Immunol.* 32: 295–302), Lol p 9 (Blaher et al. (1996) *J. Allergy Clin. Immunol.* 98: 124–132; Par J I (Costa et al. (1994) *FEBS Lett.* 341: 182–186; Sallusto et al. (1996) *J. Allergy Clin. Immunol.* 97: 627–637), Parj 2. 0101 (Duro et al. (1996) *FEBS Lett.* 399: 295–298); Bet v1 (Faber et al. (1996) *J. Biol. Chem.* 271: 19243–19250), Bet v2 (Rihs et al. (1994) *Int. Arch. Allergy Immunol.* 105: 190–194); Dac g3 (Guerin-Marchand et al. (1996) *Mol. Immunol.* 33: 797–806); Phl p 1 (Petersen et al. (1995) *J. Allergy Clin. Immunol.* 95: 987–994), Phl p 5 (Muller et al. (1996) *Int. Arch. Allergy Immunol.* 109: 352–355), Phl p 6 (Petersen et al. (1995) *Int. Arch. Allergy Immunol.* 108: 55–59); Cry j I (Sone et al. (1994) *Biochem. Biophys. Res. Commun.* 199: 619–625), Cry j II (Namba et al. (1994) *FEBS Lett.* 353: 124–128); Cor a 1 (Schenk et al. (1994) *Eur. J. Biochem.* 224: 717–722); cyn d1 (Smith et al. (1996) *J. Allergy Clin. Immunol.* 98: 331–343), cyn d7 (Suphioglu et al. (1997) *FEBS Lett.* 402: 167–172); Pha a 1 and isoforms of Pha a 5 (Suphioglu and Singh (1995) *Clin. Exp. Allergy* 25: 853–865); Cha o 1 (Suzuki et al. (1996) *Mol. Immunol.* 33: 451–460); profilin derived, e. g, from timothy grass or birch pollen (Valenta et al. (1994) *Biochem. Biophys. Res. Commun.* 199: 106–118); P0149 (Wu et al. (1996) *Plant Mol. Biol.* 32: 1037–1042); Ory s1 (Xu et al. (1995) *Gene* 164: 255–259); and Amb a V and Amb t 5 (Kim et al. (1996) *Mol. Immunol.* 33: 873–880; Zhu et al. (1995) *J. Immunol.* 155: 5064–5073).

Vaccines against food allergens can also be developed using the methods of the invention. Suitable antigens for shuffling include, for example, profilin (Rihs et al. (1994) *Int. Arch. Allergy Immunol.* 105: 190–194); rice allergenic cDNAs belonging to the alpha-amylase/trypsin inhibitor gene family (Alvarez et al. (1995) *Biochim Biophys Acta* 1251: 201–204); the main olive allergen, Ole e I (Lombardero et al. (1994) *Clin Exp Allergy* 24: 765–770); Sin a 1, the major allergen from mustard (Gonzalez De La Pena et al. (1996) *Eur J Biochem.* 237: 827–832); parvalbumin, the major allergen of salmon (Lindstrom et al. (1996) *Scand. J. Immunol.* 44: 335–344); apple allergens, such as the major allergen Mal d 1 (Vanek-Krebitz et al. (1995) *Biochem. Biophys. Res. Commun.* 214: 538–551); and peanut allergens, such as Ara h I (Burks et al. (1995) *J. Clin. Invest.* 96: 1715–1721).

The methods of the invention can also be used to develop recombinant antigens that are effective against allergies to fungi. Fungal allergens useful in these vaccines include, but are not limited to, the allergen, Cla h III, of *Cladosporium herbarum* (Zhang et al. (1995) *J. Immunol.* 154: 710–717); the allergen Psi c 2, a fungal cyclophilin, from the basidiomycete *Psilocybe cubensis* (Horner et al. (1995) *Int. Arch. Allergy Immunol.* 107: 298–300); hsp 70 cloned from a cDNA library of *Cladosporium herbarum* (Zhang et al. (1996) *Clin. Exp. Allergy* 26: 88–95); the 68 kD allergen of *Penicillium notatum* (Shen et al. (1995) *Clin. Exp. Allergy* 26: 350–356); aldehyde dehydrogenase (ALDH) (Achatz et al. (1995) *Mol. Immunol.* 32: 213–227); enolase (Achatz et al. (1995) *Mol. Immunol.* 32: 213–227); YCP4 (Id.); acidic ribosomal protein P2 (Id. ).

Other allergens that can be used in the methods of the invention include latex allergens, such as a major allergen (Hev b 5) from natural rubber latex (Akasawa et al. (1996) *J. Biol. Chem.* 271: 25389–25393; Slater et al. (1996) *J. Biol. Chem.* 271: 25394–25399).

The invention also provides a solution to another shortcoming of vaccination as a treatment for allergy and asthma. While genetic vaccination primarily induces $CD8^+$ T cell responses, induction of allergen-specific IgE responses is dependent on $CD4^+$ T cells and their help to B cells. $T_H2$-type cells are particularly efficient in inducing IgE synthesis because they secrete high levels of IL-4, IL-5 and IL-13, which direct Ig isotype switching to IgE synthesis. IL-5 also induces eosinophilia. The methods of the invention can be used to develop recombinant antigens that efficiently induce $CD4^+$ T cell responses, and direct differentiation of these cells towards the $T_H1$ phenotype.

5. Inflammatory and Autoimmune Diseases

Autoimmune diseases are characterized by immune response that attacks tissues or cells of ones own body, or pathogen-specific immune responses that also are harmful for ones own tissues or cells, or non-specific immune activation which is harmful for ones own tissues or cells. Examples of autoimmune diseases include, but are not limited to, rheumatoid arthritis, SLE, diabetes mellitus, myasthenia gravis, reactive arthritis, ankylosing spondylitis, and multiple sclerosis. These and other inflammatory conditions, including IBD, psoriasis, pancreatitis, and various immunodeficiencies, can be treated using antigens that are optimized using the methods of the invention.

These conditions are often characterized by an accumulation of inflammatory cells, such as lymphocytes, macrophages, and neutrophils, at the sites of inflammation. Altered cytokine production levels are often observed, with increased levels of cytokine production. Several autoimmune diseases, including diabetes and rheumatoid arthritis, are linked to certain MHC haplotypes. Other autoimmune-type disorders, such as reactive arthritis, have been shown to be triggered by bacteria such as Yersinia and Shigella, and evidence suggests that several other autoimmune diseases, such as diabetes, multiple sclerosis, rheumatoid arthritis, may also be initiated by viral or bacterial infections in genetically susceptible individuals.

Current strategies of treatment generally include anti-inflammatory drugs, such as NSAID or cyclosporin, and antiproliferative drugs, such as methotrexate. These therapies are non-specific, so a need exists for therapies having greater specificity, and for means to direct the immune responses towards the direction that inhibits the autoimmune process.

The present invention provides several strategies by which these needs can be fulfilled. First, the invention provides methods of obtaining antigens having greater tolerogenicity and/or have improved antigenicity. In a preferred embodiment, the antigens prepared according to the invention exhibit improved induction of tolerance by oral delivery. Oral tolerance is characterized by induction of immunological tolerance after oral administration of large quantities of antigen. In animal models, this approach has proven to be a very promising approach to treat autoimmune diseases, and clinical trials are in progress to address the efficacy of this approach in the treatment of human autoimmune diseases, such as rheumatoid arthritis and multiple sclerosis. It has also been suggested that induction of oral tolerance against viruses used in gene therapy might reduce the immunogenicity of gene therapy vectors. However, the amounts of antigen required for induction of oral tolerance are very high and the methods of the invention provide a means for obtaining antigens that exhibit a significant improvement in induction of oral tolerance.

Expression library immunization (Barry et al. (1995) Nature 377: 632) is a particularly useful method of screening for optimal antigens for use in genetic vaccines. For example, to identify autoantigens present in Yersinia, Shigella, and the like, one can screen for induction of T cell responses in HLA-B27 positive individuals. Complexes that include epitopes of bacterial antigens and MHC molecules associated with autoimmune diseases, e.g., HLA-B27 in association with Yersinia antigens can be used in the prevention of reactive arthritis and ankylosing spondylitis in HLA-B27 positive individuals.

Screening of optimized antigens can be done in animal models which are known to those of skill in the art. Examples of suitable models for various conditions include collagen induced arthritis, the NFS/sld mouse model of human Sjogren's syndrome; a 120 kD organ-specific autoantigen recently identified as an analog of human cytoskeletal protein (ox-fodrin (Haneji et al. (1997) Science 276: 604), the New Zealand Black/White F1 hybrid mouse model of human SLE, NOD mice, a mouse model of human diabetes mellitus, fas/fas ligand mutant mice, which spontaneously develop autoimmune and lymphoproliferative disorders (Watanabe-Fukunaga et al. (1992) Nature 356: 314), and experimental autoimmune encephalomyelitis (EAE), in which myelin basic protein induces a disease that resembles human multiple sclerosis.

Autoantigens that can be shuffled according to the methods of the invention and used in vaccines for treating multiple sclerosis include, but are not limited to, myelin basic protein (Stinissen et al. (1996) J. Neurosci. Res. 45: 500–511) or a fusion protein of myelin basic protein and proteolipid protein (Elliott et al. (1996) J. Clin. Invest. 98: 1602–1612), proteolipid protein (PLP) (Rosener et al. (1997) J. Neuroimmunol. 75: 28–34), 2',3'-cyclic nucleotide 3'-phosphodiesterase (CNPase) (Rosener et al. (1997) J. Neuroimmunol. 75: 28–34), the Epstein Barr virus nuclear antigen-1 (EBNA-1) (Vaughan et al. (1996) J. Neuroimmunol. 69: 95–102), HSP70 (Salvetti et al. (1996) J. Neuroimmunol. 65: 143–53; Feldmann et al. (1996) Cell 85: 307).

Target antigens that, after shuffling according to the methods of the invention, can be used to treat scleroderma, systemic sclerosis, and systemic lupus erythematosus include, for example, (-2-GPI, 50 kDa glycoprotein (Blank et al. (1994) J. Autoimmun. 7: 441–455), Ku (p70/p80) autoantigen, or its 80-kd subunit protein (Hong et al. (1994) Invest. Ophthalmol. Vis. Sci. 35: 4023–4030; Wang et al. (1994) J. Cell Sci. 107: 3223–3233), the nuclear autoantigens La (SS-B) and Ro (SS-A) (Huang et al. (1997) J. Clin. Immunol. 17: 212–219; Igarashi et al. (1995) Autoimmunity 22: 33–42; Keech et al. (1996) Clin. Exp. Immunol. 104: 255–263; Manoussakis et al. (1995) J. Autoimmun. 8: 959–969; Topfer et al. (1995) Proc. Nat'l. Acad. Sci. USA 92: 875–879), proteasome (-type subunit C9 (Feist et al. (1996) J. Exp. Med. 184: 1313–1318), Scleroderma antigens Rpp 30, Rpp 38 or Scl-70 (Eder et al. (1997) Proc. Nat'l. Acad. Sci. USA 94: 1101–1106; Hietarinta et al. (1994) Br. J. Rheumatol. 33: 323–326), the centrosome autoantigen PCM-1 (Bao et al. (1995) Autoimmunity 22: 219–228), polymyositis-scleroderma autoantigen (PM-Scl) (Kho et al. (1997) J. Biol. Chem. 272: 13426–13431), sclerodermna (and other systemic autoimmune disease) autoantigen CENP-A (Muro et al. (1996) Clin. Immunol. Immunopathol. 78: 86–89), U5, a small nuclear ribonucleoprotein (snRNP) (Okano et al. (1996) Clin. Immunol. Immunopathol. 81: 41–47), the 100-kd protein of PM-Scl autoantigen (Ge et al. (1996) Arthritis Rheum. 39: 1588–1595), the nucleolar U3- and Th(7–2) ribonucleoproteins (Verheijen et al. (1994) J. Immunol. Methods 169: 173–182), the ribosomal protein L7 (Neu et al. (1995) Clin. Exp. Immunol. 100: 198–204), hPop1 (Lygerou et al. (1996) EMBO J. 15: 5936–5948), and a 36-kd protein from nuclear matrix antigen (Deng et al. (1996) Arthritis Rheum. 39: 1300–1307).

Hepatic autoimmune disorders can also be treated using improved recombinant antigens that are prepared according to the methods described herein. Among the antigens that are useful in such treatments are the cytochromes P450 and UDP-glucuronosyl-transferases (Obermayer-Straub and Manns (1996) Baillieres Clin. Gastroenterol. 10: 501–532), the cytochromes P450 2C9 and P450 1A2 (Bourdi et al. (1996) Chem. Res. Toxicol. 9: 1159–1166; Clemente et al. (1997) J. Clin. Endocrinol. Metab. 82: 1353–1361), LC-1 antigen (Klein et al. (1996) J. Pediatr. Gastroenterol. Nutr. 23: 461–465), and a 230-kDa Golgi-associated protein (Funaki et al. (1996) Cell Struct. Funct. 21: 63–72).

For treatment of autoimmune disorders of the skin, useful antigens include, but are not limited to, the 450 kD human epidermal autoantigen (Fujiwara et al. (1996) *J. Invest. Dermatol.* 106: 1125–1130), the 230 kD and 180 kD bullous pemphigoid antigens (Hashimoto (1995) *Keio J. Med.* 44: 115–123; Murakami et al. (1996) *J. Dermatol. Sci.* 13: 112–117), pemphigus foliaceus antigen (desmoglein 1), pemphigus vulgaris antigen (desmoglein 3), BPAg2, BPAg1, and type VII collagen (Batteux et al. (1997) *J. Clin. Immunol.* 17: 228–233; Hashimoto et al. (1996) *J. Dermatol. Sci.* 12: 10–17), a 168-kDa mucosal antigen in a subset of patients with cicatricial pemphigoid (Ghohestani et al. (1996) *J. Invest. Dermatol.* 107: 136–139), and a 218-kd nuclear protein (218-kd Mi-2) (Seelig et al. (1995) *Arthritis Rheum.* 38: 1389–1399).

The methods of the invention are also useful for obtaining improved antigens for treating insulin dependent diabetes mellitus, using one or more of antigens which include, but are not limited to, insulin, proinsulin, GAD65 and GAD67, heat-shock protein 65 (hsp65), and islet-cell antigen 69 (ICA69) (French et al. (1997) *Diabetes* 46: 34–39; Roep (1996) *Diabetes* 45: 1147–1156; Schloot et al. (1997) *Diabetologia* 40: 332–338), viral proteins homologous to GAD65 (Jones and Crosby (1996) *Diabetologia* 39: 1318–1324), islet cell antigen-related protein-tyrosine phosphatase (PTP) (Cui et al. (1996) *J. Biol. Chem.* 271: 24817–24823), GM2-1 ganglioside (Cavallo et al. (1996) *J. Endocrinol.* 150: 113–120; Dotta et al. (1996) *Diabetes* 45: 1193–1196), glutamic acid decarboxylase (GAD) (Nepom (1995) *Curr. Opin. Immunol.* 7: 825–830; Panina-Bordignon et al. (1995) *J. Exp. Med.* 181: 1923–1927), an islet cell antigen (ICA69) (Karges et al. (1997) *Biochim. Biophys. Acta* 1360: 97–101; Roep et al. (1996) *Eur. J. Immunol.* 26: 1285–1289), Tep69, the single T cell epitope recognized by T cells from diabetes patients (Karges et al. (1997) *Biochim. Biophys. Acta* 1360: 97–101), ICA 512, an autoantigen of type I diabetes (Solimena et al. (1996) *EMBO J.* 15: 2102–2114), an islet-cell protein tyrosine phosphatase and the 37-kDa autoantigen derived from it in type 1 diabetes (including IA-2, IA-2) (La Gasse et al. (1997) *Mol. Med.* 3: 163–173), the 64 kDa protein from In-111 cells or human thyroid follicular cells that is immunoprecipitated with sera from patients with islet cell surface antibodies (ICSA) (Igawa et al. (1996) *Endocr. J.* 43: 299–306), phogrin, a homologue of the human transmembrane protein tyrosine phosphatase, an autoantigen of type 1 diabetes (Kawasaki et al. (1996) *Biochem. Biophys. Res. Commun.* 227: 440–447), the 40 kDa and 37 kDa tryptic fragments and their precursors IA-2 and IA-2 in IDDM (Lampasona et al. (1996) *J. Immunol.* 157: 2707–2711; Notkins et al. (1996) *J. Autoimmun.* 9: 677–682), insulin or a cholera toxoid-insulin conjugate (Bergerot et al. (1997) *Proc. Nat'l. Acad. Sci. USA* 94: 4610–4614), carboxypeptidase H, the human homologue of gp330, which is a renal epithelial glycoprotein involved in inducing Heymann nephritis in rats, and the 38-kD islet mitochondrial autoantigen (Arden et al. (1996) *J. Clin. Invest.* 97: 551–561.

Rheumatoid arthritis is another condition that is treatable using optimized antigens prepared according to the present invention. Useful antigens for rheumatoid arthritis treatment include, but are not limited to, the 45 kDa DEK nuclear antigen, in particular onset juvenile rheumatoid arthritis and iridocyclitis (Murray et al. (1997) *J. Rheumatol.* 24: 560–567), human cartilage glycoprotein-39, an autoantigen in rheumatoid arthritis (Verheijden et al. (1997) *Arthritis Rheum.* 40: 1115–1125), a 68 k autoantigen in rheumatoid arthritis (B lass et al. (1997) *Ann. Rheum. Dis.* 56: 317–322), collagen (Rosloniec et al. (1995) *J. Immunol.* 155: 4504–4511), collagen type II (Cook et al. (1996) *Arthritis Rheum.* 39: 1720–1727; Trentham (1996) *Ann. N. Y. Acad. Sci.* 778: 306–314), cartilage link protein (Guerassimov et al. (1997) *J. Rheumatol.* 24: 959–964), ezrin, radixin and moesin, which are auto-immune antigens in rheumatoid arthritis (Wagatsuma et al. (1996) *Mol. Immunol.* 33: 1171–1176), and mycobacterial heat shock protein 65 (Ragno et al. (1997) *Arthritis Rheum.* 40: 277–283).

Also among the conditions for which one can obtain an improved antigen suitable for treatment are autoimmune thyroid disorders. Antigens that are useful for these applications include, for example, thyroid peroxidase and the thyroid stimulating hormone receptor (Tandon and Weetman (1994) *J. R. Coll. Physicians Lond.* 28: 10–18), thyroid peroxidase from human Graves' thyroid tissue (Gardas et al. (1997) *Biochem. Biophys. Res. Commun.* 234: 366–370; Zimmer et al. (1997) *Histochem. Cell. Biol.* 107: 115–120), a 64-kDa antigen associated with thyroid-associated ophthalmopathy (Zhang et al. (1996) *Clin. Immunol. Immunopathol.* 80: 236–244), the human TSH receptor (Nicholson et al. (1996) *J. Mol. Endocrinol.* 16: 159–170), and the 64 kDa protein from In-111 cells or human thyroid follicular cells that is immunoprecipitated with sera from patients with islet cell surface antibodies (ICSA) (Igawa el al. (1996) *Endocr. J.* 43: 299–306).

Other conditions and associated antigens include, but are not limited to, Sjogren's syndrome (-fodrin; Haneji et al. (1997) *Science* 276: 604–607), myastenia gravis (the human M2 acetylcholine receptor or fragments thereof, specifically the second extracellular loop of the human M2 acetylcholine receptor; Fu et al. (1996) *Clin. Immunol. Immunopathol.* 78: 203–207), vitiligo (tyrosinase; Fishman et al. (1997) *Cancer* 79: 1461–1464), a 450 kD human epidermal autoantigen recognized by serum from individual with blistering skin disease, and ulcerative colitis (chromosomal proteins HMG1 and HMG2; Sobajima et al. (1997) *Clin. Exp. Immunol.* 107: 135–140).

6. Cancer

Immunotherapy has great promise for the treatment of cancer and prevention of metastasis. By inducing an immune response against cancerous cells, the body's immune system can be enlisted to reduce or eliminate cancer. Improved antigens obtained using the methods of the invention provide cancer immunotherapies of increased effectiveness compared to those that are presently available.

One approach to cancer immunotherapy is vaccination using vaccines that include or encode antigens that are specific for tumor cells or by injecting the patients with purified recombinant cancer antigens. The methods of the invention can be used for obtaining antigens that exhibit an enhancement of immune responses against known tumor-specific antigens, and also to search for novel protective antigenic sequences. Antigens having optimized expression, processing, and presentation can be obtained as described herein. The approach used for each particular cancer can vary. For treatment of hormone-sensitive cancers (for example, breast cancer and prostate cancer), methods of the invention can be used to obtain optimized hormone antagonists. For highly immunogenic tumors, including melanoma, one can screen for recombinant antigens that optimally boost the immune response against the tumor. Breast cancer, in contrast, is of relatively low immunogenicity and exhibits slow progression, so individual treatments can be designed for each patient. Prevention of metastasis is also a goal in design of cancer vaccines.

Among the tumor-specific antigens that can be used in the antigen shuffling methods of the invention are: bullous pemphigoid antigen 2, prostate mucin antigen (PMA)

(Beckett and Wright (1995) *Int. J. Cancer* 62: 703–710), tumor associated Thomsen-Friedenreich antigen (Dahlenborg et al. (1997) *Int. J. Cancer* 70: 63–71), prostate-specific antigen (PSA) (Dannull and Belldegrun (1997) *Br. J. Urol.* 1: 97–103), luminal epithelial antigen (LEA. 135) of breast carcinoma and bladder transitional cell carcinoma (TCC) (Jones et al. (1997) *Anticancer Res.* 17: 685–687), cancer-associated serum antigen (CASA) and cancer antigen 125 (CA 125) (Kierkegaard et al. (1995) *Gynecol. Oncol.* 59: 251–254), the epithelial glycoprotein 40 (EGP40) (Kievit et al. (1997) *Int. J. Cancer* 71: 237–245), squamous cell carcinoma antigen (SCC) (Lozza et al. (1997) *Anticancer Res.* 17: 525–529), cathepsin E (Mota et al. (1997) *Am. J. Pathol.* 150: 1223–1229), tyrosinase in melanoma (Fishman et al. (1997) *Cancer* 79: 1461–1464), cell nuclear antigen (PCNA) of cerebral cavemomas (Notelet et al. (1997) *Surg. Neurol.* 47: 364–370), DF3/MUC1 breast cancer antigen (Apostolopoulos et al. (1996) *Immunol. Cell. Biol.* 74: 457–464; Pandey et al. (1995) *Cancer Res.* 55: 4000–4003), carcinoembryonic antigen (Paone et al. (1996) *J. Cancer Res. Clin. Oncol.* 122: 499–503; Schlom et al. (1996) *Breast Cancer Res. Treat.* 38: 27–39), tumor-associated antigen CA 19–9 (Tolliver and O'Brien (1997) *South Med. J.* 90: 89–90; Tsuruta et al. (1997) *Urol. Int.* 58: 20–24), human melanoma antigens MART-I/Melan-A27–35 and gp100 (Kawakami and Rosenberg (1997) *Int. Rev. Immunol.* 14: 173–192; Zajac et al. (1997) *Int. J. Cancer* 71: 491–496), the T and Tn pancarcinoma (CA) glycopeptide epitopes (Springer (1995) *Crit. Rev. Oncog.* 6: 57–85), a 35 kD tumor-associated autoantigen in papillary thyroid carcinoma (Lucas et al. (1996) *Anticancer Res.* 16: 2493–2496), KH-1 adenocarcinoma antigen (Deshpande and Danishefsky (1997) *Nature* 387: 164–166), the A60 mycobacterial antigen (Maes et al. (1996) *J. Cancer Res. Clin. Oncol.* 122: 296–300), heat shock proteins (HSPs) (Blachere and Srivastava (1995) *Semin. Cancer Biol.* 6: 349–355), and MAGE, tyrosinase, melan-A and gp75 and mutant oncogene products (e.g., p53, ras, and HER-2/neu (Bueler and Mulligan (1996) *Mol. Med.* 2: 545–555; Lewis and Houghton (1995) *Semin. Cancer Biol.* 6: 321–327; Theobald et al. (1995) *Proc. Nat'l. Acad. Sci. USA* 92: 11993–11997).

7. Contraception

Genetic vaccines that contain optimized antigens obtained by the methods of the invention are also useful for contraception. For example, genetic vaccines can be obtained that encode sperm cell specific antigens, and thus induce anti-sperm immune responses. Vaccination can be achieved by, for example, administration of recombinant bacterial strains, e.g. Salmonella and the like, which express sperm antigen, as well as by induction of neutralizing anti-hCG antibodies by vaccination by DNA vaccines encoding human chorionic gonadotropin (hCG), or a fragment thereof.

Sperm antigens which can be used in the genetic vaccines include, for example, lactate dehydrogenase (LDH-C4), galactosyltransferase (GT), SP-10, rabbit sperm autoantigen (RSA), guinea pig (g)PH-20, cleavage signal protein (CS-1), HSA-63, human (h)PH-20, and AgX-1 (Zhu and Naz (1994) *Arch. Androl.* 33: 141–144), the synthetic sperm peptide, P10G (O'Rand et al. (1993) *J. Reprod. Immunol.* 25: 89–102), the 135 kD, 95 kD, 65 kD, 47 kD, 41 kD and 23 kD proteins of sperm, and the FA-1 antigen (Naz et al. (1995) *Arch. Androl.* 35: 225–231), and the 35 kD fragment of cytokeratin 1 (Lucas et al. (1996) *Anticancer Res.* 16: 2493–2496).

The methods of the invention can also be used to obtain genetic vaccines that are expressed specifically in testis. For example, polynucleotide sequences that direct expression of genes that are specific to testis can be used (e.g., fertilization antigen-1 and the like). In addition to sperm antigens, antigens expressed on oocytes or hormones regulating reproduction may be useful targets of contraceptive vaccines. For example, genetic vaccines can be used to generate antibodies against gonadotropin releasing hormone (GNRH) or zona pellucida proteins (Miller et al. (1997) *Vaccine* 15:1858–1862). Vaccinations using these molecules have been shown to be efficacious in animal models (Miller et al. (1997) *Vaccine* 15:1858–1862). Another example of a useful component of a genetic contraceptive vaccine is the ovarian zona pellucida glycoprotein ZP3 (Tung et al. (1994) *Reprod. Fertil Dev.* 6:349–355).

Methods of Selecting and Identifying Optimized Recombinant Antigens

Figure 5:
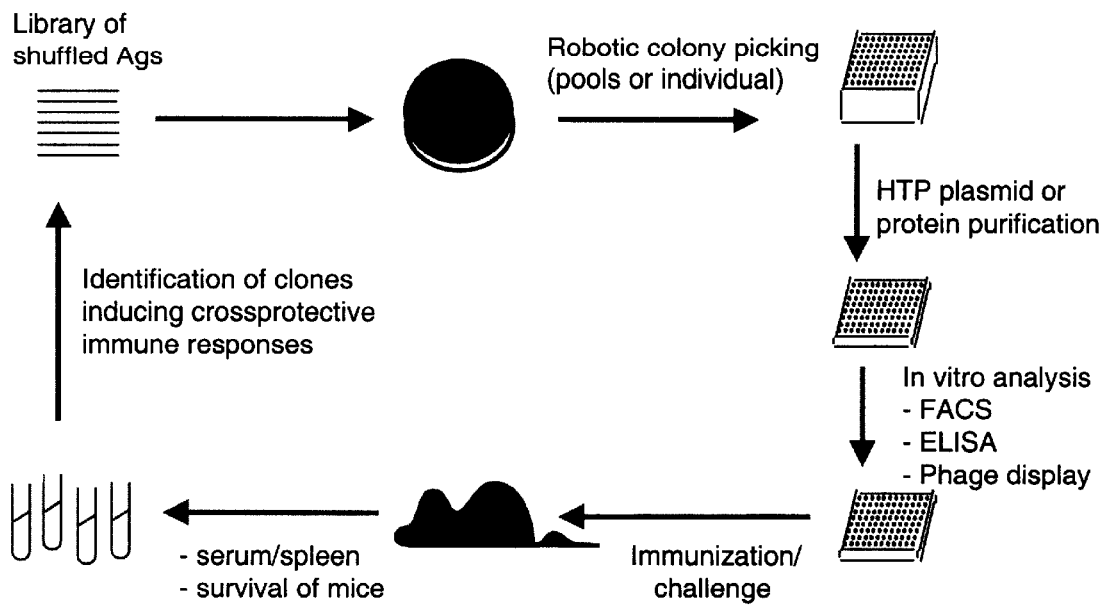
FIG. 5 shows a schematic representation of the screening strategy for antigen library screening.

Once one has performed DNA shuffling to obtain a library of polynucleotides that encode recombinant antigens, the library is subjected to selection and/or screening to identify those library members that encode antigenic peptides that have improved ability to induce an immune response to the pathogenic agent. Selection and screening of recombinant polynucleotides that encode polypeptides having an improved ability to induce an immune response can involve either in vivo and in vitro methods, but most often involves a combination of these methods. For example, in a typical embodiment the members of a library of recombinant nucleic acids are picked, either individually or as pools. The clones can be subjected to analysis directly, or can be expressed to produce the corresponding polypeptides. In a presently preferred embodiment, an in vitro screen is performed to identify the best candidate sequences for the in vivo studies. Alternatively, the library can be subjected to in vivo challenge studies directly. The analyses can employ either the nucleic acids themselves (e.g., as genetic vaccines), or the polypeptides encoded by the nucleic acids. A schematic diagram of a typical strategy is shown in FIG. 5. Both in vitro and in vivo methods are described in more detail below.

If a recombination cycle is performed in vitro, the products of recombination, i.e., recombinant segments, are sometimes introduced into cells before the screening step. Recombinant segments can also be linked to an appropriate vector or other regulatory sequences before screening. Alternatively, products of recombination generated in vitro are sometimes packaged in viruses (e.g., bacteriophage) before screening. If recombination is performed in vivo, recombination products can sometimes be screened in the cells in which recombination occurred. In other applications, recombinant segments are extracted from the cells, and optionally packaged as viruses, before screening.

Often, improvements are achieved after one round of recombination and selection. However, recursive sequence recombination can also be employed to achieve still further improvements in a desired property, or to bring about new (or "distinct") properties. Recursive sequence recombination entails successive cycles of recombination to generate molecular diversity. That is, one creates a family of nucleic acid molecules showing some sequence identity to each other but differing in the presence of mutations. In any given cycle, recombination can occur in vivo or in vitro, intracellularly or extracellularly. Furthermore, diversity resulting from recombination can be augmented in any cycle by applying prior methods of mutagenesis (e.g., error-prone PCR or cassette mutagenesis) to either the substrates or products for recombination.

In a presently preferred embodiment, polynucleotides that encode optimized recombinant antigens are subjected to molecular backcrossing, which provides a means to breed the shuffled chimeras/mutants back to a parental or wild-type sequence, while retaining the mutations that are critical to the phenotype that provides the optimized immune responses. In addition to removing the neutral mutations, molecular backcrossing can also be used to characterize which of the many mutations in an improved variant contribute most to the improved phenotype. This cannot be accomplished in an efficient library fashion by any other method. Backcrossing is performed by shuffling the improved sequence with a large molar excess of the parental sequences.

The nature of screening or selection depends on what property or characteristic is to be acquired or the property or characteristic for which improvement is sought, and many examples are discussed below. It is not usually necessary to understand the molecular basis by which particular products of recombination (recombinant segments) have acquired new or improved properties or characteristics relative to the starting substrates. For example, a gene that encodes an antigenic polypeptide can have many component sequences each having a different intended role (see, e.g., FIG. 4). Each of these component sequences can be varied and recombined simultaneously. Screening/selection can then be performed, for example, for recombinant segments that have increased ability to induce an immune response to a pathogenic agent without the need to attribute such improvement to any of the individual component sequences of the recombinant polynucleotide.

Depending on the particular screening protocol used for a desired property, initial round(s) of screening can sometimes be performed using bacterial cells due to high transfection efficiencies and ease of culture. However, especially for testing of immunogenic activity, test animals are used for library expression and screening. Similarly other types of screening which are not amenable to screening in bacterial or simple eukaryotic library cells, are performed in cells selected for use in an environment close to that of their intended use. Final rounds of screening can be performed in cells or organisms that are as close as possible to the precise cell type or organism of intended use.

If further improvement in a property is desired, at least one, and usually a collection, of recombinant segments surviving a first round of screening/selection are subject to a further round of recombination. These recombinant segments can be recombined with each other or with exogenous segments representing the original substrates or further variants thereof. Again, recombination can proceed in vitro or in vivo. If the previous screening step identifies desired recombinant segments as components of cells, the components can be subjected to further recombination in vivo, or can be subjected to further recombination in vitro, or can be isolated before performing a round of in vitro recombination. Conversely, if the previous screening step identifies desired recombinant segments in naked form or as components of viruses, these segments can be introduced into cells to perform a round of in vivo recombination. The second round of recombination, irrespective how performed, generates further recombinant segments which encompass additional diversity than is present in recombinant segments resulting from previous rounds.

The second round of recombination can be followed by a further round of screening/selection according to the principles discussed above for the first round. The stringency of screening/selection can be increased between rounds. Also, the nature of the screen and the property being screened for can vary between rounds if improvement in more than one property is desired or if acquiring more than one new property is desired. Additional rounds of recombination and screening can then be performed until the recombinant segments have sufficiently evolved to acquire the desired new or improved property or function.

The practice of this invention involves the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well-known to persons of skill. General texts which describe molecular biological techniques useful herein, including mutagenesis, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed. ), Vol. 1–3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1998) ("Ausubel")). Examples of techniques sufficient to direct persons of skill through in vitro amplification methods, including the polymerase chain reaction (PCR) the ligase chain reaction (LCR), Q-replicase amplification and other RNA polymerase mediated techniques (e.g., NASBA) are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al. (1988) *Science* 241, 1077–1080; Van Brunt (1990) *Biotechnology* 8, 291–294; Wu and Wallace (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684–685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

Oligonucleotides for use as probes, e.g., in in vitro amplification methods, for use as gene probes, or as shuffling targets (e.g., synthetic genes or gene segments) are typically synthesized chemically according to the solid phase phosphoramidite triester method described by Beaucage and Caruthers (1981) *Tetrahedron Letts.,* 22(20) :1859–1862, e.g., using an automated synthesizer, as described in Needham-VanDevanter et al. (1984) *Nucleic Acids Res.,* 12:6159–6168. Oligonucleotides can also be custom made and ordered from a variety of commercial sources known to persons of skill.

Indeed, essentially any nucleic acid with a known sequence can be custom ordered fom any of a variety of commercial sources, such as The Midland Certified Reagent Company (mcrc@oligos. com), The Grea American Gene Company (http://www.genco.com), ExpressGen Inc. (www.expressgen.com), Operon Technologies Inc.

(Ajameda, Calif.) and many others. Similarly, peptides and antibodies can be custom ordered from any of a variety of sources, such as PeptidoGenic (pkim@ccnet.com), HTI Bioproducts, Inc. (http://www.htibio.com), BMA Biomedicals Ltd (U.K.), BioSynthesis, Inc., and many others.

1. Purification and In Vitro Analysis of Recombinant Nucleic Acids and Polypeptides Once DNA shuffling has been performed, the resulting library of recombinant polynucleotides can be subjected to purification and preliminary analysis in vitro, in order to identify the most promising candidate recombinant nucleic acids. Advantageously, the assays can be practiced in a high-throughput format. For example, to purify individual shuffled recombinant antigens, clones can robotically picked into 96-well formats, grown, and, if desired, frozen for storage.

Whole cell lysates (V-antigen), periplasmic extracts, or culture supernatants (toxins) can be assayed directly by ELISA as described below, but high throughput purification is sometimes also needed. Affinity chromatography using immobilized antibodies or incorporation of a small nonimmunogenic affinity tag such as a hexahistidine peptide with immobilized metal affinity chromatography will allow rapid protein purification. High binding-capacity reagents with 96-well filter bottom plates provide a high throughput purification process. The scale of culture and purification will depend on protein yield, but initial studies will require less than 50 micrograms of protein. Antigens showing improved properties can be purified in larger scale by FPLC for re-assay and animal challenge studies.

In some embodiments, the shuffled antigen-encoding polynucleotides are assayed as genetic vaccines. Genetic vaccine vectors containing the shuffled antigen sequences can be prepared using robotic colony picking and subsequent robotic plasmid purification. Robotic plasmid purification protocols are available that allow purification of 600–800 plasmids per day. The quantity and purity of the DNA can also be analyzed in 96-well plates, for example. In a presently preferred embodiment, the amount of DNA in each sample is robotically normalized, which can significantly reduce the variation between different batches of vectors.

Once the proteins and/or nucleic acids are picked and purified as desired, they can be subjected to any of a number of in vitro analysis methods. Such screenings include, for example, phage display, flow cytometry, and ELISA assays to identify antigens that are efficiently expressed and have multiple epitopes and a proper folding pattern. In the case of bacterial toxins, the libraries may also be screened for reduced toxicity in mammalian cells.

As one example, to identify recombinant antigens that are cross-reactive, one can use a panel of monoclonal antibodies for screening. A humoral immune response generally targets multiple regions of antigenic proteins. Accordingly, monoclonal antibodies can be raised against various regions of immunogenic proteins (Alving et al. (1995) *Immunol. Rev.* 145: 5). In addition, there are several examples of monoclonal antibodies that only recognize one strain of a given pathogen, and by definition, different serotypes of pathogens are recognized by different sets of antibodies. For example, a panel of monoclonal antibodies have been raised against VEE envelope proteins, thus providing a means to recognize different subtypes of the virus (Roehrig and Bolin (1997) *J. Clin. Microbiol.* 35: 1887). Such antibodies, combined with phage display and ELISA screening, can be used to enrich recombinant antigens that have epitopes from multiple pathogen strains. Flow cytometry based cell sorting will further allow for the selection of variants that are most efficiently expressed.

Phage display provides a powerful method for selecting proteins of interest from large libraries (Bass et al. (1990) *Proteins: Struct. Funct. Genet.* 8: 309; Lowman and Wells (1991) *Methods: A Companion to Methods Enz.* 3(3) ;205–216. Lowman and Wells (1993) *J. Mol. Biol.* 234;564–578). Some recent reviews on the phage display technique include, for example, McGregor (1996) *Mol. Biotechnol.* 6(2):155–62; Dunn (1996) *Curr. Opin. Biotechnol.* 7(5):547–53; Hill et al. (1996) *Mol. Microbiol.* 20(4) :685–92; *Phage Display of Peptides and Proteins: A Laboratory Manual.* B K. Kay, J. Winter, J, McCafferty eds., Academic Press 1996; O'Neil et al. (1995) *Curr. Opin. Struct. Biol.* 5(4):443–9; Phizicky et al. (1995) *Microbiol. Rev.* 59(1):94–123; Clackson et al. (1994) *Trends Biotechnol.* 12(5):173–84; Felici et al. (1995) *Biotechnol. Annu. Rev.* 1: 149–83; Burton (1995) *Immunotechnology* 1(2) :87–94. ) See, also, Cwirla et al., *Proc. Natl. Acad. Sci. USA* 87: 6378–6382 (1990); Devlin et al., *Science* 249: 404–406 (1990), Scott & Smith, *Science* 249: 386–388 (1990); Ladner et al., U.S. Pat. No. 5,571,698. Each phage particle displays a unique variant protein on its surface and packages the gene encoding that particular variant. The shuffled genes for the antigens are fused to a protein that is expressed on the phage surface, e.g., gene III of phage M13, and cloned into phagemid vectors. In a presently preferred embodiment, a suppressible stop codon (e.g., an amber stop codon) separates the genes so that in a suppressing strain of *E. coli*, the antigen-gIIIp fusion is produced and becomes incorporated into phage particles upon infection with M13 helper phage. The same vector can direct production of the unfused antigen alone in a nonsuppressing *E. coli* for protein purification.

The genetic packages most frequently used for display libraries are bacteriophage, particularly filamentous phage, and especially phage M13, Fd and F1. Most work has involved inserting libraries encoding polypeptides to be displayed into either gIII or gVIII of these phage forming a fusion protein. See, e.g., Dower, WO 91/19818; Devlin, WO 91/18989; MacCafferty, WO 92/01047 (gene III); Huse, WO 92/06204; Kang, WO 92/18619 (gene VIII). Such a fusion protein comprises a signal sequence, usually but not necessarily, from the phage coat protein, a polypeptide to be displayed and either the gene III or gene VIII protein or a fragment thereof. Exogenous coding sequences are often inserted at or near the N-terminus of gene III or gene VIII although other insertion sites are possible.

Eukaryotic viruses can be used to display polypeptides in an analogous manner. For example, display of human heregulin fused to gp70 of Moloney murine leukemia virus has been reported by Han et al., *Proc. Natl. Acad. Sci. USA* 92: 9747–9751 (1995). Spores can also be used as replicable genetic packages. In this case, polypeptides are displayed from the outer surface of the spore. For example, spores from *B. subtilis* have been reported to be suitable. Sequences of coat proteins of these spores are provided by Donovan et al., *J. Mol. Biol.* 196, 1–10 (1987). Cells can also be used as replicable genetic packages. Polypeptides to be displayed are inserted into a gene encoding a cell protein that is expressed on the cells surface. Bacterial cells including *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli* are preferred. Details of outer surface proteins are discussed by Ladner et al., U.S. Pat. No. 5,571,698 and references cited therein. For example, the lamB protein of *E. coli* is suitable.

A basic concept of display methods that use phage or other replicable genetic package is the establishment of a physical association between DNA encoding a polypeptide to be screened and the polypeptide. This physical association is provided by the replicable genetic package, which displays a polypeptide as part of a capsid enclosing the genome of the phage or other package, wherein the polypeptide is encoded by the genome. The establishment of a physical association between polypeptides and their genetic material allows simultaneous mass screening of very large numbers of phage bearing different polypeptides. Phage displaying a polypeptide with affinity to a target, e.g., a receptor, bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means, or the polynucleotide that encodes the peptide or polypeptide can be used as part of a genetic vaccine.

Variants with specific binding properties, in this case binding to family-specific antibodies, are easily enriched by panning with immobilized antibodies. Antibodies specific for a single family are used in each round of panning to rapidly select variants that have multiple epitopes from the antigen families. For example, A-family specific antibodies can be used to select those shuffled clones that display A-specific epitopes in the first round of panning. A second round of panning with B-specific antibodies will select from the "A" clones those that display both A- and B-specific epitopes. A third round of panning with C-specific antibodies will select for variants with A, B, and C epitopes. A continual selection exists during this process for clones that express well in *E. coli* and that are stable throughout the selection. Improvements in factors such as transcription, translation, secretion, folding and stability are often observed and will enhance the utility of selected clones for use in vaccine production.

Phage ELISA methods can be used to rapidly characterize individual variants. These assays provide a rapid method for quantitation of variants without requiring purification of each protein. Individual clones are arrayed into 96-well plates, grown, and frozen for storage. Cells in duplicate plates are infected with helper phage, grown overnight and pelleted by centrifugation. The supernatants containing phage displaying particular variants are incubated with immobilized antibodies and bound clones are detected by anti-M13 antibody conjugates. Titration series of phage particles, immobilized antigen, and/or soluble antigen competition binding studies are all highly effective means to quantitate protein binding. Variant antigens displaying multiple epitopes will be further studied in appropriate animal challenge models.

Several groups have reported an in vitro ribosome display system for the screening and selection of mutant proteins with desired properties from large libraries. This technique can be used similarly to phage display to select or enrich for variant antigens with improved properties such as broad cross reactivity to antibodies and improved folding (see, e.g., Hanes et al. (1997) *Proc. Nat'l. Acad. Sci. USA* 94(10): 4937–42; Mattheakis et al. (1994) *Proc. Nat'l. Acad. Sci. USA* 91(19):9022–6; He et al. (1997) *Nucl. Acids Res.* 25(24):5132–4; Nemoto et al. (1997) *FEBS Lett.* 414(2): 405–8).

Other display methods exist to screen antigens for improved properties such as increased expression levels, broad cross reactivity, enhanced folding and stability. These include, but are not limited to display of proteins on intact *E. coli* or other cells (e.g., Francisco et al. (1993) *Proc. Nat'l. Acad. Sci. USA* 90: 1044–10448; Lu et al. (1995) *Bio/Technology* 13: 366–372). Fusions of shuffled antigens to DNA-binding proteins can link the antigen protein to its gene in an expression vector (Schatz et al. (1996) *Methods Enzymol.* 267: 171–91; Gates et al. (1996) *J. Mol. Biol.* 255: 373–86.)

The various display methods and ELISA assays can be used to screen for shuffled antigens with improved properties such as presentation of multiple epitopes, improved immunogenicity, increased expression levels, increased folding rates and efficiency, increased stability to factors such as temperature, buffers, solvents, improved purification properties, etc. Selection of shuffled antigens with improved expression, folding, stability and purification profile under a variety of chromatographic conditions can be very important improvements to incorporate for the vaccine manufacturing process.

To identify recombinant antigenic polypeptides that exhibit improved expression in a host cell, flow cytometry is a useful technique. Flow cytometry provides a method to efficiently analyze the functional properties of millions of individual cells. One can analyze the expression levels of several genes simultaneously, and flow cytometry-based cell sorting allows for the selection of cells that display properly expressed antigen variants on the cell surface or in the cytoplasm. Very large numbers ($>10^7$) of cells can be evaluated in a single vial experiment, and the pool of the best individual sequences can be recovered from the sorted cells. These methods are particularly useful in the case of, for example, Hantaan virus glycoproteins, which are generally very poorly expressed in mammalian cells. This approach provides a general solution to improve expression levels of pathogen antigens in mammalian cells, a phenomenon that is critical for the function of genetic vaccines.

To use flow cytometry to analyze polypeptides that are not expressed on the cell surface, one can engineer the recombinant polynucleotides in the library such that the polynucleotide is expressed as a fusion protein that has a region of amino acids which is targeted to the cell membrane. For example, the region can encode a hydrophobic stretch of C-terminal amino acids which signals the attachment of a phosphoinositol-glycan (PIG) terminus on the expressed protein and directs the protein to be expressed on the surface of the transfected cell (Whitehorn et al. (1995) *Biotechnology (N Y)* 13:1215–9). With an antigen that is naturally a soluble protein, this method will likely not affect the three dimensional folding of the protein in this engineered fusion with a new C-terninus. With an antigen that is naturally a transmembrane protein (e.g., a surface membrane protein on pathogenic viruses, bacteria, protozoa or tumor cells) there are at least two possibilities. First, the extracellular domain can be engineered to be in fusion with the C-terminal sequence for signaling PIG-linkage. Second, the protein can be expressed in toto relying on the signalling of the host cell to direct it efficiently to the cell surface. In a minority of cases, the antigen for expression will have an endogenous PIG terminal linkage (e.g., some antigens of pathogenic protozoa).

Those cells expressing the antigen can be identified with a fluorescent monoclonal antibody specific for the C-terminal sequence on PIG-linked forms of the surface antigen. FACS analysis allows quantitative assessment of the level of expression of the correct form of the antigen on the cell population. Cells expressing the maximal level of antigen are sorted and standard molecular biology methods are used to recover the plasmid DNA vaccine vector that conferred this reactivity. An alternative procedure that allows purification of all those cells expressing the antigen (and that may be useful prior to loading onto a cell sorter since antigen expressing cells may be a very small minority population), is to rosette or pan-purify the cells expressing surface antigen. Rosettes can be formed between antigen expressing cells and erythrocytes bearing covalently coupled antibody to the relevant antigen. These are readily purified by unit gravity sedimentation. Panning of the cell population over petri dishes bearing immobilized monoclonal antibody specific for the relevant antigen can also be used to remove unwanted cells.

In the high throughput assays of the invention, it is possible to screen up to several thousand different shuffled variants in a single day. For example, each well of a microtiter plate can be used to run a separate assay, or; if concentration or incubation time effects are to be observed, every 5–10 wells can test a single variant. Thus, a single standard microtiter plate can assay about 100 (e.g., 96) reactions. If 1536 well plates are used, then a single plate can easily assay from about 100 to about 1500 different reactions. It is possible to assay several different plates per day; assay screens for up to about 6,000–20,000 different assays (i.e., involving different nucleic acids, encoded proteins, concentrations, etc.) is possible using the integrated systems of the invention. More recently, microfluidic approaches to reagent manipulation have been developed, e.g., by Caliper Technologies *(Palo Alto, Calif.).

In one aspect, library members, e.g., cells, viral plaques, or the like, are separated on solid media to produce individual colonies (or plaques). Using an automated colony picker (e.g., the Q-bot, Genetix, U. K.), colonies or plaques are identified, picked, and up to 10,000 different mutants inoculated into 96 well microtiter dishes, optionally containing glass balls in the wells to prevent aggregation. The Q-bot does not pick an entire colony but rather inserts a pin through the center of the colony and exits with a small sampling of cells (or viruses in plaque applications). The time the pin is in the colony, the number of dips to inoculate the culture medium, and the time the pin is in that medium each effect inoculum size, and each can be controlled and optimized. The uniform process of the Q-bot decreases human handling error and increases the rate of establishing cultures (roughly 10,000/4 hours). These cultures are then shaken in a temperature and humidity controlled incubator. The glass balls in the microtiter plates act to promote uniform aeration of cells dispersal of cells, or the like, similar to the blades of a fermentor. Clones from cultures of interest can be cloned by limiting dilution. Plaques or cells constituting libraries can also be screened directly for production of proteins, either by detecting hybridization, protein activity, protein binding to antibodies, or the like.

The ability to detect a subtle increase in the performance of a shuffled library member over that of a parent strain relies on the sensitivity of the assay. The chance of finding the organisms having an improvement in ability to induce an immune response is increased by the number of individual mutants that can be screened by the assay. To increase the chances of identifying a pool of sufficient size, a prescreen that increases the number of mutants processed by 10-fold can be used. The goal of the prescreen will be to quickly identify mutants having equal or better product titers than the parent strain(s) and to move only these mutants forward to liquid cell culture for subsequent analysis.

A number of well known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass. ; Orca, Hewlett-Packard, Palo Alto, Calif. ) which mimic the manual synthetic operations performed by a scientist. Any of the above devices are suitable for use with the present invention, e.g., for high-throughput screening of molecules encoded by codon-altered nucleic acids. The nature and implementation of modifications to these devices (if any) so that they can operate as discussed herein with reference to the integrated system will be apparent to persons skilled in the relevant art.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc. ). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

The manufacturers of such systems provide detailed protocols the various high throughput. Thus, for example, Zymark Corp. provides technical bulletins describing screening systems for detecting the modulation of gene transcription, ligand binding, and the like. Microfluidic approaches to reagent manipulation have also been developed, e.g., by Caliper Technologies (Palo Alto, Calif.).

Optical images viewed (and, optionally, recorded) by a camera or other recording device (e.g., a photodiode and data storage device) are optionally further processed in any of the embodiments herein, e.g., by digitizing the image and/or storing and analyzing the image on a computer. As noted above, in some applications, the signals resulting from assays are florescent, making optical detection approaches appropriate in these instances. A variety of commercially available peripheral equipment and software is available for digitizing, storing and analyzing a digitized video or digitized optical image, e.g., using PC (Intel x86 or Pentium chip- compatible DOS , OS2 WINDOWS, WINDOWS NT or WINDOWS95 based machines), MACINTOSH, or UNIX based (e.g., SUN work station) computers.

One conventional system carries light from the assay device to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

Integrated systems for analysis in the present invention typically include a digital computer with high-throughput liquid control software, image analysis software, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled assay component. The image scanner interfaces with the image analysis software to provide a measurement of optical intensity. Typically, the intensity measurement is interpreted by the data interpretation software to show whether the optimized recombinant antigenic polypeptide products are produced.

2. Antigen Library Immunization

In a presently preferred embodiment, antigen library immunization (ALI) is used to identify optimized recombinant antigens that have improved immunogenicity. ALI involves introduction of the library of recombinant antigen-encoding nucleic acids, or the recombinant antigens encoded by the shuffled nucleic acids, into a test animal. The animals are then subjected to in vivo challenge using live pathogens. Neutralizing antibodies and cross-protective immune responses are studied after immunization with the entire libraries, pools and/or individual antigen variants.

Methods of immunizing test animals are well known to those of skill in the art. In presently preferred embodiments, test animals are immunized twice or three times at two week intervals. One week after the last immunization, the animals are challenged with live pathogens (or mixtures of pathogens), and the survival and symptoms of the animals is followed. Immunizations using test animal challenge are described in, for example, Roggenkamp et al. (1997) *Infect. Immun.* 65: 446; Woody et al. (1997) *Vaccine* 2: 133; Agren et al. (1997) *J. Immunol.* 158: 3936; Konishi et al. (1992) *Virology* 190: 454; Kinney et al. (1988) *J. Virol.* 62: 4697; Iacono-Connors et al. (1996) *Virus Res.* 43: 125; Kochel et al. (1997) *Vaccine* 15: 547; and Chu et al. (1995) *J. Virol.* 69: 6417.

The immunizations can be performed by injecting either the recombinant polynucleotides themselves, i.e., as a genetic vaccine, or by immunizing the animals with polypeptides encoded by the recombinant polynucleotides. Bacterial antigens are typically screened primarily as recombinant proteins, whereas viral antigens are preferably analyzed using genetic vaccinations.

Figure 6:
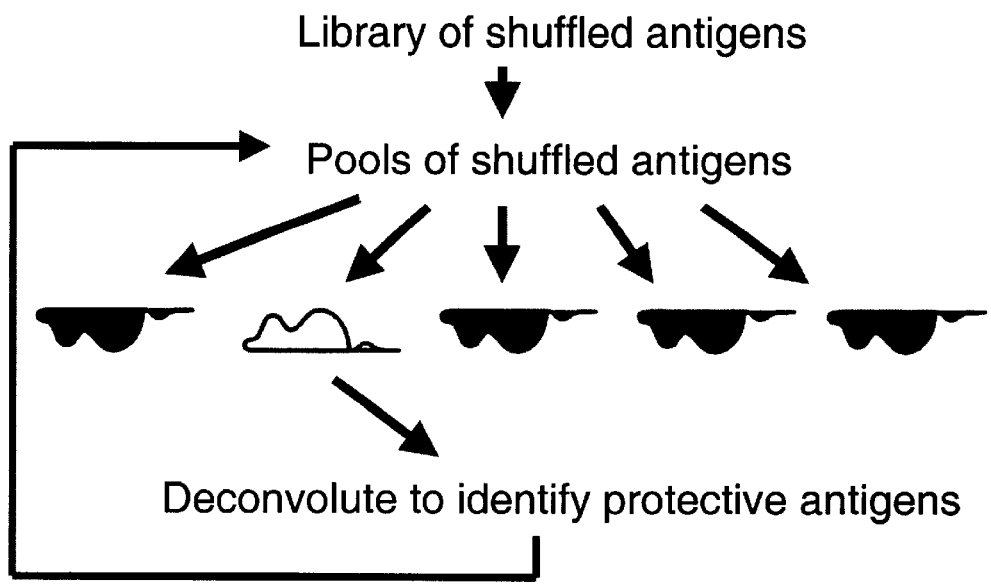
FIG. 6 shows a schematic representation of a strategy for pooling and deconvolution as used in antigen library screening.

To dramatically reduce the number of experiments required to identify individual antigens having improved immunogenic properties, one can use pooling and deconvolution, as diagrammed in FIG. 6. Pools of recombinant nucleic acids, or polypeptides encoded by the recombinant nucleic acids, are used to immunize test animals. Those pools that result in protection against pathogen challenge are then subdivided and subjected to additional analysis. The high throughput in vitro approaches described above can be used to identify the best candidate sequences for the in vivo studies.

The challenge models that can be used to screen for protective antigens include pathogen and toxin models, such as Yersinia bacteria, bacterial toxins (such as Staphylococcal and Streptococcal enterotoxins, *E. coli*/*V. cholerae* enterotoxins), Venezuelan equine encephalitis virus (VEE), Flaviviruses (Japanese encephalitis virus, Tick-borne encephalitis virus, Dengue virus), Hantaan virus, Herpes simplex, influenza virus (e.g., Influenza A virus), Vesicular Stomatitis Virus, *Pseudomonas aeruginosa*, *Salmonella typhimurium*, *Escherichia coli*, *Klebsiella pneumoniae*, *Toxoplasma gondii*, *Plasmodium yoelii*, Herpes simplex, influenza virus (e.g., Influenza A virus), and Vesicular Stomatitis Virus. However, the test animals can also be challenged with tumor cells to enable screening of antigens that efficiently protect against malignancies. Individual shuffled antigens or pools of antigens are introduced into the animals intradermally, intramuscularly, intravenously, intratracheally, anally, vaginally, orally, or intraperitoneally and antigens that can prevent the disease are chosen, when desired, for further rounds of shuffling and selection.

Eventually, the most potent antigens, based on in vivo data in test animals and comparative in vitro studies in animals and man, are chosen for human trials, and their capacity to prevent and treat human diseases is investigated.

In some embodiments, antigen library immunization and pooling of individual clones is used to immunize against a pathogen strain that was not included in the sequences that were used to generate the library. The level of crossprotection provided by different strains of a given pathogen can significantly. However, homologous titer is always higher than heterologous titer. Pooling and deconvolution is especially efficient in models where minimal protection is provided by the wild-type antigens used as starting material for shuffling (for example minimal protection by antigens A and B against strain C in FIG. 3B). This approach can be taken, for example, when evolving the V-antigen of Yersinae or Hantaan virus glycoproteins.

In some embodiments, the desired screening involves analysis of the immune response based on immunological assays known to those skilled in the art. Typically, the test animals are first immunized and blood or tissue samples are collected for example one to two weeks after the last immunization. These studies enable one to one can measure immune parameters that correlate to protective immunity, such as induction of specific antibodies (particularly IgG) and induction of specific T lymphocyte responses, in addition to determining whether an antigen or pools of antigens provides protective immunity. Spleen cells or peripheral blood mononuclear cells can be isolated from immunized test animals and measured for the presence of antigen-specific T cells and induction of cytokine synthesis. ELISA, ELISPOT and cytoplasmic cytokine staining, combined with flow cytometry, can provide such information on a single-cell level.

Common immunological tests that can be used to identify the efficacy of immunization include antibody measurements, neutralization assays and analysis of activation levels or frequencies of antigen presenting cells or lymphocytes that are specific for the antigen or pathogen. The test animals that can be used in such studies include, but are not limited to, mice, rats, guinea pigs, hamsters, rabbits, cats, dogs, pigs and monkeys. Monkey is a particularly useful test animal because the MHC molecules of monkeys and humans are very similar.

Virus neutralization assays are useful for detection of antibodies that not only specifically bind to the pathogen, but also neutralize the function of the virus. These assays are typically based on detection of antibodies in the sera of immunized animal and analysis of these antibodies for their capacity to inhibit viral growth in tissue culture cells. Such assays are known to those skilled in the art. One example of a virus neutralization assay is described by Dolin R (*J. Infect. Dis.* 1995, 172:1175–83). Virus neutralization assays provide means to screen for antigens that also provide protective immunity.

In some embodiments, shuffled antigens are screened for their capacity to induce T cell activation in vivo. More specifically, peripheral blood mononuclear cells or spleen cells from injected mice can be isolated and the capacity of cytotoxic T lymphocytes to lyse infected, autologous target cells is studied. The spleen cells can be reactivated with the specific antigen in vitro. In addition, T helper cell activation and differentiation is analyzed by measuring cell proliferation or production of $T_H1$ (IL-2 and IFN-$\gamma$) and $T_H2$ (IL-4 and IL-S) cytokines by ELISA and directly in CD4$^+$ T cells by cytoplasmic cytokine staining and flow cytometry. Based on the cytokine production profile, one can also screen for alterations in the capacity of the antigens to direct $T_H1/T_H2$ differentiation (as evidenced, for example, by changes in ratios of IL-4/IFN-γ, IL-4/IL-2, IL-5/IFN-γ, IL-5/IL-2, IL-13/IFN-γ, IL-13/IL-2). The analysis of the T cell activation induced by the antigen variants is a very useful screening method, because potent activation of specific T cells in vivo correlates to induction of protective immunity.

The frequency of antigen-specific $CD8^+$ T cells in vivo can also be directly analyzed using tetramers of MHC class I molecules expressing specific peptides derived from the corresponding pathogen antigens (Ogg and McMichael, *Curr. Opin. Immunol.* 1998, 10:393–6; Altman et al., *Science* 1996, 274:94–6). The binding of the tetramers can be detected using flow cytometry, and will provide information about the efficacy of the shuffled antigens to induce activation of specific T cells. For example, flow cytometry and tetramer stainings provide an efficient method of identifying T cells that are specific to a given antigen or peptide. Another method involves panning using plates coated with tetramers with the specific peptides. This method allows large numbers of cells to be handled in a short time, but the method only selects for highest expression levels. The higher the frequency of antigen-specific T cells in vivo is, the more efficient the immunization has been, enabling identification of the antigen variants that have the most potent capacity to induce protective immune responses. These studies are particularly useful when conducted in monkeys, or other primates, because the MHC class I molecules of humans mimic those of other primates more closely than those of mice.

Measurement of the activation of antigen presenting cells (APC) in response to immunization by antigen variants is another useful screening method. Induction of APC activation can be detected based on changes in surface expression levels of activation antigens, such as B7-1 (CD80), B7-2 (CD86), MHC class I and II, CD14, CD23, and Fc receptors, and the like.

Shuffled cancer antigens that induce cytotoxic T cells that have the capacity to kill cancer cells can be identified by measuring the capacity of T cells derived from immunized animals to kill cancer cells in vitro. Typically the cancer cells are first labeled with radioactive isotopes and the release of radioactivity is an indication of tumor cell killing after incubation in the presence of T cells from immunized animals. Such cytotoxicity assays are known in the art.

An indication of the efficacy of an antigen to activate T cells specific for, for example, cancer antigens, allergens or autoantigens, is also the degree of skin inflammation when the antigen is injected into the skin of a patient or test animal. Strong inflammation is correlated with strong activation of antigen-specific T cells. Improved activation of tumor-specific T cells may lead to enhanced killing of the tumors. In case of autoantigens, one can add immunomodulators that skew the responses towards $T_H2$, whereas in the case of allergens a $T_H1$ response is desired. Skin biopsies can be taken, enabling detailed studies of the type of immune response that occurs at the sites of each injection (in mice and monkeys large numbers of injections/antigens can be analyzed). Such studies include detection of changes in expression of cytokines, chemokines, accessory molecules, and the like, by cells upon injection of the antigen into the skin.

To screen for antigens that have optimal capacity to activate antigen-specific T cells, peripheral blood mononuclear cells from previously infected or immunized humans individuals can be used. This is a particularly useful method, because the MHC molecules that will present the antigenic peptides are human MHC molecules. Peripheral blood mononuclear cells or purified professional antigen-presenting cells (APCs) can be isolated from previously vaccinated or infected individuals or from patients with acute infection with the pathogen of interest. Because these individuals have increased frequencies of pathogen-specific T cells in circulation, antigens expressed in PBMCs or purified APCs of these individuals will induce proliferation and cytokine production by antigen-specific $CD4^+$ and $CD8^+$ T cells. Thus, antigens that simultaneously harbor epitopes from several antigens can be recognized by their capacity to stimulate T cells from various patients infected or immunized with different pathogen antigens, cancer antigens, autoantigens or allergens. One buffy coat derived from a blood donor contains lymphocytes from 0.5 liters of blood, and up to $10^4$ PBMC can be obtained, enabling very large screening experiments using T cells from one donor.

When healthy vaccinated individuals (lab volunteers) are studied, one can make,EBV-transformed B cell lines from these individuals. These cell lines can be used as antigen presenting cells in subsequent experiments using blood from the same donor; this reduces interassay and donor-to-donor variation. In addition, one can make antigen-specific T cell clones, after which antigen variants are introduced to EBV transformed B cells. The efficiency with which the transformed B cells induce proliferation of the specific T cell clones is then studied. When working with specific T cell clones, the proliferation and cytokine synthesis responses are significantly higher than when using total PBMCs, because the frequency of antigen-specific T cells among PBMC is very low.

CTL epitopes can be presented by most cells types since the class I major histocompatibility complex (MHC) surface glycoproteins are widely expressed. Therefore, transfection of cells in culture by libraries of shuffled antigen sequences in appropriate expression vectors can lead to class I epitope presentation. If specific CTLs directed to a given epitope have been isolated from an individual, then the co-culture of the transfected presenting cells and the CTLs can lead to release by the CTLs of cytokines, such as IL-2, IFN-γ, or TNF, if the epitope is presented. Higher amounts of released TNF will correspond to more efficient processing and presentation of the class I epitope from the shuffled, evolved sequence. Shuffled antigens that induce cytotoxic T cells that have the capacity to kill infected cells can also be identified by measuring the capacity of T cells derived from immunized animals to kill infected cells in vitro. Typically the target cells are first labeled with radioactive isotopes and the release of radioactivity is an indication of target cell killing after incubation in the presence of T cells from immunized animals. Such cytotoxicity assays are known in the art.

A second method for identifying optimized CTL epitopes does not require the isolation of CTLs reacting with the epitope. In this approach, cells expressing class I MHC surface glycoproteins are transfected with the library of evolved sequences as above. After suitable incubation to allow for processing and presentation, a detergent soluble extract is prepared from each cell culture and after a partial purification of the MUC-epitope complex (perhaps optional) the products are submitted to mass spectrometry (Henderson et al. (1993) *Proc. Nat'l. Acad. Sci. USA* 90: 10275–10279). Since the sequence is known of the epitope whose presentation to be increased, one can calibrate the mass spectrogram to identify this peptide. In addition, a cellular protein can be used for internal calibration to obtain a quantitative result; the cellular protein used for internal calibration could be the MHC molecule itself. Thus one can measure the amount of peptide epitope bound as a proportion of the MHC molecules.

Use of Recombinant Multivalent Antigens

The multivalent antigens of the invention are useful for treating and/or preventing the various diseases and conditions with which the respective antigens are associated. For example, the multivalent antigens can be expressed in a suitable host cell and are administered in polypeptide form. Suitable formulations and dosage regimes for vaccine delivery are well known to those of skill in the art.

In presently preferred embodiments, the optimized recombinant polynucleotides that encode improved allergens are used in conjunction with a genetic vaccine vector. The choice of vector and components can also be optimized for the particular purpose of treating allergy, for example, or other conditions. For example, the polynucleotide that encodes the recombinant antigenic polypeptide can be placed under the control of a promoter, e.g., a high activity or tissue-specific promoter. The promoter used to express the antigenic polypeptide can itself be optimized using recombination and selection methods analogous to those described herein. The vector can contain immunostimulatory sequences such as are described in copending, commonly assigned U.S. patent application Ser. No. 09/248,716, entitled "Optimization of Immunomodulatory Molecules," filed on Feb. 10, 1999. A vector engineered to direct a $T_H1$ response is preferred for many of the immune responses mediated by the antigens described herein (see, e.g., copending, commonly assigned U.S. patent application Ser. No. 09/247,888, entitled "Genetic Vaccine Vector Engineering," filed on Feb. 10, 1999. It is sometimes advantageous to employ a genetic vaccine that is targeted for a particular target cell type (e.g., an antigen presenting cell or an antigen processing cell); suitable targeting methods are described in copending, commonly assigned U.S. patent application Ser. No. 09/247,886, entitled "Targeting of Genetic Vaccine Vectors," filed on Feb. 10, 1999.

Genetic vaccines that encode the multivalent antigens described herein can be delivered to a mammal (including humans) to induce a therapeutic or prophylactic immune response. Vaccine delivery vehicles can be delivered in vivo by administration to an individual patient, typically by systemic administration (e.g., intravenous, intraperitoneal, intramuscular, subdermal, intracranial, anal, vaginal, oral, buccal route or they can be inhaled) or they can be administered by topical application. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

A large number of delivery methods are well known to those of skill in the art. Such methods include, for example liposome-based gene delivery (Debs and Zhu (1993) WO 93/24640; Mannino and Gould-Fogerite (1988) *BioTechniques* 6(7): 682–691; Rose U.S. Pat. No. 5,279,833; Brigham (1991) WO 91/06309; and Felgner et al. (1987) *Proc. Natl. Acad. Sci. USA* 84: 7413–7414), as well as use of viral vectors (e.g., adenoviral (see, e.g., Berns et al. (1995) *Ann. NY Acad. Sci.* 772: 95–104; All et al. (1994) *Gene Ther.* 1: 367–384; and Haddada et al. (1995) *Curr. Top. Microbiol. Immunol.* 199 (Pt 3): 297–306 for review), papillomaviral, retroviral (see, e.g., Buchscher et al. (1992) *J. Virol.* 66(5) 2731–2739; Johann et al. (1992) *J. Virol.* 66 (5):1635–1640 (1992); Sommerfelt et aL, (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology*, Third Edition Paul (ed) Raven Press, Ltd., New York and the references therein, and Yu et al., *Gene Therapy* (1994) supra. ), and adeno-associated viral vectors (see, West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 and Samulski (supra) for an overview of AAV vectors; see also, Lebkowski, U.S. Pat. No. 5,173,414; Tratschin et al. (1985) *Mol. Cell. Biol.* 5(11):3251–3260; Tratschin, et al. (1984) *Mol. Cell. Biol.*, 4:2072–2081; Hermonat and Muzyczka (1984) *Proc. Natl. Acad. Sci. USA*, 81:6466–6470; McLaughlin et al. (1988) *and Samulski et al.* (1989) *J. Virol,* 63:03822–3828), and the like.

"Naked" DNA and/or RNA that comprises a genetic vaccine can be introduced directly into a tissue, such as muscle. See, e.g., U.S. Pat. No. 5,580,859. Other methods such as "biolistic" or particle-mediated transformation (see, e.g., Sanford et al., U.S. Pat. Nos. 4,945,050; 5,036,006) are also suitable for introduction of genetic vaccines into cells of a mammal according to the invention. These methods are useful not only for in vivo introduction of DNA into a mammal, but also for ex vivo modification of cells for reintroduction into a mammal. As for other methods of delivering genetic vaccines, if necessary, vaccine administration is repeated in order to maintain the desired level of immunomodulation.

Genetic vaccine vectors (e.g., adenoviruses, liposomes, papillomaviruses, retroviruses, etc. ) can be administered directly to the mammal for transduction of cells in vivo. The genetic vaccines obtained using the methods of the invention can be formulated as pharmaceutical compositions for administration in any suitable manner, including parenteral (e.g., subcutaneous, intramuscular, intradermal, or intravenous), topical, oral, rectal, intrathecal, buccal (e.g., sublingual), or local administration, such as by aerosol or transdermally, for prophylactic and/or therapeutic treatment. Pretreatment of skin, for example, by use of hair-removing agents, may be useful in transdermal delivery. Suitable methods of administering such packaged nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of genetic vaccine vector in these formulations can vary widely, and will be selected primarily based on fluid volumes, viscosities, body weight and the like in accordance with the particular mode of administration selected and the patient's needs.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. It is recognized that the genetic vaccines, when administered orally, must be protected from digestion. This is typically accomplished either by complexing the vaccine vector with a composition to render it resistant to acidic and enzymatic hydrolysis or by packaging the vector in an appropriately resistant carrier such as a liposome. Means of protecting vectors from digestion are well known in the art. The pharmaceutical compositions can be encapsulated, e.g., in liposomes, or in a formulation that provides for slow release of the active ingredient.

The packaged nucleic acids, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of packaged nucleic acid can be presented in unit-dose or multi-dose sealed containers, such as ampoules and vials.

Injection solutions and suspensions can be prepared from sterile powders, granules, and tablets of the kind previously described. Cells transduced by the packaged nucleic acid can also be administered intravenously or parenterally.

The dose administered to a patient, in the context of the present invention should be sufficient to effect a beneficial therapeutic response in the patient over time. The dose will be determined by the efficacy of the particular vector employed and the condition of the patient, as well as the body weight or vascular surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of an infection or other condition, the physician evaluates vector toxicities, progression of the disease, and the production of anti-vector antibodies, if any. In general, the dose equivalent of a naked nucleic acid from a vector is from about 1 $\mu$g to 1 mg for a typical 70 kilogram patient, and doses of vectors used to deliver the nucleic acid are calculated to yield an equivalent amount of therapeutic nucleic acid. Administration can be accomplished via single or divided doses.

In therapeutic applications, compositions are administered to a patient suffering from a disease (e.g., an infectious disease or autoimmune disorder) in an amount sufficient to cure or at least partially arrest the disease and its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the proteins of this invention to effectively treat the patient.

In prophylactic applications, compositions are administered to a human or other mammal to induce an immune response that can help protect against the establishment of an infectious disease or other condition.

The toxicity and therapeutic efficacy of the genetic vaccine vectors provided by the invention are determined using standard pharmaceutical procedures in cell cultures or experimental animals. One can determine the $LD_{50}$ (the dose lethal to 50% of the population) and the $ED_{50}$ (the dose therapeutically effective in 50% of the population) using procedures presented herein and those otherwise known to those of skill in the art.

A typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Substantially higher dosages are possible in topical administration. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The multivalent antigenic polypeptides of the invention, and genetic vaccines that express the polypeptides, can be packaged in packs, dispenser devices, and kits for administering genetic vaccines to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition. For example, the label may state that the active compound within the packaging is useful for treating a particular infectious disease, autoimmune disorder, tumor, or for preventing or treating other diseases or conditions that are mediated by, or potentially susceptible to, a mammalian immune response.

EXAMPLES

The following examples are offered to illustrate, but not to limit the present invention.

Example 1

Development of Broad-Spectrum Vaccines against Bacterial Pathogens and Toxins A. Evolution of Yersinia V-antigens This Example describes the use of DNA shuffling to develop immunogens that produce strong cross-protective immune responses against a variety of Yersinia strains. Passive immunization with anti-V-antigen antibodies or active immunization with purified V-antigen can provide protection from challenge with a virulent autologous Yersinia species. However, protection against heterologous species is limited (Motin et al. (1994) *Infect. Immun.* 62: 4192).

V-antigen genes from a variety of Yersinia strains, including serotypes of *Y. pestis*, *Y. enterocolitica*, and *Y. pseudotuberculosis* are subjected to DNA shuffling as described herein. The *Yersinia pestis* V antigen coding sequence, for example, is used as a query in a database search to identify homologous genes that can be used in a family shuffling format to obtain improved antigens. Results for a BLAST search of GenBank and EMBL databases are shown in Table 1, in which each line represents a unique sequence entry listing the database, accession number, locus name, bit score and E value. See, Altschul et al. (1997) *Nucleic Acids Res.* 25:3389–3402, for a description of the search algorithm). Homologous antigens have been cloned and sequenced from a number of related yet distinct Yersinia strains and additional natural diversity is obtained by cloning antigen genes from other strains. These genes and others or fragments thereof are cloned by methods such as PCR, shuffled and screened for improved antigens.

TABLE 1

Sequences producing significant alignments

| Database/Accession No. | Gene | Score (bits) | E Value |
|---|---|---|---|
| gb\|M26405\|YEPLCR | *Yersinia pestis* lcrG, lcrV, and lcrH genes, co | 1945 | 0.0 |
| gb\|AF053946\|AF053946 | *Yersinia pestis* plasmid pCD1, complete pla | 1945 | 0.0 |
| emb\|X96802\|YPTPIVANT | *Y. pseudotuberculosis* V antigen gene | 1834 | 0.0 |
| gb\|M57893\|YEPLCRGVHP | *Yersinia pseudotuberculosis* V-antigen | 1818 | 0.0 |
| gb\|AF080155\|AF080155 | *Yersinia enterocolitica* pYV LcrV (lcrV) antigen | 1723 | 0.0 |
| emb\|X96801\|YE96PVANT | *Y. enterocolitica* V antigen gene, strain Y-... | 1667 | 0.0 |
| emb\|X96799\|YE108VANT | *Y. enterocolitica* V antigen gene, strain Y-... | 1659 | 0.0 |
| emb\|X96800\|YE527VANT | *Y. enterocolitica* V antigen gene, serotype ... | 1651 | 0.0 |
| emb\|X96798\|YE808VANT | *Y. enterocolitica* V antigen gene, strain 8081 | 1643 | 0.0 |
| emb\|X96796\|YE314VANT | *Y. enterocolitica* V antigen gene, strain WA. | 1237 | 0.0 |
| emb\|X96797\|YENCTVANT | *Y. enterocolitica* V antigen gene, strain NCTC | 1221 | 0.0 |
| gb\|S38727\|S38727 | lcrGVH operon: lcrV = V-antigen [*Yersinia pseudo.*] | 365 | 9e-99 |

Shuffled clones are selected by phage display and/or screened by ELISA to identify those recombinant nucleic acids that encode polypeptides that have multiple epitopes corresponding to the different serotypes. The shuffled antigen genes are cloned into a filamentous phage genome for polyvalent phage display or a suitable phagemid vector for monovalent phage display. A typical protocol for panning antigens by phage display is as follows.

Coat an appropriate surface (e.g., Nunc Maxisorp tube or multiwell plate) at 4° C. overnight with the target antibody, usually at a concentration of 1–10 μg/ml in PBS or other suitable buffer Rinse and Block with PBSM (PBS +3% nonfat dry milk) at 37° C. for 1–2 hr Pre-block phage if needed (PBSM, RT 1 hr)

Rinse tube and allow phage to bind (usually 1 hr @ 37° C.)

Can vary time, temp, buffer, add a competitive inhibitor, etc.

Wash extensively (15×) with PBST (PBS +0.1% TWEEN20), then PBS

Elute bound phage with low pH (e.g., 10 mM glycine), 100 mM triethylamine, competitive ligand, protease, etc. and then neutralize pH if needed.

Infect *E. coli* with eluted phage to transduce expression phagemid into new host. Titer and plate for colonies on drug plates Pool colonies into media, grow cells and infect with helper phage to produce phage for next round Phage ELISA assays are a useful method to rapidly evaluate single clones after panning of libraries. Single colonies are picked in individual wells of a multiwell plate containing 2YT media and grown as a master plate. A replicate plate is infected with helper phage and grown so that phage from a single well will display a single antigen variant. A suitable protocol for phage ELISA assays is as follows.

Coat microtiter plate with 50 μl of 1 Mg/ml target antibody 4° C. overnight

Rinse and block with PBSM for 2 hrs @ 37° C.

Rinse, add preblocked phage and allow to bind 1 hr @ 37° C.

Wash plates with PBST 3×, then PBS 3× with 2 min soaks

Add HRP(or AP)-conjugated anti-M13 antibodies for 1 hr @ 37° C.

Add substrate and measure absorbance

Identify positive clones for further evaluation

ELISA assays can also be used to screen for individual antigens with multiple epitopes or increased expression levels. Single colonies are picked in individual wells of a multiwell plate containing appropriate media and grown as a master plate so that antigens produced from a single well are a single antigen variant. A replicate plate is grown and induced for protein production, e.g., by addition of 0.5 mM IPTG for Lac repressor-based systems and grown for an appropriate time for the antigen to be produced. At this point a crude antigen preparation is made which depends on the antigen and where it is produced. Secreted proteins can be evaluated by assaying the cell supernatants after centrifugation. Periplasmic proteins are often readily released from cells by simple extraction into hyper- or hypo-tonic buffers. Intracellularly produced proteins will require some form of cell lysis such as detergent treatment to release them. A suitable protocol for ELISA assays is as follows.

Coat microtiter plate with 50 μl of 1 μg/ml target antibody 4° C. overnight

Rinse and block with PBSM for 2 hrs @ 37° C.

Rinse, add antigen prep and allow to bind 1 hr @ 37° C.

Wash plates with PBST 3×

Add HRP(or AP)-conjugated secondary antibody and incubate for 1 hr (37° C.

Add appropriate substrate and measure absorbance

Identify positive clones for further evaluation

Antibodies specific for many of the various antigens are commercially available (e.g., Toxin Technology, Inc, Sarasota, Fla.) or can be generated by immunizing suitable animals with purified antigens. Protein A or Protein G Sepharose (Pharmacia) can be used to purify immunoglobulins from the serum. Various affinity purification schemes can be used to further purify family-specific antibodies if needed such as immobilization of specific antigens to NHS-, CNBr-, or epoxy-activated sepharose beads. Other related antigens may be included soluble form to prevent binding and immobilization of cross-reactive antibodies.

The multivalent polypeptides that are identified by the initial screening protocol are purified and subjected to in vivo screening. For example, the shuffled antigens selected by a combination of any or none of these methods are purified and used to immunize animals, initially mice, which are then evaluated for improved immune responses. Typically 10 micrograms of protein is injected to a suitable location with or without appropriate adjuvant, e.g., Alhydrogel (EM Seargent Pulp and Chemical, Inc. ) and the animals are boosted with an additional dose after 2–4 weeks. At this point serum samples is drawn and evaluated by ELISA assay for the presence of antibodies that cross-react against multiple parental antigens. In this ELISA assay format the antigens are coated onto multiwell plates, then serial dilutions of each sera is allowed to bind. After washing unbound antibodies, a secondary HRP- or AP- conjugated antibody directed against the appropriate test antibody constant region, e.g., goat anti-mouse IgG Fc (Sigma) is bound. After another washing, the appropriate substrate is added, e.g., O-phenylenediamine (Sigma). The absorbance of each well is read by a plate reader at the appropriate wavelength (e.g., 490 nm for OPD) and those producing high antibody titers to multiple antigens are selected for further evaluation.

Additionally, the ability of antigens to generate neutralizing antibodies can be evaluated in an appropriate system. Antigen variants that elicit a broad cross-reactive response are evaluated further in a virulent challenge model with the appropriate pathogenic organism. For example, the multivalent polypeptides are used to immunize mice, which are then challenged with live Yersinia bacteria. Those multivalent polypeptides that protect against the challenge are identified and purified.

B. Evolution of Broad-spectrum Vaccines against Bacterial Toxins

This Example describes the use of DNA shuffling to obtain multivalent polypeptides that are effective in inducing an immune response against a broad spectrum of bacterial toxins.

1. Staphylococcus

The Group A Streptococci, which can cause diseases such as food poisoning, toxic shock syndrome, and autoimmune disorders, are highly toxic by inhalation. The family of Group A Streptococcus toxins numbers about 30 related members, making this group a suitable target for family shuffling. Accordingly, this Example describes the use of family DNA shuffling to create chimeric proteins that are capable of eliciting broad spectrum protection.

Nucleic acids that encode many diverse attenuated toxins are subjected to DNA shuffling as described herein. Table 2 shows the output of a BLAST search of GenBank, PDL, EMBL, and Swissprot using the S. aureus enterotoxin B protein to identify homologous genes that may be used in a family shuffling format to obtain improved antigens.

TABLE 2

Sequences producing significant alignments

| Database/Accession No. | Gene | Score (bits) | E Value |
|---|---|---|---|
| sp\|P01552\|ETXB_STAAU | ENTEROTOXIN TYPE B PRECURSOR (SEB) >g | 554 | e-157 |
| pdb\|1SE3\| | Staphylococcal Enterotoxin B Complexe Tri... | 504 | e-142 |
| pdb\|1SEB\|D | Staphylococcus aureus >gi\|1633348\|pdb Staphyl... | 406 | e-113 |
| sp\|P23313\|ETC3_STAAU | ENTEROTOXIN TYPE C-3 PRECURSOR (SEC3) | 376 | e-103 |
| sp\|P01553\|ETC1_STAAU | ENTEROTOXIN TYPE C-1 PRECURSOR (SEC1) | 368 | e-101 |
| sp\|P34071\|ETC2_STAAU | ENTEROTOXIN TYPE C-2 PRECURSOR (SEC2) | 361 | 2e-99 |
| gi\|295145 | (L13376) enterotoxin [Staphylococcus | 338 | 2e-92 |
| gi\|295151 | (L13379) enterotoxin [Staphylococcus | 332 | 1e-90 |
| gi\|295143 | (L13375) enterotoxin [Staphylococcus | 330 | 4e-90 |
| gi\|295149 | (L13378) enterotoxin [Staphylococcus | 329 | 1e-89 |
| pdb\|1JCK\|B | Chain B, T-Cell Receptor Beta Chain With S... | 328 | 2e-89 |
| gi\|295141 | (L13374) enterotoxin [Staphylococcus | 328 | 3e-89 |
| pdb\|1SE2\| | Staphylococcal Enterotoxin C2, Monoc. Ente... | 327 | 4e-89 |
| gi\|1906052 | (U91526) type C enterotoxin [Staphylo intermed... | 326 | 8e-89 |
| gi\|295147 | (L13377) enterotoxin [Staphylococcus | 323 | 7e-88 |
| bbs\|155101 | enterotoxin = pyrogenic toxin [Staphylo 4446, P... | 319 | 1e-86 |
| gi\|476764 | (L29565) superantigen [Streptococcus | 311 | 3e-84 |
| gi\|1245172 | (U48792) superantigen SSA [Streptococ pyogenes] >... | 310 | 4e-84 |
| gi\|1245174 | (U48793) superantigen SSA [Streptococ pyogenes] | 309 | 1e-83 |
| sp\|P08095\|SPEA_STRPY | EXOTOXIN TYPE A PRECURSOR (SCARLET FE | 225 | 2e-58 |
| gi\|47288 | (X61560) type A exotoxin [Streptococo pyogenes] >gi\|... | 211 | 3e-54 |
| pir\|\|S18783 | exotoxin type A precursor (allele 3) Streptococcu... | 211 | 4e-54 |
| pir\|\|S18786 | exotoxin type A precursor (allele 2) Streptococcu... | 209 | 2e-53 |
| pir\|\|S18789 | exotoxin A precursor (allele 4) - Str pyo... | 206 | 8e-53 |
| gi\|47328 | (X61554) type A exotoxin [Streptococo pyogenes] | 196 | 9e-50 |
| pir\|\|A26152 | streptococcal pyrogenic exotoxin type precursor -... | 185 | 2e-46 |
| sp\|P20723\|ETXD_STAAU | ENTEROTOXIN TYPE D PRECURSOR (SED) >g | 131 | 3e-30 |
| sp\|P13163\|ETXA_STAAU | ENTEROTOXIN TYPE A PRECURSOR (SEA) >g | 129 | 2e-29 |
| prf\|\|1704203A | enterotoxin A [Staphylococcus aureus] | 128 | 3e-29 |
| pdb\|1ESF\|A | Staphylococcus aureus >gi\|1633233\|pdb Staphyl... | 125 | 2e-28 |
| pir\|\|A29566 | enterotoxin A - Staphylococcus aureus | 125 | 2e-28 |
| sp\|P12993\|ETXE_STAAU | ENTEROTOXIN TYPE E PRECURSOR (SEE) >g | 118 | 3e-26 |
| gi\|510692 | (U11702) enterotoxin H [Staphylococcu >gi\|10... | 98 | 7e-20 |
| gi\|149047 | (M94872) enterotoxin D [Plasmid pIB4 | 89 | 2e-17 |
| gi\|2689563 | (U93688) enterotoxin [Staphylococcus | 76 | 2e-13 |
| gi\|153785 | (M97156) pyrogenic exotoxin C [Strept pyogenes... | 57 | 8e-08 |

TABLE 2-continued

Sequences producing significant alignments

| Database/Accession No. | Gene | Score (bits) | E Value |
|---|---|---|---|
| sp\|P13380\|SPEC_STRPY | EXOTOXIN TYPE C PRECURSOR (SPE C) | 57 | 8e-08 |
| gi\|529754 | (U02559) speC [*Streptococcus pyogenes* | 56 | 2e-07 |
| pir\|\|A30509 | exotoxin C precuror - Streptococcus >gi\|1... | 56 | 2e-07 |
| gi\|529755 | (U02560) speC [*Streptococcus pyogenes* | 55 | 4e-07 |
| pir\|\|S27240 | enterotoxin B - *Staphylococcus aureus* (fragments) | 53 | 1e-06 |

Shuffled recombinant clones are initially selected by phage display and/or screened by ELISA for the presence of multiple epitopes from the different families. Variant proteins with multiple epitopes are purified and used to for in vivo screening as described above. The mouse sera are analyzed for antibodies specific for different toxin subtypes and variants that elicit broadly cross-reactive responses will be evaluated further in challenge models.

2. *Escherichia coli* and *Vibrio cholerae*

This Example describes the use of DNA shuffling to obtain cross-reactive multivalent polypeptides that induce an immune response against the *E. coli* heat-labile toxin (LT), cholera toxin (CT), and verotoxin (VT). Nucleic acids that encode cholera and LT toxin B-chains are subjected to DNA shuffling. Table 3 shows the results of a BLAST search using the *V. cholerae* toxin B-chain to identify homologous genes that can be used in a family shuffling format to obtain improved antigens. Homologous antigens have been cloned and sequenced from a number of related yet distinct Vibrio and *E. coli* strains, and additional natural diversity can be obtained by cloning antigen genes from other strains. These genes and others or fragments thereof can be cloned by methods such as PCR, shuffled and screened for improved antigens.

TABLE 3

Sequences producing significant alignments

| Database/Accession No. | Gene | Score (bits) | E Value |
|---|---|---|---|
| sp\|P01556\|CHTB_VIBCH | CHOLERA ENTEROTOXIN, BETA CHAIN PREC | 252 | 5e-67 |
| gi\|48890 | (X58785) cholera toxin B protein (CT cholera... | 248 | 8e-66 |
| gi\|758351 | (X00171) ctx B [*Vibrio cholerae*] | 246 | 3e-65 |
| prf\|\|1001196A | toxin, cholera [*Vibrio cholerae*] | 246 | 3e-65 |
| gnl\|PID\|d1006853 | (D30052) cholera toxin [*Vibrio choler* | 244 | 1e-64 |
| pir\|\|XVVCB | cholera enterotoxin chain B precursor cholerae | 241 | 1e-63 |
| gi\|209556 | (M23050) cholera toxin subunit B prec [Artificia... | 228 | 7e-60 |
| bbs\|168005 | cholera-like enterotoxin B subunit [V cholerae,... | 211 | 1e-54 |
| sp\|P13811\|ELBH_ECOLI | HEAT-LABILE ENTEROTOXIN B CHAIN PREC | 209 | 5e-54 |
| pdb\|1XTC\|D | *Vibrio cholerae* >gi\|1827851\| pdb\|1XTC choler... | 207 | 2e-53 |

TABLE 3-continued

Sequences producing significant alignments

| Database/Accession No. | Gene | Score (bits) | E Value |
|---|---|---|---|
| pdb\|1FGB\|D | *Vibrio cholerae* >gi\|1942839\| pdb\|1FGB choler... | 207 | 2e-53 |
| pdb\|2CHB\|D | Chain D, Cholera Toxin B-Pentamer Co With Gm1... | 207 | 2e-53 |
| pdb\|1CHP\|D | *Vibrio cholerae* >gi\|1421512\| pdb\|1CHP choler... | 205 | 1e-52 |
| pdb\|1CHQ\|D | *Vibrio cholerae* >gi\|1421526\| pdb\|1CHQ choler... | 205 | 1e-52 |
| pdb\|1CT1\|D | Chain D, Cholera Toxin B-Pentamer Mut Bound ... | 204 | 1e-52 |
| sp\|P32890\|ELBP_ECOLI | HEAT-LABILE ENTEROTOXIN B CHAIN PREC | 204 | 2e-52 |
| prf\|\|0701264A | toxin LTB Cistron, heat labile [*Escher coli*] | 201 | 9e-52 |
| pir\|\|QLECB | heat-labile enterotoxin chain B prec Escheric... | 201 | 2e-51 |
| bbs\|131495 | (S60731) heat-labile enterotoxin B s B su... | 200 | 2e-51 |
| prf\|\|770190A | toxin [*Vibrio cholerae*] | 199 | 6e-51 |
| pdb\|1LTA\|D | *Escherichia coli* >gi\|494266\| pdb\|1LTA *Escherichia c...* | 179 | 4e-45 |
| pdb\|1TET\|P | *Vibrio cholerae* | 34 | 0.31 |

Those chimeric toxins that elicit high levels of neutralizing antibodies against both toxins and have improved adjuvant properties are identified. For example, shuffled clones are selected by phage display and/or screened by ELISA assays for the presence of epitopes from the different parental B-chains. Variants with multiple epitopes are purified and further studied for their capacity to act as adjuvants and to elicit cross-protective immune responses in challenge models.

Example 2

Evolution of Broad-spectrum Vaccines against *Borrelia burgdorferi*

Lyme disease is currently one of the fastest-growing infectious diseases in the United States. It is caused by infection of the spirochete bacterium *Borrelia burgdorferi*, which is carried and spread by the bite of infected ticks. Early signs of infection include skin rash and flu-like symptoms. If left untreated Lyme disease can cause arthritis, heart abnormalities, and facial paralysis. Treatment of early Lyme disease with antibiotics can stop the infection, but a lasting immunity may not develop making reinfection possible. A current vaccine requires three immunizations over a 1-year period to acquire immunity.

Both passive and active immunization with the purified *B. burgdorferi* outer surface protein A (OspA) protein has been successful in protecting against infection with *B. burgdorferi*, but has no effect against ongoing infections, since this antigen is not expressed in vertebrate hosts. OspA is normally anchored on the outside of the cell by a covalently attached lipid moiety through an amino terminal cysteine residue. In contrast, the outer surface protein C (OspC) is highly expressed by the spirochete in vertebrate hosts and vaccination of infected individuals with OspC may be an effective therapeutic in curing the infection (Zhong et al. (1997) *Proc. Nat'l. Acad. Sci. USA* 94 12533–12538.

A recent BLAST search (Altschul, et al., (1997) *Nucleic Acids Res.* 25:3389–3402) of the non-redundant GenBank, PDB, SwissProt, Spupdate, and PIR databases was used to identify homologues of the OspA outer surface protein gene.

This resulted in the identification of over 200 entries related to OspA. One hundred entries are shown in Table 4 below from different strains of *B. burgdorferi*, *B. garinii*, *B. afzelii*, *B. tanukii*, and *B. turdi* that share at least 83% DNA sequence identity to the *Borrelia burgdorferi* OspA protein. The ospA genes from these and other strains provide a source of diversity for family shuffling to obtain improved antigens for the prevention of Lyme disease. These genes are cloned by methods such as PCR, shuffled and screened for improved antigens.

TABLE 4

Sequences producing significant alignments

| Database/Accession No. | Gene | Score (bits) | E Value |
|---|---|---|---|
| dbj\|AB016977\|AB016977 | Borrelia sp. gene for outer surface prote... | 1629 | 0.0 |
| dbj\|AB016978\|AB016978 | Borrelia sp. 10MT gene for outer surface ... | 1614 | 0.0 |
| dbj\|AB016975\|AB016975 | *Borrelia turdi* gene for outer surface pro... | 1526 | 0.0 |
| dbj\|AB016976\|AB016976 | Borrelia sp. gene for outer surface prote... | 1187 | 0.0 |
| gb\|S48323\|S48323 | ospA = outer surface protein A [*Borrelia burgdor*...] | 948 | 0.0 |
| gb\|L38657\|BORFRA | *Borrelia burgdorferi* (clone N3) ospA gene frag... | 948 | 0.0 |
| emb\|X80186\|BBPTROOPS | *B. burgdorferi* PTro ospA gene | 938 | 0.0 |
| emb\|X65598\|BBOSPA1 | *B. burgdorferi* Osp A gene (TRO) | 938 | 0.0 |
| gb\|020357\|BBU20357 | *Borrelia burgdorferi* C-1-11 outer surface pr... | 876 | 0.0 |
| gb\|S88693\|S88693 | outer surface protein A [*Borrelia burgdorferi*, ...] | 858 | 0.0 |
| emb\|X66065\|BBOSPROA | *B. burgdorferi* OspA gene for outer surface p... | 839 | 0.0 |
| emb\|X85440\|BGTISOSPA | *B. garinii* ospA gene (TIsI substrain) | 839 | 0.0 |
| emb\|X85438\|BAPLJOSPA | *B. afzelii* ospA gene (PLj7 substrain) >gi\|9... | 837 | 0.0 |
| emb\|X80183\|BBPBOOSPA | *B. burgdorferi* PBo ospA gene | 829 | 0.0 |
| emb\|Z29087\|BBOSPAY | *B. burgdorferi* (VS461) OspA gene for outer su... | 821 | 0.0 |
| emb\|X85982\|BADNAOSPA | *B. afzelii* ospA gene | 821 | 0.0 |
| emb\|X62161\|BBOSPAG | *B. burgdorferi* plasmid ospA gene for outer su... | 821 | 0.0 |
| gb\|U78301\|BBU78301 | *Borrelia afzelii* major outer membrane surfac... | 821 | 0.0 |
| emb\|X65599\|BBOSPA2 | *B. burgdorferi* Osp A gene (PKO) | 819 | 0.0 |
| emb\|X70365\|BBOPSAA | *B. burgdorferi* OspA gene | 819 | 0.0 |
| emb\|X85439\|BAPLUOSPA | *B. afzelii* ospA gene (PLud substrain) | 813 | 0.0 |
| emb\|X81047\|BBOPSA | *B. burgdorferi* plasmid OspA gene | 813 | 0.0 |
| gb\|U20356\|BAU20356 | *Borrelia afzelii* BV1 outer surface protein A... | 813 | 0.0 |
| emb\|X85437\|BAPHOOSPA | *B. afzelii* ospA gene (PHo substrain) | 797 | 0.0 |
| emb\|X80253\|BBPWUDLL | *B. burgdorferi* PWud11 ospA gene | 791 | 0.0 |
| emb\|Z29086\|BBOSPAX | *B. burgdorferi* (G25) OspA gene for outer surf... | 791 | 0.0 |
| gb\|L19702\|BORMAJOSPR | *Borrelia burgdorferi* outer surface protein... | 791 | 0.0 |
| emb\|X62387\|BBSPA | *B. burgdorferi* ospA gene for outer surface prot... | 789 | 0.0 |
| emb\|X60300\|BBASPA | *B. burgdorferi* gene for OspA outer surface pro... | 785 | 0.0 |
| emb\|X62624\|BBK48OSPA | *B. burgdorferi* ospA gene | 767 | 0.0 |
| gb\|M88764\|BOROSPABA | *Borrelia burgdorferi* operon major outer mem... | 759 | 0.0 |

TABLE 4-continued

Sequences producing significant alignments

| Database/Accession No. | Gene | Score (bits) | E Value |
|---|---|---|---|
| emb\|X63412\|BBPOSPA | *B. burgdorferi* plasmid ospA gene for outer su... | 759 | 0.0 |
| gb\|L36036\|BOROSPAL | *Borrelia burgdorferi* outer surface protein A... | 743 | 0.0 |
| gb\|U20358\|BGU20358 | *Borrelia garinii* LV4 outer surface protein A... | 743 | 0.0 |
| emb\|X85442\|BB297OSPA | *B. burgdorferi* ospA gene (297 substrain) | 714 | 0.0 |
| gb\|L19701\|BOROPSAB | *Borrelia burgdorferi* major outer surface pro... | 714 | 0.0 |
| emb\|X14407\|BBOSPAB | *Borrelia burgdorferi* ospA and ospB genes for... | 706 | 0.0 |
| gb\|AE000790\|AE000790 | *Borrelia burgdorferi* plasmid lp54, complet... | 706 | 0.0 |
| gb\|U20360\|BBU20360 | *Borrelia burgdorferi* S-1-10 outer surface pr... | 706 | 0.0 |
| emb\|X69606\|BBKAOSPA | *B. burgdorferi* OspA gene >gi\|1819262\|gb\|I284... | 706 | 0.0 |
| dbj\|AB007100\|AB007100 | *Borrelia garinii* gene for outer surface p... | 702 | 0.0 |
| gb\|M57248\|BOROSPA | *B. burgdorferei* outer surface protein A (OspA)... | 698 | 0.0 |
| emb\|X80182\|BBPKAOPSA | *B. burgdorferi* PKa ospA gene | 698 | 0.0 |
| dbj\|AB007101\|AB007101 | *Borrelia garinii* gene for outer surface p... | 694 | 0.0 |
| emb\|X85443\|BBT25OSPA | *B. burgdorferi* ospA gene (T255 substrain) | 692 | 0.0 |
| emb\|X16467\|BBOSPA | *Borrelia burgdorferi* OspA gene for outer surf... | 690 | 0.0 |
| gb\|U20359\|BBU20359 | Borrelia sp. LV5 outer surface protein A pre... | 690 | 0.0 |
| gb\|AF026059\|AF026059 | *Borrelia burgdorferi* 50 kDa plasmid lipopr... | 682 | 0.0 |
| emb\|X85739\|BBDNAOSPA | *B. burgdorferi* ospA gene | 682 | 0.0 |
| emb\|X85441\|BGWABOSPA | *B. garinii* ospA gene (WABSou substrain) | 676 | 0.0 |
| gb\|U93709\|U93709 | *Borrelia garinii* outer surface protein A (ospA... | 674 | 0.0 |
| dbj\|AB007099\|AB007099 | *Borrelia garinii* gene for outer surface p... | 662 | 0.0 |
| emb\|X80251\|BBPHEIOSP | *B. burgdorferi* PHei ospA gene | 660 | 0.0 |
| gb\|U49190\|BGU49190 | *Borrelia garinii* major outer membrane surfac... | 652 | 0.0 |
| emb\|X65600\|BBOSPA3 | *B. burgdorferi* Osp A gene (HE) | 652 | 0.0 |
| dbj\|D29660\|D29660 | *Borrelia burgdorferi* gene for outer surface pr... | 652 | 0.0 |
| dbj\|AB016979\|AB016979 | *Borrelia valaisiana* gene for outer surfac... | 648 | 0.0 |
| dbj\|AB007109\|AB007109 | *Borrelia garinii* gene for outer surface p... | 646 | 0.0 |
| gb\|U93707\|U93707 | *Borrelia garinii* outer surface protein A (ospA... | 644 | 0.0 |
| dbj\|AB007102\|AB007102 | *Borrelia garinii* gene for outer surface p... | 642 | 0.0 |
| dbj\|AB001041\|AB001041 | *Borrelia garinii* DNA for outer surface pr... | 636 | e-180 |
| dbj\|AB007114\|AB007114 | *Borrelia garinii* gene for outer surface p... | 632 | e-179 |
| dbj\|AB007105\|AB007105 | *Borrelia garinii* gene for outer surface p... | 632 | e-179 |
| gb\|U93710\|U93710 | *Borrelia garinii* outer surface protein A (ospA... | 628 | e-178 |
| dbj\|AB007106\|AB007106 | *Borrelia garinii* gene for outer surface p... | 624 | e-177 |
| dbj\|AB007104\|AB007104 | *Borrelia garinii* gene for outer surface p... | 624 | e-177 |
| gb\|U93706\|U93706 | *Borrelia garinii* outer surface protein A (ospA... | 620 | e-176 |
| emb\|X80256\|BGPBROSPA | *B. garnii* PBr ospA gene | 613 | e-173 |
| dbj\|AB007108\| | *Borrelia garinii* gene for outer | 607 | e-171 |

TABLE 4-continued

Sequences producing significant alignments

| Database/Accession No. | Gene | Score (bits) | E Value |
|---|---|---|---|
| AB007108 gb\|L81129\|BOROSPAY | surface p... Borrelia burgdorferi (isolate 2-1498 297) ou... | 605 | e-171 |
| gb\|U93711\|U93711 | Borrelia garinii outer surface protein A (ospA... | 605 | e-171 |
| dbj\|AB007103\| AB007103 | Borrelia garinii gene for outer surface p... | 587 | e-165 |
| gb\|L81128\|BOROSPAZ | Borrelia burgdorferi (isolate 2-1498 Son 188... | 581 | e-164 |
| gb\|L23137\|BOROSPAC | Borrelia burgdorferi (27985CT2) OspA gene, 3... | 577 | e-162 |
| gb\|L23139\|BOROSPAE | Borrelia burgdorferi (42373NY3) OspA gene, 3... | 577 | e-162 |
| gb\|L23142\|BOROSPAI | Borrelia burgdorferi (CA3) OspA gene, 3'end ... | 577 | e-162 |
| gb\|L23136\|BOROSPAA | Borrelia burgdorferi (B19CT1) OspA gene, 3'e... | 577 | e-162 |
| gb\|U93705\|U93705 | Borrelia garinii outer surface protein A (ospA... | 569 | e-160 |
| gb\|L23140\|BOROSPAF | Borrelia burgdorferi (41552MA) OspA gene, 3'... | 569 | e-160 |
| dbj\|AB007110\| AB007110 | Borrelia garinii gene for outer surface p... | 565 | e-159 |
| gb\|L23143\|BOROSPAJ | Borrelia burgdorferi (CA7) OspA gene, 3'end ... | 561 | e-158 |
| dbj\|AB007112\| AB007112 | Borrelia garinii gene for outer surface p... | 557 | e-156 |
| emb\|X80254\| BGT25OSPA | B. garnii T25 ospA gene | 557 | e-156 |
| gb\|U93708\|U93708 | Borrelia garinii outer surface protein A (ospA... | 553 | e-155 |
| dbj\|AB007107\| AB007107 | Borrelia garinii gene for outer surface p... | 549 | e-154 |
| gb\|L23141\|BOROSPAH | Borrelia burgdorferi (21343WI) OspA gene, 3'... | 545 | e-153 |
| dbj\|AB007111\| AB007111 | Borrelia garinii gene for outer surface p... | 541 | e-152 |
| dbj\|AB007113\| AB007113 | Borrelia garinii gene for outer surface p... | 537 | e-151 |
| gb\|L23144\|BOROSPAK | Borrelia burgdorferi (CA8) OspA gene, 3'end ... | 529 | e-148 |
| gb\|U78549\|BAU78549 | Borrelia afzelii major outer membrane surfac... | 525 | e-147 |
| dbj\|AB009863\| AB009863 | Borrelia garinii gene for outer surface p... | 519 | e-145 |
| emb\|X68059\| BBOSPAGE | B. burgdorferi OspA gene for outer surface p... | 498 | e-139 |
| dbj\|AB009862\| AB009862 | Borrelia garinii gene for outer surface p... | 466 | e-129 |
| emb\|X95360\| BBOSPPFRA | B. burgdorferi ospA gene (strain PFra) | 460 | e-127 |
| emb\|X68541\|BBPHEI | B. burgdorferi (PHEI) plasmid OspA gene for ou... | 446 | e-123 |
| emb\|X68540\|BBPWUDI | B. burgdorferi (PWudI) plasmid OspA gene for ... | 414 | e-114 |
| emb\|X95358\|BGOSPPLI | B. garinii ospA gene (strain PLi) | 414 | e-114 |
| dbj\|AB009860\| AB009860 | Borrelia garinii gene for outer surface p... | 393 | e-107 |
| dbj\|AB009858\| AB009858 | Borrelia garinii gene for outer surface p... | 365 | 8e-99 |
| dbj\|AB009861\| AB009861 | Borrelia garinii gene for outer surface p... | 283 | 2e-74 |

A BLAST search with the *B. burgdorferi* OspC protein gene revealed over 200 related entries. Entries for one hundred sequences sharing at least 82% DNA sequence identity are shown in Table 5 below that provide a source of diversity for family shuffling to obtain improved therapeutics in the treatment of Lyme disease. These genes are cloned by methods such as PCR, shuffled and screened for improved antigens.

TABLE 5

Sequences producing significant alignments

| Database/Accession No. | Gene | Score (bits) | E Value |
|---|---|---|---|
| gb\|U04282\|BBU04282 | Borrelia burgdorferi GMP synthetase (guaA) g... | 1261 | 0.0 |
| gb\|L42898\|BOR31OSPC | Borrelia burgdorferi (strain 25015) | 1124 | 0.0 |
| gb\|U01894\|BBU01894 | Borrelia burgdorferi B31 outer surface prote... | 622 | e-176 |
| dbj\|D49497\|BOROSPCA | Borrelia burgdorferi gene for outer surface... | 622 | e-176 |
| gb\|AE000792\|AE000792 | Borrelia burgdorferi plasmid cp26, comple... | 622 | e-176 |
| emb\|X69596\| BBB31OSPC | B. burgdorferi ospC gene for outer surface ... | 615 | e-174 |
| gb\|AF029860\|AF029860 | Borrelia burgdorferi OC1 outer surface pro... | 523 | e-146 |
| gb\|U91798\|BBU91798 | Borrelia burgdorferi strain L5 outer surface... | 519 | e-145 |
| gb\|L42887\|BOR20OSPC | Borrelia burgdorferi (strain Ip2) outer sur... | 517 | e-145 |
| gb\|L81131\|BOROSPCY | Borrelia burgdorferi; substrain sensu strict... | 509 | e-142 |
| gb\|U91792\|BBU91792 | Borrelia burgdorferi strain HII outer surfac... | 478 | e-133 |
| gb\|U91797\|BBU91797 | Borrelia burgdorferi strain IP3 outer surfac... | 462 | e-128 |
| gb\|U91801\|BBU19801 | Borrelia burgdorferi strain P1F outer surfac... | 444 | e-123 |
| dbj\|AB001377\| AB001377 | Borrelia japonica strain NO67 DNA for Out... | 430 | e-118 |
| dbj\|AB001378\| AB001378 | Borrelia japonica strain OvKK7 DNA for Ou... | 430 | e-118 |
| emb\|X84783\| BBOSPCTXW | B. burgdorferi ospC gene (strain TXGW) | 418 | e-115 |
| dbj\|AB000355\| AB000355 | Borrelia tanukii DNA for Outer surface pr... | 418 | e-115 |
| gb\|U91799\|BBU91799 | Borrelia burgdorferi strain IP1 outer surfac... | 418 | e-115 |
| dbj\|AB001376\| AB001376 | Borrelia japonica strain Fi31o DNA for Ou... | 414 | e-114 |
| emb\|X73624\|BBOSPCC | B. burgdorferi (DK26) OspC gene | 404 | e-111 |
| emb\|X62162\|BBPCG | B. burgdorferi gene for pC protein | 398 | e-109 |
| emb\|X69590\| BBWUDOSPC | B. burgdorferi OspC gene, 3' end | 398 | e-109 |
| emb\|X81521\|BAOSPC1 | B. afzelii (strain PBo) ospC gene | 371 | e-102 |
| dbj\|AB000345\| AB000345 | Borelia afzelii DNA for Outer surface pr... | 365 | 6e-99 |
| dbj\|AB009900\| AB009900 | Borrelia afzelii gene for outer surface p... | 361 | 9e-98 |
| dbj\|AB009899\| AB009899 | Borrelia afzelii gene for outer surface p... | 357 | 1e-96 |
| emb\|X81523\|BAOSPC2 | B. afzelii (strain PLj7) ospC gene | 339 | 3e-91 |
| gb\|AF029871\|AF029871 | Borrelia burgdorferi OC12 outer surface pr... | 337 | 1e-90 |
| dbj\|AB009897\| AB009897 | Borrelia afzelii gene for outer surface p... | 337 | 1e-90 |
| dbj\|AB000354\| AB000354 | Borrelia tanukii DNA for Outer surface pr... | 337 | 1e-90 |
| gb\|L25413\|BOROSPC | Borrelia burgdorferi membrane protein (ospC) ... | 335 | 5e-90 |
| dbj\|D49502\|BOROSPCF | Borrelia afzelii gene for outer surface pro... | 335 | 5e-90 |
| emb\|X83555\| BBDNAOSPC | B. burgdorferi (B. pacificus strain) ospC gene | 333 | 2e-89 |
| gb\|L42874\|BOR10OSPC | Borrelia burgdorferi (strain Orth) outer su... | 331 | 8e-89 |
| dbj\|D49503\|BOROSPCG | Borrelia afzelii gene for outer surface pro... | 331 | 8e-89 |
| dbj\|AB009894\| AB009894 | Borrelia afzelii gene for outer surface p... | 329 | 3e-88 |
| gb\|L42890\|BOR23OSPC | Borrelia burgdorferi (strain E61) outer sur... | 329 | 3e-88 |

TABLE 5-continued

Sequences producing significant alignments

| Database/Accession No. | Gene | Score (bits) | E Value |
|---|---|---|---|
| gb\|L42892\|BOR25OSPC | *Borrelia burgdorferi* (strain acal) outer su... | 329 | 3e-88 |
| dbj\|D49501\|BOROSPCE | *Borrelia afzelii* gene for outer surface pro... | 327 | 1e-87 |
| gb\|U04240\|BBU04240 | *Borrelia burgdorferi* GMP synthetase (guaA) a... | 317 | 1e-84 |
| gb\|U04280\|BBU04280 | *Borrelia burgdorferi* GMP synthetase (guaA) g... | 317 | 1e-84 |
| dbj\|AB009901\|AB009901 | *Borrelia afzelii* gene for outer surface p... | 309 | 3e-82 |
| dbj\|AB009893\|AB009893 | *Borrelia afzelii* gene for outer surface p... | 309 | 3e-82 |
| gb\|L42883\|BOR17OSPC | *Borrelia burgdorferi* (strain JSB) outer sur... | 307 | 1e-81 |
| gb\|U04281\|BBU04281 | *Borrelia burgdorferi* HB19 outer surface prot... | 305 | 5e-81 |
| dbj\|AB009896\|AB009896 | *Borrelia afzelii* gene for outer surface p... | 305 | 5e-81 |
| emb\|X81522\|BBOSPC1 | *B. burgdorferi* (strain PBre) ospC gene | 297 | 1e-78 |
| dbj\|AB000349\|AB000349 | *Borrelia afzelii* DNA for Outer surface pr... | 297 | 1e-78 |
| emb\|X73625\|BBOSPCD | *B. burgdorferi* (DK7) OspC gene | 297 | 1e-78 |
| dbj\|D49509\|BOROSPCM | *Borrelia garinii* gene for outer surface pro... | 295 | 4e-78 |
| dbj\|AB000346\|AB000346 | *Borrelia afzelii* DNA for Outer surface pr... | 293 | 2e-77 |
| gb\|AF029870\|AF029870 | *Borrelia burgdorferi* OC11 outer surface pr... | 289 | 3e-76 |
| gb\|L42895\|BOR28OSPC | *Borrelia burgdorferi* (strain 28354) outer s... | 289 | 3e-76 |
| emb\|X81524\|BBOSPC2 | *B. burgdorferi* (strain T255) ospC gene | 289 | 3e-76 |
| dbj\|D88296\|D88296 | *Borrelia afzelii* 26 kb circular plasmid DNA fo... | 289 | 3e-76 |
| emb\|X81526\|BGOSPC2 | *B. garinii* (strain WABSou) ospC gene >gi\|8720... | 285 | 4e-75 |
| emb\|X84772\|BBOSPCD32 | *B. garinii* ospC gene (strain DK32) | 285 | 4e-75 |
| dbj\|AB009902\|AB009902 | *Borrelia afzelii* gene for outer surface p... | 285 | 4e-75 |
| dbj\|D49505\|BOROLPCI | *Borrelia garinii* gene for outer surface pro... | 281 | 7e-74 |
| gb\|U01892\|BBU01892 | *Borrelia burgdorferi* 2591 outer surface prot... | 281 | 7e-74 |
| emb\|X83552\|BADNAOSPC | *B. afzelii* (PLud strain) ospC gene | 280 | 3e-73 |
| dbj\|D49378\|BOROSPC64 | *Borrelia garinii* (strain HT64) ospC gene f... | 278 | 1e-72 |
| dbj\|D49379\|BOROSPCVS | *Borrelia afzelii* (strain VS461) ospC gene ... | 274 | 2e-71 |
| gb\|AF029864\|AF029864 | *Borrelia burgdorferi* OC5 outer surface pro... | 266 | 4e-69 |
| dbj\|AB000350\|AB000350 | *Borrelia afzelii* DNA for Outer surface pr... | 266 | 4e-69 |
| qb\|U08284\|BBU08284 | *Borrelia burgdorferi* 297 outer surface prote... | 264 | 2e-68 |
| dbj\|AB000343\|AB000343 | *Borrelia afzelii* DNA for Outer surface pr... | 260 | 2e-67 |
| dbj\|AB000353\|AB000353 | *Borrelia tanukii* DNA for Outer surface pr... | 258 | 1e-66 |
| emb\|X84779\|BBOSPCMUL | *B. burgdorferi* ospC gene (strain MUL) | 256 | 4e-66 |
| emb\|X84768\|BBOSPCD15 | *B. afzelii* ospC gene (strain DK15) | 256 | 4e-66 |
| dbj\|D88292\|D88292 | *Borrelia garinii* 26 kb circular plasmid DNA fo... | 254 | 2e-65 |
| dbj\|D49507\|BOROSPCK | *Borrelia garinii* gene for outer surface pro... | 254 | 2e-65 |
| emb\|X83556\|BGOSPCN34 | *B. garinii* (N34 strain) ospC gene | 250 | 2e-64 |
| gb\|AF029866\|AF029866 | *Borrelia burgdorferi* OC7 outer surface pro... | 250 | 2e-64 |
| dbj\|D88294\|D88294 | *Borrelia garinii* 26 kb circular plasmid DNA fo... | 250 | 2e-64 |
| gb\|L42888\|BOR21OSPC | *Borrelia burgdorferi* (strain H9) outer surf... | 248 | 9e-64 |
| gb\|AF029862\|AF029862 | *Borrelia burgdorferi* OC3 outer surface pro... | 246 | 4e-63 |
| dbj\|AB009891\|AB009891 | *Borrelia afzelii* gene for outer surface p... | 246 | 4e-63 |
| dbj\|AB009898\|AB009898 | *Borrelia afzelii* gene for outer surface p... | 246 | 4e-63 |
| gb\|AF029861\|AF029861 | *Borrelia burgdorferi* OC2 outer surface pro... | 246 | 4e-63 |
| emb\|X69593\|BBTNOSPC | *B. burgdorferi* OspC gene, 3' end | 246 | 4e-63 |
| dbj\|D49377\|BOROSPC57 | *Borrelia garinii* (strain HT57) ospC gene f... | 244 | 1e-62 |
| dbj\|D49500\|BOROSPCD | *Borrelia garinii* gene for outer surface pro... | 244 | 1e-62 |
| gb\|L42896\|BOR29OSPC | *Borrelia burgdorferi* (strain 27579) outer s... | 242 | 6e-62 |
| dbj\|D49376\|BOROSPCTC | *Borrelia garinii* (strain TCLSK) ospC gene ... | 240 | 2e-61 |
| gb\|L42873\|BOR9OSPC | *Borrelia burgdorferi* (strain SIMON) outer su... | 238 | 9e-61 |
| dbj\|D49381\|BOROSPC37 | *Borrelia garinii* (strain HT37) ospC gene f... | 238 | 9e-61 |
| dbj\|D49498\|BOROSPCB | *Borrelia garinii* gene for outer surface pro... | 238 | 9e-61 |
| emb\|X69592\|BBT25OSPC | *B. burgdorferi* OspC gene, 3' end | 232 | 6e-59 |
| emb\|X69594\|BBPBROSPC | *B. burgdorferi* OspC gene, 3' end | 228 | 9e-58 |
| dbj\|D49506\|BOROSPCJ | *Borrelia garinii* gene for outer surface pro... | 220 | 2e-55 |
| emb\|X69595\|BBPBIOSPC | *B. burgdorferi* ospC gene for outer surface ... | 220 | 2e-55 |
| emb\|X83554\|BGOSPPTRO | *B. garinii* (PTrob strain) opsC gene | 220 | 2e-55 |
| emb\|X73626\|BBOSPCE | *B. burgdorferi* (DK6) OspC gene | 220 | 2e-55 |
| gb\|L42870\|BOR6OSPC | *Borrelia burgdorferi* (strain VSDA) outer sur... | 220 | 2e-55 |
| gb\|L42894\|BOR27OSPC | *Borrelia burgdorferi* (strain 28691) outer s... | 218 | 8e-55 |
| dbj\|D49504\|BOROSPCH | *Borrelia garinii* gene for outer surface pro... | 208 | 8e-52 |
| gb\|L42868\|BOR4OSPC | *Borrelia burgdorferi* (strain ZS7) outer surf... | 206 | 3e-51 |
| dbj\|AB000358\|AB000358 | *Borrelia japonica* DNA for Outer surface p... | 204 | 1e-50 |
| dbj\|AB000351\|AB000351 | *Borrelia japonica* DNA for Outer surface p... | 204 | 1e-50 |

Example 3

Evolution of Broad-spectrum Vaccines against Mycobacterium

Tuberculosis is an ancient bacterial disease caused by *Mycobacterium tuberculosis* that continues to be an important public health problem worldwide and calls are 5 being made for an improved effort in eradication (*Morb. Mortal Wkly Rep* (1998 Aug 21, 1998; 47(RR-13): 1–6). It infects over 50 million people and over 3 million people will die from tuberculosis this year. The currently available vaccine, Bacille Calmette-Guerin (BCG) is found to be less effective in developing countries and an increasing number of multidrug-resistant (MDR) strains are being isolated.

The major immunodominant antigen of *M. tuberculosis* is the 30–35 kDa (a.k.a. antigen 85, alpha-antigen) which is normally a lipoglycoprotein on the cell surface. Other protective antigens include a 65-kDa heat shock protein, and a 36-kDa proline-rich antigen (Tascon et al. (1996) *Nat. Med.* 2: 888–92).

Table 6 shows the output of a BLAST search using the 30–35 kDa major *M. Tuberculosis* antigen (a.k.a. antigen 85, alpha-antigen) coding sequence to identify homologous genes that may be used in a family shuffling format to obtain improved antigens. Many homologous antigens have been cloned and sequenced from a large number of related yet distinct mycobacterial strains. These genes are cloned by methods such as PCR, shuffled and screened for improved antigens.

TABLE 6

Sequences producing significant alignments

| Database/Accession No. | Gene | Score (bits) | E Value |
|---|---|---|---|
| gb\|U38939\|MTU38939 | *Mycobacterium tuberculosis* 30 kDa extracellu... | 1939 | 0.0 |
| emb\|X62398\|MT85B | *M. tuberculosis* (strain Erdman) gene for 85-B a... | 1939 | 0.0 |
| emb\|Z97193\|MTCY180 | *Mycobacterium tuberculosis* H37Rv complete ge... | 1939 | 0.0 |
| emb\|X62397\|MB85B | *M. bovis* (strain 1173P2) gene for 85-B antigen | 1931 | 0.0 |
| gb\|M21839\|MSGBCGA | *M. bovis* BCG gene encoding alpha-antigen, comp... | 1869 | 0.0 |
| emb\|X53897\|MKAANTIG | *Mycobacterium kansasii* gene for alpha antigen | 819 | 0.0 |
| dbj\|D26187\|MSGAA | *Mycobacterium scrofuraceum* DNA for alpha-antig... | 706 | 0.0 |
| dbj\|D16546\|MSGAAG | *Mycobacterium intracellulare* gene for alpha-a... | 581 | e-164 |
| emb\|X63437\|MAALANT | *M. avium* gene for alpha-antigen | 569 | e-160 |
| dbj\|D14253\|MSGATCC139 | *Mycobacterium intracellulare* DNA for alph... | 533 | e-149 |
| qb\|L01095\|MSGB38COS | *M. leprae* genomic DNA DNA sequence, cosmid B38 ... | 371 | e-100 |
| emb\|X60934\|ML85BA | *M. leprae* gene for 85-B antigen | 363 | 4e-98 |
| emb\|Z11666\|MLFBPAPR | *M. leprae* fibronectin-binding protein antige... | 347 | 2e-93 |
| gb\|M27016\|MSG32KDA | *Mycobacterium tuberculosis* 32 kDa antigen gene. | 317 | 2e-84 |
| emb\|X53034\|MB32PG | *Mycobacterium bovis* gene for 32 kDa protein | 317 | 2e-84 |
| dbj\|D26486\|MSG32KDAP | *Mycobacterium bovis* genes for 32 kDa protei... | 317 | 2e-84 |
| emb\|AL022076\|MTV026 | *Mycobacterium tuberculosis* H37Rv complete g... | 311 | 2e-84 |
| gb\|U47335\|MTU47335 | *Mycobacterium tuberculosis* extracellular 32 ... | 311 | 2e-84 |
| dbj\|D78142\|MSGBCGA85B | *Mycobacterium bovis* gene for alpha antige... | 309 | 5e-82 |
| emb\|Y10378\|MG85AANT | *M. gordonae* gene encoding 85-A antigen | 303 | 3e-80 |
| dbj\|D78144\|D78144 | *Mycobacterium avium* gene for MPT51, antigen 8... | 258 | 2e-66 |
| gb\|M90648\|MSG85AA | *Mycobacterium leprae* 85-A antigen gene, compl... | 236 | 6e-60 |
| dbj\|D43841\|MSGA85CA | *Mycobacterium leprae* DNA for antigen 85 com... | 222 | 8e-56 |
| emb\|X92567\|MMARI147 | *M. marinum* gene for 32 kDa protein (partial) | 218 | 1e-54 |
| emb\|Z33658\|MA32KPI6 | *M. avium* (ATCC 19075) gene for 32 kDa protein... | 192 | 7e-47 |
| dbj\|D87323\|D87323 | *Mycobacterium avium* gene for antigen 85C and ... | 186 | 5e-45 |
| emb\|Z33657\|MA32KPI5 | *M. avium* (ATCC 15769) gene for 32 kDa protein... | 184 | 2e-44 |
| emb\|Z33662\|MI32KPI10 | *M. intracellulare* (ATCC 13950) gene for 32 k... | 168 | 1e-39 |
| emb\|X92566\|MASIA122 | *M. asiaticum* gene for 32 kDa protein (partial) | 168 | 1e-39 |
| emb\|Y07715\|MA32KPRO1 | *M. asiaticum* gene segment of 32-kDa protein | 168 | 1e-39 |
| emb\|Z50760\|MA32K511 | *M. avium* complex gene for 32 kDa protein (pa... | 168 | 1e-39 |
| emb\|Z50759\|MA32K1112 | *M. avium* complex gene for 32 kDa protein (p... | 167 | 4e-39 |
| emb\|Z50767\|MA32K769 | *M. avium* complex gene for 32 kDa protein (pa... | 161 | 3e-37 |
| emb\|Z50774\|MA32K966 | *M. avium* complex gene for 32 kDa protein (pa... | 161 | 3e-37 |
| emb\|Z33659\|MA32KPI7 | *M. avium* (ATCC 19074) gene for 32 kDa protein... | 161 | 3e-37 |
| emb\|Z33661\|MI32KPI9 | *M. intracellulare* (ATCC 35762) gene for 32 kD... | 161 | 3e-37 |
| emb\|Z50763\|MA32K559 | *M. avium* complex gene for 32 kDa protein (pa... | 161 | 3e-37 |
| emb\|Z50772\|MA32K961 | *M. avium* complex gene for 32 kDa protein (pa... | 151 | 4e-36 |
| emb\|Z50765\|MA32K576 | *M. avium* complex gene for 32 kDa protein (pa... | 153 | 6e-35 |
| emb\|Z50770\|MA32K904 | *M. avium* complex gene for 32 kDa protein (pa... | 153 | 6e-35 |
| emb\|Z33667\|MM32KPI15 | *M. malmoense* gene for 32 kDa protein (partial) | 153 | 6e-35 |
| emb\|Z50768\|MA32K814 | *M. avium* complex gene for 32 kDa protein (pa... | 153 | 6e-35 |
| emb\|Z50764\|MA32K575 | *M. avium* complex gene for 32 kDa protein (pa... | 149 | 1e-33 |
| emb\|Z50762\|MA32K558 | *M. avium* complex gene for 32 kDa protein (pa... | 145 | 2e-32 |
| emb\|X57229\|MT85CG | *Mycobacterium tuberculosis* gene for antigen 8... | 145 | 2e-32 |
| enb\|Z50761\|MA32K554 | *M. avium* complex gene for 32 kDa protein (pa... | 145 | 2e-32 |
| emb\|Z92770\|MTCI5 | *Mycobacterium tuberculosis* H37Rv complete geno... | 145 | 2e-32 |
| enb\|X92570\|MSZUL8 | *M. szulgai* gene for 32 kDa protein (partial) | 141 | 2e-31 |
| emb\|Z50758\|MA32K1076 | *M. avium* complex gene for 32 kDa protein (p... | 127 | 4e-27 |
| emb\|Z50766\|MA32K577 | *M. avium* complex gene for 32 kDa protein (pa... | 123 | 6e-26 |
| emb\|Z33654\|MB32KPI2 | *M. bovis* (HCG) gene for 32 kDa protein (parti... | 119 | 9e-25 |
| emb\|X92573\|MTRIV151 | *M. triviale* gene for 32 kDa protein (partial) | 109 | 9e-22 |
| emb\|X92583\|MCEL1236 | *M. celatum* gene for 32 kDa protein (partial) | 100 | 8e-19 |
| emb\|Z21950\|ML85APRA | *M. leprae* of 85A protein gene >gi 267923\|emb... | 90 | 8e-16 |
| gb\|L78816\|MSGB26CS | *Mycobacterium leprae* cosmid B26 DNA sequence. | 88 | 3e-15 |
| emb\|Z21951\|ML85CPRA | *M. leprae* of 85C protein gene | 88 | 3e-15 |
| gb\|M90649\|MSG85CA | *Mycobacterium leprae* 85-C antigen gene, compl... | 88 | 3e-15 |
| emb\|X92582\|MCEL1235 | *M. celatum* gene for 32 kDa protein (partial) | 86 | 1e-14 |
| emb\|X92577\|MPHLE89 | *M. phlei* gene for 32 kDa protein (partial) | 82 | 2e-13 |
| emb\|X92581\|MBRA1077 | *M. branderi* gene for 32 kDa protein (partial) | 82 | 2e-13 |
| emb\|Y07718\|MF32KPRO4 | *M. flavescens* gene segment of 32-kDa protein | 82 | 2e-13 |
| emb\|X92575\|MFORT131 | *M. fortuitum* gene for 32 kDa protein (partial) | 80 | 8e-13 |
| emb\|Z33663\|MA32KP111 | *M. avium*-intracellulare complex gene for 32... | 76 | 1e-11 |
| emb\|X92576\|MPERE132 | *M. peregrinum* gene for 32 kDa protein (partial) | 74 | 5e-11 |
| emb\|Z50776\|MAH04894 | *M. avium* complex gene for 32 kDa protein (pa... | 68 | 3e-09 |
| emb\|X92571\|MXENO201 | *M. xenopi* gene for 32 kDa protein (partial) | 68 | 3e-09 |
| emb\|Y07717\|MS32KPRO3 | *M. smegmatis* gene segment of 32-kDa protein | 66 | 1e-08 |

TABLE 6-continued

Sequences producing significant alignments

| Database/Accession No. | Gene | Score (bits) | E Value |
|---|---|---|---|
| emb\|Z50769\|MA32K822 | *M. avium* complex gene for 32 kDa protein (pa... | 60 | 7e-07 |
| emb\|Z50775\|MAH03994 | *M. avium* complex gene for 32 kDa protein (pa... | 60 | 7e-07 |
| emb\|Y07719\|MV32KPRO5 | *M. vaccae* gene segment of 32-kDa protein | 54 | 4e-05 |
| emb\|X92580\|MVAC91 | *M. vaccae* gene for 32 kDa protein (partial) | 54 | 4e-05 |
| emb\|X92574\|MNONC45 | *M. nonchromogenicum* gene for 32 kDa protein (... | 48 | 0.003 |
| emb\|X92569\|MSIMI95 | *M. simiae* gene for 32 kDa protein (partial) | 48 | 0.003 |
| emb\|AJ002150\|MTAJ2150 | *Mycobacterium tuberculosis* H37Rv, MPT51 gene | 46 | 0.011 |
| emb\|Z79700\|MTCY10D7 | *Mycobacterium tuberculosis* H37Rv complete g... | 44 | 0.043 |
| gb\|M58472\|ATUCAT | *A. tumefaciens* chloramphenicol acetyltransferas... | 42 | 0.17 |
| emb\|X92578\|MSMEG90 | *M. smegmatis* gene for 32 kDa protein (partial) | 40 | 0.66 |
| emb\|X92572\|MTER260 | *M. terrae* gene for 32 kDa protein (partial) | 40 | 0.66 |
| emb\|X92568\|MSCRO149 | *M. scrofulaceum* gene for 32 kDa protein (par... | 40 | 0.66 |
| emb\|Z33666\|MG32KPI14 | *M. gordonae* (ATCC 14470) gene for 32 kDa pro... | 40 | 0.66 |
| gb\|M17700\|FLCNPCA | Influenza C/California/78 nucleoprotein RNA (... | 38 | 2.6 |

Example 4

Evolution of Broad-spectrum Vaccines against *Helicobacter pylori*

Chronic infection of the gastroduodenal mucosae by *Helicobacter pylori* bacteria is responsible for chronic active gastritis, peptic ulcers, and gastric cancers such as adenocarcinoma and low-grade B-cell lymphoma. An increasing occurrence of antibiotic-resistant strains is limiting this therapy. The use of vaccines to both prevent and treat ongoing infections is being actively pursued (Crabtree J E (1998) *Gut* 43: 7–8; Axon A T (1998) *Gut* 43 Suppl 1: S70–3; Dubois et al. (1998) *Infect. Immun.* 66: 4340–6; Tytgat G N (1998) *Aliment. Pharmacol. Ther.* 12 Suppl 1: 123–8; Blaser M J. (1998) *BMJ*. 316: 1507–10; Marcetti et al. (1998) *Vaccine* 16: 33–7; Kleanthous et al. (1998) *Br. Med. Bull.* 54: 229–41; Wermeille et al. (1998) *Pharm. World Sci.* 20: 1–17.

Identification of appropriate Helicobacter antigens for use in preventive and therapeutic vaccines can include two-dimensional gel electrophoresis, sequence analysis, and serum profiling (McAtee et al. (1998) *Clin. Diagn. Lab. Immunol.* 5:537–42; McAtee et al. (1998) *Helicobacter* 3: 163–9). Antigenic differences between related Helicobacter species and strains can limit the use of vaccines for prevention and treatment of infections (Keenan et al. (1998) *FEMS Microbiol Lett.* 161: 21–7).

In this Example, DNA family shuffling of related yet immunologically distinct antigens allows for the isolation of complex chimeric antigens that can provide a broad cross-reactive protection against many related strains and species of Helicobacter. Mouse models of persistent infection by mouse-adapted *H. pylori* strains that have been used to evaluate therapeutic use of vaccines against infection are used to evaluate shuffled antigens (Crabtree J E (1998) *Gut* 43: 7–8; Axon A T (1998) *Gut* 43 Suppl 1:S70–3).

The vacuolating cytotoxin (VacA) and cytotoxin associated gene products (CagA) have been evaluated as a vaccine against *H. pylori* infection in animal models which supports the application of this approach in humans.

Table 7 shows the results of a BLAST search using the *H. pylori* VacA gene to identify homologous genes that can be used in a family shuffling format to obtain improved antigens. Homologous antigens have been cloned and sequenced from a number of related yet distinct *H. pylori* strains and additional natural diversity can be obtained by cloning antigen genes from other strains. These genes and others or fragments thereof are cloned by methods such as PCR, shuffled and screened for improved antigens.

TABLE 7

Sequences producing significant alignments

| Database/Accession No. | Gene | Score (bits) | E Value |
|---|---|---|---|
| gb\|U95971\|HPU95971 | *Helicobacter pylori* 95-54 (J128) inactive cy... | 7874 | 0.0 |
| gb\|AE000598\|HPAE000598 | *Helicobacter pylori* section 76 of 134 of... | 2468 | 0.0 |
| gb\|AF001358\|HPAF001358 | *Helicobacter pylori* vacuolating cytotoxi... | 2405 | 0.0 |
| emb\|Z26883\|HPCYTTOX | *H. pylori* gene for cytotoxin. | 2389 | 0.0 |
| gb\|U05677\|HPU05677 | *Helicobacter pylori* 87-203 vacuolating cytot... | 2389 | 0.0 |
| gb\|U05676\|HPU05676 | *Helicobacter pylori* 60190 cysteinyl-tRNA syn... | 2355 | 0.0 |
| gb\|U29401\|HPU29401 | *Helicobacter pylori* vacuolating cytotoxin ho... | 2345 | 0.0 |
| emb\|AJ006969\|HPY6969 | *Helicobacter pylori* vacA gene, strain Mz25... | 2103 | 0.0 |
| gb\|S72494\|S72494 | 140 kda cytotoxin [*Helicobacter pylori*, Genomi... | 2050 | 0.0 |
| gb\|U07145\|HPU07145 | *Helicobacter pylori* NCTC 11638 cysteinyl tRN... | 2050 | 0.0 |
| emb\|AJ006968\|HPY6968 | *Helicobacter pylori* vacA gene, strain Mz26... | 2032 | 0.0 |
| emb\|AJ006970\|HPY6970 | *Helicobacter pylori* vacA gene, strain Mz29... | 1992 | 0.0 |
| gb\|AF077939\|AF077939 | *Helicobacter pylori* strain 166 vacuolating... | 1834 | 0.0 |
| gb\|AF077940\|AF077940 | *Helicobacter pylori* strain 539 vacuolating... | 1814 | 0.0 |
| gb\|AF077941\|AF077941 | *Helicobacter pylori* strain 549 vacuolating... | 1778 | 0.0 |
| gb\|AF077938\|AF077938 | *Helicobacter pylori* strain 50 vacuolating ... | 1746 | 0.0 |
| gb\|U63255\|HPU63255 | *Helicobacter pylori* vacuolating cytotoxin ge... | 835 | 0.0 |
| gb\|U63270\|HPU63270 | *Helicobacter pylori* vacuolating cytotoxin ge... | 819 | 0.0 |
| gb\|U63272\|HPU63272 | *Helicobacter pylori* vacuolating cytotoxin ge... | 819 | 0.0 |
| gb\|U63283\|HPU63283 | *Helicobacter pylori* vacuolating cytotoxin ge... | 819 | 0.0 |
| gb\|U63284\|HPU63284 | *Helicobacter pylori* vacuolating cytotoxin ge... | 819 | 0.0 |
| gb\|U63262\|HPU63262 | *Helicobacter pylori* vacuolating cytotoxin ge... | 803 | 0.0 |
| gb\|U63268\|HPU63268 | *Helicobacter pylori* vacuolating cytotoxin ge... | 803 | 0.0 |
| gb\|U63273\|HPU63273 | *Helicobacter pylori* vacuolating cytotoxin ge... | 803 | 0.0 |
| gb\|U63282\|HPU63282 | *Helicobacter pylori* vacuolating cytotoxin ge... | 803 | 0.0 |
| gb\|U63259\|HPU63259 | *Helicobacter pylori* vacuolating cytotoxin ge... | 795 | 0.0 |
| gb\|U63276\|HPU63276 | *Helicobacter pylori* vacuolating cytotoxin ge... | 779 | 0.0 |
| gb\|U63287\|HPU63287 | *Helicobacter pylori* vacuolating cytotoxin ge... | 779 | 0.0 |

TABLE 7-continued

Sequences producing significant alignments

| Database/Accession No. | Gene | Score (bits) | E Value |
|---|---|---|---|
| gb\|U63263\|HPU63263 | *Helicobacter pylori* vacuolating cytotoxin ge... | 771 | 0.0 |
| gb\|U63269\|HPU63269 | *Helicobacter pylori* vacuolating cytotoxin ge... | 771 | 0.0 |
| gb\|U63286\|HPU63286 | *Helicobacter pylori* vacuolating cytotoxin ge... | 771 | 0.0 |
| gb\|U63275\|HPU63275 | *Helicobacter pylori* vacuolating cytotoxin ge... | 763 | 0.0 |
| gb\|U63279\|HPU63279 | *Helicobacter pylori* vacuolating cytotoxin ge... | 763 | 0.0 |
| gb\|U63277\|HPU63277 | *Helicobacter pylori* vacuolating cytotoxin ge... | 755 | 0.0 |
| gb\|U63280\|HPU63280 | *Helicobacter pylori* vacuolating cytotoxin ge... | 755 | 0.0 |
| gb\|U63265\|HPU63265 | *Helicobacter pylori* vacuolating cytotoxin ge... | 747 | 0.0 |
| gb\|U63267\|HPU63267 | *Helicobacter pylori* vacuolating cytotoxin ge... | 747 | 0.0 |
| gb\|U63281\|HPU63281 | *Helicobacter pylori* vacuolating cytotoxin ge... | 741 | 0.0 |
| gb\|U63261\|HPU63261 | *Helicobacter pylori* vacuolating cytotoxin ge... | 739 | 0.0 |
| gb\|U63274\|HPU63274 | *Helicobacter pylori* vacuolating cytotoxin ge... | 739 | 0.0 |
| gb\|U63285\|HPU63285 | *Helicobacter pylori* vacuolating cytotoxin ge... | 737 | 0.0 |
| emb\|AJ009430\|HPAJ9430 | *Helicobacter pylori* vacA gene (partial), ... | 737 | 0.0 |
| emb\|AJ009435\|HPAJ9435 | *Helicobacter pylori* vacA gene (partial), ... | 730 | 0.0 |
| emb\|AJ009439\|HPAJ9439 | *Helicobacter pylori* vacA gene (partial), ... | 730 | 0.0 |
| gb\|U63271\|HPU63271 | *Helicobacter pylori* vacuolating cytotoxin ge... | 724 | 0.0 |
| emb\|AJ009418\|HPAJ9418 | *Helicobacter pylori* vacA gene (partial), ... | 722 | 0.0 |
| emb\|AJ009422\|HPAJ9422 | *Helicobacter pylori* vacA gene (partial), ... | 722 | 0.0 |
| gb\|U63256\|HPU63256 | *Helicobacter pylori* vacuolating cytotoxin ge... | 716 | 0.0 |
| gb\|U63266\|HPU63266 | *Helicobacter pylori* vacuolating cytotoxin ge... | 716 | 0.0 |
| emb\|AJ009420\|HPAJ9420 | *Helicobacter pylori* vacA gene (partial), ... | 714 | 0.0 |
| emb\|AJ009424\|HPAJ9424 | *Helicobacter pylori* vacA gene (partial), ... | 714 | 0.0 |
| emb\|AJ009431\|HPAJ9431 | *Helicobacter pylori* vacA gene (partial), ... | 714 | 0.0 |
| gb\|U63260\|HPU63260 | *Helicobacter pylori* vacuolating cytotoxin ge... | 708 | 0.0 |
| gb\|U63278\|HPU63278 | *Helicobacter pylori* vacuolating cytotoxin ge... | 708 | 0.0 |
| emb\|AJ009419\|HPAJ9419 | *Helicobacter pylori* vacA gene (partial), ... | 706 | 0.0 |
| emb\|AJ009428\|HPAJ9428 | *Helicobacter pylori* vacA gene (partial), ... | 706 | 0.0 |
| emb\|AJ009437\|HPAJ9437 | *Helicobacter pylori* vacA gene (partial), ... | 706 | 0.0 |
| emb\|AJ009427\|HPAJ9427 | *Helicobacter pylori* vacA gene (partial), ... | 704 | 0.0 |
| gb\|U63257\|HPU63257 | *Helicobacter pylori* vacuolating cytotoxin ge... | 700 | 0.0 |
| emb\|AJ009423\|HPAJ9423 | *Helicobacter pylori* vacA gene (partial), ... | 698 | 0.0 |
| emb\|AJ009432\|HPAJ9432 | *Helicobacter pylori* vacA gene (partial), ... | 692 | 0.0 |
| emb\|AJ009417\|HPAJ9417 | *Helicobacter pylori* vacA gene (partial), ... | 688 | 0.0 |
| emb\|AJ009421\|HPAJ9421 | *Helicobacter pylori* vacA gene (partial), ... | 688 | 0.0 |
| emb\|AJ009426\|HPAJ9426 | *Helicobacter pylori* vacA gene (partial), ... | 688 | 0.0 |
| emb\|AJ009438\|HPAJ9438 | *Helicobacter pylori* vacA gene (partial), ... | 688 | 0.0 |
| gb\|U63264\|HPU63264 | *Helicobacter pylori* vacuolating cytotoxin ge... | 676 | 0.0 |
| emb\|AJ009433\|HPAJ9433 | *Helicobacter pylori* vacA gene (partial), ... | 666 | 0.0 |
| emb\|AJ009425\|HPAJ9425 | *Helicobacter pylori* vacA gene (partial), ... | 658 | 0.0 |
| gb\|U63258\|HPU63258 | *Helicobacter pylori* vacuolating cytotoxin ge... | 652 | 0.0 |
| emb\|AJ009442\|HPAJ9442 | *Helicobacter pylori* vacA gene (partial), ... | 626 | e-177 |
| emb\|AJ009444\|HPAJ9444 | *Helicobacter pylori* vacA gene (partial), ... | 626 | e-177 |
| gb\|U80068\|HPU80068 | *Helicobacter pylori* strain 213, vacuolating ... | 622 | e-175 |
| emb\|AJ009434\|HPAJ9434 | *Helicobacter pylori* vacA gene (partial), ... | 618 | e-174 |
| emb\|AJ009441\|HPAJ9441 | *Helicobacter pylori* vacA gene (partial), ... | 603 | e-170 |
| gb\|AF035616\|HPVCP2 | *Helicobacter pylori* strain R34A vacuolating ... | 599 | e-168 |
| emb\|AJ009447\|HPAJ9447 | *Helicobacter pylori* vacA gene (partial), ... | 587 | e-165 |
| emb\|AJ009440\|HPAJ9440 | *Helicobacter pylori* vacA gene (partial), ... | 563 | e-158 |
| emb\|AJ009436\|HPAJ9436 | *Helicobacter pylori* vacA gene (partial), ... | 555 | e-155 |
| emb\|AJ009443\|HPAJ9443 | *Helicobacter pylori* vacA gene (partial), ... | 555 | e-155 |
| emb\|AJ009446\|HPAJ9446 | *Helicobacter pylori* vacA gene (partial), ... | 555 | e-155 |
| gb\|U80067\|HPU80067 | *Helicobacter pylori* strain 184, vacuolating ... | 553 | e-155 |
| gb\|AF042735\|AF042735 | *Helicobacter pylori* JK22 vacuolating cytot... | 553 | e-155 |
| emb\|AJ009445\|HPAJ9445 | *Helicobacter pylori* vacA gene (partial), ... | 547 | e-153 |
| gb\|AF035609\|AF035609 | *Helicobacter pylori* strain R10A vacuolatin... | 547 | e-153 |
| gb\|AF042734\|AF042734 | *Helicobacter pylori* JK1 vacuolating cytoto... | 537 | e-150 |
| gb\|AF035612\|AF035612 | *Helicobacter pylori* strain R26A vacuolatin... | 347 | 9e-93 |
| gb\|AF035613\|AF035613 | *Helicobacter pylori* strain R40A vacuolatin... | 323 | 1e-85 |
| emb\|AJ006967\|HPY6967 | *Helicobacter pylori* vacA gene, strain Mz19... | 317 | 8e-84 |
| gb\|AF035615\|HPVCP1 | *Helicobacter pylori* strain R34A vacuolating ... | 315 | 3e-83 |
| gb\|AF035614\|AF035614 | *Helicobacter pylori* strain R50A vacuolatin... | 307 | 8e-81 |
| gb\|U91578\|HPU91578 | *Helicobacter pylori* strain F37 vacA gene, pa... | 109 | 4e-21 |
| gb\|U91579\|HPU91579 | *Helicobacter pylori* strain F79 vacA gene, pa... | 109 | 4e-21 |
| gb\|U91575\|HPU91575 | *Helicobacter pylori* strain F84 vacA gene, pa... | 107 | 1e-20 |
| emb\|Y14742\|HPVACA26 | *Helicobacter pylori* partial vacA gene, stra... | 101 | 9e-19 |
| gb\|U91577\|HPU91577 | *Helicobacter pylori* strain F94 vacA gene, pa... | 100 | 3e-18 |
| gb\|U91576\|HPU91576 | *Helicobacter pylori* strain F71 vacA gene, pa... | 100 | 3e-18 |
| gb\|AF035610\|AF035610 | *Helicobacter pylori* strain R13A vacuolatin... | 94 | 2e-16 |
| gb\|U91580\|HPU91580 | *Helicobacter pylori* strain F80 vacA gene, pa... | 92 | 8e-16 |
| gb\|AF035611\|AF035611 | *Helicobacter pylori* strain R59A vacuolatin... | 92 | 8e-16 |
| emb\|Y14744\|HPVACA49 | *Helicobacter pylori* partial vacA gene, stra... | 88 | 1e-14 |

Table 8 shows the results of a BLAST search using the *H. pylori* CagA gene to identify homologous genes that can be used in a family shuffling format to obtain improved antigens. Homologous antigens have been cloned and sequenced from a number of related yet distinct *H. pylori* strains and additional natural diversity can be obtained by cloning antigen genes from other strains. These genes and others or fragments thereof are be cloned by methods such as PCR, shuffled and screened for improved antigens.

TABLE 8

Sequences producing significant alignments

| Database/Accession No. | Gene | Score (bits) | E Value |
|---|---|---|---|
| gb\|AF083352\|AF083352 | *Helicobacter pylori* cytotoxin associated p... | 7041 | 0.0 |
| gb\|AE000569\| HPAE000569 | *Helicobacter pylori* section 47 of 134 of... | 5501 | 0.0 |
| gb\|L11714\| HECMAJANT | *Helicobacter pylori* major antigen gene sequ... | 4976 | 0.0 |
| emb\|X70039\|HPCAI | *H. pylori* cai gene for cytotoxicity associated ... | 4294 | 0.0 |
| gb\|U60176\|HPU60176 | *Helicobacter pylori* cag pathogenicity island... | 4294 | 0.0 |
| dbj\|AB003397\| AB003397 | *Helicobacter pylori* DNA for CagA, complet... | 4274 | 0.0 |
| gb\|U80066\|HPU80066 | *Helicobacter pylori* strain 213, cytotoxin-as... | 349 | 2e-93 |
| gb\|U80065\|HPU80065 | *Helicobacter pylori* strain 184, cytotoxin-as... | 343 | 1e-91 |
| gb\|AF043488\|AF043488 | *Helicobacter pylori* JK252 cytotoxicity ass... | 178 | 4e-42 |
| gb\|AF043487\|AF043487 | *Helicobacter pylori* JK25 cytotoxicity asso... | 170 | 1e-39 |
| gb\|AF043489\|AF043489 | *Helicobacter pylori* JK269 cytotoxicity ass... | 163 | 2e-37 |
| emb\|X70038\|HPCAIDUP | *H. pylori* DNA duplication sequence within th... | 159 | 4e-36 |
| gb\|AF043490\|AF043490 | *Helicobacter pylori* JK22 cytotoxicity asso... | 153 | 2e-34 |

Example 5

Development of Broad-Spectrum Vaccines against Malaria

This Example describes the use of DNA shuffling to generate improved vaccines against malaria infection. An excellent target for evolution by DNA shuffling is the *Plasmodium failciparum* merozoite surface protein, MSP I (Hui et al. (1996) *Infect. Immun.* 64: 1502–1509). MSP 1 is expressed on the surface of merozoites as an integral membrane protein. It is cleaved by parasite proteases just before and concomitant with rupture and release from infected cells. The cleavage appears to be obligatory for full function in MSP 1 binding to RBC receptors. The cleaved fragments remain attached to the membrane of the merozoite. Other membrane proteins on merozoites also participate in the attachment and specific invasion events. MSP1 is a proven candidate for inclusion in a vaccine against the asexual blood stage of malaria.

The genes encoding MSP1 can be isolated from various isolates of *Plasimodium falciparum* merozoites by PCR technology. Related naturally existing genes can be additionally used to increase the diversity of the starting genes. A library of shuffled MSP1 genes is generated by DNA shuffling, and this library is screened for induction of efficient immune responses.

The screening can be done by injecting individual variants into test animals, such as mice or monkeys. Either purified recombinant proteins, or DNA vaccines or viral vectors encoding the relevant genes are injected. Typically, a booster injection is given 2–3 weeks after the first injection. Thereafter, the sera of the test animals are collected and these sera are analyzed for the presence of antibodies that reduce invasion of merozoites into uninfected erythrocytes (RBC). RBC are infected by the merozoite, immediately inside the RBC, the merozoite differentiates into a ring and this matures to a schizont that contains several nascent daughter merozoites, which then burst out of the infected cell, destroying it, and go on to attach and invade another RBC. In vivo, the merozoite is likely only extracellular for seconds. In vitro, any blockade of this event can dramatically reduce the level of reinfection. Antibodies against MSP 1 bind to the surface of merozoites that are released from schizont infected RBC when they rupture and thereby reduce the ability of these merozoites to attach and engage cognate RBC receptors on the uninfected RBC surface. Merozoite attachment is reduced, merozoite entry into new RBC is reduced, and the numbers of newly invaded cells detected at the early ring stage is therefore reduced if the culture is examined several hours after the blockade of invasion test. In some assay formats a surrogate of merozoite invasion inhibition is to note the appearance of agglutinated merozoites, although this is an indirect measure of antibodies that cause reduced invasion.

The shuffled antigens that induce the most potent antibody responses reducing invasion of merozoites into uninfected erythrocytes are selected for further testing and can be subjected to new rounds of shuffling and selection. In subsequent studies, the capacity of these antigens to induce antibodies in man is investigated. Again, either purified recombinant antigens, or DNA vaccines or viral vectors encoding the relevant genes are injected and the protective immune responses are analyzed.

Example 6

Development of Broad-Spectrum Vaccines against Viral Pathogens

This Example describes the use of DNA shuffling to obtain vaccines that can induce an immune response against multiple isolates of viral pathogens.

A. Venezuelan Equine Encephalitis Virus (VEE)

VEE belongs to the alphavirus genus, which are generally transmitted by mosquitoes. However, VEE is an unusual alphavirus in that it is also highly infectious by aerosol inhalation for both humans and rodents. The disease manifestations in humans range from subclinical or mild febrile disease to serious infection and inflammation of the central nervous system. Virus clearance coincides that of production of specific anti-VEE antibodies, which are believed to be the primary mediators of protective immune responses (Schmaljohn et al. (1982) *Nature* 297: 70). VEE is an unusual virus also because its primary target outside the central nervous system is the lymphoid tissue, and therefore, replication defective variants may provide means to target vaccines or pharmaceutically useful proteins to the immune system.

At least seven subtypes of VEE are known that can be identified genetically and serologically. Based on epidemiological data, the virus isolates fall into two main categories: I-AB and I-C strains, which are associated with VEE epizootics/epidemics, and the remaining serotypes, which are associated primarily with enzootic vertebrate-mosquito cycles and circulate in specific ecological zones (Johnston and Peters, *In Fields Virology*, Third Edition, eds. B. N. Fields et al., Lippincott-Raven Publishers, Philadelphia, 1996).

The envelope protein (E) appears to be the major antigen in inducing neutralizing Abs. Accordingly, DNA shuffling is used to obtain a library of recombinant E proteins by shuffling the corresponding genes derived from various strains of VEE. These libraries and individuals chimeras/mutants thereof are subsequently screened for their capacity to induce widely cross-reacting and protective Ab responses.

B. Flaviviruses

Japanese encephalitis virus (JE), Tick-borne encephalitis virus (TBE) and Dengue virus are arthropod-borne viruses belonging to the Flavivirus family, which comprises 69 related viruses. The heterogeneity of the viruses within the family is a major challenge for vaccine development. For example, there are four major serotypes of Dengue virus, and a tetravalent vaccine that induces neutralizing Abs against all four serotypes is necessary. Moreover, non-neutralizing antibodies induced by infection or vaccination by one Dengue virus may cause enhancement of the disease during a subsequent infection by another serotype. Therefore, cross-protective, broad spectrum vaccines for TBE and JE would provide significant improvements to the existing vaccines. In this Example, the ability of DNA shuffling to efficiently generate chimeric and mutated genes is used to generate cross-protective vaccines.

1. Japanese Encephalitis Virus

Japanese encephalitis virus (JE) is a prototype of the JE antigenic complex, which comprises St. Louis encephalitis virus, Murray Valley encephalitis virus, Kunjin virus and West Nile virus (Monath and Heinz, In Fields Virology, Third Edition, eds. B. N. Fields et al., Lippincott-Raven Publishers, Philadelphia, pp 961–1034, 1996). Infections caused by JE are relatively rare, but the case-fatality is 5–40% because no specific treatment is available. JE is widely distributed in China, Japan, Philippines, far-eastern Russia and India providing a significant threat to those traveling in these areas. Currently available JE vaccine is produced from brain tissues of mice infected with single virus isolate. Side effects are observed in 10% to 30% of the vaccinees.

To obtain chimeric and/or mutated antigens that provide a protective immune response against all or most of the viruses within the JE complex, DNA shuffling is performed on viral envelope genes. The amino acid identity within the JE complex varies between 72% and 93%. In addition, significant antigenic variation has been observed among JE strains by neutralization assays, agar gel diffusion, antibody absorption and monoclonal antibody analysis (Oda (1976) Kobe J. Med. Sci. 22: 123; Kobyashi et al. (1984) Infect. Immun. 44: 117). Moreover, the amino acid divergence of the envelope protein gene among 13 strains from different Asian countries is as much as 4. 2% (Ni and Barrett (1995) J. Gen. Virol. 76: 401). The resulting library of recombinant polypeptides encoded by the shuffled genes is screened to identify those that provide a cross-protective immune response.

2. Tick-borne encephalitis Virus

The tick-borne encephalitis virus complex comprises 14 antigenically related viruses, eight of which cause human disease, including Powassan, Louping ill and Tick-borne encephalitis virus (TBE) (Monath and Heinz, In Fields Virology, Third Edition, eds. B. N. Fields et al., Lippincott-Raven Publishers, Philadelphia, pp. 961–1034, 1996). TBE has been recognized in all Central and Eastern European countries, Scandinavia and Russia, whereas Powassan occurs in Russia, Canada and the United States. The symptoms vary from flu-like illness to severe meningitis, meningoencephalitis and meningoencephalitis with a fatality rate of 1% to 2% (Gresikova and Calisher, In Monath ed., The arboviruses. ecology and epidemiology, vol. IV, Boca Raton, Fla., CRC Press, pp. 177–203, 1988).

Family DNA shuffling is used to generate chimeric envelope proteins derived from the TBE complex to generate crossprotective antigens. The envelope proteins within the family are 77–96% homologous, and viruses can be distinguished by specific mAbs (Holzmann et al., Vaccine, 10, 345, 1992). The envelope protein of Powassan is 78% identical at the amino acid level with that of TBE, and cross-protection is unlikely, although epidemiological data is limited.

Langat virus is used as a model system to analyze protective immune responses in vivo (Iacono-Connors et al. (1996) Virus Res. 43: 125). Langat virus belongs to the TBE complex, and can be used in challenge studies in BSL3 facilities. Serological studies based on recombinant envelope proteins are performed to identify immunogen variants that induce high levels of antibodies against envelope proteins derived from most or all viruses of the TBE complex.

3. Dengue Viruses

Dengue viruses are transmitted though mosquito bites, posing a significant threat to troops and civilian populations particularly in tropical areas. There are four major serotypes of Dengue virus, namely Dengue 1, 2, 3 and 4. A tetravalent vaccine that induces neutralizing antibodies against all four strains of Dengue is required to avoid antibody-mediated enhancement of the disease when the individual encounters the virus of the other strain.

The envelope protein of Dengue virus has been shown to provide an immune response that protects from a future challenge with the same strain of virus. However, the levels of neutralizing antibodies produced are relatively low and protection from live virus challenge is not always observed. For example, mice injected with genetic vaccines encoding envelope protein of Dengue-2 virus developed neutralizing antibodies when analyzed by in vitro neutralization assays, but the mice did not survive the challenge with live Dengue-2 virus (Kochel et al. (1997) Vaccine 15: 547–552). However, protective immune responses were observed in mice immunized with recombinant vaccinia virus expressing Dengue 4 virus structural proteins (Bray et al. (1989) J. Virol. 63: 2853). These studies indicate that vaccinations with E proteins work, but significant improvements in the immunogenicity of the protective antigens are required.

In this Example, DNA shuffling is performed on the genes encoding the envelope (E) protein from all four Dengue viruses and their antigenic variants. Family DNA shuffling is used to generate chimeric E protein variants that induce high titer neutralizing antibodies against all serotypes of Dengue. The E proteins of the different dengue viruses share 62% to 77% of their amino acids. Dengue 1 and Dengue 3 are most closely related (77% homologous), followed by Dengue 2 (69%) and Dengue 4 (62%). These homologies are well in the range that allows efficient family shuffling (Crameri et al. (1998) Nature 391: 288–291).

The shuffled antigen sequences are incorporated into genetic vaccine vectors, the plasmids purified, and subsequently injected into mice. The sera are collected from the mice and analyzed for the presence of high levels of cross-reactive antibodies. The best antigens are selected for further studies using in vivo challenge models to screen for chimeras/mutants that induce cross-protection against all strains of Dengue.

C. Improved Expression and Immunogenicity of Hantaan Virus Glycoproteins

One of the advantages of genetic vaccines is that vectors expressing pathogen antigens can be generated even when the given pathogen cannot be isolated in culture. An example of such potential situation was an outbreak of severe respiratory disease among rural residents of the Southwestern United States which was caused by a previously unknown hantavirus, Sin Nombre virus (Hjelle et al. (1994) *J. Virol.* 68: 592). Much RNA sequence information of the virus was obtained well before the virus could be isolated and characterized in vitro. In these situations, genetic vaccines can provide means to generate efficient vaccines in a short period of time by creating vectors encoding antigens encoded by the pathogen. However, genetic vaccines can only work if these antigens can be properly expressed in the host.

Hantaan virus belongs to the Bunyavirus family. A characteristic feature of this family is that their glycoproteins typically accumulate at the membranes of the Golgi apparatus when expressed by cloned cDNAs, thereby reducing the efficacy of corresponding genetic vaccines (Matsuoka et al. (1991) *Curr. Top. Microb. Immunol.* 169: 161–179). Poor expression of Hantaan virus glycoproteins on the cell surface is also one explanation for poor immune responses following injections of Hantaan virus genetic vaccines.

In this Example, family DNA shuffling is used to generate recombinant Hantaan virus derived glycoproteins that are efficiently expressed in human cells and that can induce protective inmmune responses against the wild-type pathogen. Nucleic acids that encode the Hantaan virus glycoprotein are shuffled with genes that encode other homologous Bunyavirus glycoproteins. The resulting library is screened to identify proteins that are readily expressed in human cells. The screening is performed using a dual marker expression vector that enables simultaneous analysis of transfection efficiency and expression of fusion proteins that are PIG-linked to the cell surface (Whitehorn et al. (1995) *Biotechnology (N Y)* 13:1215–9).

Flow cytometry based cell sorting is used to select Hantaan virus glycoprotein variants that are efficiently expressed in mammalian cells. The corresponding sequences are then obtained by PCR or plasmid recovery. These chimeras/mutants are further analyzed for their capacity to protect wild mice against Hantaan virus infections.

Example 7

DNA Shuffling of HSV-1 and HSV-2 Glycoproteins B and/or D As Means To Induce Enhanced Protective Immune Responses This Example describes the use of DNA shuffling to obtain HSV glycoprotein B (gB) and glycoprotein D (gD) polypeptides that exhibit improved ability to induce protective immune responses upon administration to a mammal. Epidemiological studies have shown that prior infections with HSV-1 give partial protection against infections with HSV-2, indicating existence of cross-reactive immune responses. Based on previous vaccination studies, the main immunogenic glycoproteins in HSV appear to be gB and gD, which are encoded by 2.7 kb and 1.2 kb genes, respectively. The gB and gD genes of HSV-1 are about 85% identical to the corresponding gene of HSV-2, and the gB genes of each share little sequence identity with the gD genes. Baboon HSV-2 gB is appr. 75% identical to human HSV-1 or -2 gB, with rather long stretches of almost 90% identity. In addition, 60–75% identity is found in portions of the genes of equine and bovine herpesviruses.

Family shuffling is employed using as substrates nucleic acids that encode gB and/or gD from HSV-1 and HSV-2. Preferably, homologous genes are obtained from HSVs of various strains. An alignment of gD nucleotide sequences from HSV-1 and two strains of HSV-2 is shown in FIG. 7. Antigens encoded by the shuffled nucleic acids are expressed and analyzed in vivo. For example, one can screen for improved induction of neutralizing antibodies and/or CTL responses against HSV-1/HSV-2. One can also detect protective immunity by challenging mice or guinea pigs with the viruses. Screening can be done using pools or individuals clones.

Example 8

Evolution of HIV Gp120 Proteins for Induction of Broad Spectrum Neutralizing Ab Responses This Example describes the use of DNA shuffling to generate immunogens that crossreact among different strains of viruses, unlike the wild-type immunogens. Shuffling two kinds of envelope sequences can generate immunogens that induce neutralizing antibodies against a third strain.

Antibody-mediated neutralization of HIV-1 is strictly type-specific. Although neutralizing activity broadens in infected individuals over time, induction of such antibodies by vaccination has been shown to be extremely difficult. Antibody-mediated protection from HIV-1 infection in vivo correlates with antibody-mediated neutralization of virus in vitro.

FIG. 8 illustrates the generation of libraries of shuffled gp120 genes. gp120 genes derived from HIV-1DH12 and HIV-1IIIB(NL43) are shuffled. The chimeric/mutant gp120 genes are then analyzed for their capacity to induce antibodies that have broad spectrum capacity to neutralize different strains of HIV. Individual shuffled gp120 genes are incorporated into genetic vaccine vectors, which are then introduced to mice by-injection or topical application onto the skin. These antigens can also be delivered as purified recombinant proteins. The immune responses are measured by analyzing the capacity of the mouse sera to neutralize HIV growth in vitro. Neutralization assays are performed against HIV-1DHl2, HIV-1IIIB and HIV-189.6. The chimeras/mutants that demonstrate broad spectrum neutralization are chosen for further rounds of shuffling and selection. Additional studies are performed in monkeys to illustrate the capacity of the shuffled gp120 genes to provide protection for subsequent infection with immunodeficiency virus.

Example 9

Antigen Shuffling of the Hepadnavirus Envelope Protein

The Hepatitis B virus (HBV) is one of a member of a family of viruses called hepadnaviruses. This Example describes the use of genomes and individual genes from this family are used for DNA shuffling, which results in antigens having improved properties.

A. Shuffling of Hepadnavirus Envelope Protein Genes

The envelope protein of the HBV assembles to form particles that carry the antigenic structures collectively known as the Hepatitis B surface antigen (HBsAg; this term is also used to designate the protein itself). Antibodies to the major antigenic site, designated the "a" epitope (which is found in the envelope domain called S), are capable of neutralizing the virus. Immunization with the HBsAg-bearing protein thus serves as a vaccine against viral infection. The HBV envelope also contains other antigenic sites that can protect against viral infection and are potentially vital components of an improved vaccine. The epitopes are part of the envelope protein domains known as preS1 and preS2 (FIG. 9).

DNA shuffling of the envelope gene from several members of the hepadnavirus family is used to obtain more immunogenic proteins. Specifically, the genes from the following hepatitis viruses are shuffled:

the human HBV viruses, subtypes ayw and adw2
a hepatitis virus isolated from chimpanzee
a hepatitis virus isolated from gibbon
a hepatitis virus isolated from woodchuck If desired, genes from other genotypes of the human virus are available for inclusion in the DNA shuffling reactions. Likewise, other animal hepadnaviruses are available.

To promote the efficiency of the formation of chimeras resulting from DNA shuffling, some artificial genes are made:

In one case, a synthetic gene is made that contains the HBV envelope sequences, except for those codons which specify amino acids found in the chimpanzee and gibbon genes. For those codons, the chimpanzee or gibbon sequence is used.

In a second case, a synthetic gene is synthesized in which the preS2 gene sequence from the human HBV adw2 strain is fused with the woodchuck S region.

In a third case, all the oligonucleotides required to chemically synthesize each of the hepadnavirus envelope genes are mixed in approximately equal quantities and allowed to anneal to form a library of sequences.

After DNA shuffling of the hepadnavirus envelope genes, either or both of two strategies are used to obtain improved HBsAg antigens.

Strategy A: Antigens are screened by immunizing mice using two possible methods. The genes are injected in the form of DNA vaccines, i.e., shuffled envelope genes carried by a plasmid that comprises the genetic regulatory elements required for expression of the envelope proteins. Alternatively, the protein is prepared from the shuffled genes and used as the immunogen.

The sequences that give rise to greater immunogenicity for either the preS1-, preS2- or S-borne HBV antigens are selected for a second round of shuffling (FIG. 10). For the second round, the best candidates are chosen based on their improved antigenicity and their other properties such as higher expression level or more efficient secretion. Screening and further rounds of shuffling are continued until a maximum optimization for one of the antigenic regions is obtained.

The individually optimized genes are then used as a combination vaccine for the induction of optimal responses to preS1-, preS2- and S-born epitopes.

Strategy B: After isolation of the individually optimized genes as in Strategy A, the preS1, preS2 and S candidates are shuffled together, or in a pairwise fashion, in further rounds to obtain genes which encode proteins that demonstrate improved immunogenicity for at least two regions containing HBsAg epitopes (FIG. 11).

B. Use of HBsAg to Carry Epitopes from Unrelated Antigens

Several of the characteristics of the HBsAg make it a useful protein to carry epitopes drawn from other, unrelated antigens. The epitopes can be either B epitopes (which induce antibodies) or T epitopes drawn from the class I type (which stimulate CD8$^+$ T lymphocytes and induced cytotoxic cells) or class II type (which induce helper T lymphocytes and are important in providing immunological memory responses.

1. B Cell Epitopes

Amino acid sequences of potential B epitopes are chosen from any pathogen. Such sequences are often known to induce antibodies, but the immunogenicity is weak or otherwise unsatisfactory for preparation of a vaccine. These sequences can also be mimotopes, which have been selected based on their ability to have a certain antigenicity or immunogenicity.

Figure 12:
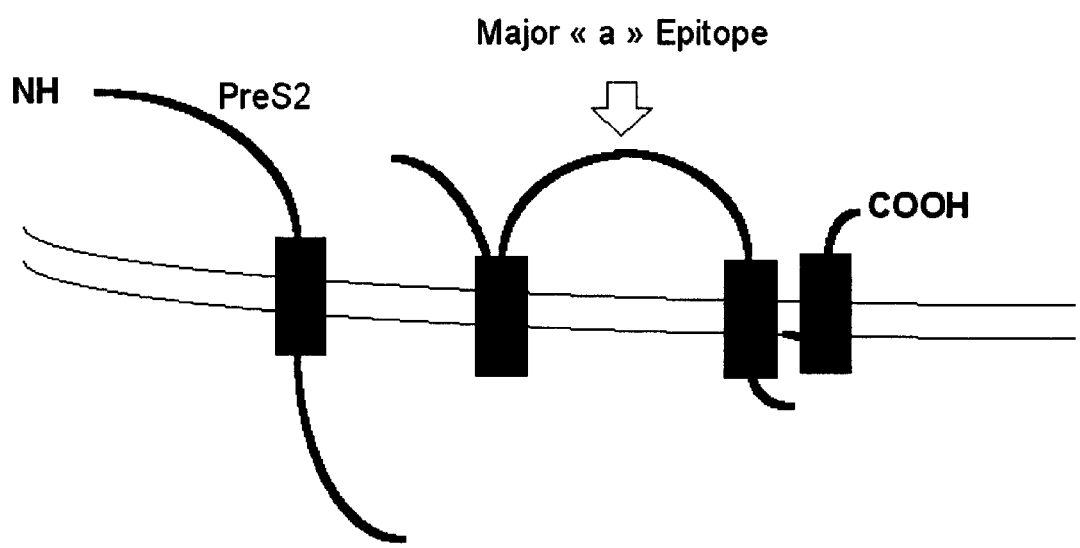
FIG. 12 shows the transmembrane organization of the HBsAg polypeptide.

The amino acid coding sequences are added to a hepadnavirus envelope gene. The heterologous sequences can either replace certain envelope sequences, or be added in addition to all the envelope sequences. The heterologous epitope sequences can be placed at any position in the envelope gene. A preferred position is the region of the envelope gene that encodes the major "a" epitope of the HBsAg (FIG. 12). This region is likely to be exposed on the external side of the particles formed by the envelope protein, and thus will expose the heterologous epitopes.

DNA shuffling is carried out on the envelope gene sequences, keeping the sequence of the heterologous epitopes constant. Screening is carried out to choose candidates that are secreted into the culture medium after transfection of plasmids from the shuffled library into cells in tissue culture.

Clones that encode a secreted protein are then tested for immunogenicity in mice either as a DNA vaccine or as a protein antigen, as described above. Clones that give an improved induction of antibodies to the heterologous epitopes are chosen for further rounds of DNA shuffling. The process is continued until the immunogenicity of the heterologous epitope is sufficient for use as a vaccine against the pathogen from which the heterologous epitopes were derived.

2. Class I Epitopes

MHC Class I epitopes are relatively short, linear peptide sequences that are generally between 6 and 12 amino acids amino acids in length, most often 9 amino acids in length. These epitopes are processed by antigen-presenting cells either after synthesis of the epitope within the cell (usually as part of a larger protein) or after uptake of soluble protein by the cells.

Polynucleotide sequences that encode one or more class I epitopes are inserted into the sequence of a hepadnavirus envelope gene either by replacing certain envelope sequences, or by inserting the epitope sequences into the envelope gene. This is typically done by modifying the gene before DNA shuffling or by including in the shuffling reaction certain oligonucleotide fragments that encode the heterologous epitopes as well as sufficient flanking hepadnavirus sequences to be incorporated into the shuffled products.

Preferably, the heterologous class I epitopes are placed into different positions in the several hepadnavirus genes used for the DNA shuffling reaction. This will optimize the chances for finding chimeric gene carrying the epitopes in an optimal position for efficient presentation.

3. Class II Epitopes

MHC Class II epitopes are generally required to be part of a protein which is taken up by antigen presenting cells, rather than synthesized within the cell. Preferably, such epitopes are incorporated into a carrier protein such as the HBV envelope that can be produced in a soluble form or which can be secreted if the gene is delivered in the form of a DNA vaccine.

Polynucleotides that encode heterologous class II epitopes are inserted into regions of the hepadnavirus envelope genes that are not involved in the transmembrane structure of the protein. DNA shuffling is performed to obtain a secreted protein that also carries the class II epitopes. When injected as a protein, or when the gene is delivered as a DNA vaccine, the protein can be taken up by antigen presenting cells for processing of the class II epitopes.

Example 10

Evolution of Broad Spectrum Vaccines against Hepatitis C Virus

Antigenic heterogeneity of different strains of Hepatitis C Virus (HCV) is a major problem in development of efficient vaccines against HCV. Antibodies or CTLs specific for one strain of HCV typically do not protects against other strains. Multivalent vaccine antigens that simultaneously protect against several strains of HCV would be of major importance when developing efficient vaccines against HCV.

The HCV envelope genes, which encode envelope proteins E1 and E2, have been shown to induce both antibody and lymphoproliferative responses against these antigens (Lee et al. (1998) *J. Virol.* 72: 8430–6), and these responses can be optimized by DNA shuffling. The hypervariable region I (HVR1) of the envelope protein E2 of HCV is the most variable antigenic fragment in the whole viral genome and is primarily responsible for the large inter- and intra-individual heterogeneity of the infecting virus (Puntoriero et al. (1998) *EMBO J.* 17: 3521–33). Therefore, the gene encoding E2 is a particularly useful target for evolution by DNA shuffling.

DNA shuffling of HCV antigens, such as nucleocapsid or envelope proteins E1, E2, provides a means to generate multivalent HCV vaccines that simultaneously protect against several strains of HCV. These antigens are shuffled using the family DNA shuffling approach. The starting genes will be obtained from various natural isolates of HCV. In addition, related genes from other viruses can be used to increase the number of different recombinants that are generated. A library of related, chimeric variants of HCV antigens are then generated and this library will be screened for induction of widely crossreactive immune responses. The screening can be done directly in vivo by injecting individual variants into test animals, such as mice or monkeys. Either purified recombinant proteins or DNA vaccines encoding the relevant genes are injected. Typically, a booster injection is given 2–3 weeks after the first injection. Thereafter, the sera of the test animals are collected and these sera are tested for the presence of antibodies that react against multiple HCV virus isolates.

Before the in vivo testing is initiated, the antigens can be pre-enriched in vitro for antigens that are recognized by polyclonal antisera derived from previously infected patients or test animals. Alternatively, monoclonal antibodies that are specific for various strains of HCV are used. The screening is performed using phage display or ELISA assays. For example, the antigen variants are expressed on bacteriophage M13 and the phage are then incubated on plates coated with antisera derived from patients or test animals infected with various HCV isolates. The phage that bind to the antibodies are then eluted and further analyzed in test animals for induction of crossreactive antibodies.

Example 11

Evolution of Chimeric Allergens that Induce Broad Immune Responses and Have Reduced Risk of Inducing Anaphylactic Reactions Specific immunotherapy of allergy is performed by injecting increasing amounts of the given allergens into the patients. The therapy typically alters the types of allergen-specific immune responses from a dominating T helper 2 ($T_H2$) type response to a dominating T helper 1 ($T_H1$) type response. However, because allergic patients have increased levels of IgE antibodies specific for the allergens, the immunotherapy of allergy involves a risk of IgE receptor mediated anaphylactic reactions.

T helper ($T_H$) cells are capable of producing a large number of different cytokines, and based on their cytokine synthesis pattern $T_H$ cells are divided into two subsets (Paul and Seder (1994) *Cell* 76: 241–251). $T_H1$ cells produce high levels of IL-2 and IFN-gamma and no or minimal levels of IL-4, IL-5 and IL-I 3. In contrast, $T_H2$ cells produce high levels of IL-4, IL-5 and IL-I 3, whereas IL-2 and IFN-gamma production is minimal or absent. $T_H1$ cells activate macrophages, dendritic cells and augment the cytolytic activity of CD8$^+$ cytotoxic T lymphocytes and NK cells (Id.), whereas $T_H2$ cells provide efficient help for B cells and they also mediate allergic responses due to the capacity of $T_H2$ cells to induce IgE isotype switching and differentiation of B cells into IgE secreting cell (De Vries and Punnonen (1996) In *Cytokine regulation of humoral immunity: basic and clinical aspects.* Eds. Snapper, C. M., John Wiley & Sons, Ltd., West Sussex, UK, pp. 195–215.

Figure 13:
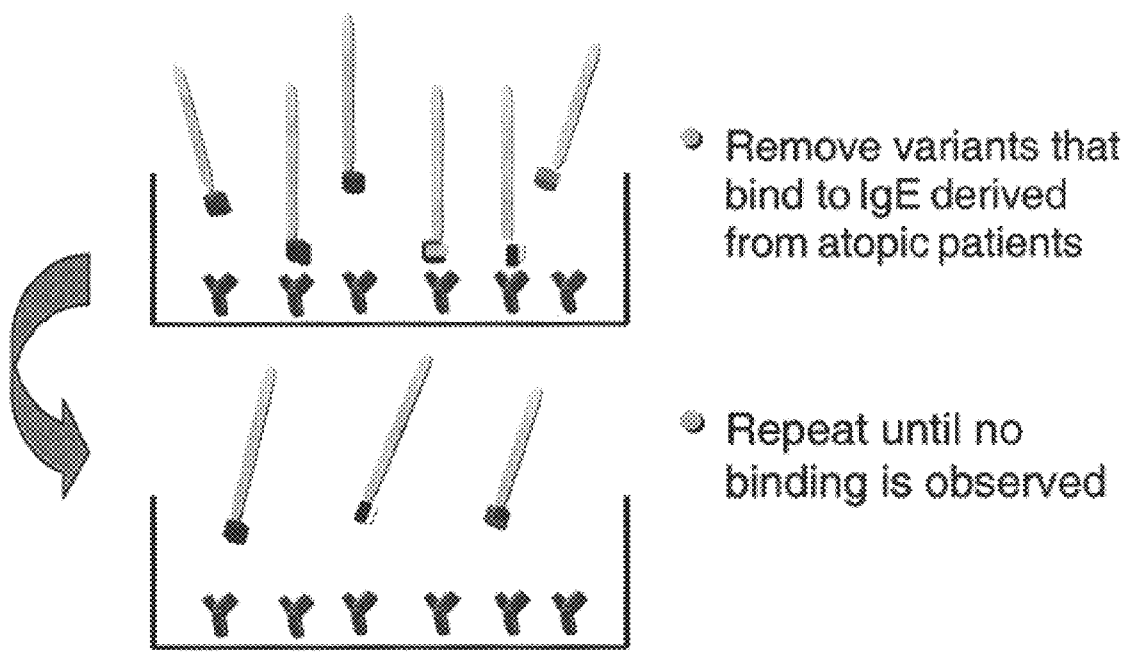
FIG. 13 shows a method for using phage display to obtain recombinant allergens that are not bound by pre-existing IgE.

This Example describes methods to generate chimeric allergens that can broadly modulate allergic immune responses. This can be achieved by DNA shuffling of related allergen genes to generate chimeric genes. In addition, chimeric/mutated allergens are less likely to be recognized by preexisting IgE antibodies of the patients. Importantly, allergen variants that are not recognized by IgE antibodies can be selected using patient sera and negative selection (FIG. 13).

Figure 14:
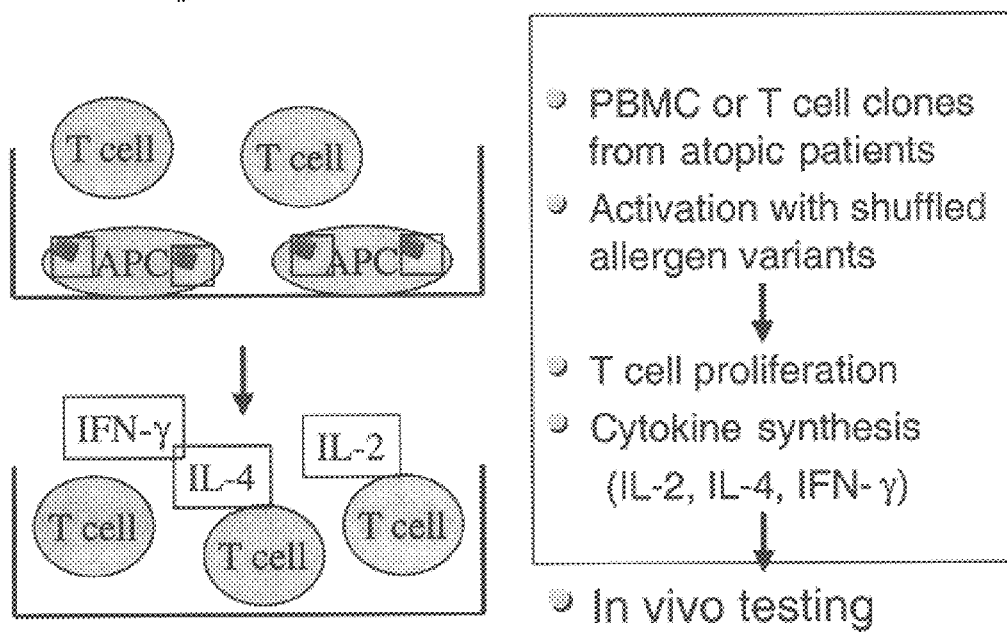
FIG. 14 shows a strategy for screening of recombinant allergens to identify those that are effective in activating TH cells. PBMC or T cell clones from atopic individuals are exposed to antigen-presenting cells that display the antigen variants obtained using the methods of the invention. To identify those allergen variants that are effective in activating T cells, the cultures are tested for induction of T cell proliferation or for a pattern of cytokine synthesis that is indicative of the particular type of T cell activation that is desired. If desired, the allergen variants that test positive in the in vitro assay can be subjected to in vivo testing.

As one example, chimeric allergen variants of Der p2, Der f2, Tyr p2 Lep d2 and Gly d2 allergens are generated. These house dust mite allergens are very common in exacerbating allergic and asthmatic symptoms, and improved means to downregulate such allergic immune responses are desired. House dust mites can be used as sources of the genes. The corresponding genes are shuffled using family DNA shuffling and a shuffled library is generated. Phage display is used to exclude allergens that are recognized by antibodies from allergic individuals. It is particularly important is to exclude variants that are recognized by IgE antibodies. Phage expressing the allergen variants are incubated with pools of sera derived from allergic individuals. The phage that are recognized by IgE antibodies are removed, and the remaining allergens are further tested in vitro and in vivo for their capacity to activate allergen-specific human T cells (FIG. 14). Because immunotherapy of allergy is believed to function through induction of a dominating $T_H1$ response as compared to allergic $T_H2$ response, efficient T cell activation and induction of a $T_H1$ type response by allergen variants is used as a measure of the efficacy of the allergens to modulate allergic T cell responses.

The optimal allergen variants are then further tested in vivo by studying skin responses after injections to the skin. A strong inflammatory response around the injection site is an indication of efficient T cell activation, and the allergen variants that induce the most efficient delayed type T cell response (typically observed 24 hours after the injection) are the best candidates for further studies in vivo to identify allergens that effectively downregulate allergic immune responses. Accordingly, these allergen variants re analyzed for their capacity to inhibit allergic responses in allergic, atopic and asthmatic individuals. The screening of allergen variants is further illustrated in FIG. 13 and FIG. 14.

Example 12

Evolution of Cancer Antigens that Induce Efficient Anti-tumor Immune Responses Several cancer cells express antigens that are present at significantly higher levels on the malignant cells than on other cells in the body. Such antigens provide excellent targets for preventive cancer vaccines and immunotherapy of cancer. The immunogenicity of such antigens can be improved by DNA shuffling. In addition, DNA shuffling provides means to improve expression levels of cancer antigens.

This Example describes methods to generate cancer antigens that can efficiently induce anti-tumor immune responses by DNA shuffling of related cancer antigen genes. Libraries of shuffled melanoma-associated glycoprotein (gp100/pmel 17) genes (Huang et al. (1998) *J. Invest. Dermatol.* 111: 662–7) are generated. The genes can be isolated from melanoma cells obtained from various patients, who may have mutations of the gene, increasing the diversity in the starting genes. In addition, a gp100 gene can be isolated from other mammalian species to further increase the diversity of starting genes. A typical method for the isolation of the genes is RT-PCR. The corresponding genes are shuffled using single gene DNA shuffling or family DNA shuffling and a shuffled library is generated.

Figure 15:
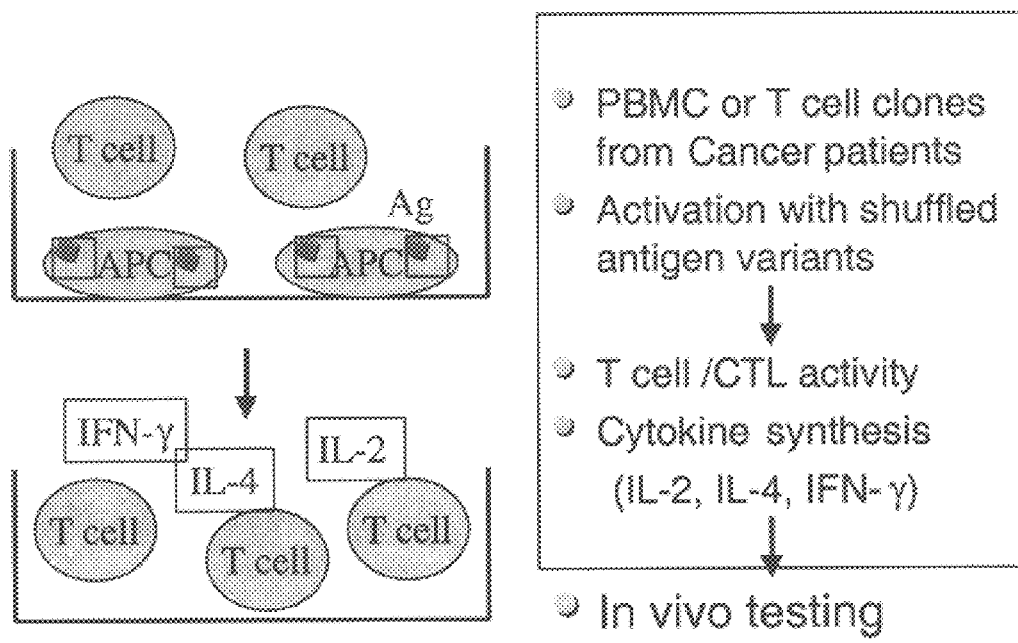
FIG. 15 shows a strategy for screening of recombinant cancer antigens to identify those that are effective in activating T cells of cancer patients.
Figure 16A:
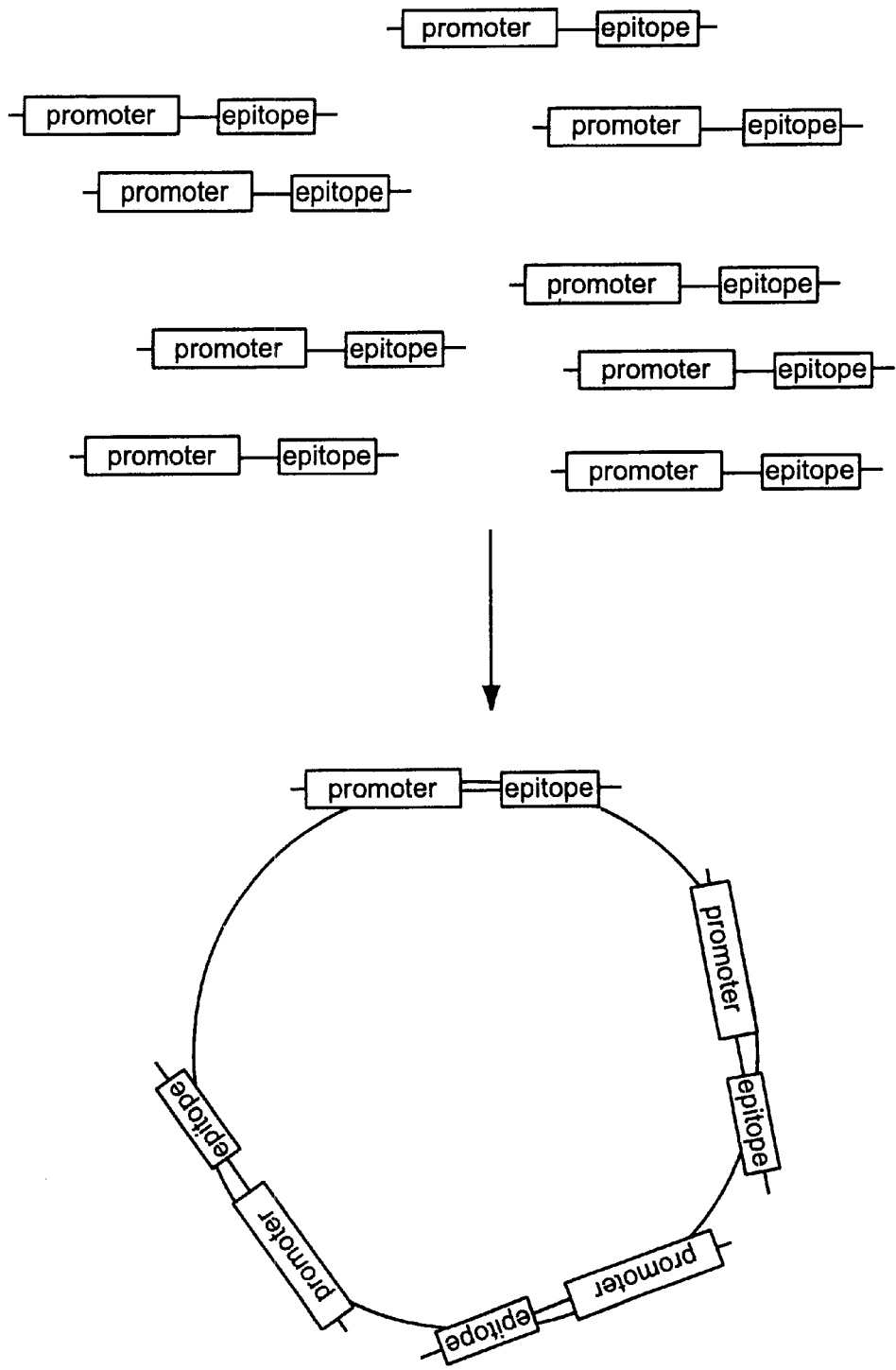
FIG. 16A and FIG. 16B show two different strategies for generating vectors that contain multiple T cell epitopes obtained, for example, by DNA shuffling.
Figure 16B:
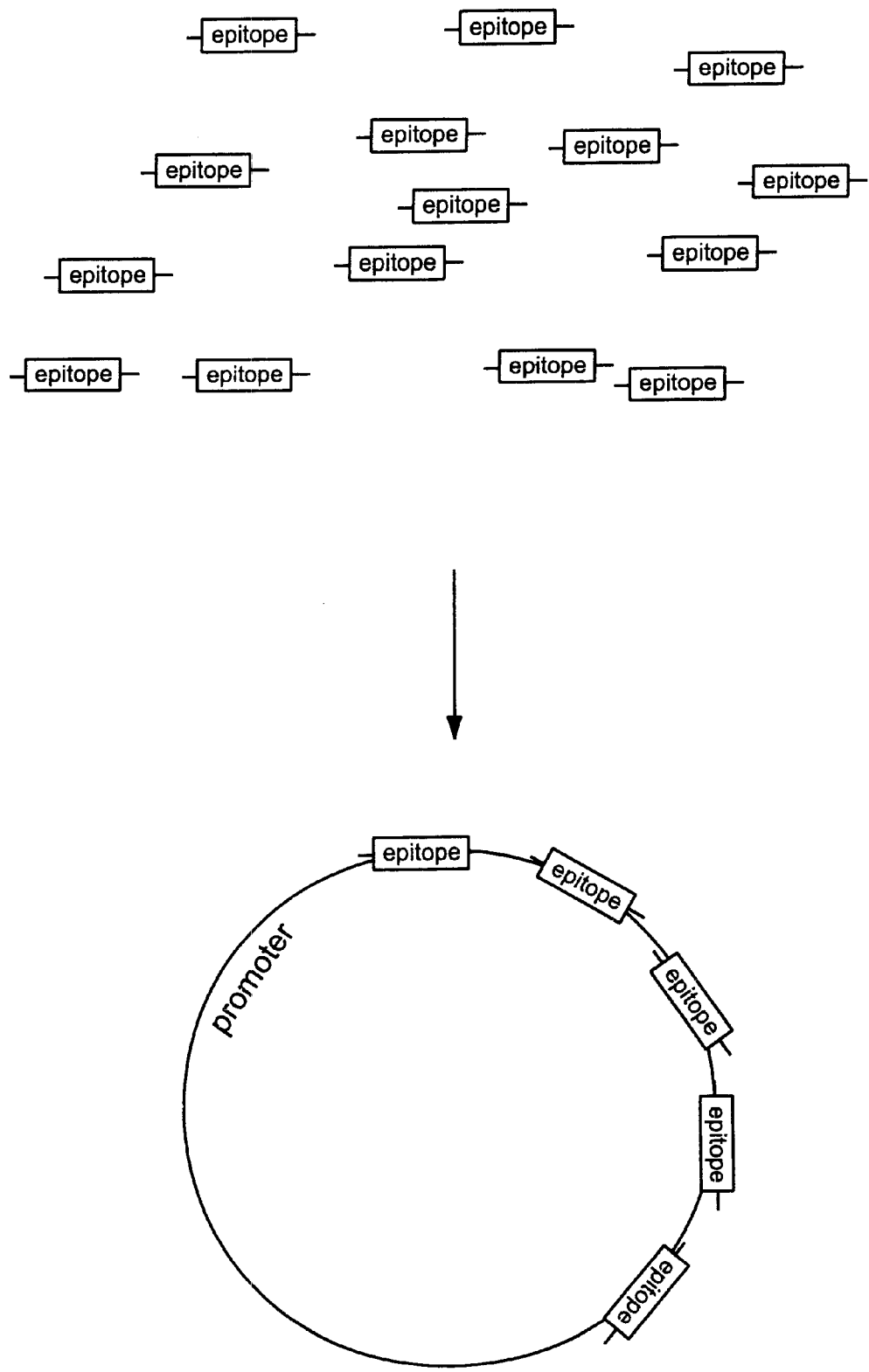

The shuffled gp100 variants, either pools or individual clones, are subsequently injected into test animals, and the immune responses are studied (FIG. 15). The shuffled antigens are either expressed in *E. coli* and recombinant, purified proteins are injected, or the antigen genes are used as components of DNA vaccines. The immune response can be analyzed for example by measuring anti-gp100 antibodies, as previous studies indicate that the antigen can induce specific antibody responses (Huang et al., supra. ). Alternatively, the test animals that can be challenged by malignant cells expressing gp100. Animals that have been efficiently immunized will generate cytotoxic T cells specific for gp100 and will survive the challenge, whereas in non-immunized or poorly immunized animals the malignant cells will efficiently grow eventually resulting in lethal expansion of the cells. Furthermore, antigens that induce cytotoxic T cells that have the capacity to kill cancer cells can be identified by measuring the capacity of T cells derived from immunized animals to kill cancer cells in vitro. Typically the cancer cells are first labeled with radioactive isotopes and the release of radioactivity is an indication of tumor cell killing after incubation in the presence of T cells from immunized animals. Such cytotoxicity assays are known in the art.

The antigens that induce highest levels of specific antibodies and/or can protect against the highest number of malignant cells can be chosen for additional rounds of shuffling and screening. Mice are useful test animals because large numbers of antigens can be studied. However, monkeys are a preferred test animal, because the MHC molecules of monkeys are very similar to those of humans.

To screen for antigens that have optimal capacity to activate antigen-specific T cells, peripheral blood mononuclear cells from previously infected or immunized humans individuals can be used. This is a particularly useful method, because the MHC molecules that will present the antigenic peptides are human MHC molecules. Shuffled cancer antigens that induce cytotoxic T cells that have the capacity to kill cancer cells can be identified by measuring the capacity of T cells derived from immunized animals to kill cancer cells in vitro. Typically the cancer cells are first labeled with radioactive isotopes and the release of radioactivity is an indication of tumor cell killing after incubation in the presence of T cells from immunized animals. Such cytotoxicity assays are known in the art.

Example 13

Evolution of Autoantigens that Induce Efficient Immune Responses

Autoimmune diseases are characterized by an immune response directed against self antigens expressed by the host. Autoimmune responses are generally mediated by $T_H1$ cells that produce high levels of IL-2 and IFN-gamma. Vaccines that can direct autoantigen specific T cells towards $T_H2$ phenotype producing increased levels of IL-4 and IL-5 would be beneficial. For such vaccines to work, the vaccine antigens have to be able to efficiently activate specific T cells. DNA shuffling can be used to generate antigens that have such properties. To optimally induce $T_H2$ cell differentiation it may be beneficial to coadminister cytokines that have been shown to enhance $T_H2$ cell activation and differentiation, such as IL-4 (Racke et al. (1994) *J. Exp. Med.* 180: 1961–66).

This Example describes methods for generating autoantigens that can efficiently induce immune responses. DNA shuffling is performed on related autoantigen genes. For example, libraries of shuffled myelin basic proteins, or fragments thereof (Zamvil and Steinman (1990) *Ann. Rev. Immunol.* 8: 579–621); Brocke et al. (1996) *Nature* 379: 343–46) are generated. MBP is considered to be an important autoantigen in patients with multiple sclerosis (MS). The genes encoding MBP from at least bovine, mouse, rat, guinea pig and human have been isolated providing an excellent starting point for family shuffling. A typical method for the isolation of the genes is RT-PCR. The shuffled MBP variants, either pools or individual clones, are subsequently injected into test animals, and the immune responses are studied. The shuffled antigens are either expressed in *E. coli* and recombinant, purified proteins are injected, or the antigen genes are used as components of DNA vaccines or viral vectors. The immune response can be analyzed for example by measuring anti-MBP antibodies by ELISA. Alternatively, the lymphocytes derived from immunized test animals are activated with MBP, and the T cell proliferation or cytokine synthesis is studies. A sensitive assays for cytokine synthesis is ELISPOT (McCutcheon et al. (1997) *J. Immunol. Methods* 210: 149–66). Mice are useful test animals because large numbers of antigens can be studied. However, monkeys are a preferred test animal, because the MHC molecules of monkeys are very similar to those of humans.

To screen for antigens that have optimal capacity to activate MBP specific T cells peripheral blood mononuclear cells from patients with MS can also be used. This is a particularly useful method, because the MHC molecules that will present the antigenic peptides are human MHC molecules. Shuffled antigens that activate MBP specific T cells can be identified by measuring the capacity of T cells derived from MS patients to proliferate or produce cytokines upon culture in the presence of the antigen variants. Such assays are known in the art. One such assay is ELISPOT (McCutcheon et al., supra. ). An indication of the efficacy of an MBP variant to activate specific T cells is also the degree of skin inflammation when the antigen is injected into the skin of a patient with MS. Strong inflammation is correlated with strong activation of antigen-specific T cells. Improved activation of MBP specific T cells, particularly in the presence of IL-4, is likely to result in enhanced $T_H2$ cell responses, which are beneficial in the treatment of MS patients.

Example 14

Method of Optimizing the Immunogenicity of Hepatitis B Surface Antigen

This Example describes methods by which the envelope protein sequence of the hepatitis B virus can be evolved to provide a more immunogenic surface antigen. Such a protein is important for vaccination of low responders and for immunotherapy of chronic hepatitis B.

Background

Current HBV vaccines (Merck, SKB) are based on the immunogenicity of the viral envelope protein and contain the Major (or Small) form of the envelope protein produced as particles in yeast. These particles induce antibodies to the major surface antigen (HBsAg) which can protect against infection when antibody levels are at least 10 milli-International Units per milliliter (mU/ml). These recombinant protein preparations are not capable of inducing humoral immunity in chronic carriers (some 300 million cases worldwide) the induction of which would be important to control virus spread. Moreover, certain individuals respond poorly to the vaccine (up to 30–50% of vaccinees in some groups) and do not develop protective levels of antibody. The inclusion of the natural epitope sequences contained in the Middle or Large forms of the viral envelope protein has been used as a method to increase the immunogenicity of vaccine preparations. An alternative method is to introduce new (i.e., not present in the natural virus sequence) helper T-cell epitopes into the HBsAg sequence using DNA shuffling technology.

Method

DNA sequences of HBsAg from different subtypes of HBV (e.g., ayw and adr) and the related woodchuck hepatitis virus are prepared for shuffling. Comparison of the genes encoding these proteins suggests that recombination would occur at least ten times within 850 base pairs when shuffling the ayw and woodchuck hepatitis virus (WHV) DNA sequences. Nucleotide and amino acid sequences of portions of different subtypes of HBV are shown in FIG. 17.

The sequence of the main HBsAg B-cell antigenic site (the "a" epitope) can be retained in the protein sequence by including the coding sequences of the external "a" loop in the final protein preparation. Peptide analogue(s) for the "a" epitope of HBsAg have been described (Neurath et al. (1984) *J. Virol. Methods* 9:341–346), and the immunogenicity of the "a" epiiope has been demonstrated (Bhatnagar et al. (1982) *Proc. Nat'l. Acad. Sci. USA* 79: 4400–4404). HBsAg and WHsAg share the major "a" determinant, and chimps can be protected by both antigens (Cote et al. (1986) *J. Virol.* 60: 895–901). Likewise, important CTL epitopes can be included in the protein in a defined way.

One can also easily introduce B or T (helper or CTL) epitopes from other antigens into the shuffled HBsAg sequence. This may focus the immune response to certain epitopes, independent of other potentially dominant epitopes from the same protein. Furthermore, the availability of the "a" loop on the HBsAg may provide a region of the envelope protein into which other artificial antigens or mimotopes could be included.

In all cases where a novel HBV envelope sequence is prepared to include a specific epitope (from HBV, another pathogen or a tumor cell), shuffling of the surrounding sequences in the HBV envelope will serve to optimize expression of the protein and help to ensure that the immune response is directed to the desired epitope.

Several methods of analyzing and utilizing shuffled HBsAg sequences are described below.

A. Modulating Expression Levels of HBsAg

Shuffled HBsAg sequences are introduced into cells in culture and the ability to direct expression of secreted HBsAg (measured with clinical kits for HBsAg expression) is evaluated. This can be used to identify shuffled HBsAg sequences which exhibit optimized HBsAg expression levels. Such coding sequences are particularly interesting for DNA vaccination.

B. Circumventing Low Responsiveness to the HBsAg

Shuffled HBsAg sequences are evaluated for their ability to induce an immune response to the clinically relevant HBsAg epitopes. This can be done using mice of the H-2s and H-2f haplotypes, which respond poorly or not at all to HBsAg protein immunization. In these experiments, one can verify that antibodies are generated to the main "a" epitope in the S protein, and a second protective epitope in the PreS2 region (a linear sequence).

The PreS2 and S coding sequences for the envelope protein (HBsAg) from the HBV ayw subtype (plasmid pCAG-M-Kan; Whalen) and the WHV (plasmid pWHV8 from ATCC) are amplified from the two plasmids by PCR and shuffled. Examples of suitable primers for PCR amplification are shown in FIG. 18. The shuffled library of sequences is cloned into an HBsAg-expression vector and individual colonies are chosen for preparation of plasmid DNA. The DNA is administered to the test animals and vectors which induce the desired immune response are identified and recovered.

C. Presentation of Natural HBsAg CTL Epitopes by Evolved HBsAg Proteins

This example describes methods of using the evolved HBsAg protein to present natural HBsAg CTL epitopes. Shuffling is used to increase overall immunogenicity of the HBsAg protein, as discussed above. However, some of the evolved HBsAg sequences are replaced with class I or class II epitope sequences from the natural HBsAg protein in order to stimulate immunoreactivity specifically to these natural viral epitopes. Alternatively, the natural viral epitopes can be added to the evolved protein without loss of immunogenicity of the evolved HBsAg.

D. Expression of Tumor-derived CTL Epitopes by Evolved HBsAg Proteins

This example describes methods of using the evolved HBsAg protein is used to express tumor-derived CTL epitopes. The overall immunogenicity of the HBsAg protein is increased by shuffling. However, some of the evolved HBsAg sequences are replaced with class I or class II epitope sequences from tumor cells in order to stimulate immunoreactivity specifically to these natural viral epitopes. Alternatively, the tumor cells epitopes can be added to the evolved protein without loss of immunogenicity of the evolved HBsAg.

E. Expression of Mimotope Sequences by the HBsAg

This example describes the use of an evolved HBsAg protein for expression of mimotope sequences. Again, the evolved HBsAg protein is used to increase overall immunogenicity of the protein. However, some of the evolved HBsAg sequences are replaced with mimotope sequences to stimulate immunoreactivity specifically to the natural sequence which cross reacts with the mimotope. Alternatively, the mimotope sequences can be added to the evolved protein without loss of immunogenicity of the evolved HBsAg.

Example 15

Fusion Proteins of the HBsAg Polypeptide and HIV gp120 Protein

This Example describes the preparation of fusion proteins ("chimeras") formed from the HBsAg polypeptide and the extracellular fragment gp120 of the HIV envelope protein, and their use as vaccines.
Background When used as a vaccine, recombinant monomeric gp120 has failed to induce antibodies that have strong neutralizing activity with primary isolates of the HIV virus. It has been suggested that oligomeric forms of the HIV envelope protein which expose certain regions of the tertiary structure would be better able to elicit virus-neutralizing antibodies (Parrin et al. (1997) *Immunol. Lett.* 57: 105–1 12; VanCott et al. (1997) *J. Virol.* 71: 4319–4330;

In this Example, DNA shuffling is applied to this problem, in order to obtain gp120 polypeptides which adopt conformations slightly different from those of previous preparations of recombinant gp120. To allow the individual gp120 molecules to interact as oligomers, a fusion is prepared between gp120 sequences (on the N-terminus of the fusion) and HBsAg sequences (on the C-terminal of the fusion).

The N-terminal peptide sequence of the S region of the HBsAg polypeptide is a transmembrane structure which is locked into the membrane of the endoplasmic reticulum. The actual N-terminus of the S region as well as the preS2 sequences are located in the lumenal part of the ER. They are found on the outside of the final HBsAg particles. By placing the gp120 sequences on the N-terminus of the HBsAg preS2 or S sequences, the gp120 sequences are also located on the outside of the particles. The gp120 molecules can thus be brought together in three-dimensional space to interact as in the virus.

Since the exact conformation of the final chimera which will have the most appropriate immunogenicity cannot be predicted, DNA shuffling is employed. The sequences of the HBsAg polypeptide, which functions as a scaffold, and of gp120 are both shuffled. Screening of the shuffled products can be performed by ELISA assay using antibodies (polyclonal or monoclonal) which have previously been determined to have virus neutralizing activity.
Method The sequences encoding the gp120 fragment of the HIV envelope protein are preferably prepared as a synthetic gene to include codons which are optimal for gene expression in mammals. The gp120 sequence will typically include a signal sequence on its N-terminal end.

The gp120 sequences are inserted into the preS2 region of an HBsAg-expressing plasmid. In the preS2 region of the plasmid pMKan and its derivatives, an EcoRI site and an XhoI site are available for cloning. The gp120 sequences can be inserted between these two sites, which brings the gp120 closer to the start of the S coding sequences, or into the EcoRl site alone, which leaves a spacer sequence of about 50 amino acids between the gp120 sequence and the start of the S region of the HBsAg. These two different cloning strategies will give rise to chimeric molecules in which the gp120 sequences are located at different distances from the transmembrane region of the HBsAg sequence. This may be advantageous in allowing the gp120 sequences to adopt conformations which are more suitable immunogens than monomeric gp120.

DNA shuffling of the entire chimeric sequence is carried out. Family shuffling is preferred; this involves the preparation of several gp120-HBsAg fusion proteins in which different gp120 and HBsAg (or WHV) sequences are used. An alignment of HBsAg nucleotide sequences is shown in FIG. 19. After shuffling of the different sequences, the products are cloned into an expression vector such as pMKan. Pools of clones from the library of shuffled products are transfected into cultured cells and the secretion of chimeric proteins is assayed with broadly reactive antibodies to gp120. Positive clones can be further evaluated with particular antibodies that have demonstrated HIV neutralizing activity, for example the anti-CD4 binding domain recombinant human monoclonal antibody, IgGlb12 (Kessler et al. (1997) *AIDS Res. Hum. Retroviruses.* 1: 13: 575–582; Roben et al. (1994) *J. Virol.* 68: 4821–4828). Candidate clones can then be used to immunize mice and the antiserum obtained is evaluated for HIV virus-neutralizing activity in in vitro assays.

Figure 20:
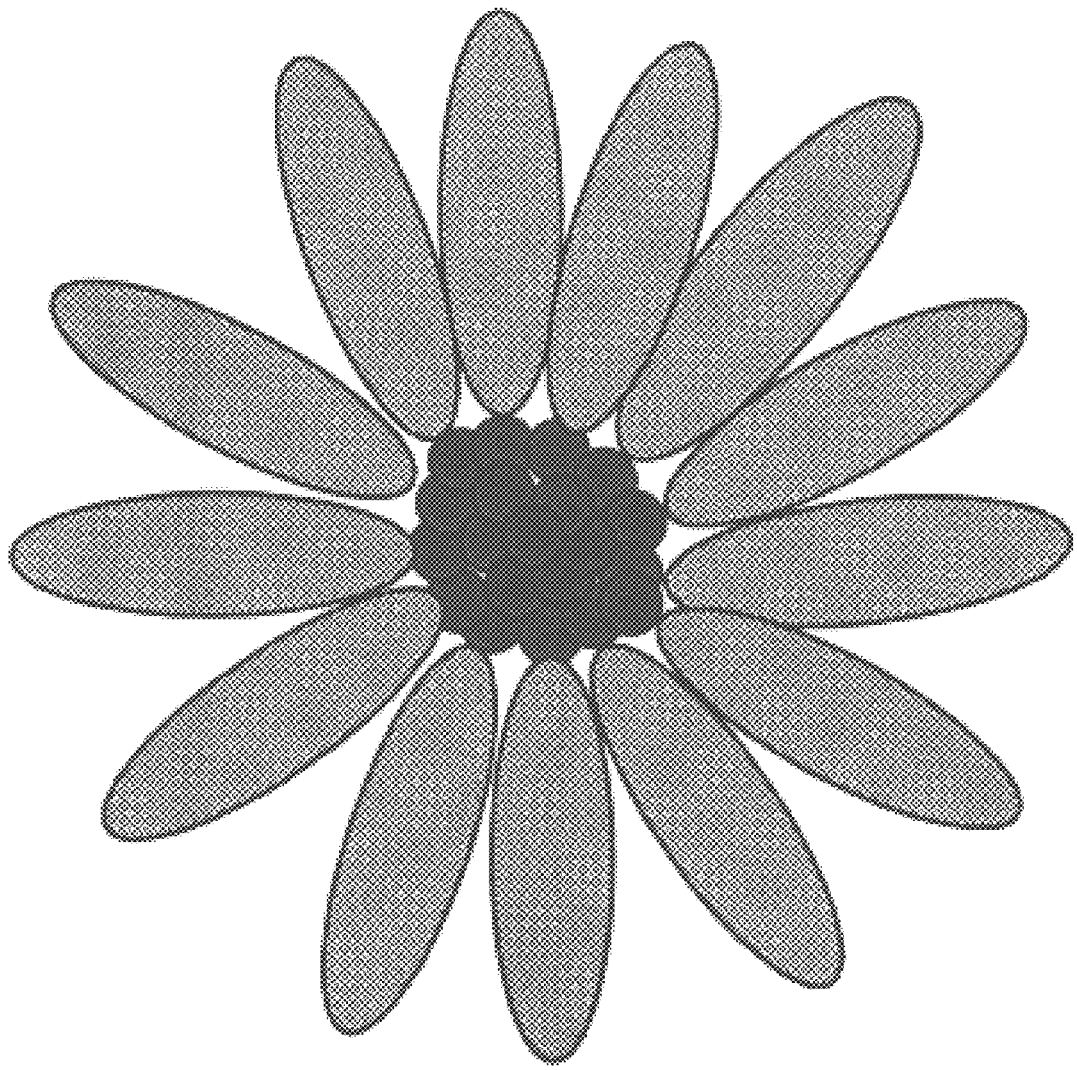
FIG. 20 shows a diagram of multimeric particles that assemble when an appropriate number of chimeric polypeptides and native HBsAg S monomers are mixed.

Because the gp120 molecule (approx. 1100 amino acids) is larger in size than the monomeric HBsAg preS2+S protein (282 amino acids), it is likely that not every HBsAg monomer in an aggregated particle will contain a gp120 sequence. Internal initiation of protein synthesis can take place on the HBsAg coding sequences at the initiator methionine that marks the beginning of the S region. Thus, the chimeric molecule (which contains the gp120 sequences) will be mixed in the cell with the S region and the multimeric particles should assemble with an appropriate number of chimeric polypeptides and native HBsAg S monomers. Alternatively, an S-expressing plasmid can be mixed with the plasmid expressing the chimera, or a single plasmid which expresses the chimera and the S form can be constructed. A diagram of the resulting particles is shown in FIG. 20.

Example 16

DNA Shuffling of HSV-1 and HSV-2 Glycoproteins B and/or D as Means to Induce Enhanced Protective Immune Responses This Example describes the use of DNA shuffling to obtain HSV glycoprotein B (gB) and glycoprotein D (gD) polypeptides that exhibit improved ability to induce protective immune responses upon administration to a mammal. Epidemiological studies have shown that prior infections with HSV-1 give partial protection against infections with HSV-2, indicating existence of cross-reactive immune responses. Based on previous vaccination studies, the main immunogenic glycoproteins in HSV appear to be gB and gD, which are encoded by 2.7 kb and 1.2 kb genes, respectively. The gB and gD genes of HSV-1 are about 85% identical to the corresponding gene of HSV-2, and the gB genes of each share little sequence identity with the gD genes. Baboon HSV-2 gB is appr. 75% identical to human HSV-1 or –2 gB, with rather long stretches of almost 90% identity. In addition, 60–75% identity is found in portions of the genes of equine and bovine herpesviruses.

Family shuffling is employed using as substrates nucleic acids that encode gB and/or gD from HSV-1 and HSV-2. Preferably, homologous genes are obtained from HSVs of various strains. An alignment of gD nucleotide sequences from HSV-1 and two strains of HSV-2 is shown in FIG. 7. Antigens encoded by the shuffled nucleic acids are expressed and analyzed in vivo. For example, one can screen for improved induction of neutralizing antibodies and/or CTL responses against HSV-1/HSV-2. One can also detect protective immunity by challenging mice or guinea pigs with the viruses. Screening can be done using pools or individuals clones.

Example 17

Evolution of HIV Gp120 Proteins for Induction of Broad Spectrum Neutralizing Ab Responses This Example describes the use of DNA shuffling to generate immunogens that crossreact among different strains of viruses, unlike the wild-type immunogens. Shuffling two kinds of envelope sequences can generate immunogens that induce neutralizing antibodies against a third strain.

Antibody-mediated neutralization of HIV-1 is strictly type-specific. Although neutralizing activity broadens in infected individuals over time, induction of such antibodies by vaccination has been shown to be extremely difficult. Antibody-mediated protection from HIV-1 infection in vivo correlates with antibody-mediated neutralization of virus in vitro.

FIG. 8 illustrates the generation of libraries of shuffled gp120 genes. gp120 genes derived from HIV-1DH12 and HIV-1IIIB(NL43) are shuffled. The chimeric/mutant gp120 genes are then analyzed for their capacity to induce antibodies that have broad spectrum capacity to neutralize different strains of HIV. Individual shuffled gp120 genes are incorporated into genetic vaccine vectors, which are then introduced to mice by injection or topical application onto the skin. These antigens can also be delivered as purified recombinant proteins. The immune responses are measured by analyzing the capacity of the mouse sera to neutralize HIV growth in vitro. Neutralization assays are performed against HIV-1DHI2, HIV-1IIIB and HIV-189.6. The chimeras/mutants that demonstrate broad spectrum neutralization are chosen for further rounds of shuffling and selection. Additional studies are performed in monkeys to illustrate the capacity of the shuffled gp120 genes to provide protection for subsequent infection with immunodeficiency virus.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

---

What is claimed is:

1. A recombinant multivalent antigenic polypeptide that comprises multiple non-contiguous subsequences of at least a first antigenic polypeptide of a first flavivirus or alphavirus and multiple noncontiguous subsequences of at least a second antigenic polypeptide of a second flavivirus or alphavirus, each subsequence being positioned relative to its position in the first or second antigenic polypeptide,
wherein the recombinant multivalent antigenic polypeptide induces an immune response against each of the first and second antigenic polypeptides that is greater than the immune response induced by any one of the first and second antigenic polypeptides against any other of the first and second antigenic polypeptides.

2. The multivalent antigenic polypeptide of claim 1, wherein the multivalent antigenic polypeptide comprises multiple non-contiguous subsequences of at least a third antigenic polypeptide of a third flavivirus or alphavirus.

3. The multivalent antigenic polypeptide of claim 1, wherein at least the first and second antigenic polypeptides are from a virus selected from the group consisting of a Venezuelan equine encephalitis virus or a related alphavirus, a virus of the Japanese encephalitis virus complex, a virus of the tick-borne encephalitis virus complex, a Dengue virus, a yellow fever virus, a St. Louis encephalitis virus, and a Murray Valley encephalitis virus.

4. The multivalent antigenic polypeptide of claim 3, wherein at least the first and second antigenic polypeptides are envelope proteins.

5. The multivalent antigenic polypeptide of claim 1, wherein at least the first and second antigenic polypeptides comprise different serotypes of a flavivirus or alphavirus.

6. The multivalent antigenic polypeptide of claim 1, wherein at least the first and second antigenic polypeptides comprise different species of a flavivirus or alphavirus.

7. The multivalent antigenic polypeptide of claim 1, wherein the multivalent antigenic polypeptide induces an immune response to the first and second antigenic polypeptides that is greater than the immune response induced by any one of the first and second antigenic polypeptides against any of the first and second antigenic polypeptides.

8. The multivalent antigenic polypeptide of claim 1, wherein the multivalent antigenic polypeptide induces an immune response that is cross reactive against at least the first and second antigenic polypeptides and at least a third antigenic polypeptide of a flavivirus or alphavirus.

9. The multivalent antigenic polypeptide of claim 1, wherein the multivalent antigenic polypeptide induces an immune response that is cross reactive against at least two different serotypes, strains, or species of a flavivirus or alphavirus.

10. The multivalent antigenic polypeptide of claim 9, wherein the multivalent antigenic polypeptide induces an immune response that is cross reactive against at least three different serotypes, strains, or species of a flavivirus or alphavirus, wherein at least the first and second antigenic polypeptides are from two of the three different serotypes, strains, or species.

11. The multivalent antigenic polypeptide of claim 9, wherein the multivalent antigenic polypeptide induces an immune response that protects against a disease condition caused by one or more of the two different serotypes, strains, or species.

12. A recombinant multivalent antigenic polypeptide comprising multiple non-contiguous subsequences of at least a first antigenic polypeptide of at least a first flavivirus or alphavirus and multiple non-contiguous subsequences of at least a second antigenic polypeptide of at least a second flavivirus or alphavirus, each subsequence being positioned relative to its position in the first or second antigenic polypeptide, wherein the recombinant multivalent antigenic polypeptide is prepared by the method comprising:

(1) recombining at least a first nucleic acid comprising a nucleotide sequence that encodes the first antigenic polypeptide and at least a second nucleic acid comprising a nucleotide sequence that encodes the second antigenic polypeptide, wherein at least the first and second nucleic acids differ from each other in two or more nucleotides, to produce a library of recombinant nucleic acids; and (2) screening the library of recombinant nucleic acids for at least one optimized recombinant nucleic acid that encodes a recombiant multivalent antigenic polypeptide that induces an imnmune response against each of the first and second flaviviruses or alphaviruses that is greater than the immune response induced by the first antigenic polypeptide against the second flavivirus or alphavirus and the immune response induced by the second antigenic polypeptide against the first flavivirus or alphavirus.

13. The recombinant multivalent antigenic polypeptide of claim 12, wherein the method further comprises:

(3) recombining at least one optimized recombinant nucleic acid with at least a third nucleic acid comprising a nucleotide sequence that encodes at least a third antigenic polypeptide of at least a third flavivirus or alphavirus, wherein the third nucleic acid is the same or different from the first and second nucleic acids, to produce a further library of recombinant nucleic acids;

(4) screening the further library of recombinant nucleic acids for at least one further optimized recombinant nucleic acid that encodes a recombinant multivalent antigenic polypeptide that induces an immune response against each of the first, second and third flaviviruses or alphaviruses that is greater than the immune response induced by (i) the first antigenic polypeptide against the second or third flavivirus or alphavirus, (ii) the second antigenic polypeptide against the first or third flavivirus or alphavirus, and (iii) the third antigenic polypeptide against the first or second flavivirus or alphavirus; and (5) repeating (3) and (4), as necessary, for a further optimized recombinant multivalent antigenic polypeptide that induces an immune response against each of the first, second and third flaviviruses or alphaviruses that is greater than the immune response induced by (i) the first antigenic polypeptide against the second or third flavivirus or alphavirus, (ii) the second antigenic polypeptide against the first or third flavivirus or alphavirus, and (iii) the third antigenic polypeptide against the first or second flavivirus or alphavirus.

14. The recombinant multivalent antigenic polypeptide of claim 12, wherein at least the first and second antigenic polypeptides comprise different serotypes of a flavivirus or alphavirus.

15. The recombinant multivalent antigenic polypeptide of claim 12, wherein at least the first and second antigenic polypeptides comprise different species or strains of a flavivirus or alphavirus.

16. The recombinant multivalent antigenic polypeptide of claim 14, wherein the recombinant multivalent antigenic polypeptide induces a neutralizing antibody response against at least one of the different serotypes.

17. The recombinant multivalent antigenic polypeptide of claim 12, wherein the first and second nucleic acids encode at least first and second antigenic polypeptides of at least one virus selected from the group consisting of a Venezuelan equine encephalitis virus or a related alphavirus, a virus of the Japanese encephalitis virus complex, a virus of the tick-borne encephalitis virus complex, a Dengue virus, a yellow fever virus, a St. Louis encephalitis virus, and a Murray Valley encephalitis virus.

18. The multivalent antigenic polypeptide of claim 1, wherein the multivalent antigenic polypeptide induces an immune response against each of the first and second flaviviruses or alphaviruses that is greater than the immune response induced by the first antigenic polypeptide against the second flavivirus or alphavirus and the immune response induced by the second antigenic polypeptide against the first flavivirus or alphavirus.

19. The multivalent antigenic polypeptide of claim 18, wherein the multivalent antigenic polypeptide induces an immune response against each of the first and second flaviviruses or alphaviruses that is greater than the immune response induced by the first or second antigenic polypeptide against the first or second flavivirus or alphavirus.

20. The multivalent antigenic polypeptide of claim 1, wherein the multivalent antigenic polypeptide induces production of neutralizing antibodies against each of the first and second antigenic polypeptides.

21. The multivalent antigenic polypeptide of claim 1, wherein the multivalent antigenic polypeptide induces production of neutralizing antibodies against each of the first and second flaviviruses or viruses.

22. The recombinant multivalent antigenic polypeptide of claim 12, wherein (2) comprises screening the library of recombinant nucleic acids for at least one optimized recombinant nucleic acid that encodes a recombinant multivalent antigenic polypeptide that induces an immune response against any of the first and second flavivirus or alphavirus that is greater than the immune response induced by any of the first and second antigenic polypeptides against any of the first and second flaviviruses or alphaviruses.

23. The recombinant multivalent antigenic polypeptide of claim 15, wherein the recombinant multivalent antigenic polypeptide induces a neutralizing antibody response against at least one of the different species or strains.

24. A recombinant multivalent antigenic polypeptide that comprises multiple non-contiguous subsequences of at least a first antigenic polypeptide of at least a first flavivirus or alphavirus, multiple non-contiguous subsequences of at least a second antigenic polypeptide of at least a second flavivirus or alphavirus, and multiple non-contiguous subsequences of at least a third antigenic polypeptide of at least a third flavivirus or alphavirus, each subsequence being positioned relative to its position in the first, second, or third antigenic polypeptide, wherein the recombinant multivalent antigenic polypeptide induces:

(i) an immune response against the first flavivirus or alphavirus that is greater than the immune response induced by the second or third antigenic polypeptide against the first flavivirus or alphavirus;

(ii) an immune response against the second flavivirus or alphavirus that is greater than the immune response induced by the first or third antigenic polypeptide against the second flavivirus or alphavirus; and (iii) an immune response against the third flavivirus or alphavirus that is greater than the immune response induced by the first or second antigenic polypeptide against the third flavivirus or alphavirus.

25. The multivalent antigenic polypeptide of claim 24, wherein the multivalent antigenic polypeptide induces an immune response against any of the first, second, or third flavivirus or alphavirus that is greater than the immune response induced by any of the first, second, or third antigenic polypeptide against any of the first, second, or third flavivirus or alphavirus.

26. The multivalent antigenic polypeptide of claim 25, wherein the multivalent antigenic polypeptide induces production of neutralizing antibodies against one or more of the first, second, and third flaviviruses or alphaviruses.

27. A multivalent antigenic polypeptide comprising multiple non-contiguous subsequences of a first antigenic polypeptide of a dengue-1 virus multiple non-contiguous subsequences of a second antigenic polypeptide of a dengue-2 virus, multiple non-contiguous subsequences of a third antigenic polypeptide of a dengue-3 virus, and multiple non-contiguous subsequences of a fourth antigenic polypeptide of a dengue-4 virus, each subsequence being positioned relative to its position in the first, second, third, or fourth antigenic polypeptide, wherein the multivalent antigenic polypeptide induces an immune response against each of a dengue-1 virus, dengue-2 virus, dengue-3 virus, and dengue-4 virus that is greater than:

(i) the immune response induced by the first antigenic polypeptide against a dengue-2 virus, dengue-3 virus, or dengue-4 virus;

(ii) the immune response induced by the second antigenic polypeptide against a dengue-1 virus, dengue-3 virus, or dengue-4 virus;

(iii) the immune response induced by the third antigenic polypeptide against a dengue-1 virus, dengue-2 virus, or dengue-4 virus; and (iv) the immune response induced by the fourth antigenic polypeptide against a dengue-1 virus, dengue-2 virus, or dengue-3 virus.

28. The multivalent antigenic polypeptide of claim 27, wherein the multivalent antigenic polypeptide induces an immune response against each of a dengue-1 virus, dengue-2 virus, dengue-3 virus, and dengue-4 virus that is greater than the immune response induced by any of the first, second, third and fourth antigenic polypeptides against any of dengue-1 virus, dengue-2 virus, dengue-3 virus, or dengue-4 virus.

29. The multivalent antigenic polypeptide of claim 27, wherein the multivalent antigenic polypeptide induces production of neutralizing antibodies against at least one of a dengue-1 virus, dengue-2 virus, dengue-3 virus, and dengue-4 virus.

30. The multivalent antigenic polypeptide of claim 27, wherein each of the first, second, third, and fourth antigenic polypeptides comprises an envelope protein, a premembrane protein, or both an envelope protein and a premembrane protein.

31. A chimeric dengue virus polypeptide comprising multiple non-contiguous subsequences of an envelope protein of a dengue-1 virus, multiple non-contiguous subsequences of an envelope protein of a dengue-2 virus, multiple non-contiguous subsequences of an envelope protein of a dengue-3 virus, and multiple non-contiguous subsequences of an envelope protein of a dengue-4 virus, each subsequence being positioned relative to its position in the respective envelope protein, wherein the chimeric dengue virus polypeptide induces production of neutralizing antibodies against each of dengue-1 virus, dengue-2 virus, dengue-3 virus, and dengue-4 virus.

32. The multivalent antigenic polypeptide of claim 24, wherein the multivalent antigenic polypeptide is present as a component of a virus or a viral vector.

33. The multivalent antigenic polypeptide of claim 27, wherein the multivalent antigenic polypeptide is present as a component of a virus or a viral vector.

34. The chimeric dengue virus polypeptide of claim 31, wherein the chimeric dengue virus polypeptide is present as a component of a virus or a viral vector.

35. A composition comprising the recombinant multivalent antigenic polypeptide of claim 1 and a carrier.

36. A composition comprising the multivalent antigenic polypeptide of claim 27 and a carrier.

37. A composition comprising the chimreric dengue virus polypeptide of claim 31 and a carrier.

38. The multivalent antigenic polypeptide of claim 4, wherein the first and second flaviviruses or alphaviruses are different serotypes, strains, or species.

39. The multivalent antigenic polypeptide of claim 7, wherein the first and second flaviviruses or alphaviruses are different serotypes, strains, or species, and at least the first and second antigenic polypeptides comprise envelope proteins.

40. The multivalent antigenic polypeptide of claim 24, wherein the first and second flaviviruses or alphaviruses are different serotepes, strains, or species, and at least the first and second antigenic polypeptides comprise envelope proteins.

41. The multivalent antigenic polypeptide of claim 25, wherein the first and second flaviviruses or alphaviruses are different serotypes, strains, or species, and at least the first and second antigenic polypeptides comprise envelope proteins.

42. A chimeric flavivirus or alphavirus polypeptide comprising multiple non-contiguous subsequences of an envelope protein of at least a first flavivirus or alphavirus, multiple non-contiguous subsequences of an envelope protein of at least a second flavivirus or alphavirus, and multiple non-contiguous subsequences of an envelope protein of at least a third flavivirus or alphavirus, each subsequence being positioned relative to its position in the respective envelope protein, wherein the chimeric flavivirus or alphavirus polypeptide induces production of neutralizing antibodies against each of the first, second, and third flaviviruses or alphaviruses.

43. The chimeric flavivirus or alphavirus polypeptide of claim 42, wherein the chimeric flavivirus or alphavirus polypeptide is present as a component of a virus or a viral vector.

44. A chimeric antigenic polypeptide comprising multiple non-contiguous subsequences of at least a first antigenic polypeptide of at least a first flavivirus or alphavirus and multiple non-contiguous subsequences of at least a second antigenic polypeptide of at least a second flavivirus or alphavirus, each subsequence being positioned relative to its position in the respective antigenic polypeptide, wherein the chimeric antigenic polypeptide includes production of neutralizing antibodies against at least the first and second antigenic polypeptides or first and second flaviviruses or alphaviruses.

45. The chimeric antigenic polypeptide of claim 44, wherein at least the first and second antigenic polypeptides comprise different serotypes of a flavivirus or alphavirus.

46. The chimeric antigenic polypeptide of claim 45, wherein the chimeric antigenic polypeptide comprises multiple non-contiguous subsequences of at least a third antigenic polypeptide of at least a third flavivirus or alphavirus and induces production of neutralizing antibodies against at least the first, second, and third antigenic polypeptides or first, second, and third flaviviruses or alphaviruses.

47. The chimeric antigenic polypeptide of claim 46, wherein the chimeric antigenic polypeptide is present as a component of a virus or a viral vector.

* * * * *

SEQUENCE LISTING

<160> NUMBER OF SEQ ID NOS: 25

<210> SEQ ID NO 1
<211> LENGTH: 1185
<212> TYPE: DNA
<213> ORGANISM: Herpes Simplex Virus 1
<220> FEATURE:
<223> OTHER INFORMATION: glycoprotein D-1 (gD-1) from Herpes Simplex
      Virus 1 (HSV-1)

<400> SEQUENCE: 1

```
atgggggga ctgccgccag gttggggcc gtgattttgt ttgtcgtcat agtgggcctc      60 catgggtcc gcggcaaata tgccttggcg gatgcctctc tcaagatggc cgaccccaat     120
cgctttcgcg gcaaagacct tccggtcctg gaccagctga ccgaccctcc ggggtccgg    180 cgcgtgtacc acatccaggc gggcctaccg gacccgttcc agcccccag cctcccgatc     240 acggtttact acgccgtgtt ggagcgcgcc tgccgcagcg tgctcctaaa cgcaccgtcg     300
gaggcccccc agattgtccg cggggcctcc gaagacgtcc ggaaacaacc ctacaacctg     360
accatcgctt ggtttcggat gggaggcaac tgtgctatcc ccatcacggt catggagtac     420
accgaatgct cctacaacaa gtctctgggg gcctgtccca tccgaacgca gccccgctgg     480
aactactatg acagcttcag cgccgtcagc gaggataacc tggggttcct gatgcacgcc     540
cccgcgtttg agaccgccgg cacgtacctg cggctcgtga agataaacga ctggacggag     600
attacacagt ttatcctgga gcaccgagcc aagggctcct gtaagtacgc cctcccgctg     660
cgcatccccc cgtcagcctg cctctccccc caggcctacc agcagggggt gacggtggac     720
agcatcggga tgctgccccg cttcatcccc gagaaccagc gcaccgtcgc cgtatacagc     780
ttgaagatcg ccgggtggca cgggcccaag gccccataca cgagcaccct gctgccccg     840 gagctgtccg agaccccaa cgccacgcag ccagaactcg ccccggaaga ccccgaggat     900
tcggccctct tggaggaccc cgtggggacg gtggcgccgc aaatcccacc aaactggcac     960
atcccgtcga tccaggacgc cgcgacgcct taccatcccc cggccacccc gaacaacatg    1020
ggcctgatcg ccggcgcggt gggcggcagt ctcctggcag ccctggtcat tgcggaatt    1080
```

-continued

```
gtgtactgga tgcaccgccg cactcggaaa gccccaaagc gcatacgcct cccccacatc   1140
cgggaagacg accagccgtc ctcgcaccag cccttgtttt actag                   1185

<210> SEQ ID NO 2
<211> LENGTH: 1180
<212> TYPE: DNA
<213> ORGANISM: Herpes Simplex Virus 2
<220> FEATURE:
<223> OTHER INFORMATION: glycoprotein D-1 (gD-1) from Herpes Simplex
      Virus 2 (HSV-2)

<400> SEQUENCE: 2
atggggcgtt tgacctccgg cgtcgggacg gcggccctgc tagttgtcgc ggtgggactc     60
cgcgtcgtct gcgccaaata cgccttagca gacccctcgc ttaagatggc cgatcccaat    120
cgatttcgcg ggaagaacct tccggttttg gaccagctga ccgacccccc cggggtgaag    180
cgtgtttacc acattcagcc gagcctggag gacccgttcc agccccccag catcccgatc    240
actgtgtact acgcagtgct ggaacgtgcc tgccgcagcg tgctcctaca tgccccatcg    300
gaggcccccc agatcgtgcg cggggcttcg gacgaggccc gaaagcacac gtacaacctg    360
accatcgcct ggtatcgcat gggagacaat tgcgctatcc ccatcacggt tatggaatac    420
accgagtgcc cctacaacaa gtcgttgggg gtctgcccca tccgaacgca gccccgctgg    480
agctactatg acagctttag cgccgtcagc gaggataacc tgggattcct gatgcacgcc    540
cccgccttcg agaccgcggg tacgtacctg cggctagtga agataaacga ctggacggag    600
atcacacaat ttatcctgga gcaccgggcc cgcgcctcct gcaagtacgc tctccccctg    660
cgcatccccc cggcagcgtg cctcacctcg aaggcctacc aacagggcgt gacggtcgac    720
agcatcggga tgttaccccg ctttactccc gaaaaccagc gcaccgtcgc cctatacagc    780
ttaaaaatcg ccgggtggca cggccccaag cccccgtaca ccagcaccct gctgccgccg    840
gagctgtccg acaccaccaa cgccacgcaa cccgaactcg ttccggaaga ccccgaggac    900
tcggccctct tagaggatcc cgccgggacg gtgtcttcgc agatcccccc aaactggcac    960
atcccgtcga tccaggacgt cgcgccgcac cacgcccccg ccgccccagc caacccgggc   1020
ctgatcatcg gcgcgctggc cggcagtacc ctggcggcgc tggtcatcgg cggtattgcg   1080
ttttgggtac gccgccggcg ctcagtggcc cccaagcgcc tacgtctccc ccacatccgg   1140
gatgacgacg cgcccccctc gcaccagcca ttgttttact                         1180

<210> SEQ ID NO 3
<211> LENGTH: 1242
<212> TYPE: DNA
<213> ORGANISM: Herpes Simplex Virus 2
<220> FEATURE:
<223> OTHER INFORMATION: glycoprotein D-2 (gD-2) from Herpes Simplex
      Virus 2 (HSV-2)

<400> SEQUENCE: 3
atggggcgtt tgacctccgg cgtcgggacg gcggccctgc tagttgtcgc ggtgggactc     60
cgcgtcgtct gcgccaaata cgccttagca gacccctcgc ttaagatggc cgatcccaat    120
cgatttcgcg ggaagaacct tccggttttg gaccagctga ccgacccccc cggggtgaag    180
cgtgtttacc acattcagcc gagcctggag gacccgttcc agccccccag catcccgatc    240
actgtgtact acgcagtgct ggaacgtgcc tgccgcagcg tgctcctaca tgccccatcg    300
gaggcccccc agatcgtgcg cggggcttcg gacgaggccc gaaagcacac gtacaacctg    360
accatcgcct ggtatcgcat gggagacaat tgcgctatcc ccatcacggt tatggaatac    420
```

```
accgagtgcc cctacaacaa gtcgttgggg gtctgcccca tccgaacgca gccccgctgg    480
agctactatg acagctttag cgccgtcagc gaggataacc tgggattcct catgcacgcc    540
cccgccttcg agaccgcggg tacgtacctg cggctagtga agataaacga ctggacggag    600
atcacacaat ttatcctgga gcaccgggcc cgcgcctcct gcaagtacgc tctccccctg    660
cgcatccccc cggcagcgtg cctcacctcg aaggcctacc aacagggcgt gacggtcgac    720
agcatcggga tgttaccccg ctttatcccc gaaaaccagc gcaccgtcgc cctatacagc    780
ttaaaaatcg ccgggtggca cggccccaag cccccgtaca ccagcaccct gctgccgccg    840
gagctgtccg acaccaccaa cgccacgcaa cccgaactcg ttccggaaga ccccgaggac    900
tcggccctct tagaggatcc cgccgggacg tgtcttcgc agatcccccc aaactggcac    960
atcccgtcga tccaggacgt cgcgccgcac cacgcccccg ccgccccag caacccgggc   1020 ctgatcatcg gcgcgctggc cggcagtacc ctggcggcg tggtcatcgg cggtattgcg   1080
ttttgggtac gccgccgcgc tcagatggcc cccaagcgcc tacgtctccc ccacatccgg   1140
gatgacgacg cgcccccctc gcaccagcca ttgttttact agaggagttt ccccgttccc   1200
gtgtacctct gggcccgtgt gggagggtgg ccggggtatt tg                     1242
```

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence:primer 6025F

<400> SEQUENCE: 4

```
caagcttctc tatcaaagca gtaagtagta c                                   31
```

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:primer 7773R

<400> SEQUENCE: 5

```
cttcctgctg ctcccaagaa cccaa                                          25
```

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:primer 6196F

<400> SEQUENCE: 6

```
atagaaagag cagaagacag tggca                                          25
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:primer 7746R

<400> SEQUENCE: 7

```
aacaaagctc ctattcccac tgctc                                          25
```

<210> SEQ ID NO 8

```
<211> LENGTH: 32
<212> TYPE: DNA
<213> ORGANISM: Artificial Sequence
<220> FEATURE:
<223> OTHER INFORMATION: Description of Artificial Sequence:primer
      BssH2-6205F

<400> SEQUENCE: 8
ttggcgcgca gaagacagtg gcaatgagag tg                                        32

<210> SEQ ID NO 9
<211> LENGTH: 846
<212> TYPE: DNA
<213> ORGANISM: Hepatitis B virus
<220> FEATURE:
<221> NAME/KEY: CDS
<222> LOCATION: (1)..(846)
<223> OTHER INFORMATION: PreS2-S coding region of hepatitis B virus adr
      surface antigen (HBsAg)

<400> SEQUENCE: 9
```

| | | | | | | | | | | | | | | | | |
|---|---|---|---|---|---|---|---|---|---|---|---|---|---|---|---|---|
| atg | cag | tgg | aac | tcc | aca | aca | ttc | cac | caa | gct | ctg | cta | gac | ccc | aga | 48 |
| Met | Gln | Trp | Asn | Ser | Thr | Thr | Phe | His | Gln | Ala | Leu | Leu | Asp | Pro | Arg | |
| 1 | | | | 5 | | | | | 10 | | | | | 15 | | |
| gtg | agg | ggc | cta | tac | ttt | cct | gct | ggt | ggc | tcc | agt | tcc | gga | aca | gta | 96 |
| Val | Arg | Gly | Leu | Tyr | Phe | Pro | Ala | Gly | Gly | Ser | Ser | Ser | Gly | Thr | Val | |
| | | | 20 | | | | | 25 | | | | | 30 | | | |
| aac | cct | gtt | ccg | act | act | gcc | tca | ccc | ata | tcg | tca | atc | ttc | tcg | agg | 144 |
| Asn | Pro | Val | Pro | Thr | Thr | Ala | Ser | Pro | Ile | Ser | Ser | Ile | Phe | Ser | Arg | |
| | 35 | | | | | 40 | | | | | 45 | | | | | |
| act | ggg | gac | cct | gca | ccg | aac | atg | gag | aac | aca | tca | gga | ttc | cta | | 192 |
| Thr | Gly | Asp | Pro | Ala | Pro | Asn | Met | Glu | Asn | Thr | Thr | Ser | Gly | Phe | Leu | |
| | 50 | | | | 55 | | | | | 60 | | | | | | |
| gga | ccc | ctg | ctc | gtg | tta | cag | gcg | ggg | ttt | ttc | ttg | ttg | aca | aga | atc | 240 |
| Gly | Pro | Leu | Leu | Val | Leu | Gln | Ala | Gly | Phe | Phe | Leu | Leu | Thr | Arg | Ile | |
| 65 | | | | | 70 | | | | | 75 | | | | | 80 | |
| ctc | aca | ata | cca | cag | agt | cta | cac | tcg | tgg | tgg | act | tct | ctc | aat | ttt | 288 |
| Leu | Thr | Ile | Pro | Gln | Ser | Leu | His | Ser | Trp | Trp | Thr | Ser | Leu | Asn | Phe | |
| | | | | 85 | | | | | 90 | | | | | 95 | | |
| cta | ggg | gca | gca | ccc | acg | tgt | ctt | ggc | caa | aat | tcg | cag | tcc | cca | acc | 336 |
| Leu | Gly | Ala | Ala | Pro | Thr | Cys | Leu | Gly | Gln | Asn | Ser | Gln | Ser | Pro | Thr | |
| | | | 100 | | | | | 105 | | | | | 110 | | | |
| tcc | aat | cac | tca | cca | acc | tct | tgt | cct | cca | att | tgt | cct | ggt | tat | cgt | 384 |
| Ser | Asn | His | Ser | Pro | Thr | Ser | Cys | Pro | Pro | Ile | Cys | Pro | Gly | Tyr | Arg | |
| | | 115 | | | | | 120 | | | | | 125 | | | | |
| tgg | atg | tgt | ctg | cgg | cgt | ttt | atc | ata | ttc | ctc | ttc | atc | ctg | ctg | cta | 432 |
| Trp | Met | Cys | Leu | Arg | Arg | Phe | Ile | Ile | Phe | Leu | Phe | Ile | Leu | Leu | Leu | |
| | 130 | | | | | 135 | | | | | 140 | | | | | |
| tgc | ctc | atc | ttc | ttg | ttg | gtt | ctt | ctg | gac | tac | caa | ggt | atg | ttg | tct | 480 |
| Cys | Leu | Ile | Phe | Leu | Leu | Val | Leu | Leu | Asp | Tyr | Gln | Gly | Met | Leu | Ser | |
| 145 | | | | | 150 | | | | | 155 | | | | | 160 | |
| gtt | tgt | cct | cta | ctt | cca | aga | aca | tca | act | acc | agc | acg | gga | cca | tgc | 528 |
| Val | Cys | Pro | Leu | Leu | Pro | Arg | Thr | Ser | Thr | Thr | Ser | Thr | Gly | Pro | Cys | |
| | | | | 165 | | | | | 170 | | | | | 175 | | |
| aag | acc | tgc | acg | att | cct | gct | caa | gga | acc | tct | atg | ttt | ccc | tct | tct | 576 |
| Lys | Thr | Cys | Thr | Ile | Pro | Ala | Gln | Gly | Thr | Ser | Met | Phe | Pro | Ser | Ser | |
| | | | 180 | | | | | 185 | | | | | 190 | | | |
| tgc | tgt | aca | aaa | cct | tcg | gac | gga | aac | tgc | act | tgt | att | ccc | atc | cca | 624 |
| Cys | Cys | Thr | Lys | Pro | Ser | Asp | Gly | Asn | Cys | Thr | Cys | Ile | Pro | Ile | Pro | |
| | | 195 | | | | | 200 | | | | | 205 | | | | |
| tca | tct | tgg | gct | ttc | gca | aga | ttc | cta | tgg | gag | tgg | gcc | tca | gtc | cgt | 672 |
| Ser | Ser | Trp | Ala | Phe | Ala | Arg | Phe | Leu | Trp | Glu | Trp | Ala | Ser | Val | Arg | |
| | 210 | | | | | 215 | | | | | 220 | | | | | |

-continued

```
ttc tcc tgg ctc agt tta cta gtg cca ttt gtt cag tgg ttc gta ggg       720
Phe Ser Trp Leu Ser Leu Val Pro Phe Val Gln Trp Phe Val Gly
225             230             235             240 ctt tcc ccc act gtt tgg ctt tca gtt ata tgg atg atg tgg tat tgg       768
Leu Ser Pro Thr Val Trp Leu Ser Val Ile Trp Met Met Trp Tyr Trp
            245             250             255 ggg cca agt ctg tac aac atc ttg agt ccc ttt tta cct cta tta cca       816
Gly Pro Ser Leu Tyr Asn Ile Leu Ser Pro Phe Leu Pro Leu Leu Pro
        260             265             270 att ttc ttt tgt ctt tgg gta tac att tga                               846
Ile Phe Phe Cys Leu Trp Val Tyr Ile
        275             280
```

<210> SEQ ID NO 10
<211> LENGTH: 281
<212> TYPE: PRT
<213> ORGANISM: Hepatitis B virus

<400> SEQUENCE: 10

```
Met Gln Trp Asn Ser Thr Thr Phe His Gln Ala Leu Leu Asp Pro Arg
 1               5                  10                  15

Val Arg Gly Leu Tyr Phe Pro Ala Gly Gly Ser Ser Ser Gly Thr Val
            20                  25                  30

Asn Pro Val Pro Thr Thr Ala Ser Pro Ile Ser Ser Ile Phe Ser Arg
        35                  40                  45

Thr Gly Asp Pro Ala Pro Asn Met Glu Asn Thr Thr Ser Gly Phe Leu
    50                  55                  60

Gly Pro Leu Leu Val Leu Gln Ala Gly Phe Phe Leu Leu Thr Arg Ile
65                  70                  75                  80

Leu Thr Ile Pro Gln Ser Leu His Ser Trp Trp Thr Ser Leu Asn Phe
                85                  90                  95

Leu Gly Ala Ala Pro Thr Cys Leu Gly Gln Asn Ser Gln Ser Pro Thr
            100                 105                 110

Ser Asn His Ser Pro Thr Ser Cys Pro Pro Ile Cys Pro Gly Tyr Arg
        115                 120                 125

Trp Met Cys Leu Arg Arg Phe Ile Ile Phe Leu Phe Ile Leu Leu Leu
    130                 135                 140

Cys Leu Ile Phe Leu Leu Val Leu Leu Asp Tyr Gln Gly Met Leu Ser
145                 150                 155                 160

Val Cys Pro Leu Leu Pro Arg Thr Ser Thr Thr Ser Thr Gly Pro Cys
                165                 170                 175

Lys Thr Cys Thr Ile Pro Ala Gln Gly Thr Ser Met Phe Pro Ser Ser
            180                 185                 190

Cys Cys Thr Lys Pro Ser Asp Gly Asn Cys Thr Cys Ile Pro Ile Pro
        195                 200                 205

Ser Ser Trp Ala Phe Ala Arg Phe Leu Trp Glu Trp Ala Ser Val Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Ile Trp Met Met Trp Tyr Trp
                245                 250                 255

Gly Pro Ser Leu Tyr Asn Ile Leu Ser Pro Phe Leu Pro Leu Leu Pro
            260                 265                 270

Ile Phe Phe Cys Leu Trp Val Tyr Ile
        275                 280
```

<210> SEQ ID NO 11
<211> LENGTH: 846
<212> TYPE: DNA
<213> ORGANISM: Hepatitis B virus
<220> FEATURE:
<221> NAME/KEY: CDS
<222> LOCATION: (1)..(846)
<223> OTHER INFORMATION: PreS2-S coding region of hepatitis B virus ayw surface antigen (HBsAg)

<400> SEQUENCE: 11

```
atg cag tgg aat tcc aca acc ttc cac caa act ctg caa gat ccc aga      48
Met Gln Trp Asn Ser Thr Thr Phe His Gln Thr Leu Gln Asp Pro Arg
 1               5                  10                  15 gtg aga ggc ctg tat ttc cct gct ggt ggc tcc agt tca gga aca gta      96
Val Arg Gly Leu Tyr Phe Pro Ala Gly Gly Ser Ser Ser Gly Thr Val
                20                  25                  30 aac cct gtt ctg act act gcc tct ccc tta tcg tca atc ttc tcg agg     144
Asn Pro Val Leu Thr Thr Ala Ser Pro Leu Ser Ser Ile Phe Ser Arg
            35                  40                  45 att ggg gac cct gcg ctg aac atg gag aac atc aca tca gga ttc cta     192
Ile Gly Asp Pro Ala Leu Asn Met Glu Asn Ile Thr Ser Gly Phe Leu
        50                  55                  60 gga ccc ctt ctc gtg tta cag gcg ggt ttt ttc ttg ttg aca aga atc     240
Gly Pro Leu Leu Val Leu Gln Ala Gly Phe Phe Leu Leu Thr Arg Ile
 65                  70                  75                  80 ctc aca ata ccg cag agt cta gac tcg tgg tgg act tct ctc aat ttt     288
Leu Thr Ile Pro Gln Ser Leu Asp Ser Trp Trp Thr Ser Leu Asn Phe
                85                  90                  95 cta ggg gga act acc gtg tgt ctt ggc caa aat tcg cag tcc cca acc     336
Leu Gly Gly Thr Thr Val Cys Leu Gly Gln Asn Ser Gln Ser Pro Thr
               100                 105                 110 tcc aat cac tca cca acc tct tgt cct cca act tgt cct ggt tat cgc     384
Ser Asn His Ser Pro Thr Ser Cys Pro Pro Thr Cys Pro Gly Tyr Arg
           115                 120                 125 tgg atg tgt ctg cgg cgt ttt atc atc ttc ctc ttc atc ctg ctg cta     432
Trp Met Cys Leu Arg Arg Phe Ile Ile Phe Leu Phe Ile Leu Leu Leu
       130                 135                 140 tgc ctc atc ttc ttg ttg gtt ctt ctg gac tat caa ggt atg ttg ccc     480
Cys Leu Ile Phe Leu Leu Val Leu Leu Asp Tyr Gln Gly Met Leu Pro
145                 150                 155                 160 gtt tgt cct cta att cca gga tcc tca aca acc agc acg gga cca tgc     528
Val Cys Pro Leu Ile Pro Gly Ser Ser Thr Thr Ser Thr Gly Pro Cys
                165                 170                 175 cgg acc tgc atg act act gct caa gga acc tct atg tat ccc tcc tgt     576
Arg Thr Cys Met Thr Thr Ala Gln Gly Thr Ser Met Tyr Pro Ser Cys
            180                 185                 190 tgc tgt acc aaa cct tcg gac gga aat tgc acc tgt att ccc atc cca     624
Cys Cys Thr Lys Pro Ser Asp Gly Asn Cys Thr Cys Ile Pro Ile Pro
        195                 200                 205 tca tcc tgg gct ttc gga aaa ttc cta tgg gag tgg gcc tca gcc cgt     672
Ser Ser Trp Ala Phe Gly Lys Phe Leu Trp Glu Trp Ala Ser Ala Arg
    210                 215                 220 ttc tcc tgg ctc agt tta cta gtg cca ttt gtt cag tgg ttc gta ggg     720
Phe Ser Trp Leu Ser Leu Leu Val Pro Phe Val Gln Trp Phe Val Gly
225                 230                 235                 240 ctt tcc ccc act gtt tgg ctt tca gtt ata tgg atg atg tgg tat tgg     768
Leu Ser Pro Thr Val Trp Leu Ser Val Ile Trp Met Met Trp Tyr Trp
                245                 250                 255 ggg cca agt ctg tac agc atc ttg agt ccc ttt tta ccg ctg tta cca     816
Gly Pro Ser Leu Tyr Ser Ile Leu Ser Pro Phe Leu Pro Leu Leu Pro
```

```
                    260                 265                 270
att ttc ttt tgt ctt tgg gta tac att taa                              846
Ile Phe Phe Cys Leu Trp Val Tyr Ile
        275                 280

<210> SEQ ID NO 12
<211> LENGTH: 281
<212> TYPE: PRT
<213> ORGANISM: Hepatitis B virus

<400> SEQUENCE: 12

Met Gln Trp Asn Ser Thr Thr Phe His Gln Thr Leu Gln Asp Pro Arg
  1               5                  10                  15

Val Arg Gly Leu Tyr Phe Pro Ala Gly Gly Ser Ser Ser Gly Thr Val
             20                  25                  30

Asn Pro Val Leu Thr Thr Ala Ser Pro Leu Ser Ser Ile Phe Ser Arg
         35                  40                  45

Ile Gly Asp Pro Ala Leu Asn Met Glu Asn Ile Thr Ser Gly Phe Leu
     50                  55                  60

Gly Pro Leu Leu Val Leu Gln Ala Gly Phe Phe Leu Leu Thr Arg Ile
 65                  70                  75                  80

Leu Thr Ile Pro Gln Ser Leu Asp Ser Trp Trp Thr Ser Leu Asn Phe
                 85                  90                  95

Leu Gly Gly Thr Thr Val Cys Leu Gly Gln Asn Ser Gln Ser Pro Thr
            100                 105                 110

Ser Asn His Ser Pro Thr Ser Cys Pro Pro Thr Cys Pro Gly Tyr Arg
        115                 120                 125

Trp Met Cys Leu Arg Arg Phe Ile Ile Phe Leu Phe Ile Leu Leu Leu
    130                 135                 140

Cys Leu Ile Phe Leu Leu Val Leu Leu Asp Tyr Gln Gly Met Leu Pro
145                 150                 155                 160

Val Cys Pro Leu Ile Pro Gly Ser Ser Thr Thr Ser Thr Gly Pro Cys
                165                 170                 175

Arg Thr Cys Met Thr Thr Ala Gln Gly Thr Ser Met Tyr Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Gly Lys Phe Leu Trp Glu Trp Ala Ser Ala Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Ile Trp Met Met Trp Tyr Trp
                245                 250                 255

Gly Pro Ser Leu Tyr Ser Ile Leu Ser Pro Phe Leu Pro Leu Leu Pro
            260                 265                 270

Ile Phe Phe Cys Leu Trp Val Tyr Ile
        275                 280

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence:forward HBV
      ayw PCR primer

<400> SEQUENCE: 13
```

```
ccgggaattc ctcgacacca tgcagtggaa ttccacaacc                          40

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence:reverse HBV
      ayw PCR primer

<400> SEQUENCE: 14
ccggggtacc caaagacaaa agaaaattgg taacagcgg                           39

<210> SEQ ID NO 15
<211> LENGTH: 849
<212> TYPE: DNA
<213> ORGANISM: Woodchuck hepatitis B virus
<220> FEATURE:
<221> NAME/KEY: CDS
<222> LOCATION: (1)..(849)
<223> OTHER INFORMATION: Woodchuck hepatitis B virus (WHV8) surface
      antigen

<400> SEQUENCE: 15 atg aaa aat cag act ttt cat ctc cag ggg ttc gta gac gga tta cga        48
Met Lys Asn Gln Thr Phe His Leu Gln Gly Phe Val Asp Gly Leu Arg
 1               5                  10                  15 gac ttg aca aca acg gaa cgc caa cac aat gcc tat gga gat cct ttt        96
Asp Leu Thr Thr Thr Glu Arg Gln His Asn Ala Tyr Gly Asp Pro Phe
             20                  25                  30 aca aca cta agc cct gcg gtt cct act gta tcc acc ata ttg tct cct       144
Thr Thr Leu Ser Pro Ala Val Pro Thr Val Ser Thr Ile Leu Ser Pro
         35                  40                  45 ccc tcg acg act ggg gac cct gca ctg tca ccg gag atg tca cca tca       192
Pro Ser Thr Thr Gly Asp Pro Ala Leu Ser Pro Glu Met Ser Pro Ser
     50                  55                  60 agt ctc cta gga ctc ctc gca gga tta cag gtg gtg tat ttc ttg tgg       240
Ser Leu Leu Gly Leu Leu Ala Gly Leu Gln Val Val Tyr Phe Leu Trp
 65                  70                  75                  80 aca aaa atc cta aca ata gct cag aat cta gat tgg tgg tgg act tct       288
Thr Lys Ile Leu Thr Ile Ala Gln Asn Leu Asp Trp Trp Trp Thr Ser
                 85                  90                  95 ctc agt ttt cca ggg ggc ata cca gag tgc act ggc caa aat tcg cag       336
Leu Ser Phe Pro Gly Gly Ile Pro Glu Cys Thr Gly Gln Asn Ser Gln
            100                 105                 110 ttc caa act tgc aaa cac ttg cca acc tcc tgt cca cca act tgc aat       384
Phe Gln Thr Cys Lys His Leu Pro Thr Ser Cys Pro Pro Thr Cys Asn
        115                 120                 125 ggc ttt cgt tgg atg tat ctg cgg cgt ttt atc ata tac cta tta gtc       432
Gly Phe Arg Trp Met Tyr Leu Arg Arg Phe Ile Ile Tyr Leu Leu Val
    130                 135                 140 ctg ctg ctg tgc ctc atc ttc ttg ttg gtt ctc ctg gac tgg aaa ggt       480
Leu Leu Leu Cys Leu Ile Phe Leu Leu Val Leu Leu Asp Trp Lys Gly
145                 150                 155                 160 tta ata cct gtc tgt cct ctt caa ccc aca aca gaa aca aca gtc aat       528
Leu Ile Pro Val Cys Pro Leu Gln Pro Thr Thr Glu Thr Thr Val Asn
                165                 170                 175 tgc aga caa tgc aca atc tct gca caa gac atg tat act cct cct tac       576
Cys Arg Gln Cys Thr Ile Ser Ala Gln Asp Met Tyr Thr Pro Pro Tyr
            180                 185                 190 tgt tgt tgt tta aaa cct acg gca gga aat tgc act tgt tgg ccc atc       624
Cys Cys Cys Leu Lys Pro Thr Ala Gly Asn Cys Thr Cys Trp Pro Ile
        195                 200                 205
```

```
cct tca tca tgg gct tta gga aat tac cta tgg gag tgg gcc tta gcc       672
Pro Ser Ser Trp Ala Leu Gly Asn Tyr Leu Trp Glu Trp Ala Leu Ala
    210                 215                 220 cgt ttc tct tgg ctc aat tta cta gtg ccc ttg ctt caa tgg tta gga       720
Arg Phe Ser Trp Leu Asn Leu Leu Val Pro Leu Gln Trp Leu Gly
225                 230                 235                 240 gga att tcc ctc att gcg tgg ttt ttg ctt ata tgg atg att tgg ttt       768
Gly Ile Ser Leu Ile Ala Trp Phe Leu Leu Ile Trp Met Ile Trp Phe
                245                 250                 255 tgg ggg ccc gca ctt ctg agc atc tta ccg cca ttt att ccc ata ttt       816
Trp Gly Pro Ala Leu Leu Ser Ile Leu Pro Pro Phe Ile Pro Ile Phe
    260                 265                 270 gtt ctg ttt ttc ttg att tgg gta tac att tga                           849
Val Leu Phe Phe Leu Ile Trp Val Tyr Ile
            275                 280

<210> SEQ ID NO 16
<211> LENGTH: 282
<212> TYPE: PRT
<213> ORGANISM: Woodchuck hepatitis B virus

<400> SEQUENCE: 16

Met Lys Asn Gln Thr Phe His Leu Gln Gly Phe Val Asp Gly Leu Arg
 1               5                  10                  15

Asp Leu Thr Thr Thr Glu Arg Gln His Asn Ala Tyr Gly Asp Pro Phe
                20                  25                  30

Thr Thr Leu Ser Pro Ala Val Pro Thr Val Ser Thr Ile Leu Ser Pro
            35                  40                  45

Pro Ser Thr Thr Gly Asp Pro Ala Leu Ser Pro Glu Met Ser Pro Ser
        50                  55                  60

Ser Leu Leu Gly Leu Leu Ala Gly Leu Gln Val Val Tyr Phe Leu Trp
65                  70                  75                  80

Thr Lys Ile Leu Thr Ile Ala Gln Asn Leu Asp Trp Trp Thr Ser
                85                  90                  95

Leu Ser Phe Pro Gly Gly Ile Pro Glu Cys Thr Gly Asn Ser Gln
                100                 105                 110

Phe Gln Thr Cys Lys His Leu Pro Thr Ser Cys Pro Pro Thr Cys Asn
            115                 120                 125

Gly Phe Arg Trp Met Tyr Leu Arg Arg Phe Ile Ile Tyr Leu Leu Val
        130                 135                 140

Leu Leu Leu Cys Leu Ile Phe Leu Leu Val Leu Leu Asp Trp Lys Gly
145                 150                 155                 160

Leu Ile Pro Val Cys Pro Leu Gln Pro Thr Thr Glu Thr Thr Val Asn
                165                 170                 175

Cys Arg Gln Cys Thr Ile Ser Ala Gln Asp Met Tyr Thr Pro Pro Tyr
            180                 185                 190

Cys Cys Cys Leu Lys Pro Thr Ala Gly Asn Cys Thr Cys Trp Pro Ile
        195                 200                 205

Pro Ser Ser Trp Ala Leu Gly Asn Tyr Leu Trp Glu Trp Ala Leu Ala
    210                 215                 220

Arg Phe Ser Trp Leu Asn Leu Leu Val Pro Leu Leu Gln Trp Leu Gly
225                 230                 235                 240

Gly Ile Ser Leu Ile Ala Trp Phe Leu Leu Ile Trp Met Ile Trp Phe
                245                 250                 255

Trp Gly Pro Ala Leu Leu Ser Ile Leu Pro Pro Phe Ile Pro Ile Phe
            260                 265                 270
```

Val Leu Phe Phe Leu Ile Trp Val Tyr Ile
        275                 280

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence:forward WHV
      PCR primer

<400> SEQUENCE: 17
ccgggaattc tcatctccag gggttcgtag acggattacg                             40

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence:reverse WHV
      PCR primer

<400> SEQUENCE: 18
ccggggtacc caaatcaaga aaacagaac aaatatggg                               39

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:AYWSHFOR
      primer

<400> SEQUENCE: 19
gccggcagga aggaaatggg                                                   20

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:AYWSHREV
      primer

<400> SEQUENCE: 20
ctgctattgt cttcccaatc ctc                                               23

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:WHVSHFOR
      primer

<400> SEQUENCE: 21
cgggacatac cacgtggttt ag                                                22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence:WHVSHREV
      primer

<400> SEQUENCE: 22

```
ggcattaaag cagcgtatcc ac                                              22

<210> SEQ ID NO 23
<211> LENGTH: 16
<212> TYPE: PRT
<213> ORGANISM: Plasmodium berghei
<220> FEATURE:
<221> NAME/KEY: PEPTIDE
<222> LOCATION: (1)..(16)
<223> OTHER INFORMATION: circumsporozoite (CS) protein-based B-epitope

<400> SEQUENCE: 23

Pro Pro Pro Pro Asn Pro Asn Asp Pro Pro Pro Pro Asn Pro Asn Asp
 1               5                  10                  15

<210> SEQ ID NO 24
<211> LENGTH: 20
<212> TYPE: PRT
<213> ORGANISM: Plasmodium yoelii
<220> FEATURE:
<221> NAME/KEY: PEPTIDE
<222> LOCATION: (1)..(20)
<223> OTHER INFORMATION: circumsporozoite (CS) protein-based B-epitope

<400> SEQUENCE: 24

Gln Gly Pro Gly Ala Pro Gln Gly Pro Gly Ala Pro Gln Gly Pro Gly
 1               5                  10                  15

Ala Pro Gln Gly
            20

<210> SEQ ID NO 25
<211> LENGTH: 12
<212> TYPE: PRT
<213> ORGANISM: Plasmodium berghei
<220> FEATURE:
<221> NAME/KEY: PEPTIDE
<222> LOCATION: (1)..(12)
<223> OTHER INFORMATION: T-helper epitope

<400> SEQUENCE: 25

Lys Gln Ile Arg Asp Ser Ile Thr Glu Glu Trp Ser
 1               5                  10
```